United States Patent
Attar et al.

(10) Patent No.: US 12,077,592 B2
(45) Date of Patent: Sep. 3, 2024

(54) GPRC5D CHIMERIC ANTIGEN RECEPTORS AND CELLS EXPRESSING THE SAME

(71) Applicant: Janssen Biotech, Inc., Horsham, PA (US)

(72) Inventors: Ricardo Attar, Lawrenceville, NJ (US); Rajkumar Ganesan, Blue Bell, PA (US); Francois Gaudet, Princeton, NJ (US); Bradley J. Heidrich, Gilbertsville, PA (US); Carmen Baca Jones, Ambler, PA (US); John Lee, North Wales, PA (US); Yingzhe Li, Dresher, PA (US); Sanjaya Singh, Blue Bell, PA (US); Sathya Venkataramani, Blue Bell, PA (US)

(73) Assignee: Janssen Biotech, Inc., Horsham, PA (US)

( * ) Notice: Subject to any disclaimer, the term of this patent is extended or adjusted under 35 U.S.C. 154(b) by 647 days.

(21) Appl. No.: 16/743,188

(22) Filed: Jan. 15, 2020

(65) Prior Publication Data
US 2020/0231686 A1    Jul. 23, 2020

Related U.S. Application Data

(60) Provisional application No. 62/793,973, filed on Jan. 18, 2019.

(51) Int. Cl.
| | |
|---|---|
| *C07K 16/28* | (2006.01) |
| *A61K 9/00* | (2006.01) |
| *A61P 35/00* | (2006.01) |
| *A61K 39/00* | (2006.01) |

(52) U.S. Cl.
CPC ........ *C07K 16/2866* (2013.01); *A61K 9/0019* (2013.01); *A61P 35/00* (2018.01); *A61K 2039/505* (2013.01); *A61K 2039/54* (2013.01); *A61K 2039/545* (2013.01); *C07K 2317/24* (2013.01); *C07K 2317/53* (2013.01); *C07K 2317/565* (2013.01); *C07K 2317/622* (2013.01); *C07K 2317/73* (2013.01); *C07K 2317/74* (2013.01); *C07K 2319/02* (2013.01); *C07K 2319/03* (2013.01); *C07K 2319/30* (2013.01); *C07K 2319/33* (2013.01)

(58) Field of Classification Search
CPC ............ C07K 16/2866; C07K 2317/24; C07K 2317/53; C07K 2317/565; C07K 2317/622; C07K 2317/73; C07K 2317/74; C07K 2319/02; C07K 2319/03; C07K 2319/30; A61K 9/0019; A61K 2039/505; A61K 2039/54; A61K 2039/545; A61P 35/00

See application file for complete search history.

(56) References Cited

U.S. PATENT DOCUMENTS

| | | | |
|---|---|---|---|
| 3,832,253 | A | 8/1974 | Palma et al. |
| 3,854,480 | A | 12/1974 | Zaffaroni |
| 4,452,775 | A | 6/1984 | Kent |
| 4,667,014 | A | 5/1987 | Nestor, Jr. et al. |
| 4,748,034 | A | 5/1988 | de Rham |
| 5,225,539 | A | 7/1993 | Winter |
| 5,239,660 | A | 8/1993 | Ooi |
| 5,545,806 | A | 8/1996 | Lonberg et al. |
| 5,569,825 | A | 10/1996 | Lonberg et al. |
| 5,585,089 | A | 12/1996 | Queen et al. |
| 5,639,641 | A | 6/1997 | Pedersen et al. |
| 5,693,761 | A | 12/1997 | Queen et al. |
| 5,714,352 | A | 2/1998 | Jakobovits |
| 6,265,150 | B1 | 7/2001 | Terstappen et al. |
| 7,695,936 | B2 | 4/2010 | Carter et al. |
| 2002/0197266 | A1 | 12/2002 | Debinski |
| 2007/0287170 | A1 | 12/2007 | Davis et al. |
| 2009/0182127 | A1 | 7/2009 | Kjaergaard et al. |
| 2010/0015133 | A1 | 1/2010 | Igawa et al. |
| 2010/0286374 | A1 | 11/2010 | Kannan et al. |
| 2011/0123532 | A1 | 5/2011 | Gurney et al. |
| 2012/0149876 | A1 | 6/2012 | Von Kreudenstein et al. |
| 2020/0231686 | A1 | 7/2020 | Attar et al. |
| 2020/0268797 | A1* | 8/2020 | Ganesan ................ C12N 13/00 |

FOREIGN PATENT DOCUMENTS

| | | |
|---|---|---|
| CL | 201900146 A1 | 4/2019 |
| EP | 0 239 400 B1 | 9/1987 |
| EP | 0 3 581 651 A1 | 12/2019 |
| EP | 0 391 1677 A1 | 11/2021 |
| GB | 2188638 A | 10/1987 |
| WO | WO 2004/111233 A1 | 12/2004 |
| WO | WO 2008/119353 A1 | 10/2008 |
| WO | WO 2008/119353 A8 | 10/2008 |
| WO | WO 2009/085462 A1 | 7/2009 |
| WO | WO 2011/131746 A2 | 10/2011 |
| WO | WO 2011/131746 A3 | 10/2011 |
| WO | WO 2011/143545 A1 | 11/2011 |

(Continued)

OTHER PUBLICATIONS

Mariuzza (Annu. Rev. Biophys. Biophys. Chem., 16: 139-159, 1987).*
Zhang et al. (Biomarker Research, 5(22): 1-6, 2017).*
Altschul, S.F., et al., "Basic Local Alignment Search Tool", J. Mol. Biol, (1990), vol. 215, pp. 403-410.

(Continued)

*Primary Examiner* — Nelson B Moseley, II

(57) ABSTRACT

The present disclosure provides for chimeric antigen receptors (CARs) that specifically target a G-protein coupled receptor, G-protein coupled receptor family C group 5 member D (GPRC5D), and immunoresponsive cells comprising such CARs, for the treatment of cancer.

36 Claims, 28 Drawing Sheets
Specification includes a Sequence Listing.

(56) References Cited

FOREIGN PATENT DOCUMENTS

| WO | WO 2013/063419 | * | 5/2013 | ............ A61K 48/00 |
|----|----------------|---|--------|------------------------|
| WO | WO 2016/090312 A1 | | 6/2016 | |
| WO | WO 2017/015490 | * | 1/2017 | ............ A61K 35/17 |
| WO | WO 2018/017786 A2 | | 1/2018 | |
| WO | WO 2018/147245 A1 | | 8/2018 | |
| WO | WO 2019/094626 | * | 11/2018 | ............ A61K 49/14 |
| WO | WO 2019/060695 A1 | | 3/2019 | |
| WO | WO 2020/148677 A1 | | 7/2020 | |

OTHER PUBLICATIONS

Bird, R.E., et al., "Single-Chain Antigen-Binding Proteins", Science, (1988), vol. 242, pp. 423-426.

Brash, D.E., et al., "Strontium Phosphate Transfection of Human Cells in Primary Culture: Stable Expression of the Simian Virus 40 Large-T-Antigen Gene in Primary Human Bronchial Epithelial Cells", Molecular and Cellular Biology, (1987), vol. 7, No. 8, pp. 2031-2034.

Chothia, C., et al., "Canonical Structures for the Hypervariable Regions of Immunoglobulins", J. Mol. Biol., (1987), vol. 196, pp. 901-917.

Haskard, D.O., et al., "The Production of Human Monoclonal Autoantibodies from Patients with Rheumatoid Arthritis by the EBV-Hybridoma Techique", Journal of Immunological Methods, (1984), vol. 74, pp. 361-367.

Hudecz, F., "Synthesis of Peptide Bioconjugates", Methods Mol. Biol., (2005), vol. 298, pp. 209-223.

Huse, W.D., et al., "Generation of a Large Combinatorial Library of the Immunoglobulin Repertoire in Phage Lambda", Science, (1989), vol. 246, pp. 1275-1281.

Huston, J.S., et al., Protein engineering of antibody binding sites: Recovery of specific activity in an anti-digoxin single-chain Fv analogue produced in *Escherichia coli*, Proc. Natl. Acad. Sci. USA, (1988), vol. 85, pp. 5879-5883.

Johnston, S.A., "Biolistic transformation: microbes to mice", Nature, (1990), vol. 346, pp. 776-777.

Kirin, S.I., et al., "Amino Acid and Peptide Bioconjugates of Copper(II) and Zinc(II) Complexes with a Modified N,N-Bis(2-picoly)amine Ligand", Inorganic Chemistry, (2005), vol. 44, No. 15, pp. 5405-5415.

Knappik, A., et al., "Fully Synthetic Human Combinatorial Antibody Libraries (HuCAL) Based on Modular Consensus Frameworks and CDRs Randomized with Trinucleotides", J. Mol. Biol., (2000), vol. 296, pp. 57-86.

Kohler, G., et al., "Derivation of specific antibody-producing tissue culture and tumor lines by cell fusion", Eur. J. Immunol., (1976), vol. 6, pp. 511-519.

Lefranc, M.P., et al., "IMGT unique numbering for immunoglobulin and T cell receptor variable domains and Ig superfamily V-like domains", Developmental and Comparative Immunology, (2003), vol. 27, pp. 55-77.

Lefranc, M.P., et al., "IMGTR, the international ImMunoGeneTics information system®", Nucleic Acids of Research, (2009), vol. 37, pp. D1006-D1012.

Myers, E.W., et al., "Optimal alignments in linear space", CABIOS, (1988), vol. 4, No. 1, pp. 11-17.

Murray, E.J.,"Gene Transfer and Expression Protocols", Methods in Lolecular Biology, (1991), vol. 7, Table of Contents.

Needleman, S.B., et al., "A General Method Applicable to the Search for Similarities in the Amino Acid Sequence of Two Proteins", J. Mol. Biol., (1970), vol. 48, pp. 443-453.

Pedersen, J.T., et al., "Comparison of Surface Accessible Residues in Human and Murine Immunoglobulin Fv Domains", J. Mol. Biol., (1994), vol. 235, pp. 959-973.

Roder, J.C., et al., "The EBV-Hybridoma Technique", Methods in Enzymology, (1986), vol. 121, pp. 140-167.

Rosenberg, S.A., et al., "Use of Tumor-Infiltrating Lymphocytes and Interleukin-2 in the Immunotherapy of Patients with Metastatic Melanoma", New England Journal of Medicine, (1988), vol. 319, p. 1676.

Shi, L., et al., "De Novo Selection of High-Affinity Antibodies from Synthetic Fab Libraries Displayed on Phage as pIX Fusion Proteins", J. Mol. Biol., (2010), vol. 397, pp. 385-396.

Wu, T.T., et al., "An Analysis of the Sequences of the Variable Regions of Bence Jones Proteins and Myeloma Light Chains and Their Implications for Antibody Complementarity", J. Exp. Med., (1970), vol. 132, pp. 211-250.

Smith, E.L., et al., "Car T Cell Therapy targeting G protein-coupled receptor class C group 5 Member D (GPRC5D), a novel target for the immunotherapy of multiple myeloma", (2018), Blood, vol. 132, No. supplement 1, p. 589.

Smith, E.L., et al., "GPRC5D is a target for the immunotherapy of multiple myeloma with rationally designed Car T cells", (2019), Sci.Transl.Med, vol. 11, No. eaau7746, pp. 1-14.

International Search Report from PCT/IB2020/050310 dated Apr. 23, 2020.

* cited by examiner

A.

B.

ically in ASCII format and is hereby incorporated by reference in its entirety. Said ASCII copy, created on Jan. 9, 2020, is named JBI6043WOPCT1_SL.txt and is 150,002 bytes in size.

```
                              SEQUENCE LISTING

<160> NUMBER OF SEQ ID NOS: 127

<210> SEQ ID NO 1
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gln Gly Thr Lys Val Glu Ile Lys
            100                 105

<210> SEQ ID NO 2
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Phe Ile Gly Trp Val Arg Gln Met Pro Gly Lys Gly Leu Glu Trp Met
        35                  40                  45

Gly Ile Ile Tyr Pro Gly Lys Ser Asp Thr Arg Tyr Ser Pro Ser Phe
    50                  55                  60
```

```
Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg Val Tyr Ser Phe Gly Gly Arg His Lys Ala Leu Phe Asp Tyr
            100                 105                 110

Trp Gly Gln Gly Thr Leu Val Thr Val Ser Ser
            115                 120
```

<210> SEQ ID NO 3
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

```
Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Ser Ile Ser Ser Tyr
             20                  25                  30

Leu Asn Trp Tyr Gln Gln Lys Pro Gly Lys Ala Pro Lys Leu Leu Ile
         35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro Leu
                 85                  90                  95

Thr Phe Gly Gln Gly Thr Lys Val Glu Ile Lys
            100                 105
```

<210> SEQ ID NO 4
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

```
Gln Val Gln Leu Val Gln Ser Gly Ala Glu Val Lys Lys Pro Gly Ser
  1               5                  10                  15

Ser Val Lys Val Ser Cys Lys Ala Ser Gly Gly Thr Phe Ser Ser Tyr
             20                  25                  30

Ala Ile Ser Trp Val Arg Gln Ala Pro Gly Gln Gly Leu Glu Trp Met
         35                  40                  45

Gly Gly Ile Ile Pro Ile Phe Gly Thr Ala Asn Tyr Ala Gln Lys Phe
 50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Glu Ser Arg Trp Arg Gly Tyr Lys Leu Asp Tyr Trp Gly Gln
            100                 105                 110

Gly Thr Leu Val Thr Val Ser Ser
            115                 120
```

<210> SEQ ID NO 5
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Ala Thr His
            20                  25                  30

Val Gly Trp Tyr Gln Gln Lys Pro Gly Lys Ala Pro Lys Arg Leu Ile
        35                  40                  45

Tyr Ser Ala Ser Tyr Arg Tyr Ser Gly Val Pro Ser Arg Phe Ser Gly
    50                  55                  60

Ser Gly Ser Gly Thr Glu Phe Thr Leu Thr Ile Ser Asn Leu Gln Pro
65                  70                  75                  80

Glu Asp Phe Ala Thr Tyr Tyr Cys Gln Gln Tyr Asn Arg Tyr Pro Tyr
                85                  90                  95

Thr Phe Gly Gln Gly Thr Lys Leu Glu Ile Lys
            100                 105

<210> SEQ ID NO 6
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
            20                  25                  30

Thr Met Asn Trp Val Arg Gln Ala Pro Gly Gln Gly Leu Glu Trp Met
        35                  40                  45

Gly Leu Ile Asn Pro Tyr Asn Ser Asp Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Val Ala Leu Arg Val Ala Leu Asp Tyr Trp Gly Gln Gly Thr
            100                 105                 110

Leu Val Thr Val Ser Ser
        115

<210> SEQ ID NO 7
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

```
Gly Thr Glu Gly Lys Ser Ser Gly Ser Gly Ser Glu Ser Lys Ser Thr
1               5                   10                  15
```

<210> SEQ ID NO 8
<211> LENGTH: 246
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gln Gly Thr Lys Val Glu Ile Lys Gly Thr Glu Gly Lys
            100                 105                 110

Ser Ser Gly Ser Gly Ser Glu Ser Lys Ser Thr Glu Val Gln Leu Val
        115                 120                 125

Gln Ser Gly Ala Glu Val Lys Lys Pro Gly Glu Ser Leu Lys Ile Ser
    130                 135                 140

Cys Lys Gly Ser Gly Tyr Ser Phe Thr Ser Tyr Phe Ile Gly Trp Val
145                 150                 155                 160

Arg Gln Met Pro Gly Lys Gly Leu Glu Trp Met Gly Ile Ile Tyr Pro
                165                 170                 175

Gly Lys Ser Asp Thr Arg Tyr Ser Pro Ser Phe Gln Gly Gln Val Thr
            180                 185                 190

Ile Ser Ala Asp Lys Ser Ile Ser Thr Ala Tyr Leu Gln Trp Ser Ser
        195                 200                 205

Leu Lys Ala Ser Asp Thr Ala Met Tyr Tyr Cys Ala Arg Val Tyr Ser
    210                 215                 220

Phe Gly Gly Arg His Lys Ala Leu Phe Asp Tyr Trp Gly Gln Gly Thr
225                 230                 235                 240

Leu Val Thr Val Ser Ser
                245
```

<210> SEQ ID NO 9
<211> LENGTH: 243
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30
```

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro Leu
                 85                  90                  95

Thr Phe Gly Gln Gly Thr Lys Val Glu Ile Lys Gly Thr Glu Gly Lys
            100                 105                 110

Ser Ser Gly Ser Gly Ser Glu Ser Lys Ser Thr Gln Val Gln Leu Val
            115                 120                 125

Gln Ser Gly Ala Glu Val Lys Lys Pro Gly Ser Ser Val Lys Val Ser
130                 135                 140

Cys Lys Ala Ser Gly Gly Thr Phe Ser Ser Tyr Ala Ile Ser Trp Val
145                 150                 155                 160

Arg Gln Ala Pro Gly Gln Gly Leu Glu Trp Met Gly Gly Ile Ile Pro
                165                 170                 175

Ile Phe Gly Thr Ala Asn Tyr Ala Gln Lys Phe Gln Gly Arg Val Thr
            180                 185                 190

Ile Thr Ala Asp Glu Ser Thr Ser Thr Ala Tyr Met Glu Leu Ser Ser
            195                 200                 205

Leu Arg Ser Glu Asp Thr Ala Val Tyr Tyr Cys Ala Arg Glu Ser Arg
        210                 215                 220

Trp Arg Gly Tyr Lys Leu Asp Tyr Trp Gly Gln Gly Thr Leu Val Thr
225                 230                 235                 240

Val Ser Ser

<210> SEQ ID NO 10
<211> LENGTH: 241
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Asp Ile Gln Met Thr Gln Ser Pro Ser Ser Leu Ser Ala Ser Val Gly
 1               5                  10                  15

Asp Arg Val Thr Ile Thr Cys Lys Ala Ser Gln Asn Val Ala Thr His
                20                  25                  30

Val Gly Trp Tyr Gln Gln Lys Pro Gly Lys Ala Pro Lys Arg Leu Ile
            35                  40                  45

Tyr Ser Ala Ser Tyr Arg Tyr Ser Gly Val Pro Ser Arg Phe Ser Gly
 50                  55                  60

Ser Gly Ser Gly Thr Glu Phe Thr Leu Thr Ile Ser Asn Leu Gln Pro
 65                  70                  75                  80

Glu Asp Phe Ala Thr Tyr Tyr Cys Gln Gln Tyr Asn Arg Tyr Pro Tyr
                 85                  90                  95

Thr Phe Gly Gln Gly Thr Lys Leu Glu Ile Lys Gly Thr Glu Gly Lys
            100                 105                 110

Ser Ser Gly Ser Gly Ser Glu Ser Lys Ser Thr Gln Val Gln Leu Val
            115                 120                 125

Gln Ser Gly Ala Glu Val Lys Lys Pro Gly Ala Ser Val Lys Val Ser
130                 135                 140

Cys Lys Ala Ser Gly Tyr Ser Phe Thr Gly Tyr Thr Met Asn Trp Val
145                 150                 155                 160

Arg Gln Ala Pro Gly Gln Gly Leu Glu Trp Met Gly Leu Ile Asn Pro
                165                 170                 175

Tyr Asn Ser Asp Thr Asn Tyr Ala Gln Lys Leu Gln Gly Arg Val Thr
            180                 185                 190

Met Thr Thr Asp Thr Ser Thr Ser Thr Ala Tyr Met Glu Leu Arg Ser
        195                 200                 205

Leu Arg Ser Asp Asp Thr Ala Val Tyr Tyr Cys Ala Arg Val Ala Leu
        210                 215                 220

Arg Val Ala Leu Asp Tyr Trp Gly Gln Gly Thr Leu Val Thr Val Ser
225                 230                 235                 240

Ser

<210> SEQ ID NO 11
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Met Ala Trp Val Trp Thr Leu Leu Phe Leu Met Ala Ala Ala Gln Ser
1               5                   10                  15

Ile Gln Ala

<210> SEQ ID NO 12
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 13
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Arg Val Lys Phe Ser Arg Ser Ala Asp Ala Pro Ala Tyr Lys Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

-continued

Asp Lys Met Ala Glu Ala Tyr Ser Glu Ile Gly Met Lys Gly Glu Arg
 65                  70                  75                  80

Arg Arg Gly Lys Gly His Asp Gly Leu Tyr Gln Gly Leu Ser Thr Ala
                 85                  90                  95

Thr Lys Asp Thr Tyr Asp Ala Leu His Met Gln Ala Leu Pro Pro Arg
            100                 105                 110

<210> SEQ ID NO 14
<211> LENGTH: 154
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu Arg Val Lys Phe Ser Arg
        35                  40                  45

Ser Ala Asp Ala Pro Ala Tyr Lys Gln Gly Gln Asn Gln Leu Tyr Asn
    50                  55                  60

Glu Leu Asn Leu Gly Arg Arg Glu Glu Tyr Asp Val Leu Asp Lys Arg
 65                 70                  75                  80

Arg Gly Arg Asp Pro Glu Met Gly Gly Lys Pro Arg Arg Lys Asn Pro
                85                  90                  95

Gln Glu Gly Leu Tyr Asn Glu Leu Gln Lys Asp Lys Met Ala Glu Ala
            100                 105                 110

Tyr Ser Glu Ile Gly Met Lys Gly Glu Arg Arg Arg Gly Lys Gly His
        115                 120                 125

Asp Gly Leu Tyr Gln Gly Leu Ser Thr Ala Thr Lys Asp Thr Tyr Asp
    130                 135                 140

Ala Leu His Met Gln Ala Leu Pro Pro Arg
145                 150

<210> SEQ ID NO 15
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Ile Tyr Ile Trp Ala Pro Leu Ala Gly Thr Cys Gly Val Leu Leu Leu
1               5                   10                  15

Ser Leu Val Ile Thr Leu Tyr Cys
            20

<210> SEQ ID NO 16
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Thr Ser Thr Pro Ala Pro Arg Pro Pro Thr Pro Ala Pro Thr Ile Ala

```
1               5                   10                  15
Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
            35                  40                  45
```

<210> SEQ ID NO 17
<211> LENGTH: 265
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

```
Met Ala Trp Val Trp Thr Leu Leu Phe Leu Met Ala Ala Ala Gln Ser
1               5                   10                  15

Ile Gln Ala Glu Ile Val Leu Thr Gln Ser Pro Ala Thr Leu Ser Leu
            20                  25                  30

Ser Pro Gly Glu Arg Ala Thr Leu Ser Cys Arg Ala Ser Gln Ser Val
            35                  40                  45

Ser Ser Tyr Leu Ala Trp Tyr Gln Gln Lys Pro Gly Gln Ala Pro Arg
    50                  55                  60

Leu Leu Ile Tyr Asp Ala Ser Asn Arg Ala Thr Gly Ile Pro Ala Arg
65                  70                  75                  80

Phe Ser Gly Ser Gly Ser Gly Thr Asp Phe Thr Leu Thr Ile Ser Ser
                85                  90                  95

Leu Glu Pro Glu Asp Phe Ala Val Tyr Tyr Cys Gln Gln Arg Ser Asn
            100                 105                 110

Trp Pro Leu Thr Phe Gly Gln Gly Thr Lys Val Glu Ile Lys Gly Thr
        115                 120                 125

Glu Gly Lys Ser Ser Gly Ser Gly Ser Glu Ser Lys Ser Thr Glu Val
130                 135                 140

Gln Leu Val Gln Ser Gly Ala Glu Val Lys Lys Pro Gly Glu Ser Leu
145                 150                 155                 160

Lys Ile Ser Cys Lys Gly Ser Gly Tyr Ser Phe Thr Ser Tyr Phe Ile
                165                 170                 175

Gly Trp Val Arg Gln Met Pro Gly Lys Gly Leu Glu Trp Met Gly Ile
            180                 185                 190

Ile Tyr Pro Gly Lys Ser Asp Thr Arg Tyr Ser Pro Ser Phe Gln Gly
        195                 200                 205

Gln Val Thr Ile Ser Ala Asp Lys Ser Ile Ser Thr Ala Tyr Leu Gln
    210                 215                 220

Trp Ser Ser Leu Lys Ala Ser Asp Thr Ala Met Tyr Tyr Cys Ala Arg
225                 230                 235                 240

Val Tyr Ser Phe Gly Gly Arg His Lys Ala Leu Phe Asp Tyr Trp Gly
                245                 250                 255

Gln Gly Thr Leu Val Thr Val Ser Ser
            260                 265
```

<210> SEQ ID NO 18
<211> LENGTH: 262
<212> TYPE: PRT
<213> ORGANISM: Artificial Sequence
<220> FEATURE:
<223> OTHER INFORMATION: Description of Artificial Sequence: Synthetic
      polypeptide -continued

<400> SEQUENCE: 18

Met Ala Trp Val Trp Thr Leu Leu Phe Leu Met Ala Ala Ala Gln Ser
1               5                   10                  15

Ile Gln Ala Asp Ile Gln Met Thr Gln Ser Pro Ser Ser Leu Ser Ala
            20                  25                  30

Ser Val Gly Asp Arg Val Thr Ile Thr Cys Arg Ala Ser Gln Ser Ile
        35                  40                  45

Ser Ser Tyr Leu Asn Trp Tyr Gln Gln Lys Pro Gly Lys Ala Pro Lys
    50                  55                  60

Leu Leu Ile Tyr Ala Ala Ser Ser Leu Gln Ser Gly Val Pro Ser Arg
65                  70                  75                  80

Phe Ser Gly Ser Gly Ser Gly Thr Asp Phe Thr Leu Thr Ile Ser Ser
                85                  90                  95

Leu Gln Pro Glu Asp Phe Ala Thr Tyr Tyr Cys Gln Gln Ser Tyr Ser
            100                 105                 110

Thr Pro Leu Thr Phe Gly Gln Gly Thr Lys Val Glu Ile Lys Gly Thr
        115                 120                 125

Glu Gly Lys Ser Ser Gly Ser Gly Ser Glu Ser Lys Ser Thr Gln Val
    130                 135                 140

Gln Leu Val Gln Ser Gly Ala Glu Val Lys Lys Pro Gly Ser Ser Val
145                 150                 155                 160

Lys Val Ser Cys Lys Ala Ser Gly Gly Thr Phe Ser Ser Tyr Ala Ile
                165                 170                 175

Ser Trp Val Arg Gln Ala Pro Gly Gln Gly Leu Glu Trp Met Gly Gly
            180                 185                 190

Ile Ile Pro Ile Phe Gly Thr Ala Asn Tyr Ala Gln Lys Phe Gln Gly
        195                 200                 205

Arg Val Thr Ile Thr Ala Asp Glu Ser Thr Ser Thr Ala Tyr Met Glu
    210                 215                 220

Leu Ser Ser Leu Arg Ser Glu Asp Thr Ala Val Tyr Tyr Cys Ala Arg
225                 230                 235                 240

Glu Ser Arg Trp Arg Gly Tyr Lys Leu Asp Tyr Trp Gly Gln Gly Thr
                245                 250                 255

Leu Val Thr Val Ser Ser
            260

<210> SEQ ID NO 19
<211> LENGTH: 260
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Met Ala Trp Val Trp Thr Leu Leu Phe Leu Met Ala Ala Ala Gln Ser
1               5                   10                  15

Ile Gln Ala Asp Ile Gln Met Thr Gln Ser Pro Ser Ser Leu Ser Ala
            20                  25                  30

Ser Val Gly Asp Arg Val Thr Ile Thr Cys Lys Ala Ser Gln Asn Val
        35                  40                  45

Ala Thr His Val Gly Trp Tyr Gln Gln Lys Pro Gly Lys Ala Pro Lys
    50                  55                  60

Arg Leu Ile Tyr Ser Ala Ser Tyr Arg Tyr Ser Gly Val Pro Ser Arg
65                  70                  75                  80

Phe Ser Gly Ser Gly Ser Gly Thr Glu Phe Thr Leu Thr Ile Ser Asn
                85                  90                  95

Leu Gln Pro Glu Asp Phe Ala Thr Tyr Tyr Cys Gln Gln Tyr Asn Arg
            100                 105                 110

Tyr Pro Tyr Thr Phe Gly Gln Gly Thr Lys Leu Glu Ile Lys Gly Thr
        115                 120                 125

Glu Gly Lys Ser Ser Gly Ser Gly Ser Glu Ser Lys Ser Thr Gln Val
130                 135                 140

Gln Leu Val Gln Ser Gly Ala Glu Val Lys Lys Pro Gly Ala Ser Val
145                 150                 155                 160

Lys Val Ser Cys Lys Ala Ser Gly Tyr Ser Phe Thr Gly Tyr Thr Met
                165                 170                 175

Asn Trp Val Arg Gln Ala Pro Gly Gln Gly Leu Glu Trp Met Gly Leu
            180                 185                 190

Ile Asn Pro Tyr Asn Ser Asp Thr Asn Tyr Ala Gln Lys Leu Gln Gly
        195                 200                 205

Arg Val Thr Met Thr Thr Asp Thr Ser Thr Ser Thr Ala Tyr Met Glu
        210                 215                 220

Leu Arg Ser Leu Arg Ser Asp Asp Thr Ala Val Tyr Tyr Cys Ala Arg
225                 230                 235                 240

Val Ala Leu Arg Val Ala Leu Asp Tyr Trp Gly Gln Gly Thr Leu Val
                245                 250                 255

Thr Val Ser Ser
            260

<210> SEQ ID NO 20
<211> LENGTH: 265
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Met Ala Trp Val Trp Thr Leu Leu Phe Leu Met Ala Ala Ala Gln Ser
1               5                   10                  15

Ile Gln Ala Glu Val Gln Leu Val Gln Ser Gly Ala Glu Val Lys Lys
            20                  25                  30

Pro Gly Glu Ser Leu Lys Ile Ser Cys Lys Gly Ser Gly Tyr Ser Phe
        35                  40                  45

Thr Ser Tyr Phe Ile Gly Trp Val Arg Gln Met Pro Gly Lys Gly Leu
    50                  55                  60

Glu Trp Met Gly Ile Ile Tyr Pro Gly Lys Ser Asp Thr Arg Tyr Ser
65                  70                  75                  80

Pro Ser Phe Gln Gly Gln Val Thr Ile Ser Ala Asp Lys Ser Ile Ser
                85                  90                  95

Thr Ala Tyr Leu Gln Trp Ser Ser Leu Lys Ala Ser Asp Thr Ala Met
            100                 105                 110

Tyr Tyr Cys Ala Arg Val Tyr Ser Phe Gly Gly Arg His Lys Ala Leu
        115                 120                 125

Phe Asp Tyr Trp Gly Gln Gly Thr Leu Val Thr Val Ser Ser Gly Thr
    130                 135                 140

Glu Gly Lys Ser Ser Gly Ser Gly Ser Glu Ser Lys Ser Thr Glu Ile
145                 150                 155                 160

Val Leu Thr Gln Ser Pro Ala Thr Leu Ser Leu Ser Pro Gly Glu Arg
                165                 170                 175

```
Ala Thr Leu Ser Cys Arg Ala Ser Gln Ser Val Ser Ser Tyr Leu Ala
            180                 185                 190

Trp Tyr Gln Gln Lys Pro Gly Gln Ala Pro Arg Leu Leu Ile Tyr Asp
        195                 200                 205

Ala Ser Asn Arg Ala Thr Gly Ile Pro Ala Arg Phe Ser Gly Ser Gly
    210                 215                 220

Ser Gly Thr Asp Phe Thr Leu Thr Ile Ser Ser Leu Glu Pro Glu Asp
225                 230                 235                 240

Phe Ala Val Tyr Tyr Cys Gln Gln Arg Ser Asn Trp Pro Leu Thr Phe
                245                 250                 255

Gly Gln Gly Thr Lys Val Glu Ile Lys
            260                 265

<210> SEQ ID NO 21
<211> LENGTH: 262
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Met Ala Trp Val Trp Thr Leu Leu Phe Leu Met Ala Ala Ala Gln Ser
1               5                   10                  15

Ile Gln Ala Gln Val Gln Leu Val Gln Ser Gly Ala Glu Val Lys Lys
            20                  25                  30

Pro Gly Ser Ser Val Lys Val Ser Cys Lys Ala Ser Gly Gly Thr Phe
        35                  40                  45

Ser Ser Tyr Ala Ile Ser Trp Val Arg Gln Ala Pro Gly Gln Gly Leu
    50                  55                  60

Glu Trp Met Gly Gly Ile Ile Pro Ile Phe Gly Thr Ala Asn Tyr Ala
65                  70                  75                  80

Gln Lys Phe Gln Gly Arg Val Thr Ile Thr Ala Asp Glu Ser Thr Ser
                85                  90                  95

Thr Ala Tyr Met Glu Leu Ser Ser Leu Arg Ser Glu Asp Thr Ala Val
            100                 105                 110

Tyr Tyr Cys Ala Arg Glu Ser Arg Trp Arg Gly Tyr Lys Leu Asp Tyr
        115                 120                 125

Trp Gly Gln Gly Thr Leu Val Thr Val Ser Ser Gly Thr Glu Gly Lys
    130                 135                 140

Ser Ser Gly Ser Gly Ser Glu Ser Lys Ser Thr Asp Ile Gln Met Thr
145                 150                 155                 160

Gln Ser Pro Ser Ser Leu Ser Ala Ser Val Gly Asp Arg Val Thr Ile
                165                 170                 175

Thr Cys Arg Ala Ser Gln Ser Ile Ser Ser Tyr Leu Asn Trp Tyr Gln
            180                 185                 190

Gln Lys Pro Gly Lys Ala Pro Lys Leu Leu Ile Tyr Ala Ala Ser Ser
        195                 200                 205

Leu Gln Ser Gly Val Pro Ser Arg Phe Ser Gly Ser Gly Ser Gly Thr
    210                 215                 220

Asp Phe Thr Leu Thr Ile Ser Ser Leu Gln Pro Glu Asp Phe Ala Thr
225                 230                 235                 240

Tyr Tyr Cys Gln Gln Ser Tyr Ser Thr Pro Leu Thr Phe Gly Gln Gly
                245                 250                 255

Thr Lys Val Glu Ile Lys
            260
```

<210> SEQ ID NO 22
<211> LENGTH: 260
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 22

Met Ala Trp Val Trp Thr Leu Leu Phe Leu Met Ala Ala Ala Gln Ser
1               5                   10                  15

Ile Gln Ala Gln Val Gln Leu Val Gln Ser Gly Ala Glu Val Lys Lys
            20                  25                  30

Pro Gly Ala Ser Val Lys Val Ser Cys Lys Ala Ser Gly Tyr Ser Phe
        35                  40                  45

Thr Gly Tyr Thr Met Asn Trp Val Arg Gln Ala Pro Gly Gln Gly Leu
    50                  55                  60

Glu Trp Met Gly Leu Ile Asn Pro Tyr Asn Ser Asp Thr Asn Tyr Ala
65                  70                  75                  80

Gln Lys Leu Gln Gly Arg Val Thr Met Thr Thr Asp Thr Ser Thr Ser
                85                  90                  95

Thr Ala Tyr Met Glu Leu Arg Ser Leu Arg Ser Asp Asp Thr Ala Val
            100                 105                 110

Tyr Tyr Cys Ala Arg Val Ala Leu Arg Val Ala Leu Asp Tyr Trp Gly
        115                 120                 125

Gln Gly Thr Leu Val Thr Val Ser Ser Gly Thr Glu Gly Lys Ser Ser
    130                 135                 140

Gly Ser Gly Ser Glu Ser Lys Ser Thr Asp Ile Gln Met Thr Gln Ser
145                 150                 155                 160

Pro Ser Ser Leu Ser Ala Ser Val Gly Asp Arg Val Thr Ile Thr Cys
                165                 170                 175

Lys Ala Ser Gln Asn Val Ala Thr His Val Gly Trp Tyr Gln Gln Lys
            180                 185                 190

Pro Gly Lys Ala Pro Lys Arg Leu Ile Tyr Ser Ala Ser Tyr Arg Tyr
        195                 200                 205

Ser Gly Val Pro Ser Arg Phe Ser Gly Ser Gly Ser Gly Thr Glu Phe
    210                 215                 220

Thr Leu Thr Ile Ser Asn Leu Gln Pro Glu Asp Phe Ala Thr Tyr Tyr
225                 230                 235                 240

Cys Gln Gln Tyr Asn Arg Tyr Pro Tyr Thr Phe Gly Gln Gly Thr Lys
                245                 250                 255

Leu Glu Ile Lys
            260

<210> SEQ ID NO 23

<400> SEQUENCE: 23

000

<210> SEQ ID NO 24
<211> LENGTH: 246
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 24

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Phe Ile Gly Trp Val Arg Gln Met Pro Gly Lys Gly Leu Glu Trp Met
        35                  40                  45

Gly Ile Ile Tyr Pro Gly Lys Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Val Tyr Ser Phe Gly Gly Arg His Lys Ala Leu Phe Asp Tyr
            100                 105                 110

Trp Gly Gln Gly Thr Leu Val Thr Val Ser Ser Gly Thr Glu Gly Lys
        115                 120                 125

Ser Ser Gly Ser Gly Ser Glu Ser Lys Ser Thr Glu Ile Val Leu Thr
    130                 135                 140

Gln Ser Pro Ala Thr Leu Ser Leu Ser Pro Gly Glu Arg Ala Thr Leu
145                 150                 155                 160

Ser Cys Arg Ala Ser Gln Ser Val Ser Ser Tyr Leu Ala Trp Tyr Gln
                165                 170                 175

Gln Lys Pro Gly Gln Ala Pro Arg Leu Leu Ile Tyr Asp Ala Ser Asn
            180                 185                 190

Arg Ala Thr Gly Ile Pro Ala Arg Phe Ser Gly Ser Gly Ser Gly Thr
        195                 200                 205

Asp Phe Thr Leu Thr Ile Ser Ser Leu Glu Pro Glu Asp Phe Ala Val
    210                 215                 220

Tyr Tyr Cys Gln Gln Arg Ser Asn Trp Pro Leu Thr Phe Gly Gln Gly
225                 230                 235                 240

Thr Lys Val Glu Ile Lys
            245
```

<210> SEQ ID NO 25
<211> LENGTH: 243
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 25

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95
```

Ala Arg Glu Ser Arg Trp Arg Gly Tyr Lys Leu Asp Tyr Trp Gly Gln
            100                 105                 110

Gly Thr Leu Val Thr Val Ser Gly Thr Glu Gly Lys Ser Ser Gly
            115                 120                 125

Ser Gly Ser Glu Ser Lys Ser Thr Asp Ile Gln Met Thr Gln Ser Pro
130                 135                 140

Ser Ser Leu Ser Ala Ser Val Gly Asp Arg Val Thr Ile Thr Cys Arg
145                 150                 155                 160

Ala Ser Gln Ser Ile Ser Ser Tyr Leu Asn Trp Tyr Gln Gln Lys Pro
                165                 170                 175

Gly Lys Ala Pro Lys Leu Leu Ile Tyr Ala Ala Ser Ser Leu Gln Ser
            180                 185                 190

Gly Val Pro Ser Arg Phe Ser Gly Ser Gly Ser Gly Thr Asp Phe Thr
            195                 200                 205

Leu Thr Ile Ser Ser Leu Gln Pro Glu Asp Phe Ala Thr Tyr Tyr Cys
        210                 215                 220

Gln Gln Ser Tyr Ser Thr Pro Leu Thr Phe Gly Gln Gly Thr Lys Val
225                 230                 235                 240

Glu Ile Lys

<210> SEQ ID NO 26
<211> LENGTH: 241
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
            20                  25                  30

Thr Met Asn Trp Val Arg Gln Ala Pro Gly Gln Gly Leu Glu Trp Met
        35                  40                  45

Gly Leu Ile Asn Pro Tyr Asn Ser Asp Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Val Ala Leu Arg Val Ala Leu Asp Tyr Trp Gly Gln Gly Thr
            100                 105                 110

Leu Val Thr Val Ser Ser Gly Thr Glu Gly Lys Ser Ser Gly Ser Gly
            115                 120                 125

Ser Glu Ser Lys Ser Thr Asp Ile Gln Met Thr Gln Ser Pro Ser Ser
130                 135                 140

Leu Ser Ala Ser Val Gly Asp Arg Val Thr Ile Thr Cys Lys Ala Ser
145                 150                 155                 160

Gln Asn Val Ala Thr His Val Gly Trp Tyr Gln Gln Lys Pro Gly Lys
                165                 170                 175

Ala Pro Lys Arg Leu Ile Tyr Ser Ala Ser Tyr Arg Tyr Ser Gly Val
            180                 185                 190

Pro Ser Arg Phe Ser Gly Ser Gly Ser Gly Thr Glu Phe Thr Leu Thr
            195                 200                 205

```
Ile Ser Asn Leu Gln Pro Glu Asp Phe Ala Thr Tyr Tyr Cys Gln Gln
        210                 215                 220

Tyr Asn Arg Tyr Pro Tyr Thr Phe Gly Gln Gly Thr Lys Leu Glu Ile
225                 230                 235                 240

Lys

<210> SEQ ID NO 27
<211> LENGTH: 488
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Met Ala Trp Val Trp Thr Leu Leu Phe Leu Met Ala Ala Ala Gln Ser
1               5                   10                  15

Ile Gln Ala Glu Ile Val Leu Thr Gln Ser Pro Ala Thr Leu Ser Leu
            20                  25                  30

Ser Pro Gly Glu Arg Ala Thr Leu Ser Cys Arg Ala Ser Gln Ser Val
        35                  40                  45

Ser Ser Tyr Leu Ala Trp Tyr Gln Gln Lys Pro Gly Gln Ala Pro Arg
    50                  55                  60

Leu Leu Ile Tyr Asp Ala Ser Asn Arg Ala Thr Gly Ile Pro Ala Arg
65                  70                  75                  80

Phe Ser Gly Ser Gly Ser Gly Thr Asp Phe Thr Leu Thr Ile Ser Ser
                85                  90                  95

Leu Glu Pro Glu Asp Phe Ala Val Tyr Tyr Cys Gln Gln Arg Ser Asn
            100                 105                 110

Trp Pro Leu Thr Phe Gly Gln Gly Thr Lys Val Glu Ile Lys Gly Thr
        115                 120                 125

Glu Gly Lys Ser Ser Gly Ser Gly Ser Glu Ser Lys Ser Thr Glu Val
    130                 135                 140

Gln Leu Val Gln Ser Gly Ala Glu Val Lys Lys Pro Gly Glu Ser Leu
145                 150                 155                 160

Lys Ile Ser Cys Lys Gly Ser Gly Tyr Ser Phe Thr Ser Tyr Phe Ile
                165                 170                 175

Gly Trp Val Arg Gln Met Pro Gly Lys Gly Leu Glu Trp Met Gly Ile
            180                 185                 190

Ile Tyr Pro Gly Lys Ser Asp Thr Arg Tyr Ser Pro Ser Phe Gln Gly
        195                 200                 205

Gln Val Thr Ile Ser Ala Asp Lys Ser Ile Ser Thr Ala Tyr Leu Gln
    210                 215                 220

Trp Ser Ser Leu Lys Ala Ser Asp Thr Ala Met Tyr Tyr Cys Ala Arg
225                 230                 235                 240

Val Tyr Ser Phe Gly Gly Arg His Lys Ala Leu Phe Asp Tyr Trp Gly
                245                 250                 255

Gln Gly Thr Leu Val Thr Val Ser Ser Thr Ser Thr Pro Ala Pro Arg
            260                 265                 270

Pro Pro Thr Pro Ala Pro Thr Ile Ala Ser Gln Pro Leu Ser Leu Arg
        275                 280                 285

Pro Glu Ala Cys Arg Pro Ala Ala Gly Gly Ala Val His Thr Arg Gly
    290                 295                 300

Leu Asp Phe Ala Cys Asp Ile Tyr Ile Trp Ala Pro Leu Ala Gly Thr
305                 310                 315                 320
```

```
Cys Gly Val Leu Leu Leu Ser Leu Val Ile Thr Leu Tyr Cys Lys Arg
                325                 330                 335

Gly Arg Lys Lys Leu Leu Tyr Ile Phe Lys Gln Pro Phe Met Arg Pro
            340                 345                 350

Val Gln Thr Thr Gln Glu Glu Asp Gly Cys Ser Cys Arg Phe Pro Glu
        355                 360                 365

Glu Glu Glu Gly Gly Cys Glu Leu Arg Val Lys Phe Ser Arg Ser Ala
370                 375                 380

Asp Ala Pro Ala Tyr Lys Gln Gly Gln Asn Gln Leu Tyr Asn Glu Leu
385                 390                 395                 400

Asn Leu Gly Arg Arg Glu Glu Tyr Asp Val Leu Asp Lys Arg Arg Gly
                405                 410                 415

Arg Asp Pro Glu Met Gly Gly Lys Pro Arg Arg Lys Asn Pro Gln Glu
            420                 425                 430

Gly Leu Tyr Asn Glu Leu Gln Lys Asp Lys Met Ala Glu Ala Tyr Ser
        435                 440                 445

Glu Ile Gly Met Lys Gly Glu Arg Arg Arg Gly Lys Gly His Asp Gly
    450                 455                 460

Leu Tyr Gln Gly Leu Ser Thr Ala Thr Lys Asp Thr Tyr Asp Ala Leu
465                 470                 475                 480

His Met Gln Ala Leu Pro Pro Arg
                485

<210> SEQ ID NO 28
<211> LENGTH: 485
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Met Ala Trp Val Trp Thr Leu Leu Phe Leu Met Ala Ala Ala Gln Ser
1               5                   10                  15

Ile Gln Ala Asp Ile Gln Met Thr Gln Ser Pro Ser Ser Leu Ser Ala
            20                  25                  30

Ser Val Gly Asp Arg Val Thr Ile Thr Cys Arg Ala Ser Gln Ser Ile
        35                  40                  45

Ser Ser Tyr Leu Asn Trp Tyr Gln Gln Lys Pro Gly Lys Ala Pro Lys
    50                  55                  60

Leu Leu Ile Tyr Ala Ala Ser Ser Leu Gln Ser Gly Val Pro Ser Arg
65                  70                  75                  80

Phe Ser Gly Ser Gly Ser Gly Thr Asp Phe Thr Leu Thr Ile Ser Ser
                85                  90                  95

Leu Gln Pro Glu Asp Phe Ala Thr Tyr Tyr Cys Gln Gln Ser Tyr Ser
            100                 105                 110

Thr Pro Leu Thr Phe Gly Gln Gly Thr Lys Val Glu Ile Lys Gly Thr
        115                 120                 125

Glu Gly Lys Ser Ser Gly Ser Gly Ser Glu Ser Lys Ser Thr Gln Val
    130                 135                 140

Gln Leu Val Gln Ser Gly Ala Glu Val Lys Lys Pro Gly Ser Ser Val
145                 150                 155                 160

Lys Val Ser Cys Lys Ala Ser Gly Gly Thr Phe Ser Ser Tyr Ala Ile
                165                 170                 175

Ser Trp Val Arg Gln Ala Pro Gly Gln Gly Leu Glu Trp Met Gly Gly
```

```
                180             185             190
Ile Ile Pro Ile Phe Gly Thr Ala Asn Tyr Ala Gln Lys Phe Gln Gly
            195             200             205

Arg Val Thr Ile Thr Ala Asp Glu Ser Thr Ser Thr Ala Tyr Met Glu
    210             215             220

Leu Ser Ser Leu Arg Ser Glu Asp Thr Ala Val Tyr Tyr Cys Ala Arg
225             230             235             240

Glu Ser Arg Trp Arg Gly Tyr Lys Leu Asp Tyr Trp Gly Gln Gly Thr
            245             250             255

Leu Val Thr Val Ser Ser Thr Ser Pro Ala Pro Arg Pro Pro Thr
                260             265             270

Pro Ala Pro Thr Ile Ala Ser Gln Pro Leu Ser Leu Arg Pro Glu Ala
            275             280             285

Cys Arg Pro Ala Ala Gly Gly Ala Val His Thr Arg Gly Leu Asp Phe
290             295             300

Ala Cys Asp Ile Tyr Ile Trp Ala Pro Leu Ala Gly Thr Cys Gly Val
305             310             315             320

Leu Leu Leu Ser Leu Val Ile Thr Leu Tyr Cys Lys Arg Gly Arg Lys
            325             330             335

Lys Leu Leu Tyr Ile Phe Lys Gln Pro Phe Met Arg Pro Val Gln Thr
            340             345             350

Thr Gln Glu Glu Asp Gly Cys Ser Cys Arg Phe Pro Glu Glu Glu Glu
            355             360             365

Gly Gly Cys Glu Leu Arg Val Lys Phe Ser Arg Ser Ala Asp Ala Pro
            370             375             380

Ala Tyr Lys Gln Gly Gln Asn Gln Leu Tyr Asn Glu Leu Asn Leu Gly
385             390             395             400

Arg Arg Glu Glu Tyr Asp Val Leu Asp Lys Arg Arg Gly Arg Asp Pro
            405             410             415

Glu Met Gly Gly Lys Pro Arg Arg Lys Asn Pro Gln Glu Gly Leu Tyr
            420             425             430

Asn Glu Leu Gln Lys Asp Lys Met Ala Glu Ala Tyr Ser Glu Ile Gly
            435             440             445

Met Lys Gly Glu Arg Arg Arg Gly Lys Gly His Asp Gly Leu Tyr Gln
            450             455             460

Gly Leu Ser Thr Ala Thr Lys Asp Thr Tyr Asp Ala Leu His Met Gln
465             470             475             480

Ala Leu Pro Pro Arg
            485

<210> SEQ ID NO 29
<211> LENGTH: 483
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Met Ala Trp Val Trp Thr Leu Leu Phe Leu Met Ala Ala Ala Gln Ser
1               5                   10                  15

Ile Gln Ala Asp Ile Gln Met Thr Gln Ser Pro Ser Ser Leu Ser Ala
            20                  25                  30

Ser Val Gly Asp Arg Val Thr Ile Thr Cys Lys Ala Ser Gln Asn Val
            35                  40                  45
```

```
Ala Thr His Val Gly Trp Tyr Gln Gln Lys Pro Gly Lys Ala Pro Lys
 50                  55                  60

Arg Leu Ile Tyr Ser Ala Ser Tyr Arg Tyr Ser Gly Val Pro Ser Arg
 65                  70                  75                  80

Phe Ser Gly Ser Gly Ser Gly Thr Glu Phe Thr Leu Thr Ile Ser Asn
                 85                  90                  95

Leu Gln Pro Glu Asp Phe Ala Thr Tyr Tyr Cys Gln Gln Tyr Asn Arg
            100                 105                 110

Tyr Pro Tyr Thr Phe Gly Gln Gly Thr Lys Leu Glu Ile Lys Gly Thr
        115                 120                 125

Glu Gly Lys Ser Ser Gly Ser Gly Ser Glu Ser Lys Ser Thr Gln Val
130                 135                 140

Gln Leu Val Gln Ser Gly Ala Glu Val Lys Lys Pro Gly Ala Ser Val
145                 150                 155                 160

Lys Val Ser Cys Lys Ala Ser Gly Tyr Ser Phe Thr Gly Tyr Thr Met
                165                 170                 175

Asn Trp Val Arg Gln Ala Pro Gly Gln Gly Leu Glu Trp Met Gly Leu
            180                 185                 190

Ile Asn Pro Tyr Asn Ser Asp Thr Asn Tyr Ala Gln Lys Leu Gln Gly
        195                 200                 205

Arg Val Thr Met Thr Thr Asp Thr Ser Thr Ser Thr Ala Tyr Met Glu
    210                 215                 220

Leu Arg Ser Leu Arg Ser Asp Asp Thr Ala Val Tyr Tyr Cys Ala Arg
225                 230                 235                 240

Val Ala Leu Arg Val Ala Leu Asp Tyr Trp Gly Gln Gly Thr Leu Val
                245                 250                 255

Thr Val Ser Ser Thr Ser Thr Pro Ala Pro Arg Pro Pro Thr Pro Ala
            260                 265                 270

Pro Thr Ile Ala Ser Gln Pro Leu Ser Leu Arg Pro Glu Ala Cys Arg
        275                 280                 285

Pro Ala Ala Gly Gly Ala Val His Thr Arg Gly Leu Asp Phe Ala Cys
    290                 295                 300

Asp Ile Tyr Ile Trp Ala Pro Leu Ala Gly Thr Cys Gly Val Leu Leu
305                 310                 315                 320

Leu Ser Leu Val Ile Thr Leu Tyr Cys Lys Arg Gly Arg Lys Lys Leu
                325                 330                 335

Leu Tyr Ile Phe Lys Gln Pro Phe Met Arg Pro Val Gln Thr Thr Gln
            340                 345                 350

Glu Glu Asp Gly Cys Ser Cys Arg Phe Pro Glu Glu Glu Glu Gly Gly
        355                 360                 365

Cys Glu Leu Arg Val Lys Phe Ser Arg Ser Ala Asp Ala Pro Ala Tyr
    370                 375                 380

Lys Gln Gly Gln Asn Gln Leu Tyr Asn Glu Leu Asn Leu Gly Arg Arg
385                 390                 395                 400

Glu Glu Tyr Asp Val Leu Asp Lys Arg Arg Gly Arg Asp Pro Glu Met
                405                 410                 415

Gly Gly Lys Pro Arg Arg Lys Asn Pro Gln Glu Gly Leu Tyr Asn Glu
            420                 425                 430

Leu Gln Lys Asp Lys Met Ala Glu Ala Tyr Ser Glu Ile Gly Met Lys
        435                 440                 445

Gly Glu Arg Arg Arg Gly Lys Gly His Asp Gly Leu Tyr Gln Gly Leu
    450                 455                 460

Ser Thr Ala Thr Lys Asp Thr Tyr Asp Ala Leu His Met Gln Ala Leu
```

-continued

```
                465                 470                 475                 480

Pro Pro Arg

<210> SEQ ID NO 30
<211> LENGTH: 488
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Met Ala Trp Val Trp Thr Leu Leu Phe Leu Met Ala Ala Ala Gln Ser
1               5                   10                  15

Ile Gln Ala Glu Val Gln Leu Val Gln Ser Gly Ala Glu Val Lys Lys
            20                  25                  30

Pro Gly Glu Ser Leu Lys Ile Ser Cys Lys Gly Ser Gly Tyr Ser Phe
        35                  40                  45

Thr Ser Tyr Phe Ile Gly Trp Val Arg Gln Met Pro Gly Lys Gly Leu
    50                  55                  60

Glu Trp Met Gly Ile Ile Tyr Pro Gly Lys Ser Asp Thr Arg Tyr Ser
65                  70                  75                  80

Pro Ser Phe Gln Gly Gln Val Thr Ile Ser Ala Asp Lys Ser Ile Ser
                85                  90                  95

Thr Ala Tyr Leu Gln Trp Ser Ser Leu Lys Ala Ser Asp Thr Ala Met
            100                 105                 110

Tyr Tyr Cys Ala Arg Val Tyr Ser Phe Gly Gly Arg His Lys Ala Leu
        115                 120                 125

Phe Asp Tyr Trp Gly Gln Gly Thr Leu Val Thr Val Ser Ser Gly Thr
    130                 135                 140

Glu Gly Lys Ser Ser Gly Ser Gly Ser Glu Ser Lys Ser Thr Glu Ile
145                 150                 155                 160

Val Leu Thr Gln Ser Pro Ala Thr Leu Ser Leu Ser Pro Gly Glu Arg
                165                 170                 175

Ala Thr Leu Ser Cys Arg Ala Ser Gln Ser Val Ser Ser Tyr Leu Ala
            180                 185                 190

Trp Tyr Gln Gln Lys Pro Gly Gln Ala Pro Arg Leu Leu Ile Tyr Asp
        195                 200                 205

Ala Ser Asn Arg Ala Thr Gly Ile Pro Ala Arg Phe Ser Gly Ser Gly
    210                 215                 220

Ser Gly Thr Asp Phe Thr Leu Thr Ile Ser Ser Leu Glu Pro Glu Asp
225                 230                 235                 240

Phe Ala Val Tyr Tyr Cys Gln Gln Arg Ser Asn Trp Pro Leu Thr Phe
                245                 250                 255

Gly Gln Gly Thr Lys Val Glu Ile Lys Thr Ser Thr Pro Ala Pro Arg
            260                 265                 270

Pro Pro Thr Pro Ala Pro Thr Ile Ala Ser Gln Pro Leu Ser Leu Arg
        275                 280                 285

Pro Glu Ala Cys Arg Pro Ala Ala Gly Gly Ala Val His Thr Arg Gly
    290                 295                 300

Leu Asp Phe Ala Cys Asp Ile Tyr Ile Trp Ala Pro Leu Ala Gly Thr
305                 310                 315                 320

Cys Gly Val Leu Leu Leu Ser Leu Val Ile Thr Leu Tyr Cys Lys Arg
                325                 330                 335

Gly Arg Lys Lys Leu Leu Tyr Ile Phe Lys Gln Pro Phe Met Arg Pro
```

```
                    340                 345                 350
Val Gln Thr Thr Gln Glu Glu Asp Gly Cys Ser Cys Arg Phe Pro Glu
            355                 360                 365

Glu Glu Glu Gly Gly Cys Glu Leu Arg Val Lys Phe Ser Arg Ser Ala
        370                 375                 380

Asp Ala Pro Ala Tyr Lys Gln Gly Gln Asn Gln Leu Tyr Asn Glu Leu
385                 390                 395                 400

Asn Leu Gly Arg Arg Glu Glu Tyr Asp Val Leu Asp Lys Arg Arg Gly
                405                 410                 415

Arg Asp Pro Glu Met Gly Gly Lys Pro Arg Arg Lys Asn Pro Gln Glu
            420                 425                 430

Gly Leu Tyr Asn Glu Leu Gln Lys Asp Lys Met Ala Glu Ala Tyr Ser
        435                 440                 445

Glu Ile Gly Met Lys Gly Glu Arg Arg Arg Gly Lys Gly His Asp Gly
    450                 455                 460

Leu Tyr Gln Gly Leu Ser Thr Ala Thr Lys Asp Thr Tyr Asp Ala Leu
465                 470                 475                 480

His Met Gln Ala Leu Pro Pro Arg
                485

<210> SEQ ID NO 31
<211> LENGTH: 485
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Met Ala Trp Val Trp Thr Leu Leu Phe Leu Met Ala Ala Ala Gln Ser
1               5                   10                  15

Ile Gln Ala Gln Val Gln Leu Val Gln Ser Gly Ala Glu Val Lys Lys
            20                  25                  30

Pro Gly Ser Ser Val Lys Val Ser Cys Lys Ala Ser Gly Gly Thr Phe
        35                  40                  45

Ser Ser Tyr Ala Ile Ser Trp Val Arg Gln Ala Pro Gly Gln Gly Leu
    50                  55                  60

Glu Trp Met Gly Gly Ile Ile Pro Ile Phe Gly Thr Ala Asn Tyr Ala
65                  70                  75                  80

Gln Lys Phe Gln Gly Arg Val Thr Ile Thr Ala Asp Glu Ser Thr Ser
                85                  90                  95

Thr Ala Tyr Met Glu Leu Ser Ser Leu Arg Ser Glu Asp Thr Ala Val
            100                 105                 110

Tyr Tyr Cys Ala Arg Glu Ser Arg Trp Arg Gly Tyr Lys Leu Asp Tyr
        115                 120                 125

Trp Gly Gln Gly Thr Leu Val Thr Val Ser Ser Gly Thr Glu Gly Lys
    130                 135                 140

Ser Ser Gly Ser Gly Ser Glu Ser Lys Ser Thr Asp Ile Gln Met Thr
145                 150                 155                 160

Gln Ser Pro Ser Ser Leu Ser Ala Ser Val Gly Asp Arg Val Thr Ile
                165                 170                 175

Thr Cys Arg Ala Ser Gln Ser Ile Ser Ser Tyr Leu Asn Trp Tyr Gln
            180                 185                 190

Gln Lys Pro Gly Lys Ala Pro Lys Leu Leu Ile Tyr Ala Ala Ser Ser
        195                 200                 205
```

```
Leu Gln Ser Gly Val Pro Ser Arg Phe Ser Gly Ser Gly Ser Gly Thr
    210                 215                 220

Asp Phe Thr Leu Thr Ile Ser Ser Leu Gln Pro Glu Asp Phe Ala Thr
225                 230                 235                 240

Tyr Tyr Cys Gln Gln Ser Tyr Ser Thr Pro Leu Thr Phe Gly Gln Gly
                245                 250                 255

Thr Lys Val Glu Ile Lys Thr Ser Thr Pro Ala Pro Arg Pro Pro Thr
            260                 265                 270

Pro Ala Pro Thr Ile Ala Ser Gln Pro Leu Ser Leu Arg Pro Glu Ala
        275                 280                 285

Cys Arg Pro Ala Ala Gly Gly Ala Val His Thr Arg Gly Leu Asp Phe
290                 295                 300

Ala Cys Asp Ile Tyr Ile Trp Ala Pro Leu Ala Gly Thr Cys Gly Val
305                 310                 315                 320

Leu Leu Leu Ser Leu Val Ile Thr Leu Tyr Cys Lys Arg Gly Arg Lys
                325                 330                 335

Lys Leu Leu Tyr Ile Phe Lys Gln Pro Phe Met Arg Pro Val Gln Thr
            340                 345                 350

Thr Gln Glu Glu Asp Gly Cys Ser Cys Arg Phe Pro Glu Glu Glu Glu
        355                 360                 365

Gly Gly Cys Glu Leu Arg Val Lys Phe Ser Arg Ser Ala Asp Ala Pro
370                 375                 380

Ala Tyr Lys Gln Gly Gln Asn Gln Leu Tyr Asn Glu Leu Asn Leu Gly
385                 390                 395                 400

Arg Arg Glu Glu Tyr Asp Val Leu Asp Lys Arg Arg Gly Arg Asp Pro
                405                 410                 415

Glu Met Gly Gly Lys Pro Arg Arg Lys Asn Pro Gln Glu Gly Leu Tyr
            420                 425                 430

Asn Glu Leu Gln Lys Asp Lys Met Ala Glu Ala Tyr Ser Glu Ile Gly
        435                 440                 445

Met Lys Gly Glu Arg Arg Arg Gly Lys Gly His Asp Gly Leu Tyr Gln
450                 455                 460

Gly Leu Ser Thr Ala Thr Lys Asp Thr Tyr Asp Ala Leu His Met Gln
465                 470                 475                 480

Ala Leu Pro Pro Arg
                485

<210> SEQ ID NO 32
<211> LENGTH: 483
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Met Ala Trp Val Trp Thr Leu Leu Phe Leu Met Ala Ala Ala Gln Ser
1               5                   10                  15

Ile Gln Ala Gln Val Gln Leu Val Gln Ser Gly Ala Glu Val Lys Lys
            20                  25                  30

Pro Gly Ala Ser Val Lys Val Ser Cys Lys Ala Ser Gly Tyr Ser Phe
        35                  40                  45

Thr Gly Tyr Thr Met Asn Trp Val Arg Gln Ala Pro Gly Gln Gly Leu
    50                  55                  60

Glu Trp Met Gly Leu Ile Asn Pro Tyr Asn Ser Asp Thr Asn Tyr Ala
65                  70                  75                  80
```

```
Gln Lys Leu Gln Gly Arg Val Thr Met Thr Thr Asp Thr Ser Thr Ser
                85                  90                  95

Thr Ala Tyr Met Glu Leu Arg Ser Leu Arg Ser Asp Asp Thr Ala Val
            100                 105                 110

Tyr Tyr Cys Ala Arg Val Ala Leu Arg Val Ala Leu Asp Tyr Trp Gly
        115                 120                 125

Gln Gly Thr Leu Val Thr Val Ser Ser Gly Thr Glu Gly Lys Ser Ser
130                 135                 140

Gly Ser Gly Ser Glu Ser Lys Ser Thr Asp Ile Gln Met Thr Gln Ser
145                 150                 155                 160

Pro Ser Ser Leu Ser Ala Ser Val Gly Asp Arg Val Thr Ile Thr Cys
                165                 170                 175

Lys Ala Ser Gln Asn Val Ala Thr His Val Gly Trp Tyr Gln Gln Lys
            180                 185                 190

Pro Gly Lys Ala Pro Lys Arg Leu Ile Tyr Ser Ala Ser Tyr Arg Tyr
        195                 200                 205

Ser Gly Val Pro Ser Arg Phe Ser Gly Ser Gly Ser Gly Thr Glu Phe
        210                 215                 220

Thr Leu Thr Ile Ser Asn Leu Gln Pro Glu Asp Phe Ala Thr Tyr Tyr
225                 230                 235                 240

Cys Gln Gln Tyr Asn Arg Tyr Pro Tyr Thr Phe Gly Gln Gly Thr Lys
                245                 250                 255

Leu Glu Ile Lys Thr Ser Thr Pro Ala Pro Arg Pro Pro Thr Pro Ala
            260                 265                 270

Pro Thr Ile Ala Ser Gln Pro Leu Ser Leu Arg Pro Glu Ala Cys Arg
        275                 280                 285

Pro Ala Ala Gly Gly Ala Val His Thr Arg Gly Leu Asp Phe Ala Cys
        290                 295                 300

Asp Ile Tyr Ile Trp Ala Pro Leu Ala Gly Thr Cys Gly Val Leu Leu
305                 310                 315                 320

Leu Ser Leu Val Ile Thr Leu Tyr Cys Lys Arg Gly Arg Lys Lys Leu
                325                 330                 335

Leu Tyr Ile Phe Lys Gln Pro Phe Met Arg Pro Val Gln Thr Thr Gln
            340                 345                 350

Glu Glu Asp Gly Cys Ser Cys Arg Phe Pro Glu Glu Glu Glu Gly Gly
        355                 360                 365

Cys Glu Leu Arg Val Lys Phe Ser Arg Ser Ala Asp Ala Pro Ala Tyr
        370                 375                 380

Lys Gln Gly Gln Asn Gln Leu Tyr Asn Glu Leu Asn Leu Gly Arg Arg
385                 390                 395                 400

Glu Glu Tyr Asp Val Leu Asp Lys Arg Arg Gly Arg Asp Pro Glu Met
                405                 410                 415

Gly Gly Lys Pro Arg Arg Lys Asn Pro Gln Glu Gly Leu Tyr Asn Glu
            420                 425                 430

Leu Gln Lys Asp Lys Met Ala Glu Ala Tyr Ser Glu Ile Gly Met Lys
        435                 440                 445

Gly Glu Arg Arg Arg Gly Lys Gly His Asp Gly Leu Tyr Gln Gly Leu
        450                 455                 460

Ser Thr Ala Thr Lys Asp Thr Tyr Asp Ala Leu His Met Gln Ala Leu
465                 470                 475                 480

Pro Pro Arg
```

<210> SEQ ID NO 33
<211> LENGTH: 1407
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 33

| | | | | | |
|---|---|---|---|---|---|
| gagatcgtgc | tgacccagag | cccagccacc | ctgagcctga | gcccaggcga | gcgcgccacc | 60 |
| ctgagctgcc | gcgcctctca | gagcgtgagc | agctacctgg | cttggtatca | gcagaagccc | 120 |
| ggacaggccc | cacgcctgct | gatctacgac | gccagcaacc | gcgccaccgg | catcccagcc | 180 |
| cgcttcagcg | gcagcggcag | cggcaccgac | ttcaccctga | ccatcagcag | cctggagcca | 240 |
| gaggacttcg | ccgtgtacta | ctgccagcag | cgcagcaact | ggccactgac | cttcggccag | 300 |
| ggcaccaagg | tggagatcaa | gggtacagag | ggcaagtcta | gtggaagtgg | tagcgaaagt | 360 |
| aagagtaccg | aggtgcagct | ggtgcagagc | ggcgctgagg | tcaaaaagcc | aggcgaaagc | 420 |
| cttaaaatat | catgcaaagg | aagtggatat | tcctttacca | gctacttcat | cggctgggtg | 480 |
| cgccagatgc | caggcaaggg | cctggagtgg | atgggcatca | tctacccagg | caagagcgac | 540 |
| acccgctaca | gcccaagctt | ccagggccag | gtgaccatca | gcgccgacaa | gagcatcagc | 600 |
| accgcctacc | tgcagtggag | cagcctgaag | gccagcgaca | ccgccatgta | ctactgcgcc | 660 |
| cgcgtgtaca | gcttcggcgg | ccgccacaag | gccctgttcg | actactgggg | ccagggcacc | 720 |
| ctggtgaccg | tgagcagcac | tagtacccca | gccccacgcc | ctcccacccc | tgctcctaca | 780 |
| atagcatccc | agcccttgtc | acttcgcccc | gaagcatgca | gaccagccgc | aggcggtgct | 840 |
| gtgcataccc | gaggactgga | cttcgcctgc | gacatctaca | tctgggcccc | actggccggc | 900 |
| acctgcggcg | tgctgctgct | gagcctggtg | atcaccctgt | actgcaagcg | cggccgcaag | 960 |
| aagctgctgt | acatcttcaa | gcagccattc | atgcgcccag | tgcagaccac | ccaggaggag | 1020 |
| gacggctgca | gctgccgctt | cccagaggag | gaggagggcg | gctgcgagct | gcgcgtgaag | 1080 |
| ttcagccgca | gcgccgacgc | cccagcctac | aagcagggcc | agaaccagct | gtacaacgag | 1140 |
| ctgaacctgg | gccgccgcga | ggagtacgac | gtgctggaca | gcgccgcgg | ccgcgaccca | 1200 |
| gagatgggcg | gcaagccacg | ccgcaagaac | ccacaggagg | gcctgtacaa | cgagctgcag | 1260 |
| aaggacaaga | tggccgaggc | ctacagcgag | atcggcatga | agggcgagcg | ccgccgcggc | 1320 |
| aagggccacg | acggcctgta | ccagggcctg | agcaccgcca | ccaaggacac | ctacgacgcc | 1380 |
| ctgcacatgc | aggccctgcc | accacgc | | | | 1407 |

<210> SEQ ID NO 34
<211> LENGTH: 1398
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 34

| | | | | | |
|---|---|---|---|---|---|
| gacatccaga | tgacccagag | cccaagcagc | ctgagcgcca | gcgtgggcga | ccgcgtaacc | 60 |
| attacttgtc | gggcttccca | aagcattagt | agctatttga | attggtatca | acaaaaacca | 120 |
| ggcaaggccc | caaagctgct | gatctacgcc | gcctctagcc | tgcagagcgg | agtgccaagc | 180 |
| cgcttcagcg | gcagcggcag | cggcaccgac | ttcaccctga | ccatcagcag | cctgcagcca | 240 |
| gaggacttcg | ccacctacta | ctgccagcag | agctacagca | ccccactgac | cttcggccag | 300 |

```
ggcaccaagg tggagatcaa gggtacagag ggcaagtcta gtggaagtgg tagcgaaagt      360
aagagtaccc aggtgcagct ggtgcagagc ggcgccgagg tgaagaagcc aggcagcagc      420
gtgaaggtga gctgcaaggc cagcggcggc accttcagca gctacgccat cagctgggtg      480
cgccaggccc caggccaggg actggagtgg atgggcggca tcatcccaat cttcggcacc      540
gccaactacg cccagaagtt ccagggccgc gtgaccatca ccgccgacga gagcaccagc      600
accgcctaca tggagctgag cagcctgcgc agcgaggaca ccgccgtgta ctactgcgca      660
cgcgagagcc gctggcgcgg ctacaagctg gactactggg gccagggcac cctggtgacc      720
gtgagcagca ctagtacccc agccccacgc cctcccaccc ctgctcctac aatagcatcc      780
cagcccttgt cacttcgccc cgaagcatgc agaccagccc aggcggtgc tgtgcatacc       840 cgaggactgg acttcgcctg cgacatctac atctgggccc cactggccgg cacctgcggc      900
gtgctgctgc tgagcctggt gatcaccctg tactgcaagc gcggccgcaa gaagctgctg      960
tacatcttca gcagccatt catgcgccca gtgcagacca cccaggagga ggacggctgc     1020
agctgccgct tcccagagga ggaggagggc ggctgcgagc tgcgcgtgaa gttcagccgc     1080
agcgccgacg ccccagccta caagcagggc cagaaccagc tgtacaacga gctgaacctg     1140
ggccgccgcg aggagtacga cgtgctggac aagcgccgcg gccgcgaccc agagatgggc     1200
ggcaagccac gccgcaagaa cccacaggag ggcctgtaca acgagctgca gaaggacaag     1260
atggccgagg cctacagcga gatcggcatg aagggcgagc gccgccgcgg caagggccac     1320
gacggcctgt accagggcct gagcaccgcc accaaggaca cctacgacgc cctgcacatg     1380
caggccctgc caccacgc                                                   1398
```

<210> SEQ ID NO 35
<211> LENGTH: 1392
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 35

```
gacatccaga tgacccagag cccaagcagc ctgagcgcca gcgtgggcga ccgcgttaca       60
ataacttgta aagcaagcca aaatgttgct actcacgtcg gatggtatca gcaaaagcca      120
ggcaaggccc caaagcgcct gatctacagc gccagctacc gctacagcgg agtgccaagc      180
cgcttcagcg gcagcggcag cggcaccgag ttcaccctga ccatcagcaa cctgcagcca      240
gaggacttcg ccacctacta ctgccagcag tacaaccgct acccatacac cttcggccag      300
ggcaccaagc tggagatcaa gggtacagag ggcaagtcta gtggaagtgg tagcgaaagt      360
aagagtaccc aggtgcagct ggtgcagagc ggagccgagg tgaagaagcc aggcgccagc      420
gtgaaggtga gctgcaaggc cagcggctac agcttcaccg gctacaccat gaactgggtg      480
cgccaggccc caggccaggg actggagtgg atggcctga tcaacccata caacagcgac      540
accaactacg cccagaagct gcaggccgc gtgaccatga ccaccgacac cagcaccagc      600
accgcctaca tggagctgcg cagcctgcgc agcgacgaca ccgccgtgta ctactgcgcc      660
cgcgtggccc tgcgcgtggc cctggactac tggggacagg gcaccctggt gaccgtgagc      720
agcactagta ccccagcccc acgccctccc accctgctc ctacaatagc atcccagccc      780
ttgtcacttc gccccgaagc atgcagacca gccgaggcg tgctgtgca tacccgagga      840 ctggacttcg cctgcgacat ctacatctgg gccccactgg ccggcacctg cggcgtgctg      900
```

```
ctgctgagcc tggtgatcac cctgtactgc aagcgcggcc gcaagaagct gctgtacatc    960
ttcaagcagc cattcatgcg cccagtgcag accacccagg aggaggacgg ctgcagctgc   1020
cgcttcccag aggaggagga gggcggctgc gagctgcgcg tgaagttcag ccgcagcgcc   1080
gacgccccag cctacaagca gggccagaac cagctgtaca cgagctgaa cctgggccgc    1140 cgcgaggagt acgacgtgct ggacaagcgc cgcggccgcg acccagagat gggcggcaag   1200
ccacgccgca agaacccaca ggagggcctg tacaacgagc tgcagaagga caagatggcc   1260
gaggcctaca gcgagatcgg catgaagggc gagcgccgcc gcggcaaggg ccacgacggc   1320
ctgtaccagg gcctgagcac cgccaccaag gacacctacg acgccctgca catgcaggcc   1380
ctgccaccac gc                                                       1392
```

<210> SEQ ID NO 36
<211> LENGTH: 1407
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 36

```
gaggtgcagc tggtgcagag cggcgctgag gtcaaaaagc caggcgaaag ccttaaaata     60
tcatgcaaag gaagtggata ttcctttacc agctacttca tcggctgggt gcgccagatg    120
ccaggcaagg gcctggagtg gatgggcatc atctacccag gcaagagcga cacccgctac    180
agcccaagct tccagggcca ggtgaccatc agcgccgaca gagcatcag caccgcctac     240 ctgcagtgga gcagcctgaa ggccagcgac accgccatgt actactgcgc ccgcgtgtac    300
agcttcggcg ccgccacaa ggccctgttc gactactggg gccagggcac cctggtgacc     360
gtgagcagcg gtacagaggg caagtctagt ggaagtggta gcgaaagtaa gagtaccgag    420
atcgtgctga cccagagccc agccacccctg agcctgagcc caggcgagcg cgccaccctg    480
agctgccgcg cctctcagag cgtgagcagc tacctggctt ggtatcagca aagcccgga     540 caggcccccac gcctgctgat ctacgacgcc agcaaccgcg ccaccggcat cccagcccgc    600
ttcagcggca gcggcagcgg caccgacttc accctgacca tcagcagcct ggagccagag    660
gacttcgccg tgtactactg ccagcagcgc agcaactggc cactgacctt cggccagggc    720
accaaggtgg agatcaagac tagtacccca gccccacgcc ctcccacccc tgctcctaca    780
atagcatccc agcccttgtc acttcgcccc gaagcatgca gaccagccgc aggcggtgct    840
gtgcataccc gaggactgga cttcgcctgc gacatctaca tctgggcccc actggccggc    900
acctgcggcg tgctgctgct gagcctggtg atcaccctgt actgcaagcg cggccgcaag    960
aagctgctgt acatcttcaa gcagccattc atgcgcccag tgcagaccac ccaggaggag   1020
gacggctgca gctgccgctt cccagaggag gaggagggcg gctgcgagct gcgcgtgaag   1080
ttcagccgca gcgccgacgc cccagcctac aagcagggcc agaaccagct gtacaacgag   1140
ctgaacctgg gccgccgcga ggagtacgac gtgctggaca agcgccgcgg ccgcgaccca   1200
gagatgggcg gcaagccacg ccgcaagaac ccacaggagg gcctgtacaa cgagctgcag   1260
aaggacaaga tggccgaggc ctacagcgag atcggcatga agggcgagcg ccgccgcggc   1320
aagggccacg acggcctgta ccagggcctg agcaccgcca ccaaggacac ctacgacgcc   1380
ctgcacatgc aggccctgcc accacgc                                        1407
```

<210> SEQ ID NO 37

<211> LENGTH: 1398
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 37

| | |
|---|---|
| caggtgcagc tggtgcagag cggcgccgag gtgaagaagc aggcagcag cgtgaaggtg | 60 |
| agctgcaagg ccagcggcgg caccttcagc agctacgcca tcagctgggt gcgccaggcc | 120 |
| ccaggccagg gactggagtg gatgggcggc atcatcccaa tcttcggcac cgccaactac | 180 |
| gcccagaagt tccagggccg cgtgaccatc accgccgacg agagcaccag caccgcctac | 240 |
| atggagctga gcagcctgcg cagcgaggac accgccgtgt actactgcgc acgcgagagc | 300 |
| cgctggcgcg gctacaagct ggactactgg ggccagggca ccctggtgac cgtgagcagc | 360 |
| ggtacagagg gcaagtctag tggaagtggt agcgaaagta agagtaccga catccagatg | 420 |
| acccagagcc caagcagcct gagcgccagc gtgggcgacc gcgtaaccat tacttgtcgg | 480 |
| gcttcccaaa gcattagtag ctatttgaat tggtatcaac aaaaaccagg caaggcccca | 540 |
| aagctgctga tctacgccgc tctagcctg cagagcggag tgccaagcc cttcagcggc | 600 |
| agcggcagcg gcaccgactt caccctgacc atcagcagcc tgcagccaga ggacttcgcc | 660 |
| acctactact gccagcagag ctacagcacc ccactgacct tcggccaggg caccaaggtg | 720 |
| gagatcaaga ctagtacccc agcccacgc cctcccaccc ctgctcctac aatagcatcc | 780 |
| cagcccttgt cacttcgccc cgaagcatgc agaccagccg caggcggtgc tgtgcatacc | 840 |
| cgaggactgg acttcgcctg cgacatctac atctgggccc cactggccgg cacctgcggc | 900 |
| gtgctgctgc tgagcctggt gatcaccctg tactgcaagc gcggccgcaa gaagctgctg | 960 |
| tacatcttca gcagccatt catgcgccca gtgcagacca cccaggagga ggacggctgc | 1020 |
| agctgccgct tcccagagga ggaggagggc ggctgcgagc tgcgcgtgaa gttcagccgc | 1080 |
| agcgccgacg ccccagccta caagcagggc cagaaccagc tgtacaacga gctgaacctg | 1140 |
| ggccgccgcg aggagtacga cgtgctggac aagcgccgcg gccgcgaccc agagatgggc | 1200 |
| ggcaagccac gccgcaagaa cccacaggag ggcctgtaca cgagctgca gaaggacaag | 1260 |
| atggccgagg cctacagcga gatcggcatg aagggcgagc gccgccgcgg caagggccac | 1320 |
| gacgccctgt accagggcct gagcaccgcc accaaggaca cctacgacgc cctgcacatg | 1380 |
| caggccctgc caccacgc | 1398 |

<210> SEQ ID NO 38
<211> LENGTH: 1392
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 38

| | |
|---|---|
| caggtgcagc tggtgcagag cggagccgag gtgaagaagc aggcgccag cgtgaaggtg | 60 |
| agctgcaagg ccagcggcta cagcttcacc ggctacacca tgaactgggt gcgccaggcc | 120 |
| ccaggccagg gactggagtg gatgggcctg atcaacccat acaacagcga caccaactac | 180 |
| gcccagaagc tgcagggccg cgtgaccatg accaccgaca ccagcaccag caccgcctac | 240 |
| atggagctgc gcagcctgcg cagcgacgac accgccgtgt actactgcgc ccgcgtggcc | 300 |
| ctgcgcgtgg ccctggacta ctggggacag ggcaccctgg tgaccgtgag cagcggtaca | 360 |

```
gagggcaagt ctagtggaag tggtagcgaa agtaagagta ccgacatcca gatgacccag      420
agcccaagca gcctgagcgc cagcgtgggc gaccgcgtta caataacttg taaagcaagc      480
caaaatgttg ctactcacgt cggatggtat cagcaaaagc caggcaaggc cccaaagcgc      540
ctgatctaca gcgccagcta ccgctacagc ggagtgccaa gccgcttcag cggcagcggc      600
agcggcaccg agttcaccct gaccatcagc aacctgcagc cagaggactt cgccacctac      660
tactgccagc agtacaaccg ctacccatac accttcggcc agggcaccaa gctggagatc      720
aagactagta ccccagcccc acgccctccc accccctgctc ctacaatagc atcccagccc      780
ttgtcacttc gccccgaagc atgcagacca gccgcaggcg gtgctgtgca cacccgagga      840
ctggacttcg cctgcgacat ctacatctgg gccccactgg ccggcacctg cggcgtgctg      900
ctgctgagcc tggtgatcac cctgtactgc aagcgcggcc gcaagaagct gctgtacatc      960
ttcaagcagc cattcatgcg cccagtgcag accacccagg aggaggacgg ctgcagctgc     1020
cgcttcccag aggaggagga gggcggctgc gagctgcgcg tgaagttcag ccgcagcgcc     1080
gacgccccag cctacaagca gggccagaac cagctgtaca acgagctgaa cctgggccgc     1140
cgcgaggagt acgacgtgct ggacaagcgc cgcggccgcg acccagagat gggcggcaag     1200
ccacgccgca gaaccccaca ggagggcctg tacaacgagc tgcagaagga caagatggcc     1260
gaggcctaca gcgagatcgg catgaagggc gagcgccgcc gcggcaaggg ccacgacggc     1320
ctgtaccagg gcctgagcac cgccaccaag gacacctacg acgccctgca catgcaggcc     1380
ctgccaccac gc                                                        1392

<210> SEQ ID NO 39
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Gly Gly Thr Phe Ser Ser Tyr
1               5

<210> SEQ ID NO 40
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Glu Ser Arg Trp Arg Gly Tyr Lys Leu Asp Tyr
1               5                   10

<210> SEQ ID NO 41
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Ile Pro Ile Phe Gly Thr
1               5
```

```
<210> SEQ ID NO 42
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Gly Tyr Ser Phe Thr Ser Tyr
1               5

<210> SEQ ID NO 43
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Tyr Pro Gly Lys Ser Asp
1               5

<210> SEQ ID NO 44
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Val Tyr Ser Phe Gly Gly Arg His Lys Ala Leu Phe Asp Tyr
1               5                   10

<210> SEQ ID NO 45
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Gly Tyr Ser Phe Thr Gly Tyr
1               5

<210> SEQ ID NO 46
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Asn Pro Tyr Asn Ser Asp
1               5

<210> SEQ ID NO 47
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 47

Val Ala Leu Arg Val Ala Leu Asp Tyr
1               5

<210> SEQ ID NO 48
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Arg Ala Ser Gln Ser Ile Ser Ser Tyr Leu Asn
1               5                   10

<210> SEQ ID NO 49
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Ala Ala Ser Ser Leu Gln Ser
1               5

<210> SEQ ID NO 50
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Gln Gln Ser Tyr Ser Thr Pro Leu Thr
1               5

<210> SEQ ID NO 51
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Arg Ala Ser Gln Ser Val Ser Ser Tyr Leu Ala
1               5                   10

<210> SEQ ID NO 52
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Asp Ala Ser Asn Arg Ala Thr
1               5

<210> SEQ ID NO 53
<211> LENGTH: 9
<212> TYPE: PRT
```

<213> ORGANISM: Artificial Sequence
<220> FEATURE:
<223> OTHER INFORMATION: Description of Artificial Sequence: Synthetic
      peptide

<400> SEQUENCE: 53

Gln Gln Arg Ser Asn Trp Pro Leu Thr
1               5

<210> SEQ ID NO 54
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Lys Ala Ser Gln Asn Val Ala Thr His Val Gly
1               5                   10

<210> SEQ ID NO 55
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Ser Ala Ser Tyr Arg Tyr Ser
1               5

<210> SEQ ID NO 56
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Gln Gln Tyr Asn Arg Tyr Pro Tyr Thr
1               5

<210> SEQ ID NO 57
<211> LENGTH: 345
<212> TYPE: PRT
<213> ORGANISM: Homo sapiens

<400> SEQUENCE: 57

Met Tyr Lys Asp Cys Ile Glu Ser Thr Gly Asp Tyr Phe Leu Leu Cys
1               5                   10                  15

Asp Ala Glu Gly Pro Trp Gly Ile Ile Leu Glu Ser Leu Ala Ile Leu
                20                  25                  30

Gly Ile Val Val Thr Ile Leu Leu Leu Ala Phe Leu Phe Leu Met
            35                  40                  45

Arg Lys Ile Gln Asp Cys Ser Gln Trp Asn Val Leu Pro Thr Gln Leu
    50                  55                  60

Leu Phe Leu Leu Ser Val Leu Gly Leu Phe Gly Leu Ala Phe Ala Phe
65                  70                  75                  80

Ile Ile Glu Leu Asn Gln Gln Thr Ala Pro Val Arg Tyr Phe Leu Phe
                85                  90                  95

Gly Val Leu Phe Ala Leu Cys Phe Ser Cys Leu Leu Ala His Ala Ser

```
                  100                 105                 110
Asn Leu Val Lys Leu Val Arg Gly Cys Val Ser Phe Ser Trp Thr Thr
            115                 120                 125
Ile Leu Cys Ile Ala Ile Gly Cys Ser Leu Leu Gln Ile Ile Ala
        130                 135                 140
Thr Glu Tyr Val Thr Leu Ile Met Thr Arg Gly Met Met Phe Val Asn
145                 150                 155                 160
Met Thr Pro Cys Gln Leu Asn Val Asp Phe Val Val Leu Leu Val Tyr
            165                 170                 175
Val Leu Phe Leu Met Ala Leu Thr Phe Phe Val Ser Lys Ala Thr Phe
        180                 185                 190
Cys Gly Pro Cys Glu Asn Trp Lys Gln His Gly Arg Leu Ile Phe Ile
        195                 200                 205
Thr Val Leu Phe Ser Ile Ile Ile Trp Val Val Trp Ile Ser Met Leu
        210                 215                 220
Leu Arg Gly Asn Pro Gln Phe Gln Arg Gln Pro Gln Trp Asp Asp Pro
225                 230                 235                 240
Val Val Cys Ile Ala Leu Val Thr Asn Ala Trp Val Phe Leu Leu Leu
                245                 250                 255
Tyr Ile Val Pro Glu Leu Cys Ile Leu Tyr Arg Ser Cys Arg Gln Glu
                260                 265                 270
Cys Pro Leu Gln Gly Asn Ala Cys Pro Val Thr Ala Tyr Gln His Ser
            275                 280                 285
Phe Gln Val Glu Asn Gln Glu Leu Ser Arg Ala Arg Asp Ser Asp Gly
        290                 295                 300
Ala Glu Glu Asp Val Ala Leu Thr Ser Tyr Gly Thr Pro Ile Gln Pro
305                 310                 315                 320
Gln Thr Val Asp Pro Thr Gln Glu Cys Phe Ile Pro Gln Ala Lys Leu
                325                 330                 335
Ser Pro Gln Gln Asp Ala Gly Gly Val
            340                 345

<210> SEQ ID NO 58
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Gly Gly Ser Leu Ser Ser Ser Ser Tyr
1               5

<210> SEQ ID NO 59
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Tyr Tyr Ser Gly Asn
1               5

<210> SEQ ID NO 60
<211> LENGTH: 15
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 60

His Val Gly Tyr Ser Tyr Gly Arg Arg Phe Trp Tyr Phe Asp Leu
1               5                   10                  15

<210> SEQ ID NO 61
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Arg Ala Ser Gln Ser Val Ser Ser Tyr Leu Ala
1               5                   10

<210> SEQ ID NO 62
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Asp Ala Ser Asn Arg Ala Thr
1               5

<210> SEQ ID NO 63
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Gln Gln Arg Ser Asn Trp Pro Pro Thr
1               5

<210> SEQ ID NO 64
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Leu Ser Ser Ser
                20                  25                  30

Ser Tyr Trp Trp Gly Trp Thr Arg Gln Pro Pro Gly Arg Gly Leu Glu
        35                  40                  45

Trp Ile Gly Thr Met Tyr Tyr Ser Gly Asn Ile Tyr Tyr Asn Pro Ser
    50                  55                  60

Leu Gln Ser Arg Ala Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
```

```
                85                  90                  95
Cys Ala Arg His Val Gly Tyr Ser Tyr Gly Arg Arg Phe Trp Tyr Phe
            100                 105                 110

Asp Leu Trp Gly Arg Gly Thr Leu Val Thr Val Ser Ser
            115                 120                 125

<210> SEQ ID NO 65
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Thr Phe Gly Gln Gly Thr Lys Val Glu Ile Lys
            100                 105

<210> SEQ ID NO 66
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Gly Phe Ser Leu Thr Asn Ile Arg Met
1               5

<210> SEQ ID NO 67
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Phe Ser Asn Asp Glu
1               5

<210> SEQ ID NO 68
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68
```

```
Met Arg Leu Pro Tyr Gly Met Asp Val
1               5
```

<210> SEQ ID NO 69
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

```
Arg Ser Ser Gln Ser Leu Val His Ser Asp Gly Asn Thr Tyr Leu Ser
1               5                   10                  15
```

<210> SEQ ID NO 70
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

```
Lys Ile Ser Asn Arg Phe Phe
1               5
```

<210> SEQ ID NO 71
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

```
Met Gln Ala Thr Gln Phe Pro His Thr
1               5
```

<210> SEQ ID NO 72
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

```
Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Thr Asn Ile
            20                  25                  30

Arg Met Ser Val Ser Trp Ile Arg Gln Pro Pro Gly Lys Ala Leu Glu
        35                  40                  45

Trp Leu Ala His Ile Phe Ser Asn Asp Glu Lys Ser Tyr Ser Ser Ser
    50                  55                  60

Leu Lys Ser Arg Leu Thr Ile Ser Arg Asp Thr Ser Lys Ser Gln Val
65                  70                  75                  80

Val Leu Thr Leu Thr Asn Val Asp Pro Val Asp Thr Ala Thr Tyr Tyr
                85                  90                  95

Cys Ala Arg Met Arg Leu Pro Tyr Gly Met Asp Val Trp Gly Gln Gly
            100                 105                 110

Thr Thr Val Thr Val Ser Ser
        115
```

<210> SEQ ID NO 73
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Ser Leu Val His Ser
            20                  25                  30

Asp Gly Asn Thr Tyr Leu Ser Trp Leu Gln Gln Arg Pro Gly Gln Pro
        35                  40                  45

Pro Arg Leu Leu Ile Tyr Lys Ile Ser Asn Arg Phe Phe Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Thr Gln Phe Pro His Thr Phe Gly Gln Gly Thr Lys Leu Glu Ile Lys
            100                 105                 110

<210> SEQ ID NO 74
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Gly Gly Ser Glu Gly Lys Ser Ser Gly Ser Gly Ser Glu Ser Lys Ser
1               5                   10                  15

Thr Gly Gly Ser
            20

<210> SEQ ID NO 75
<211> LENGTH: 252
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Leu Ser Ser Ser
            20                  25                  30

Ser Tyr Trp Trp Gly Trp Thr Arg Gln Pro Pro Gly Arg Gly Leu Glu
        35                  40                  45

Trp Ile Gly Thr Met Tyr Tyr Ser Gly Asn Ile Tyr Tyr Asn Pro Ser
    50                  55                  60

Leu Gln Ser Arg Ala Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg His Val Gly Tyr Ser Tyr Gly Arg Arg Phe Trp Tyr Phe
            100                 105                 110

Asp Leu Trp Gly Arg Gly Thr Leu Val Thr Val Ser Ser Gly Gly Ser
            115                 120                 125

Glu Gly Lys Ser Ser Gly Ser Gly Ser Glu Ser Lys Ser Thr Gly Gly
            130                 135                 140

Ser Glu Ile Val Leu Thr Gln Ser Pro Ala Thr Leu Ser Leu Ser Pro
145                 150                 155                 160

Gly Glu Arg Ala Thr Leu Ser Cys Arg Ala Ser Gln Ser Val Ser Ser
                165                 170                 175

Tyr Leu Ala Trp Tyr Gln Gln Lys Pro Gly Gln Ala Pro Arg Leu Leu
            180                 185                 190

Ile Tyr Asp Ala Ser Asn Arg Ala Thr Gly Ile Pro Ala Arg Phe Ser
            195                 200                 205

Gly Ser Gly Ser Gly Thr Asp Phe Thr Leu Thr Ile Ser Ser Leu Glu
            210                 215                 220

Pro Glu Asp Phe Ala Val Tyr Tyr Cys Gln Gln Arg Ser Asn Trp Pro
225                 230                 235                 240

Pro Thr Phe Gly Gln Gly Thr Lys Val Glu Ile Lys
                245                 250

<210> SEQ ID NO 76
<211> LENGTH: 252
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Thr Phe Gly Gln Gly Thr Lys Val Glu Ile Lys Gly Ser Glu Gly
            100                 105                 110

Lys Ser Ser Gly Ser Gly Ser Glu Ser Lys Ser Thr Gly Gly Ser Gln
        115                 120                 125

Leu Gln Leu Gln Glu Ser Gly Pro Gly Leu Val Lys Pro Ser Glu Thr
    130                 135                 140

Leu Ser Leu Thr Cys Thr Val Ser Gly Gly Ser Leu Ser Ser Ser Ser
145                 150                 155                 160

Tyr Trp Trp Gly Trp Thr Arg Gln Pro Pro Gly Arg Gly Leu Glu Trp
                165                 170                 175

Ile Gly Thr Met Tyr Tyr Ser Gly Asn Ile Tyr Tyr Asn Pro Ser Leu
            180                 185                 190

Gln Ser Arg Ala Thr Ile Ser Val Asp Thr Ser Lys Asn Gln Phe Ser
        195                 200                 205

```
Leu Lys Leu Ser Ser Val Thr Ala Ala Asp Thr Ala Val Tyr Tyr Cys
        210                 215                 220

Ala Arg His Val Gly Tyr Ser Tyr Gly Arg Arg Phe Trp Tyr Phe Asp
225                 230                 235                 240

Leu Trp Gly Arg Gly Thr Leu Val Thr Val Ser Ser
                245                 250
```

<210> SEQ ID NO 77
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

```
Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Thr Asn Ile
            20                  25                  30

Arg Met Ser Val Ser Trp Ile Arg Gln Pro Pro Gly Lys Ala Leu Glu
        35                  40                  45

Trp Leu Ala His Ile Phe Ser Asn Asp Glu Lys Ser Tyr Ser Ser Ser
    50                  55                  60

Leu Lys Ser Arg Leu Thr Ile Ser Arg Asp Thr Ser Lys Ser Gln Val
65                  70                  75                  80

Val Leu Thr Leu Thr Asn Val Asp Pro Val Asp Thr Ala Thr Tyr Tyr
                85                  90                  95

Cys Ala Arg Met Arg Leu Pro Tyr Gly Met Asp Val Trp Gly Gln Gly
            100                 105                 110

Thr Thr Val Thr Val Ser Ser Gly Gly Ser Glu Gly Lys Ser Ser Gly
        115                 120                 125

Ser Gly Ser Glu Ser Lys Ser Thr Gly Gly Ser Asp Ile Val Met Thr
130                 135                 140

Gln Thr Pro Leu Ser Ser Pro Val Thr Leu Gly Gln Pro Ala Ser Ile
145                 150                 155                 160

Ser Cys Arg Ser Ser Gln Ser Leu Val His Ser Asp Gly Asn Thr Tyr
                165                 170                 175

Leu Ser Trp Leu Gln Gln Arg Pro Gly Gln Pro Pro Arg Leu Leu Ile
            180                 185                 190

Tyr Lys Ile Ser Asn Arg Phe Phe Gly Val Pro Asp Arg Phe Ser Gly
        195                 200                 205

Ser Gly Ala Gly Thr Asp Phe Thr Leu Lys Ile Ser Arg Val Glu Ala
    210                 215                 220

Glu Asp Val Gly Val Tyr Tyr Cys Met Gln Ala Thr Gln Phe Pro His
225                 230                 235                 240

Thr Phe Gly Gln Gly Thr Lys Leu Glu Ile Lys
                245                 250
```

<210> SEQ ID NO 78
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

```
Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Ser Leu Val His Ser
            20                  25                  30

Asp Gly Asn Thr Tyr Leu Ser Trp Leu Gln Gln Arg Pro Gly Gln Pro
        35                  40                  45

Pro Arg Leu Leu Ile Tyr Lys Ile Ser Asn Arg Phe Phe Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Thr Gln Phe Pro His Thr Phe Gly Gln Gly Thr Lys Leu Glu Ile Lys
            100                 105                 110

Gly Gly Ser Glu Gly Lys Ser Ser Gly Ser Gly Ser Glu Ser Lys Ser
        115                 120                 125

Thr Gly Gly Ser Gln Val Thr Leu Lys Glu Ser Gly Pro Val Leu Val
130                 135                 140

Lys Pro Thr Glu Thr Leu Thr Leu Thr Cys Thr Val Ser Gly Phe Ser
145                 150                 155                 160

Leu Thr Asn Ile Arg Met Ser Val Ser Trp Ile Arg Gln Pro Pro Gly
                165                 170                 175

Lys Ala Leu Glu Trp Leu Ala His Ile Phe Ser Asn Asp Glu Lys Ser
            180                 185                 190

Tyr Ser Ser Ser Leu Lys Ser Arg Leu Thr Ile Ser Arg Asp Thr Ser
        195                 200                 205

Lys Ser Gln Val Val Leu Thr Leu Thr Asn Val Asp Pro Val Asp Thr
210                 215                 220

Ala Thr Tyr Tyr Cys Ala Arg Met Arg Leu Pro Tyr Gly Met Asp Val
225                 230                 235                 240

Trp Gly Gln Gly Thr Thr Val Thr Val Ser Ser
                245                 250

<210> SEQ ID NO 79
<211> LENGTH: 271
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

Met Ala Trp Val Trp Thr Leu Leu Phe Leu Met Ala Ala Ala Gln Ser
1               5                   10                  15

Ile Gln Ala Gln Leu Gln Leu Gln Glu Ser Gly Pro Gly Leu Val Lys
            20                  25                  30

Pro Ser Glu Thr Leu Ser Leu Thr Cys Thr Val Ser Gly Gly Ser Leu
        35                  40                  45

Ser Ser Ser Ser Tyr Trp Trp Gly Trp Thr Arg Gln Pro Pro Gly Arg
    50                  55                  60

Gly Leu Glu Trp Ile Gly Thr Met Tyr Tyr Ser Gly Asn Ile Tyr Tyr
65                  70                  75                  80

Asn Pro Ser Leu Gln Ser Arg Ala Thr Ile Ser Val Asp Thr Ser Lys
            85                  90                  95

Asn Gln Phe Ser Leu Lys Leu Ser Ser Val Thr Ala Ala Asp Thr Ala
```

```
            100                 105                 110
Val Tyr Tyr Cys Ala Arg His Val Gly Tyr Ser Tyr Gly Arg Arg Phe
        115                 120                 125

Trp Tyr Phe Asp Leu Trp Gly Arg Gly Thr Leu Val Thr Val Ser Ser
130                 135                 140

Gly Gly Ser Glu Gly Lys Ser Ser Gly Ser Gly Ser Glu Ser Lys Ser
145                 150                 155                 160

Thr Gly Gly Ser Glu Ile Val Leu Thr Gln Ser Pro Ala Thr Leu Ser
                165                 170                 175

Leu Ser Pro Gly Glu Arg Ala Thr Leu Ser Cys Arg Ala Ser Gln Ser
            180                 185                 190

Val Ser Ser Tyr Leu Ala Trp Tyr Gln Gln Lys Pro Gly Gln Ala Pro
        195                 200                 205

Arg Leu Leu Ile Tyr Asp Ala Ser Asn Arg Ala Thr Gly Ile Pro Ala
    210                 215                 220

Arg Phe Ser Gly Ser Gly Ser Gly Thr Asp Phe Thr Leu Thr Ile Ser
225                 230                 235                 240

Ser Leu Glu Pro Glu Asp Phe Ala Val Tyr Tyr Cys Gln Gln Arg Ser
                245                 250                 255

Asn Trp Pro Pro Thr Phe Gly Gln Gly Thr Lys Val Glu Ile Lys
            260                 265                 270

<210> SEQ ID NO 80
<211> LENGTH: 271
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Met Ala Trp Val Trp Thr Leu Leu Phe Leu Met Ala Ala Ala Gln Ser
1               5                   10                  15

Ile Gln Ala Glu Ile Val Leu Thr Gln Ser Pro Ala Thr Leu Ser Leu
            20                  25                  30

Ser Pro Gly Glu Arg Ala Thr Leu Ser Cys Arg Ala Ser Gln Ser Val
        35                  40                  45

Ser Ser Tyr Leu Ala Trp Tyr Gln Gln Lys Pro Gly Gln Ala Pro Arg
    50                  55                  60

Leu Leu Ile Tyr Asp Ala Ser Asn Arg Ala Thr Gly Ile Pro Ala Arg
65                  70                  75                  80

Phe Ser Gly Ser Gly Ser Gly Thr Asp Phe Thr Leu Thr Ile Ser Ser
                85                  90                  95

Leu Glu Pro Glu Asp Phe Ala Val Tyr Tyr Cys Gln Gln Arg Ser Asn
            100                 105                 110

Trp Pro Pro Thr Phe Gly Gln Gly Thr Lys Val Glu Ile Lys Gly Gly
        115                 120                 125

Ser Glu Gly Lys Ser Ser Gly Ser Gly Ser Glu Ser Lys Ser Thr Gly
    130                 135                 140

Gly Ser Gln Leu Gln Leu Gln Glu Ser Gly Pro Gly Leu Val Lys Pro
145                 150                 155                 160

Ser Glu Thr Leu Ser Leu Thr Cys Thr Val Ser Gly Gly Ser Leu Ser
                165                 170                 175

Ser Ser Ser Tyr Trp Trp Gly Trp Thr Arg Gln Pro Pro Gly Arg Gly
            180                 185                 190
```

```
Leu Glu Trp Ile Gly Thr Met Tyr Tyr Ser Gly Asn Ile Tyr Tyr Asn
            195                 200                 205

Pro Ser Leu Gln Ser Arg Ala Thr Ile Ser Val Asp Thr Ser Lys Asn
        210                 215                 220

Gln Phe Ser Leu Lys Leu Ser Ser Val Thr Ala Ala Asp Thr Ala Val
225                 230                 235                 240

Tyr Tyr Cys Ala Arg His Val Gly Tyr Ser Tyr Gly Arg Arg Phe Trp
                245                 250                 255

Tyr Phe Asp Leu Trp Gly Arg Gly Thr Leu Val Thr Val Ser Ser
                260                 265                 270

<210> SEQ ID NO 81
<211> LENGTH: 270
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Met Ala Trp Val Trp Thr Leu Leu Phe Leu Met Ala Ala Ala Gln Ser
1               5                   10                  15

Ile Gln Ala Gln Val Thr Leu Lys Glu Ser Gly Pro Val Leu Val Lys
            20                  25                  30

Pro Thr Glu Thr Leu Thr Leu Thr Cys Thr Val Ser Gly Phe Ser Leu
        35                  40                  45

Thr Asn Ile Arg Met Ser Val Ser Trp Ile Arg Gln Pro Pro Gly Lys
    50                  55                  60

Ala Leu Glu Trp Leu Ala His Ile Phe Ser Asn Asp Glu Lys Ser Tyr
65                  70                  75                  80

Ser Ser Ser Leu Lys Ser Arg Leu Thr Ile Ser Arg Asp Thr Ser Lys
                85                  90                  95

Ser Gln Val Val Leu Thr Leu Thr Asn Val Asp Pro Val Asp Thr Ala
            100                 105                 110

Thr Tyr Tyr Cys Ala Arg Met Arg Leu Pro Tyr Gly Met Asp Val Trp
        115                 120                 125

Gly Gln Gly Thr Thr Val Thr Val Ser Ser Gly Ser Glu Gly Lys
    130                 135                 140

Ser Ser Gly Ser Gly Ser Glu Ser Lys Ser Thr Gly Gly Ser Asp Ile
145                 150                 155                 160

Val Met Thr Gln Thr Pro Leu Ser Ser Pro Val Thr Leu Gly Gln Pro
                165                 170                 175

Ala Ser Ile Ser Cys Arg Ser Ser Gln Ser Leu Val His Ser Asp Gly
            180                 185                 190

Asn Thr Tyr Leu Ser Trp Leu Gln Gln Arg Pro Gly Gln Pro Pro Arg
        195                 200                 205

Leu Leu Ile Tyr Lys Ile Ser Asn Arg Phe Phe Gly Val Pro Asp Arg
    210                 215                 220

Phe Ser Gly Ser Gly Ala Gly Thr Asp Phe Thr Leu Lys Ile Ser Arg
225                 230                 235                 240

Val Glu Ala Glu Asp Val Gly Val Tyr Tyr Cys Met Gln Ala Thr Gln
                245                 250                 255

Phe Pro His Thr Phe Gly Gln Gly Thr Lys Leu Glu Ile Lys
            260                 265                 270

<210> SEQ ID NO 82
```

<211> LENGTH: 270
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Met Ala Trp Val Trp Thr Leu Leu Phe Leu Met Ala Ala Ala Gln Ser
1               5                   10                  15

Ile Gln Ala Asp Ile Val Met Thr Gln Thr Pro Leu Ser Ser Pro Val
            20                  25                  30

Thr Leu Gly Gln Pro Ala Ser Ile Ser Cys Arg Ser Ser Gln Ser Leu
        35                  40                  45

Val His Ser Asp Gly Asn Thr Tyr Leu Ser Trp Leu Gln Gln Arg Pro
    50                  55                  60

Gly Gln Pro Pro Arg Leu Leu Ile Tyr Lys Ile Ser Asn Arg Phe Phe
65                  70                  75                  80

Gly Val Pro Asp Arg Phe Ser Gly Ser Gly Ala Gly Thr Asp Phe Thr
                85                  90                  95

Leu Lys Ile Ser Arg Val Glu Ala Glu Asp Val Gly Val Tyr Tyr Cys
            100                 105                 110

Met Gln Ala Thr Gln Phe Pro His Thr Phe Gly Gln Gly Thr Lys Leu
        115                 120                 125

Glu Ile Lys Gly Gly Ser Glu Gly Lys Ser Ser Gly Ser Gly Ser Glu
    130                 135                 140

Ser Lys Ser Thr Gly Gly Ser Gln Val Thr Leu Lys Glu Ser Gly Pro
145                 150                 155                 160

Val Leu Val Lys Pro Thr Glu Thr Leu Thr Leu Thr Cys Thr Val Ser
                165                 170                 175

Gly Phe Ser Leu Thr Asn Ile Arg Met Ser Val Ser Trp Ile Arg Gln
            180                 185                 190

Pro Pro Gly Lys Ala Leu Glu Trp Leu Ala His Ile Phe Ser Asn Asp
        195                 200                 205

Glu Lys Ser Tyr Ser Ser Ser Leu Lys Ser Arg Leu Thr Ile Ser Arg
    210                 215                 220

Asp Thr Ser Lys Ser Gln Val Val Leu Thr Leu Thr Asn Val Asp Pro
225                 230                 235                 240

Val Asp Thr Ala Thr Tyr Tyr Cys Ala Arg Met Arg Leu Pro Tyr Gly
                245                 250                 255

Met Asp Val Trp Gly Gln Gly Thr Thr Val Thr Val Ser Ser
            260                 265                 270

<210> SEQ ID NO 83
<211> LENGTH: 475
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Leu Ser Ser
            20                  25                  30

Ser Tyr Trp Trp Gly Trp Thr Arg Gln Pro Pro Gly Arg Gly Leu Glu
        35                  40                  45

Trp Ile Gly Thr Met Tyr Tyr Ser Gly Asn Ile Tyr Tyr Asn Pro Ser
 50                  55                  60

Leu Gln Ser Arg Ala Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                     85                  90                  95

Cys Ala Arg His Val Gly Tyr Ser Tyr Gly Arg Arg Phe Trp Tyr Phe
                 100                 105                 110

Asp Leu Trp Gly Arg Gly Thr Leu Val Thr Val Ser Ser Gly Gly Ser
             115                 120                 125

Glu Gly Lys Ser Ser Gly Ser Gly Ser Glu Ser Lys Ser Thr Gly Gly
         130                 135                 140

Ser Glu Ile Val Leu Thr Gln Ser Pro Ala Thr Leu Ser Leu Ser Pro
145                 150                 155                 160

Gly Glu Arg Ala Thr Leu Ser Cys Arg Ala Ser Gln Ser Val Ser Ser
                 165                 170                 175

Tyr Leu Ala Trp Tyr Gln Gln Lys Pro Gly Gln Ala Pro Arg Leu Leu
             180                 185                 190

Ile Tyr Asp Ala Ser Asn Arg Ala Thr Gly Ile Pro Ala Arg Phe Ser
         195                 200                 205

Gly Ser Gly Ser Gly Thr Asp Phe Thr Leu Thr Ile Ser Ser Leu Glu
     210                 215                 220

Pro Glu Asp Phe Ala Val Tyr Tyr Cys Gln Gln Arg Ser Asn Trp Pro
225                 230                 235                 240

Pro Thr Phe Gly Gln Gly Thr Lys Val Glu Ile Lys Thr Ser Thr Pro
                 245                 250                 255

Ala Pro Arg Pro Pro Thr Pro Ala Pro Thr Ile Ala Ser Gln Pro Leu
             260                 265                 270

Ser Leu Arg Pro Glu Ala Cys Arg Pro Ala Ala Gly Gly Ala Val His
         275                 280                 285

Thr Arg Gly Leu Asp Phe Ala Cys Asp Ile Tyr Ile Trp Ala Pro Leu
     290                 295                 300

Ala Gly Thr Cys Gly Val Leu Leu Leu Ser Leu Val Ile Thr Leu Tyr
305                 310                 315                 320

Cys Lys Arg Gly Arg Lys Lys Leu Leu Tyr Ile Phe Lys Gln Pro Phe
                 325                 330                 335

Met Arg Pro Val Gln Thr Thr Gln Glu Glu Asp Gly Cys Ser Cys Arg
             340                 345                 350

Phe Pro Glu Glu Glu Glu Gly Gly Cys Glu Leu Arg Val Lys Phe Ser
         355                 360                 365

Arg Ser Ala Asp Ala Pro Ala Tyr Lys Gln Gly Gln Asn Gln Leu Tyr
     370                 375                 380

Asn Glu Leu Asn Leu Gly Arg Arg Glu Glu Tyr Asp Val Leu Asp Lys
385                 390                 395                 400

Arg Arg Gly Arg Asp Pro Glu Met Gly Gly Lys Pro Arg Arg Lys Asn
                 405                 410                 415

Pro Gln Glu Gly Leu Tyr Asn Glu Leu Gln Lys Asp Lys Met Ala Glu
             420                 425                 430

Ala Tyr Ser Glu Ile Gly Met Lys Gly Glu Arg Arg Arg Gly Lys Gly
         435                 440                 445

His Asp Gly Leu Tyr Gln Gly Leu Ser Thr Ala Thr Lys Asp Thr Tyr
     450                 455                 460

Asp Ala Leu His Met Gln Ala Leu Pro Pro Arg
465                 470                 475

<210> SEQ ID NO 84
<211> LENGTH: 475
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Thr Phe Gly Gln Gly Thr Lys Val Glu Ile Lys Gly Gly Ser Glu Gly
            100                 105                 110

Lys Ser Ser Gly Ser Gly Ser Glu Ser Lys Ser Thr Gly Gly Ser Gln
        115                 120                 125

Leu Gln Leu Gln Glu Ser Gly Pro Gly Leu Val Lys Pro Ser Glu Thr
130                 135                 140

Leu Ser Leu Thr Cys Thr Val Ser Gly Ser Leu Ser Ser Ser Ser Ser
145                 150                 155                 160

Tyr Trp Trp Gly Trp Thr Arg Gln Pro Pro Gly Arg Gly Leu Glu Trp
                165                 170                 175

Ile Gly Thr Met Tyr Tyr Ser Gly Asn Ile Tyr Tyr Asn Pro Ser Leu
            180                 185                 190

Gln Ser Arg Ala Thr Ile Ser Val Asp Thr Ser Lys Asn Gln Phe Ser
        195                 200                 205

Leu Lys Leu Ser Ser Val Thr Ala Ala Asp Thr Ala Val Tyr Tyr Cys
210                 215                 220

Ala Arg His Val Gly Tyr Ser Tyr Gly Arg Arg Phe Trp Tyr Phe Asp
225                 230                 235                 240

Leu Trp Gly Arg Gly Thr Leu Val Thr Val Ser Ser Thr Ser Thr Pro
                245                 250                 255

Ala Pro Arg Pro Pro Thr Pro Ala Pro Thr Ile Ala Ser Gln Pro Leu
            260                 265                 270

Ser Leu Arg Pro Glu Ala Cys Arg Pro Ala Ala Gly Gly Ala Val His
        275                 280                 285

Thr Arg Gly Leu Asp Phe Ala Cys Asp Ile Tyr Ile Trp Ala Pro Leu
290                 295                 300

Ala Gly Thr Cys Gly Val Leu Leu Leu Ser Leu Val Ile Thr Leu Tyr
305                 310                 315                 320

Cys Lys Arg Gly Arg Lys Lys Leu Leu Tyr Ile Phe Lys Gln Pro Phe
                325                 330                 335

Met Arg Pro Val Gln Thr Thr Gln Glu Glu Asp Gly Cys Ser Cys Arg
            340                 345                 350

```
Phe Pro Glu Glu Glu Gly Gly Cys Glu Leu Arg Val Lys Phe Ser
            355                 360                 365

Arg Ser Ala Asp Ala Pro Ala Tyr Lys Gln Gly Gln Asn Gln Leu Tyr
        370                 375                 380

Asn Glu Leu Asn Leu Gly Arg Arg Glu Glu Tyr Asp Val Leu Asp Lys
385                 390                 395                 400

Arg Arg Gly Arg Asp Pro Glu Met Gly Gly Lys Pro Arg Arg Lys Asn
                405                 410                 415

Pro Gln Glu Gly Leu Tyr Asn Glu Leu Gln Lys Asp Lys Met Ala Glu
                420                 425                 430

Ala Tyr Ser Glu Ile Gly Met Lys Gly Glu Arg Arg Arg Gly Lys Gly
            435                 440                 445

His Asp Gly Leu Tyr Gln Gly Leu Ser Thr Ala Thr Lys Asp Thr Tyr
        450                 455                 460

Asp Ala Leu His Met Gln Ala Leu Pro Pro Arg
465                 470                 475

<210> SEQ ID NO 85
<211> LENGTH: 474
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Thr Asn Ile
            20                  25                  30

Arg Met Ser Val Ser Trp Ile Arg Gln Pro Pro Gly Lys Ala Leu Glu
        35                  40                  45

Trp Leu Ala His Ile Phe Ser Asn Asp Glu Lys Ser Tyr Ser Ser Ser
    50                  55                  60

Leu Lys Ser Arg Leu Thr Ile Ser Arg Asp Thr Ser Lys Ser Gln Val
65                  70                  75                  80

Val Leu Thr Leu Thr Asn Val Asp Pro Val Asp Thr Ala Thr Tyr Tyr
                85                  90                  95

Cys Ala Arg Met Arg Leu Pro Tyr Gly Met Asp Val Trp Gly Gln Gly
            100                 105                 110

Thr Thr Val Thr Val Ser Ser Gly Gly Ser Glu Gly Lys Ser Ser Gly
        115                 120                 125

Ser Gly Ser Glu Ser Lys Ser Thr Gly Gly Ser Asp Ile Val Met Thr
    130                 135                 140

Gln Thr Pro Leu Ser Ser Pro Val Thr Leu Gly Gln Pro Ala Ser Ile
145                 150                 155                 160

Ser Cys Arg Ser Ser Gln Ser Leu Val His Ser Asp Gly Asn Thr Tyr
                165                 170                 175

Leu Ser Trp Leu Gln Gln Arg Pro Gly Gln Pro Pro Arg Leu Leu Ile
            180                 185                 190

Tyr Lys Ile Ser Asn Arg Phe Phe Gly Val Pro Asp Arg Phe Ser Gly
        195                 200                 205

Ser Gly Ala Gly Thr Asp Phe Thr Leu Lys Ile Ser Arg Val Glu Ala
    210                 215                 220

Glu Asp Val Gly Val Tyr Tyr Cys Met Gln Ala Thr Gln Phe Pro His
```

```
                225                 230                 235                 240
        Thr Phe Gly Gln Gly Thr Lys Leu Glu Ile Lys Thr Ser Thr Pro Ala
                        245                 250                 255

Pro Arg Pro Pro Thr Pro Ala Pro Thr Ile Ala Ser Gln Pro Leu Ser
                        260                 265                 270

Leu Arg Pro Glu Ala Cys Arg Pro Ala Ala Gly Gly Ala Val His Thr
                        275                 280                 285

Arg Gly Leu Asp Phe Ala Cys Asp Ile Tyr Ile Trp Ala Pro Leu Ala
                        290                 295                 300

Gly Thr Cys Gly Val Leu Leu Leu Ser Leu Val Ile Thr Leu Tyr Cys
        305                 310                 315                 320

Lys Arg Gly Arg Lys Lys Leu Leu Tyr Ile Phe Lys Gln Pro Phe Met
                        325                 330                 335

Arg Pro Val Gln Thr Thr Gln Glu Glu Asp Gly Cys Ser Cys Arg Phe
                        340                 345                 350

Pro Glu Glu Glu Glu Gly Gly Cys Glu Leu Arg Val Lys Phe Ser Arg
                        355                 360                 365

Ser Ala Asp Ala Pro Ala Tyr Lys Gln Gly Gln Asn Gln Leu Tyr Asn
                        370                 375                 380

Glu Leu Asn Leu Gly Arg Arg Glu Glu Tyr Asp Val Leu Asp Lys Arg
        385                 390                 395                 400

Arg Gly Arg Asp Pro Glu Met Gly Gly Lys Pro Arg Arg Lys Asn Pro
                        405                 410                 415

Gln Glu Gly Leu Tyr Asn Glu Leu Gln Lys Asp Lys Met Ala Glu Ala
                        420                 425                 430

Tyr Ser Glu Ile Gly Met Lys Gly Glu Arg Arg Arg Gly Lys Gly His
                        435                 440                 445

Asp Gly Leu Tyr Gln Gly Leu Ser Thr Ala Thr Lys Asp Thr Tyr Asp
                        450                 455                 460

Ala Leu His Met Gln Ala Leu Pro Pro Arg
        465                 470

<210> SEQ ID NO 86
<211> LENGTH: 474
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86

Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Ser Leu Val His Ser
                20                  25                  30

Asp Gly Asn Thr Tyr Leu Ser Trp Leu Gln Gln Arg Pro Gly Gln Pro
            35                  40                  45

Pro Arg Leu Leu Ile Tyr Lys Ile Ser Asn Arg Phe Phe Gly Val Pro
        50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Thr Gln Phe Pro His Thr Phe Gly Gln Gly Thr Lys Leu Glu Ile Lys
                100                 105                 110
```

Gly Gly Ser Glu Gly Lys Ser Ser Gly Ser Glu Ser Lys Ser
            115                 120                 125

Thr Gly Ser Gln Val Thr Leu Lys Glu Ser Gly Pro Val Leu Val
            130                 135                 140

Lys Pro Thr Glu Thr Leu Thr Leu Thr Cys Thr Val Ser Gly Phe Ser
145                 150                 155                 160

Leu Thr Asn Ile Arg Met Ser Val Ser Trp Ile Arg Gln Pro Pro Gly
                165                 170                 175

Lys Ala Leu Glu Trp Leu Ala His Ile Phe Ser Asn Asp Glu Lys Ser
            180                 185                 190

Tyr Ser Ser Leu Lys Ser Arg Leu Thr Ile Ser Arg Asp Thr Ser
            195                 200                 205

Lys Ser Gln Val Val Leu Thr Leu Thr Asn Val Asp Pro Val Asp Thr
210                 215                 220

Ala Thr Tyr Tyr Cys Ala Arg Met Arg Leu Pro Tyr Gly Met Asp Val
225                 230                 235                 240

Trp Gly Gln Gly Thr Thr Val Thr Val Ser Ser Thr Ser Thr Pro Ala
                245                 250                 255

Pro Arg Pro Pro Thr Pro Ala Pro Thr Ile Ala Ser Gln Pro Leu Ser
            260                 265                 270

Leu Arg Pro Glu Ala Cys Arg Pro Ala Ala Gly Gly Ala Val His Thr
            275                 280                 285

Arg Gly Leu Asp Phe Ala Cys Asp Ile Tyr Ile Trp Ala Pro Leu Ala
            290                 295                 300

Gly Thr Cys Gly Val Leu Leu Leu Ser Leu Val Ile Thr Leu Tyr Cys
305                 310                 315                 320

Lys Arg Gly Arg Lys Lys Leu Leu Tyr Ile Phe Lys Gln Pro Phe Met
                325                 330                 335

Arg Pro Val Gln Thr Thr Gln Glu Glu Asp Gly Cys Ser Cys Arg Phe
            340                 345                 350

Pro Glu Glu Glu Glu Gly Gly Cys Glu Leu Arg Val Lys Phe Ser Arg
            355                 360                 365

Ser Ala Asp Ala Pro Ala Tyr Lys Gln Gly Gln Asn Gln Leu Tyr Asn
370                 375                 380

Glu Leu Asn Leu Gly Arg Arg Glu Glu Tyr Asp Val Leu Asp Lys Arg
385                 390                 395                 400

Arg Gly Arg Asp Pro Glu Met Gly Gly Lys Pro Arg Arg Lys Asn Pro
                405                 410                 415

Gln Glu Gly Leu Tyr Asn Glu Leu Gln Lys Asp Lys Met Ala Glu Ala
            420                 425                 430

Tyr Ser Glu Ile Gly Met Lys Gly Glu Arg Arg Arg Gly Lys Gly His
            435                 440                 445

Asp Gly Leu Tyr Gln Gly Leu Ser Thr Ala Thr Lys Asp Thr Tyr Asp
450                 455                 460

Ala Leu His Met Gln Ala Leu Pro Pro Arg
465                 470

<210> SEQ ID NO 87
<211> LENGTH: 1485
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 87

```
atggcttggg tgtggacctt gctattcctg atggcagctg cccaaagtat acaggcccaa      60
ctccagctgc aagaatctgg tcctggactc gtaaaaccat cagaaaccct ctcattgacc     120
tgcacagtga gtggtggatc attgtcttcc agcagctatt ggtgggggtg gactcgacag     180
ccaccaggtc gcggtctcga gtggataggt acaatgtatt acagtggtaa catttattac     240
aaccctagcc tccaaagccg ggcaaccatc tctgttgaca catccaagaa tcaatttagc     300
ctgaaattgt ctagtgtgac tgctgctgat acagctgttt attattgcgc taggcatgtc     360
ggatactctt atggtcgtag attctggtac ttcgatttgt ggggtcgcgg gaccttggta     420
acagtctcct ccgaggatca gaggggaaa tcttccggta gcggcagtga atcaaagtca      480
actggtggtt ccgaaatcgt gctgactcag tcacccgcaa ctctttcact gagtcctgga     540
gaacgtgcta ctctgtcatg tcgggcttct cagtcagtaa gttcttattt ggcatggtac     600
cagcaaaagc ccggccaagc cccccgactc ttgatatacg atgcatcaaa ccgtgccact     660
ggaatcccag cacggttttc cggaagtggt tccggaaccg acttcaccct caccatatcc     720
agtttggagc ccgaggactt cgcagtttac tattgtcaac aacggtccaa ctggccccc      780
acatttggac aaggcaccaa agtcgaaata aagactagta ccccagcccc acgccctccc     840
accoctgctc ctacaatagc atcccagccc ttgtcacttc gccccgaagc atgcagacca     900
gccgcaggcg gtgctgtgca tacccgagga ctggacttcg cctgcgacat ctacatctgg     960
gccccactgg ccggcacctg cggcgtgctg ctgctgagcc tggtgatcac cctgtactgc    1020
aagcgcggcc gcaagaagct gctgtacatc ttcaagcagc cattcatgcg cccagtgcag    1080
accacccagg aggaggacgg ctgcagctgc cgcttcccag aggaggagga gggcggctgc    1140
gagctgcgcg tgaagttcag ccgcagcgcc gacgccccag cctacaagca gggccagaac    1200
cagctgtaca acgagctgaa cctgggccgc cgcgaggagt acgacgtgct ggacaagcgc    1260
cgcggccgcg acccagagat gggcggcaag ccacgccgca gaacccaca ggagggcctg     1320
tacaacgagc tgcagaagga caagatggcc gaggcctaca gcgagatcgg catgaagggc    1380
gagcgccgcc gcggcaaggg ccacgacggc ctgtaccagg gcctgagcac cgccaccaag    1440
gacacctacg acgccctgca catgcaggcc ctgccaccac gctga                    1485
```

<210> SEQ ID NO 88
<211> LENGTH: 1485
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 88

```
atggcttggg tgtggacctt gctattcctg atggcagctg cccaaagtat acaggccgaa      60
atcgtactga ctcaaagtcc cgctactctc agtctgtcac ccggcgagag agccacactg     120
tcatgccgcg ccagccaatc agtcagttcc taccttgctt ggtatcagca gaaacctggc     180
caagcacctc ggctgcttat ctacgacgcc agcaatcgcg ccactggtat cccagctcgg     240
ttttcaggta gcggcagtgg gacagacttt accttgacta ttagctctct tgaacccgaa     300
gactttgccg tttattactg ccagcaacgg tcaaactggc ctcccacttt tggccaagga     360
accaaagtag agataaaagg tggttcagaa ggtaaatcaa gtgggtccgg ttccgaaagt     420
aagtccaccg gaggctctca actccagttg caggaaagtg gcctgggct tgtaaaacca     480
agcgagacat tgtctctcac atgcactgta tcaggggat ctctttcaag ttcctcttat     540
```

```
tggtggggt  ggactcgtca  acccccggt   aggggtctcg  aatggatcgg  taccatgtat       600
tattctggga  atatatacta  taatccaagc  cttcaaagta  gagctactat  atccgtggac       660
acatccaaga  atcagttctc  cttgaaactt  tctagcgtga  ccgccgccga  tactgctgtc       720
tactactgcg  cacggcatgt  gggatactcc  tacgggagac  ggttctggta  tttcgacttg       780
tggggtcgcg  gtacactcgt  tacagtgtcc  tctactagta  ccccagcccc  acgccctccc       840
acccctgctc  ctacaatagc  atcccagccc  ttgtcacttc  gccccgaagc  atgcagacca       900
gccgcaggcg  gtgctgtgca  tacccgagga  ctggacttcg  cctgcgacat  ctacatctgg       960
gccccactgg  ccggcacctg  cggcgtgctg  ctgctgagcc  tggtgatcac  cctgtactgc      1020
aagcgcggcc  gcaagaagct  gctgtacatc  ttcaagcagc  cattcatgcg  cccagtgcag      1080
accacccagg  aggaggacgg  ctgcagctgc  cgcttcccag  aggaggagga  gggcggctgc      1140
gagctgcgcg  tgaagttcag  ccgcagcgcc  gacgccccag  cctacaagca  gggccagaac      1200
cagctgtaca  acgagctgaa  cctgggccgc  cgcgaggagt  acgacgtgct  ggacaagcgc      1260
cgcggccgcg  acccagagat  gggcggcaag  ccacgccgca  agaacccaca  ggagggcctg      1320
tacaacgagc  tgcagaagga  caagatggcc  gaggcctaca  gcgagatcgg  catgaagggc      1380
gagcgccgcc  gcggcaaggg  ccacgacggc  ctgtaccagg  gcctgagcac  cgccaccaag      1440
gacacctacg  acgccctgca  catgcaggcc  ctgccaccac  gctga                      1485

<210> SEQ ID NO 89
<211> LENGTH: 1482
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 89
atggcttggg  tgtggacctt  gctattcctg  atggcagctg  cccaaagtat  acaggcccaa        60
gtaacactca  aggagagcgg  accagtcttg  gtgaaaccaa  ctgagacctt  gactttgaca       120
tgtactgtaa  gtggcttcag  ccttaccaac  atcaggatgt  cagtatcttg  gataaggcaa       180
ccacctggca  aggcactcga  atggctggca  cacatctttt  ctaacgacga  aaaatcctat       240
tcttccagtc  tcaaaagtcg  ccttaccatc  agccgagata  ccagtaagag  tcaagtagtt       300
cttacattga  ccaatgtaga  tccagttgat  acagccacat  actactgcgc  acgaatgcgg       360
cttccatacg  gcatggatgt  atggggacag  ggaactactg  ttaccgttag  ttccggcggc       420
tccgagggca  agagcagcgg  cagcggcagc  gagagcaaga  gcaccggcgg  cagcgacatt       480
gtgatgaccc  aaacacctct  tagtagtcct  gtaactctcg  gacagccagc  ttcaatatct       540
tgtcgctcaa  gtcaatccct  cgtccattcc  gacggcaaca  cctacctctc  ttggctccaa       600
cagagacccg  gccagcctcc  cagacttctc  atctacaaaa  tcagtaacag  gttcttcggc       660
gtccctgaca  ggttcagtgg  atctggagca  ggtacagatt  tcaccttgaa  gataagtaga       720
gtggaggctg  aggacgtagg  cgtctattat  tgtatgcaag  ctacccaatt  cccacataca       780
ttcggccaag  gcactaaatt  ggaaataaaa  actagtaccc  cagccccacg  ccctcccacc       840
cctgctccta  caatagcatc  ccagcccttg  tcacttcgcc  cgaagcatg  cagaccagcc       900 gcaggcggtg  ctgtgcatac  ccgaggactg  gacttcgcct  gcgacatcta  catctgggcc       960
ccactggccg  gcacctgcgg  cgtgctgctg  ctgagcctgg  tgatcaccct  gtactgcaag      1020
cgcggccgca  agaagctgct  gtacatcttc  aagcagccat  tcatgcgccc  agtgcagacc      1080
```

| | |
|---|---|
| acccaggagg aggacggctg cagctgccgc ttcccagagg aggaggaggg cggctgcgag | 1140 |
| ctgcgcgtga agttcagccg cagcgccgac gccccagcct acaagcaggg ccagaaccag | 1200 |
| ctgtacaacg agctgaacct gggccgccgc gaggagtacg acgtgctgga caagcgccgc | 1260 |
| ggccgcgacc cagagatggg cggcaagcca cgccgcaaga acccacagga gggcctgtac | 1320 |
| aacgagctgc agaaggacaa gatggccgag gcctacagcg agatcggcat gaagggcgag | 1380 |
| cgccgccgcg gcaagggcca cgacggcctg taccagggcc tgagcaccgc caccaaggac | 1440 |
| acctacgacg ccctgcacat gcaggccctg ccaccacgct ga | 1482 |

<210> SEQ ID NO 90
<211> LENGTH: 1482
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 90

| | |
|---|---|
| atggcttggg tgtggacctt gctattcctg atggcagctg cccaaagtat acaggccgac | 60 |
| attgtgatga cccaaacacc tcttagtagt cctgtaactc tcggacagcc agcttcaata | 120 |
| tcttgtcgct caagtcaatc cctcgtccat ccgacggca cacctacct ctcttggctc | 180 |
| caacagagac ccggccagcc tcccagactt ctcatctaca aaatcagtaa caggttcttc | 240 |
| ggcgtccctg acaggttcag tggatctgga gcaggtacag atttcaccctt gaagataagt | 300 |
| agagtggagg ctgaggacgt aggcgtctat tattgtatgc aagctaccca attcccacat | 360 |
| acattcggcc aaggcactaa attggaaata aaaggcggct ccgagggcaa gagcagcggc | 420 |
| agcggcagcg agagcaagag caccggcggc agccaagtaa cactcaagga gagcggacca | 480 |
| gtcttggtga aaccaactga gaccttgact ttgacatgta ctgtaagtgg cttcagcctt | 540 |
| accaacatca ggatgtcagt atcttggata aggcaaccac ctggcaaggc actcgaatgg | 600 |
| ctggcacaca tcttttctaa cgacgaaaaa tcctattctt ccagtctcaa aagtcgcctt | 660 |
| accatcagcc gagataccag taagagtcaa gtagttctta cattgaccaa tgtagatcca | 720 |
| gttgatacag ccacatacta ctgcgcacga atgcggcttc catacggcat ggatgtatgg | 780 |
| ggacagggaa ctactgttac cgttagttcc actagtaccc cagccccacg ccctcccacc | 840 |
| cctgctccta caatagcatc ccagcccttg tcacttcgcc ccgaagcatg cagaccagcc | 900 |
| gcaggcggtg ctgtgcatac ccgaggactg gacttcgcct gcgacatcta catctgggcc | 960 |
| ccactggccg gcacctgcgg cgtgctgctg ctgagcctgg tgatcaccct gtactgcaag | 1020 |
| cgcggccgca gaagctgct gtacatcttc aagcagccat tcatgcgccc agtgcagacc | 1080 |
| acccaggagg aggacggctg cagctgccgc ttcccagagg aggaggaggg cggctgcgag | 1140 |
| ctgcgcgtga agttcagccg cagcgccgac gccccagcct acaagcaggg ccagaaccag | 1200 |
| ctgtacaacg agctgaacct gggccgccgc gaggagtacg acgtgctgga caagcgccgc | 1260 |
| ggccgcgacc cagagatggg cggcaagcca cgccgcaaga acccacagga gggcctgtac | 1320 |
| aacgagctgc agaaggacaa gatggccgag gcctacagcg agatcggcat gaagggcgag | 1380 |
| cgccgccgcg gcaagggcca cgacggcctg taccagggcc tgagcaccgc caccaaggac | 1440 |
| acctacgacg ccctgcacat gcaggccctg ccaccacgct ga | 1482 |

<210> SEQ ID NO 91
<211> LENGTH: 20

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Gly Gly Ser Glu Gly Lys Ser Ser Gly Ser Gly Ser Glu Ser Lys Ser
1               5                   10                  15

Thr Gly Gly Ser
            20

<210> SEQ ID NO 92
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Gly Gly Gly Ser Gly Gly Gly Ser
1               5

<210> SEQ ID NO 93
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Gly Gly Gly Ser Gly Gly Gly Ser Gly Gly Gly Ser
1               5                   10

<210> SEQ ID NO 94
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Gly Gly Gly Ser Gly Gly Gly Ser Gly Gly Gly Ser Gly Gly Gly Ser
1               5                   10                  15

<210> SEQ ID NO 95
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Gly Gly Gly Ser Gly Gly Gly Ser Gly Gly Gly Ser Gly Gly Gly Ser
1               5                   10                  15

Gly Gly Gly Ser
            20

<210> SEQ ID NO 96
<211> LENGTH: 15
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 96

Gly Gly Gly Gly Ser Gly Gly Gly Gly Ser Gly Gly Gly Gly Ser
1               5                   10                  15

<210> SEQ ID NO 97
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Gly Gly Gly Gly Ser Gly Gly Gly Gly Ser Gly Gly Gly Gly Ser Gly
1               5                   10                  15

Gly Gly Gly Ser
            20

<210> SEQ ID NO 98
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 99
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Gly Ser Thr Ser Gly Ser Gly Lys Pro Gly Ser Gly Glu Gly Ser Thr
1               5                   10                  15

Lys Gly

<210> SEQ ID NO 100
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Ile Arg Pro Arg Ala Ile Gly Gly Ser Lys Pro Arg Val Ala
1               5                   10

<210> SEQ ID NO 101
<211> LENGTH: 15
<212> TYPE: PRT
<213> ORGANISM: Artificial Sequence
<220> FEATURE:
<223> OTHER INFORMATION: Description of Artificial Sequence: Synthetic

```
peptide

<400> SEQUENCE: 101

Gly Lys Gly Gly Ser Gly Lys Gly Gly Ser Gly Lys Gly Gly Ser
1               5                   10                  15

<210> SEQ ID NO 102
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Gly Gly Lys Gly Ser Gly Gly Lys Gly Ser Gly Gly Lys Gly Ser
1               5                   10                  15

<210> SEQ ID NO 103
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Gly Gly Gly Lys Ser Gly Gly Gly Lys Ser Gly Gly Gly Lys Ser
1               5                   10                  15

<210> SEQ ID NO 104
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Gly Lys Gly Lys Ser Gly Lys Gly Lys Ser Gly Lys Gly Lys Ser
1               5                   10                  15

<210> SEQ ID NO 105
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Gly Gly Gly Lys Ser Gly Gly Lys Gly Ser Gly Lys Gly Gly Ser
1               5                   10                  15

<210> SEQ ID NO 106
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Gly Lys Pro Gly Ser Gly Lys Pro Gly Ser Gly Lys Pro Gly Ser
1               5                   10                  15

<210> SEQ ID NO 107
```

```
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Gly Lys Pro Gly Ser Gly Lys Pro Gly Ser Gly Lys Pro Gly Ser Gly
1               5                   10                  15

Lys Pro Gly Ser
            20

<210> SEQ ID NO 108
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Gly Lys Gly Lys Ser Gly Lys Gly Lys Ser Gly Lys Gly Lys Ser Gly
1               5                   10                  15

Lys Gly Lys Ser
            20

<210> SEQ ID NO 109
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Ser Thr Ala Gly Asp Thr His Leu Gly Gly Glu Asp Phe Asp
1               5                   10

<210> SEQ ID NO 110
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Gly Glu Gly Gly Ser Gly Glu Gly Gly Ser Gly Glu Gly Gly Ser
1               5                   10                  15

<210> SEQ ID NO 111
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Gly Gly Glu Gly Ser Gly Gly Glu Gly Ser Gly Gly Glu Gly Ser
1               5                   10                  15

<210> SEQ ID NO 112
<211> LENGTH: 15
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 112

Gly Glu Gly Glu Ser Gly Glu Gly Glu Ser Gly Glu Gly Glu Ser
1               5                   10                  15

<210> SEQ ID NO 113
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Gly Gly Gly Glu Ser Gly Gly Glu Gly Ser Gly Glu Gly Gly Ser
1               5                   10                  15

<210> SEQ ID NO 114
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Gly Glu Gly Glu Ser Gly Glu Gly Glu Ser Gly Glu Gly Glu Ser Gly
1               5                   10                  15

Glu Gly Glu Ser
            20

<210> SEQ ID NO 115
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Gly Ser Thr Ser Gly Ser Gly Lys Pro Gly Ser Gly Glu Gly Ser Thr
1               5                   10                  15

Lys Gly

<210> SEQ ID NO 116
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Pro Arg Gly Ala Ser Lys Ser Gly Ser Ala Ser Gln Thr Gly Ser Ala
1               5                   10                  15

Pro Gly Ser

<210> SEQ ID NO 117
<211> LENGTH: 19
<212> TYPE: PRT
<213> ORGANISM: Artificial Sequence
<220> FEATURE:
<223> OTHER INFORMATION: Description of Artificial Sequence: Synthetic
```

```
                              peptide

<400> SEQUENCE: 117

Gly Thr Ala Ala Ala Gly Ala Gly Ala Ala Gly Gly Ala Ala Ala Gly
1               5                   10                  15

Ala Ala Gly

<210> SEQ ID NO 118
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Gly Thr Ser Gly Ser Ser Gly Ser Gly Ser Gly Ser Gly Ser Gly Ser
1               5                   10                  15

Gly Gly Gly

<210> SEQ ID NO 119
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Gly Lys Pro Gly Ser Gly Lys Pro Gly Ser Gly Lys Pro Gly Ser Gly
1               5                   10                  15

Lys Pro Gly Ser
            20

<210> SEQ ID NO 120
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Gly Ser Gly Ser
1

<210> SEQ ID NO 121
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Ala Pro Ala Pro Ala Pro Ala Pro Ala Pro
1               5                   10

<210> SEQ ID NO 122
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 122

Ala Pro Ala Pro Ala Pro Ala Pro Ala Pro Ala Pro Ala Pro Ala Pro
1               5                   10                  15

Ala Pro Ala Pro
            20

<210> SEQ ID NO 123
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 123

Ala Glu Ala Ala Ala Lys Glu Ala Ala Ala Lys Glu Ala Ala Ala Ala
1               5                   10                  15

Lys Glu Ala Ala Ala Ala Lys Glu Ala Ala Ala Lys Ala Ala Ala
            20                  25                  30

<210> SEQ ID NO 124
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Glu Pro Lys Ser Cys Asp Lys Thr His Thr Cys Pro Pro Cys Pro
1               5                   10                  15

<210> SEQ ID NO 125
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Glu Arg Lys Cys Cys Val Glu Cys Pro Pro Cys Pro
1               5                   10

<210> SEQ ID NO 126
<211> LENGTH: 62
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 126

Glu Leu Lys Thr Pro Leu Gly Asp Thr Thr His Thr Cys Pro Arg Cys
1               5                   10                  15

Pro Glu Pro Lys Ser Cys Asp Thr Pro Pro Cys Pro Arg Cys Pro
            20                  25                  30

Glu Pro Lys Ser Cys Asp Thr Pro Pro Cys Pro Arg Cys Pro Glu
        35                  40                  45

Pro Lys Ser Cys Asp Thr Pro Pro Cys Pro Arg Cys Pro
    50                  55                  60

<210> SEQ ID NO 127
<211> LENGTH: 12

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Glu Ser Lys Tyr Gly Pro Pro Cys Pro Ser Cys Pro
1               5                   10
```

GPRC5D CHIMERIC ANTIGEN RECEPTORS AND CELLS EXPRESSING THE SAME

CROSS-REFERENCE TO RELATED APPLICATIONS

This application claims the benefit of U.S. Provisional Application Ser. No. 62/793,973, filed 18 Jan. 2019. The entire content of the aforementioned application is incorporated herein by reference in its entirety.

SEQUENCE LISTING

The instant application contains a Sequence Listing which has been submitted electronically in ASCII format and is hereby incorporated by reference in its entirety. Said ASCII copy, created on Jan. 9, 2020, is named JBI6043WOPCT1_SL.txt and is 150,002 bytes in size.

TECHNICAL FIELD

The invention relates to GPRC5D-targeting chimeric antigen receptors (CARs) comprising GPRC5D single-chain variable fragments and engineered GPRC5D-targeting immune cells expressing the CARs. Also provided are nucleic acids and expression vectors encoding the CARs, recombinant cells containing the vectors, and compositions comprising the engineered immune cells expressing the GPRC5D-targeting CARs. Methods of making the CARs, and engineered immune cells, and methods of using the engineered immune cells to treat conditions including cancer are also provided.

BACKGROUND

T cell therapy utilizes isolated T cells that have been genetically modified to enhance their specificity for a specific tumor associated antigen. Genetic modification may involve the expression of a chimeric antigen receptor (CAR) or an exogenous T cell receptor to provide new antigen specificity onto the T cell. T cells expressing chimeric antigen receptors (CAR-T cells) can induce tumor immunoreactivity. There is a need for better cancer therapies utilizing CAR-T cells.

SUMMARY

Disclosed herein are chimeric antigen receptors (CARs), e.g., CARs that target a G-protein coupled receptor, G-protein coupled receptor family C group 5 member D (GPRC5D), cells comprising the CARs, vectors encoding the CARs, e.g., recombinant expression vectors, and nucleic acid molecules encoding the CARs, methods of making the CARs, compositions, polypeptides, proteins, nucleic acids, host cells, populations of cells and methods of treating disorders, e.g., cancer, using the disclosed CARs.

In one aspect, the disclosure provides a CAR, comprising an extracellular antigen-binding domain, a transmembrane domain and an intracellular signaling domain, wherein the extracellular antigen-binding domain comprises:
  a heavy chain complementarity determining region 1 (CDR1) having the amino acid sequence of SEQ ID NO: 66, a heavy chain CDR2 having the amino acid sequence of SEQ ID NO: 67, and a heavy chain CDR3 having the amino acid sequence of SEQ ID NO: 68;
  a heavy chain complementarity determining region 1 (CDR1) having the amino acid sequence of SEQ ID NO: 58, a heavy chain CDR2 having the amino acid sequence of SEQ ID NO: 59, and a heavy chain CDR3 having the amino acid sequence of SEQ ID NO: 60;
  a heavy chain complementarity determining region 1 (CDR1) having the amino acid sequence of SEQ ID NO: 39, a heavy chain CDR2 having the amino acid sequence of SEQ ID NO: 40, and a heavy chain CDR3 having the amino acid sequence of SEQ ID NO: 41;
  a heavy chain CDR1 having the amino acid sequence of SEQ ID NO: 42, a heavy chain CDR2 having the amino acid sequence of SEQ ID NO: 43, and a heavy chain CDR3 having the amino acid sequence of SEQ ID NO: 44; or
  a heavy chain CDR1 having the amino acid sequence of SEQ ID NO: 45, a heavy chain CDR2 having the amino acid sequence of SEQ ID NO: 46, and a heavy chain CDR3 having the amino acid sequence of SEQ ID NO: 47;
wherein the extracellular antigen-binding domain binds the GPRC5D antigen.

In one embodiment:
the extracellular antigen-binding domain comprises the heavy chain CDR1 having the amino acid sequence of SEQ ID NO: 66, the heavy chain CDR2 having the amino acid sequence of SEQ ID NO: 67, and the heavy chain CDR3 having the amino acid sequence of SEQ ID NO: 68, and further comprises a light chain CDR1 having the amino acid sequence of SEQ ID NO: 69, a light chain CDR2 having the amino acid sequence of SEQ ID NO: 70, and a light chain CDR3 having the amino acid sequence of SEQ ID NO: 71;
the extracellular antigen-binding domain comprises the heavy chain CDR1 having the amino acid sequence of SEQ ID NO: 58, the heavy chain CDR2 having the amino acid sequence of SEQ ID NO: 59, and the heavy chain CDR3 having the amino acid sequence of SEQ ID NO: 60, and further comprises a light chain CDR1 having the amino acid sequence of SEQ ID NO: 61, a light chain CDR2 having the amino acid sequence of SEQ ID NO: 62, and a light chain CDR3 having the amino acid sequence of SEQ ID NO: 63
the extracellular antigen-binding domain comprises the heavy chain CDR1 having the amino acid sequence of SEQ ID NO: 39, the heavy chain CDR2 having the amino acid sequence of SEQ ID NO: 40, and the heavy chain CDR3 having the amino acid sequence of SEQ ID NO: 41, and further comprises a light chain CDR1 having the amino acid sequence of SEQ ID NO: 48, a light chain CDR2 having the amino acid sequence of SEQ ID NO: 49, and a light chain CDR3 having the amino acid sequence of SEQ ID NO: 50;
the extracellular antigen-binding domain comprises the heavy chain CDR1 having the amino acid sequence of SEQ ID NO: 42, the heavy chain CDR2 having the amino acid sequence of SEQ ID NO: 43, and the heavy chain CDR3 having the amino acid sequence of SEQ ID NO: 44, and further comprises a light chain CDR1 having the amino acid sequence of SEQ ID NO: 51, a light chain CDR2 having the amino acid sequence of SEQ ID NO: 52, and a light chain CDR3 having the amino acid sequence of SEQ ID NO: 53; or
the extracellular antigen-binding domain comprises the heavy chain CDR1 having the amino acid sequence of SEQ ID NO: 45, the heavy chain CDR2 having the amino acid sequence of SEQ ID NO: 46, and the heavy chain CDR3 having the amino acid sequence of SEQ ID NO: 47, and further comprises a light chain CDR1 having the amino acid sequence of SEQ ID NO: 54, a light chain CDR2 having the amino acid sequence of SEQ ID NO: 55, and a light chain CDR3 having the amino acid sequence of SEQ ID NO: 56.

In one embodiment, the extracellular antigen-binding domain comprises a light chain variable region (LCVR) comprising an amino acid sequence selected from the group consisting of SEQ ID NOS: 73, 65, 1, 3 and 5, or a heavy chain variable region (HCVR) comprising an amino acid sequence selected from the group consisting of SEQ ID NOS: 72, 64, 2, 4, and 6, or a combination of a LCVR comprising an amino acid sequence selected from the group consisting of SEQ ID NOS: 73, 65, 1, 3 and 5, and a HCVR comprising an amino acid sequence selected from the group consisting of SEQ ID NOS: 72, 64, 2, 4, and 6.

In one embodiment, the extracellular antigen-binding domain comprises:
  a light chain variable region comprising an amino acid sequence of SEQ ID NO: 73 and a heavy chain variable region comprising an amino acid sequence of SEQ ID NO: 72;
  a light chain variable region comprising an amino acid sequence of SEQ ID NO: 65 and a heavy chain variable region comprising an amino acid sequence of SEQ ID NO: 64;
  a light chain variable region comprising an amino acid sequence of SEQ ID NO: 1 and a heavy chain variable region comprising an amino acid sequence of SEQ ID NO: 2;
  a light chain variable region comprising an amino acid sequence of SEQ ID NO: 3 and a heavy chain variable region comprising an amino acid sequence of SEQ ID NO: 4; or
  a light chain variable region comprising an amino acid sequence of SEQ ID NO: 5 and a heavy chain variable region comprising an amino acid sequence of SEQ ID NO: 6.

In one embodiment, the extracellular antigen-binding domain comprises a single-chain variable fragment (scFv). In some embodiments, the scFv comprises a linker polypeptide between the light chain variable region and the heavy chain variable region.

In one embodiment, the linker polypeptide comprises an amino acid sequence of SEQ ID NO: 7.

In one embodiment, the scFv comprises an amino acid sequence selected from the group consisting of SEQ ID NOS: 78, 77, 75, 76, 8, 9, 10, 24, 25, and 26.

In one embodiment, the extracellular antigen-binding domain comprises a signal polypeptide. In some embodiments, the signal polypeptide comprises an amino acid sequence of SEQ ID NO: 11.

In one embodiment, the intracellular signaling domain comprises a polypeptide component selected from the group consisting of a TNF receptor superfamily member 9 (CD137) component, a T-cell surface glycoprotein CD3 zeta chain (CD3z) component, a cluster of differentiation (CD27) component, a cluster of differentiation superfamily member (such as, e.g., CD28 or inducible T-cell co-stimulator (ICOS)) component, and a combination thereof.

In one embodiment, the CD137 component comprises an amino acid sequence of SEQ ID NO: 12.

In one embodiment, the CD3z component comprises an amino acid sequence of SEQ ID NO: 13.

In one embodiment, the intracellular signaling domain comprises an amino acid sequence of SEQ ID NO: 14.

In one embodiment, the transmembrane domain comprises a CD8a transmembrane region (CD8a-TM) polypeptide. In some embodiments, the CD8a-TM polypeptide comprises an amino acid sequence of SEQ ID NO: 15.

In one embodiment, the CAR further comprises a hinge region linking the transmembrane domain to the extracellular antigen-binding domain. In some embodiments, the hinge region is a CD8a-hinge region. In some embodiments, CD8a-hinge region comprises an amino acid sequence of SEQ ID NO: 16.

In one embodiment, the extracellular antigen-binding domain comprises an amino acid sequence selected from the group consisting of SEQ ID NOS: 82, 81, 80, 79, 17, 18, 19, 20, 21, and 22.

In one embodiment, a CAR of the present disclosure comprises an amino acid sequence selected from the group consisting of SEQ ID NOS: 86, 85, 83, 84, 27, 28, 29, 30, 31 and 32.

In one aspect, the disclosure provides isolated lymphocytes expressing the CARs as described herein. In some embodiments, the lymphocyte is a T lymphocyte. In some embodiments, the T lymphocyte is a naïve T cell. In some embodiments, the T lymphocyte is a memory stem T cell. In some embodiments, the T lymphocyte is a central memory T cell. In some embodiments, the T lymphocyte is CD4+. In some embodiments, the T lymphocyte is CD8+. In some embodiments, the T lymphocyte is CD4+ and CD8+.

In one aspect, the disclosure provides isolated nucleic acid molecules encoding any of the CARs described herein. In some embodiments, the nucleic acid molecule comprises a nucleic acid sequence selected from the group consisting of SEQ ID NOS: 90, 89, 87, 88, 33, 34, 35, 36, 37, and 38. In some embodiments, the isolated nucleic acid molecule comprises a nucleotide sequence that is at least about 80%, 81%, 82%, 83%, 84%, 85%, 86%, 87%, 88%, 89%, 90%, 91%, 92%, 93%, 94%, 95%, 96%, 97%, 98%, or 99% identical to a nucleotide sequence of SEQ ID NOS: 90, 89, 87, 88, 33, 34, 35, 36, 37, or 38. In one embodiment, the present disclosure provides a vector comprising the nucleic acid molecule. In one embodiment, the present disclosure provides a cell expressing the nucleic acid molecule.

In one aspect, the present disclosure provides compositions, e.g., pharmaceutical compositions, comprising an effective amount of the lymphocyte expressing one or more of the CARs described and a pharmaceutically acceptable excipient.

In one aspect, the present disclosure provides a CAR according to the present disclosure for use in a method of therapy.

In one aspect, the present disclosure provides a lymphocyte according to the present disclosure for use in a method of therapy. In one aspect, the present disclosure provides a composition, e.g. a pharmaceutic composition, according to the present disclosure for use in a method of therapy.

In one aspect, the present disclosure provides a CAR according to the present disclosure for use in a method of treating cancer. In one aspect, the present disclosure provides a lymphocyte according to the present disclosure for use in a method of treating cancer. In one aspect, the present disclosure provides a composition, e.g. a pharmaceutic composition, according to the present disclosure for use in a method of treating cancer. In one embodiment, the cancer is selected from the group consisting of a bladder cancer, a metastatic bladder cancer, a esophageal cancer, a non-small-cell lung adenocarcinoma, a non-small cell lung squamous cell carcinoma, a prostate cancer, a urothelial carcinoma, a small cell lung cancer, an endometrial cancer, a cholangiocarcinoma, a hepatocellular carcinoma, sarcomas, solid tumors of squamous origin, a lung cancer, a gastric cancer, a colon cancer, a hepatocellular carcinoma, a renal cell carcinoma, a bladder urothelial carcinoma, a metastatic melanoma, a breast cancer, an ovarian cancer, a cervical cancer, a head and neck cancer, a pancreatic cancer, a glioma, a glioblastoma, a non-Hodgkin's lymphoma (NHL), an acute lymphocytic leukemia (ALL), a chronic lymphocytic leukemia (CLL), a chronic myelogenous leukemia (CIVIL), a smoldering multiple myeloma (SMM), a multiple myeloma (MM), an acute myeloid leukemia (AML), and combinations thereof. In one embodiment, the cancer being treated is multiple myeloma.

In one aspect, the present disclosure provides methods of treating a subject having cancer, the methods comprising administering a therapeutically effective amount of a lymphocyte expressing one or more of the CARs described to a subject in need thereof, whereby the lymphocyte induces killing of cancer cells in the subject. In one embodiment, the cancer is selected from the group consisting of a bladder cancer, a metastatic bladder cancer, a esophageal cancer, a non-small-cell lung adenocarcinoma, a non-small cell lung squamous cell carcinoma, a prostate cancer, a urothelial carcinoma, a small cell lung cancer, an endometrial cancer, a cholangiocarcinoma, a hepatocellular carcinoma, sarcomas, solid tumors of squamous origin, a lung cancer, a gastric cancer, a colon cancer, a hepatocellular carcinoma, a renal cell carcinoma, a bladder urothelial carcinoma, a metastatic melanoma, a breast cancer, an ovarian cancer, a cervical cancer, a head and neck cancer, a pancreatic cancer, a glioma, a glioblastoma, a non-Hodgkin's lymphoma (NHL), an acute lymphocytic leukemia (ALL), a chronic lymphocytic leukemia (CLL), a chronic myelogenous leukemia (CIVIL), a smoldering multiple myeloma (SMM), a multiple myeloma (MM), an acute myeloid leukemia (AML), and combinations thereof. In one embodiment, the cancer being treated in a subject is multiple myeloma.

In one aspect, a method of targeted killing of a cancer cell is disclosed, the method comprising contacting the cancer cell with a lymphocyte expressing one or more of the CARs described, whereby the lymphocyte induces killing of the cancer cell. In some embodiments, the cancer cell is selected from the group consisting of a lung cancer cell, a gastric cancer cell, a colon cancer cell, a hepatocellular carcinoma cell, a renal cell carcinoma cell, a bladder urothelial carcinoma cell, a metastatic melanoma cell, a breast cancer cell, an ovarian cancer cell, a cervical cancer cell, a head and neck cancer cell, a pancreatic cancer cell, a glioma cell, a glioblastoma cell, and a non-Hodgkin's lymphoma (NHL) cell, an acute lymphocytic leukemia (ALL) cell, a chronic lymphocytic leukemia (CLL) cell, a chronic myelogenous leukemia (CIVIL) cell, a smoldering multiple myeloma (SMM) cell, a multiple myeloma (MM) cell, an acute myeloid leukemia (AML) cell, and combinations thereof. In one embodiment, the cancer cell is a multiple myeloma cell.

BRIEF DESCRIPTION OF THE DRAWINGS

The foregoing will be apparent from the following more particular description of example embodiments, as illustrated in the accompanying drawings.

FIGS. 9A-9C show bar graphs, with the data collectively demonstrating that GPRC5D GC5B680-N68S-LH CAR was detected by flow cytometry in both CD4 and CD8 T cells, and that the CD4/CD8 proportion was not very different from an untransduced population. FIG. 9A shows the percentage of a mock (untransduced) cell population comprised by each of $CD8^+$ and $CD4^+$ cells. FIGS. 9B-9C each, respectively, show the percentage of CAR" cells (transduced cells not expressing GPRC5D CAR) comprised by each of CD8+ and $CD4^+$ cells and the percentage of $CAR^+$ cells (transduced cells expressing GPRC5D CAR) comprised by each of $CD8^+$ and $CD4^+$ cells. FIG. 9D illustrates a flow cytogram prepared from one donor illustrating a gating strategy for selection of different indicated memory populations in a CAR-T population using surface markers (CD45RA and CD62L). FIGS. 9E and 9F depict bar plots showing that GPRC5D GC5B680-N68S-LH was expressed mostly on $T_{N/SCM}$ and $T_{CM}$, which have been shown to have increased proliferative capacity, survival, and therapeutic efficacy. The values shown in FIGS. 9A-9C and 9E-9F represent the mean±SD with 6 healthy donors.

DETAILED DESCRIPTION

Figure 1:
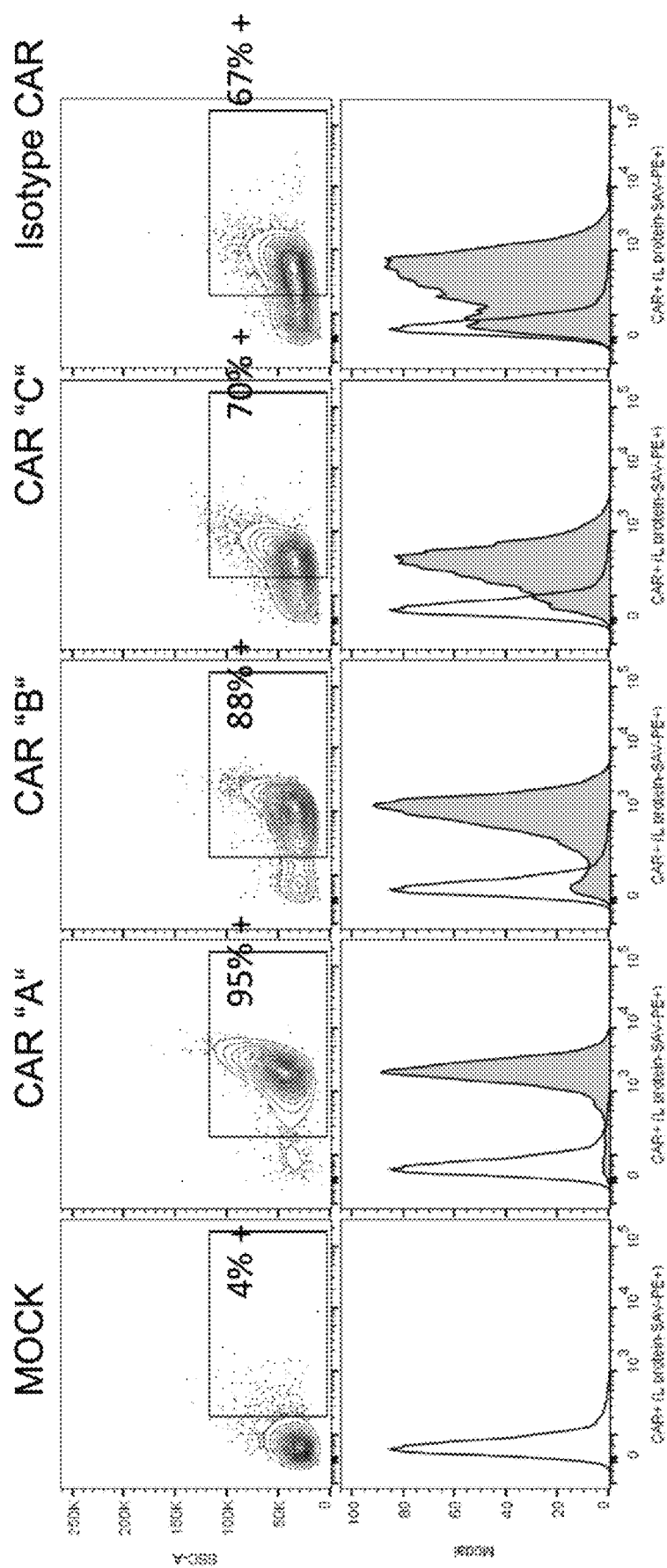
FIG. 1 shows flow cytometric analyses of primary human pan T cells electroporated with no mRNA (mock) or 10 μg of mRNA expressing either an α-GPRC5D scFv CAR or isotype control CAR. 24 hours post-electroporation, CAR surface expression was measured by flow cytometry following stain with biotinylated L-protein and streptavidin-conjugated PE. Open histogram is mock, filled grey histogram is CAR-T population.
Figure 1:
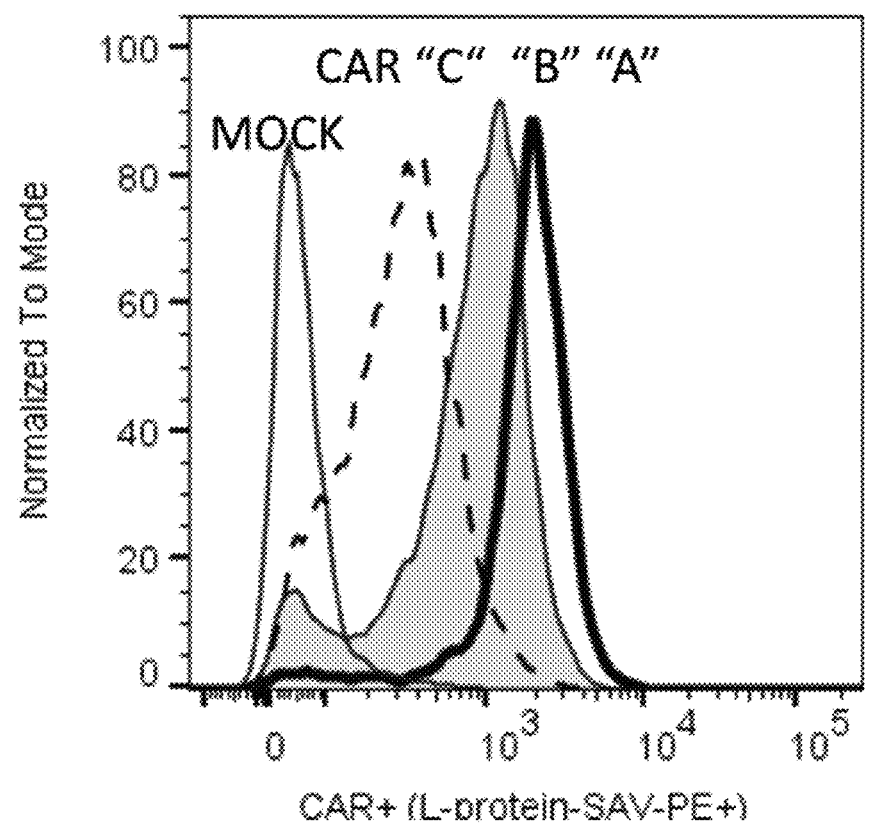

A description of example embodiments follows.

The present disclosure provides for chimeric antigen receptors (CARs) that target a G-protein coupled receptor G-protein coupled receptor family C group 5 member D (GPRC5D), cells comprising such CARs, and methods of treating cancer (e.g., hematologic malignancies and solid tumors) using the CARs described herein.

The CARs of the invention have antigen specificity for GPRC5D (e.g., a human GPRC5D polypeptide having the amino acid sequence of SEQ ID NO: 57, or fragments thereof). The phrases "have antigen specificity" and "elicit antigen-specific response" as used herein mean that the CAR can specifically bind to and immunologically recognize an antigen, such that binding of the CAR to the GPRC5D antigen elicits an immune response. Methods of testing the CARs for antigen specificity and for the ability to recognize target cells are known in the art.

The disclosure also provides related nucleic acids, recombinant expression vectors, host cells, populations of cells, antibodies, or antigen binding portions thereof, and pharmaceutical compositions relating to the CARs of the invention.

Several aspects of the invention are described below, with reference to examples for illustrative purposes only. It should be understood that numerous specific details, relationships, and methods are set forth to provide a full understanding of the invention. One having ordinary skill in the relevant art, however, will readily recognize that the invention can be practiced without one or more of the specific details or practiced with other methods, protocols, reagents, cell lines and animals. The present invention is not limited by the illustrated ordering of acts or events, as some acts may occur in different orders and/or concurrently with other acts or events. Furthermore, not all illustrated acts, steps or events are required to implement a methodology in accordance with the present invention. Many of the techniques and procedures described, or referenced herein, are well understood and commonly employed using conventional methodology by those skilled in the art.

Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. It will be further understood that terms, such as those defined in commonly-used dictionaries, should be interpreted as having a meaning that is consistent with their meaning in the context of the relevant art and/or as otherwise defined herein.

The terminology used herein is for the purpose of describing particular embodiments only and is not intended to be limiting. As used herein, the indefinite articles "a", "an" and "the" should be understood to include plural reference unless the context clearly indicates otherwise.

Chimeric Antigen Receptors

The present invention relates generally to the use of T cells genetically modified to stably express a desired chimeric antigen receptor. A chimeric antigen receptor (CAR) is an artificially constructed hybrid protein or polypeptide containing the antigen binding domains of an antibody (scFv) linked to T-cell signaling domains. Characteristics of CARs can include their ability to redirect T-cell specificity and reactivity toward a selected target in a non-MHC-restricted manner, exploiting the antigen-binding properties of monoclonal antibodies. The non-MHC-restricted antigen recognition gives T cells expressing CARs the ability to recognize antigens independent of antigen processing, thus bypassing a major mechanism of tumor evasion. Moreover, when expressed in T-cells, CARs advantageously do not dimerize with endogenous T cell receptor (TCR) alpha and beta chains.

The CARs described herein provide recombinant polypeptide constructs comprising at least an extracellular antigen binding domain, a transmembrane domain and an intracellular signaling domain (also referred to herein as "a cytoplasmic signaling domain") comprising a functional signaling domain derived from a stimulatory molecule as defined below. T cells expressing a CAR are referred to herein as CAR T cells, CAR-T cells or CAR modified T cells, and these terms are used interchangeably herein. The cell can be genetically modified to stably express an antibody binding domain on its surface, conferring novel antigen specificity that is MHC independent.

In some instances, the T cell is genetically modified to stably express a CAR that combines an antigen recognition domain of a specific antibody with an intracellular domain of the CD3-zeta chain or FcγRI protein into a single chimeric protein. In one embodiment, the stimulatory molecule is the zeta chain associated with the T cell receptor complex.

An "intracellular signaling domain," as the term is used herein, refers to an intracellular portion of a molecule. It is the functional portion of the protein which acts by transmitting information within the cell to regulate cellular activity via defined signaling pathways by generating second messengers or functioning as effectors by responding to such messengers. The intracellular signaling domain generates a signal that promotes an immune effector function of the CAR containing cell, e.g., a CAR-T cell. Examples of immune effector function, e.g., in a CAR-T cell, include cytolytic activity and helper activity, including the secretion of cytokines.

In an embodiment, the intracellular signaling domain can comprise a primary intracellular signaling domain. Example primary intracellular signaling domains include those derived from the molecules responsible for primary stimulation, or antigen dependent simulation. In an embodiment, the intracellular signaling domain can comprise a costimulatory intracellular domain. Example costimulatory intracellular signaling domains include those derived from molecules responsible for costimulatory signals, or antigen independent stimulation. For example, in the case of a CAR-T, a primary intracellular signaling domain can comprise a cytoplasmic sequence of a T cell receptor, and a costimulatory intracellular signaling domain can comprise cytoplasmic sequence from co-receptor or costimulatory molecule.

A primary intracellular signaling domain can comprise a signaling motif which is known as an immunoreceptor tyrosine-based activation motif or ITAM. Examples of ITAM containing primary cytoplasmic signaling sequences include, but are not limited to, those derived from CD3-zeta, FcR gamma, FcR beta, CD3 gamma, CD3 delta, CD3 epsilon, CD5, CD22, CD79a, CD79b, and CD66d DAP10 and DAP12.

The primary intracellular signaling domain can be derived from the signaling domains of for example CD3-zeta, CD3 epsilon, CD22, CD79a, CD66d, CD39 DAP10, DAP12, Fc epsilon receptor I gamma chain (FCER1G), FcR beta, CD3 delta, CD3 gamma, CD5, CD226, or CD79B.

The term "zeta" or alternatively "zeta chain", "CD3-zeta" or "TCR-zeta" is defined as the protein provided as GenBank Acc. No. BAG36664.1, or the equivalent residues from a non-human species, e.g., murine, rabbit, primate, mouse, rodent, monkey, ape and the like, and a "zeta stimulatory domain" or alternatively a "CD3-zeta stimulatory domain" or a "TCR-zeta stimulatory domain" is defined as the amino acid residues from the cytoplasmic domain of the zeta chain that are sufficient to functionally transmit an initial signal necessary for T cell activation. In one aspect, the cytoplasmic domain of zeta comprises residues 52 through 164 of GenBank Acc. No. BAG36664.1 or the equivalent residues from a non-human species, e.g., mouse, rodent, monkey, ape and the like, that are functional orthologs thereof.

In a preferred embodiment, the intracellular signaling domain comprises a CD3-zeta stimulatory domain. In one aspect, the "zeta stimulatory domain" or a "CD3-zeta stimulatory domain" is the sequence provided as SEQ ID NO: 13.

The term "costimulatory molecule" refers to the cognate binding partner on a T cell that specifically binds with a costimulatory ligand, thereby mediating a costimulatory response by the T cell, such as, but not limited to, proliferation. Costimulatory molecules are cell surface molecules other than antigen receptors or their ligands that are required for an efficient immune response. Costimulatory molecules include, but are not limited to an MHC class 1 molecule, BTLA and a Toll ligand receptor, as well as OX40, CD2, CD27, CD28, CDS, ICAM-1, LFA-1 (CD11a/CD18), 4-1BB (CD137), CD30, CD40, CD54 (ICAM), CD83, CD134 (OX40), CD150 (SLAMF1), CD152 (CTLA4), CD223 (LAG3), CD270 (HVEM), CD278 (ICOS), DAP10, LAT, NKD2C SLP76, TRIM, BTLA, GITR, CD226, HVEM, and ZAP70.

A costimulatory intracellular signaling domain can be the intracellular portion of a costimulatory molecule. A costimulatory molecule can be represented in the following protein families: TNF receptor proteins, Immunoglobulin-like proteins, cytokine receptors, integrins, signaling lymphocytic activation molecules (SLAM proteins), and activating NK cell receptors. Examples of such molecules include CD27, CD28, 4-1BB (CD137), OX40, GITR, CD30, CD40, ICOS, BAFFR, HVEM, lymphocyte function-associated antigen-1 (LFA-1), CD2, CD7, LIGHT, NKG2C, SLAMF7, NKp80, CD160, B7-H3, and a ligand that specifically binds with CD83, and the like.

The intracellular signaling domain can comprise the entire intracellular portion, or the entire native intracellular signaling domain, of the molecule from which it is derived, or a functional fragment thereof.

The term "4-1BB" refers to a member of the TNFR superfamily with an amino acid sequence provided as GenBank Acc. No. AAA62478.2, or the equivalent residues from a non-human species, e.g., mouse, rodent, monkey, ape and the like; and a "4-1BB co-stimulatory domain" is defined as amino acid residues 214-255 of GenBank accession no. AAA62478.2, or the equivalent residues from a non-human species, e.g., mouse, rodent, monkey, ape and the like. In one aspect, the "4-1BB costimulatory domain" is the sequence provided as SEQ ID NO: 12 or the equivalent residues from a non-human species, e.g., mouse, rodent, monkey, ape and the like.

In some embodiments, the cytoplasmic signaling domain further comprises one or more functional signaling domains derived from at least one costimulatory molecule as defined herein. In one embodiment, the costimulatory molecule is chosen from 4-1BB (i.e., CD137), CD27, CD3-zeta and/or CD28. CD28 is a T cell marker important in T cell co-stimulation. CD27 is a member of the tumor necrosis factor receptor superfamily and acts as a co-stimulatory immune checkpoint molecule. 4-1BB transmits a potent costimulatory signal to T cells, promoting differentiation and enhancing long-term survival of T lymphocytes. CD3-zeta associates with TCRs to produce a signal and contains immunoreceptor tyrosine-based activation motifs (ITAMs).

In a preferred embodiment, the intracellular signaling domain comprises a costimulatory intracellular signaling domain, wherein the costimulatory intracellular signaling domain is a 4-1BB costimulatory domain. In a preferred embodiment the 4-1BB co-stimulatory domain is the sequence provided as SEQ ID NO: 12.

In one embodiment, a transmembrane domain that naturally is associated with one of the domains in the CAR is used. In another embodiment, the transmembrane domain can be selected or modified by amino acid substitution to avoid binding of such domains to the transmembrane domains of the same or different surface membrane proteins to minimize interactions with other members of the receptor complex. In one example embodiment, the transmembrane domain is the CD8a transmembrane domain.

In one embodiment, the CAR comprises a hinge domain comprising a CD8a hinge domain.

In one embodiment, the CAR comprises a CD8a hinge domain and a CD8a transmembrane domain.

In one embodiment, the CAR comprises a hinge domain comprising a CD8a hinge domain and an intracellular signaling domain comprising CD28, 4-1BB, and CD3-zeta.

CARs described herein provide recombinant polypeptide constructs comprising at least an extracellular antigen binding domain, a transmembrane domain and an intracellular signaling domain (also referred to herein as "a cytoplasmic signaling domain") comprising, e.g., a functional signaling domain derived from a stimulatory molecule as defined below In one embodiment, the CAR comprises a chimeric fusion protein comprising an extracellular antigen recognition domain, a transmembrane domain and an intracellular signaling domain comprising a functional signaling domain derived from a stimulatory molecule. In one embodiment, the CAR comprises a chimeric fusion protein comprising an extracellular antigen recognition domain, a transmembrane domain and an intracellular signaling domain comprising a functional signaling domain derived from a co-stimulatory molecule and a functional signaling domain derived from a stimulatory molecule. In one embodiment, the CAR comprises a chimeric fusion protein comprising an extracellular antigen recognition domain, a transmembrane domain and an intracellular signaling domain comprising at least two functional signaling domains derived from one or more co-stimulatory molecule(s) and a functional signaling domain derived from a stimulatory molecule.

The CARs of the invention can be designed to comprise the CD28 and/or 4-1BB signaling domain by itself or be combined with any other desired cytoplasmic domain(s) useful in the context of the CARs of the invention. In one embodiment, the cytoplasmic domain of the CAR can further comprise the signaling domain of CD3-zeta. For example, the cytoplasmic domain of the CAR can include but is not limited to CD3-zeta, 4-1BB and CD28 signaling modules and combinations thereof.

In a preferred embodiment, the CAR comprises a CD8a hinge domain, a CD8a transmembrane domain, and an intracellular signaling domain comprising the signaling domain of CD3-zeta.

In a preferred embodiment, the CAR comprises a CD8a hinge domain, a CD8a transmembrane domain, and an intracellular signaling domain comprising the signaling domain of CD3-zeta and a 4-1BB costimulatory domain.

Accordingly, the invention provides CAR T cells and methods of their use for adoptive therapy.

The disclosure further provides variants, e.g., functional variants, of the CARs, nucleic acids, polypeptides, and proteins described herein. "Variant" refers to a polypeptide or a polynucleotide that differs from a reference polypeptide or a reference polynucleotide by one or more modifications for example, substitutions, insertions or deletions. The term "functional variant" as used herein refers to a CAR, polypeptide, or protein having substantial or significant sequence identity or similarity to a parent CAR, polypeptide, or protein, which functional variant retains the biological activity of the CAR, polypeptide, or protein for which it is a variant. Functional variants encompass, e.g., those variants of the CAR, polypeptide, or protein described herein (the parent CAR, polypeptide, or protein) that retain the ability to recognize target cells to a similar extent, the same extent, or to a higher extent, as the parent CAR, polypeptide, or protein. In reference to the parent CAR, polypeptide, or protein, the functional variant can, for example, be at least about 30%, about 40%, about 50%, about 60%, about 75%, about 80%, about 85%, about 90%, about 91%, about 92%, about 93%, about 94%, about 95%, about 96%, about 97%, about 98%, about 99% or more identical in amino acid sequence to the parent CAR, polypeptide, or protein.

Herein, the structure of polypeptides is in places defined on the basis of % sequence identity with a recited reference sequence (with a given SEQ ID NO). In this context, % sequence identity between two amino acid sequences may be determined by comparing these two sequences aligned in an optimum manner and in which the amino acid sequence to be compared can comprise additions or deletions with respect to the reference sequence for an optimum alignment between these two sequences. The percentage of identity is calculated by determining the number of identical positions for which the amino acid residue is identical between the two sequences, by dividing this number of identical positions by the total number of positions in the comparison window and by multiplying the result obtained by 100 in order to obtain the percentage of identity between these two sequences. Typically, the comparison window with correspond to the full length of the sequence being compared. For example, it is possible to use the BLAST program, "BLAST 2 sequences" (Tatusova et al, "Blast 2 sequences—a new tool for comparing protein and nucleotide sequences", FEMS Microbiol Lett. 174:247-250) available on the site http://www.ncbi.nlm.nih.gov/gorf/b12.html, the parameters used being those given by default (in particular for the parameters "open gap penalty": 5, and "extension gap penalty": 2; the matrix chosen being, for example, the matrix "BLOSUM 62" proposed by the program), the percentage of identity between the two sequences to be compared being calculated directly by the program. Determining sequence identity of a query sequence to a reference sequence is within the ability of the skilled person and can be performed using commercially available analysis software such as BLAST.

A functional variant can, for example, comprise the amino acid sequence of the parent CAR, polypeptide, or protein with at least one conservative amino acid substitution. In another embodiment, the functional variants can comprise the amino acid sequence of the parent CAR, polypeptide, or protein with at least one non-conservative amino acid substitution. In this case, the non-conservative amino acid substitution may not interfere with or inhibit the biological activity of the functional variant. The non-conservative amino acid substitution may enhance the biological activity of the functional variant such that the biological activity of the functional variant is increased as compared to the parent CAR, polypeptide, or protein.

Amino acid substitutions of the inventive CARs may be conservative amino acid substitutions. Conservative amino acid substitutions are known in the art, and include amino acid substitutions in which one amino acid having certain physical and/or chemical properties is exchanged for another amino acid that has the same or similar chemical or physical properties. For example, the conservative amino acid substitution can be an acidic amino acid substituted for another acidic amino acid (e.g., Asp or Glu), an amino acid with a nonpolar side chain substituted for another amino acid with a nonpolar side chain (e.g., Ala, Gly, Val, Ile, Leu, Met, Phe, Pro, Trp, Val, etc.), a basic amino acid substituted for another basic amino acid (Lys, Arg, etc.), an amino acid with a polar side chain substituted for another amino acid with a polar side chain (Asn, Cys, Gln, Ser, Thr, Tyr, etc.), etc.

The CAR, polypeptide, or protein can consist essentially of the specified amino acid sequence or sequences described herein, such that other components e.g., other amino acids, do not materially change the biological activity of the functional variant.

The CARs, polypeptides, and proteins of embodiments of the disclosure (including functional portions and functional variants) can be of any length, i.e., can comprise any number of amino acids, provided that the CARs, polypeptides, or proteins (or functional portions or functional variants thereof) retain their biological activity, e.g., the ability to specifically bind to an antigen, detect diseased cells (e.g., cancer cells) in a host, or treat or prevent disease in a host, etc. For example, the polypeptide can be about 50 to about 5000 amino acids long, such as about 50, about 70, about 75, about 100, about 125, about 150, about 175, about 200, about 225, about 250, about 275, about 300, about 325, about 350, about 375, about 400, about 425, about 450, about 475, about 500, about 525, about 550, about 575, about 600, about 625, about 650, about 675, about 700, about 725, about 750, about 775, about 800, about 825, about 850, about 875, about 900, about 925, about 950, about 975, about 1000 or more amino acids in length. The polypeptides of the invention also include oligopeptides.

The CARs, polypeptides, and proteins of embodiments of the invention (including functional portions and functional variants of the invention) can comprise synthetic amino acids in place of one or more naturally-occurring amino acids. Such synthetic amino acids are known in the art, and include, for example, aminocyclohexane carboxylic acid, norleucine, α-amino n-decanoic acid, homoserine, S-acetylaminomethyl-cysteine, trans-3- and trans-4-hydroxyproline, 4-aminophenylalanine, 4-nitrophenylalanine, α-(2-amino-2-norbornane)-carboxylic acid, α,γ-diaminobutyric acid, α,β-diaminopropionic acid, homophenylalanine, 4-chlorophenylalanine, 4-carboxyphenylalanine, β-phenylserine β-hydroxyphenylalanine, phenylglycine, α-naphthylalanine, cyclohexylalanine, cyclohexylglycine, N'-benzyl-N'-methyl-lysine, N',N'-dibenzyl-lysine, 6-hydroxylysine, ornithine, α-aminocyclopentane carboxylic acid, α-aminocyclohexane carboxylic acid, α-aminocycloheptane carboxylic acid, indoline-2-carboxylic acid, 1,2,3,4-tetrahydroisoquinoline-3-carboxylic acid, aminomalonic acid, aminomalonic acid monoamide, and α-tert-butylglycine.

The CARs, polypeptides, and proteins of embodiments of the invention (including functional portions and functional variants) can be subject to post-translational modifications. They can be glycosylated, esterified, N-acylated, amidated, carboxylated, phosphorylated, esterified, cyclized via, e.g., a disulfide bridge, or converted into an acid addition salt. In some embodiments, they are dimerized or polymerized, or conjugated.

The CARs, polypeptides, and/or proteins of embodiments of the invention (including functional portions and functional variants thereof) can be obtained by methods known in the art. Suitable methods of de novo synthesizing polypeptides and proteins are described in references, such as Chan et al., *Fmoc Solid Phase Peptide Synthesis*, Oxford University Press, Oxford, United Kingdom, 2000; *Peptide and Protein Drug Analysis*, ed. Reid, R., Marcel Dekker, Inc., 2000; and Epitope Mapping, ed. Westwood et al., Oxford University Press, Oxford, United Kingdom, 2001. Also, polypeptides and proteins can be recombinantly produced using the nucleic acids described herein using standard recombinant methods. See, for instance, Sambrook et al., *Molecular Cloning: A Laboratory Manual*, 3rd ed., Cold Spring Harbor Press, Cold Spring Harbor, N.Y. 2001; and Ausubel et al., *Current Protocols in Molecular Biology*, Greene Publishing Associates and John Wiley & Sons, N Y, 1994. Further, some of the CARs, polypeptides, and proteins of the invention (including functional portions and functional variants thereof) can be isolated and/or purified from a source, such as a plant, a bacterium, an insect, a mammal, etc. Methods of isolation and purification are known in the art. Alternatively, the CARs, polypeptides, and/or proteins described herein (including functional portions and functional variants thereof) can be commercially synthesized. In this respect, the CARs, polypeptides, and proteins can be synthetic, recombinant, isolated, and/or purified.

Examples of modified nucleotides that can be used to generate the recombinant nucleic acids utilized to produce the polypeptides described herein include, but are not limited to, 5-fluorouracil, 5-bromouracil, 5-chlorouracil, 5-iodouracil, hypoxanthine, xanthine, 4-acetylcytosine, 5-(carboxyhydroxymethyl) uracil, carboxymethylaminomethyl-2-thiouridine, 5-carboxymethylaminomethyluracil, dihydrouracil, $N^6$-substituted adenine, 7-methylguanine, 5-methylaminomethyluracil, 5-methoxyaminomethyl-2-thiouracil, beta-D-mannosylqueosine, 5"-methoxycarboxymethyluracil, 5-methoxyuracil, 2-methylthio-$N^6$-isopentenyladenine, uracil-5-oxyacetic acid (v), wybutoxosine, pseudouracil, queosine, beta-D-galactosylqueosine, inosine, $N^6$-isopentenyladenine, 1-methylguanine, 1-methylinosine, 2,2-dimethylguanine, 2-methyladenine, 2-methylguanine, 3-methylcytosine, 5-methylcytosine, 2-thiocytosine, 5-methyl-2-thiouracil, 2-thiouracil, 4-thiouracil, 5-methyluracil, uracil-5-oxyacetic acid methylester, 3-(3-amino-3-N-2-carboxypropyl) uracil, and 2,6-diaminopurine.

The nucleic acid can comprise any isolated or purified nucleotide sequence which encodes any of the CARs, polypeptides, or proteins, or functional portions or functional variants thereof. Alternatively, the nucleotide sequence can comprise a nucleotide sequence which is degenerate to any of the sequences or a combination of degenerate sequences.

Some embodiments of the invention also provide an isolated or purified nucleic acid comprising a nucleotide sequence which is complementary to the nucleotide sequence of any of the nucleic acids described herein or a nucleotide sequence which hybridizes under stringent conditions to the nucleotide sequence of any of the nucleic acids described herein.

The nucleotide sequence which hybridizes under stringent conditions may hybridize under high stringency conditions. By "high stringency conditions" is meant that the nucleotide sequence specifically hybridizes to a target sequence (the nucleotide sequence of any of the nucleic acids described herein) in an amount that is detectably stronger than non-specific hybridization. High stringency conditions include conditions which would distinguish a polynucleotide with an exact complementary sequence, or one containing only a few scattered mismatches from a random sequence that happened to have a few small regions (e.g., 3-12 bases) that matched the nucleotide sequence. Such small regions of complementarity are more easily melted than a full-length complement of 14-17 or more bases, and high stringency hybridization makes them easily distinguishable. Relatively high stringency conditions would include, for example, low salt and/or high temperature conditions, such as provided by about 0.02-0.1 M NaCl or the equivalent, at temperatures of about 50-70° C. Such high stringency conditions tolerate little, if any, mismatch between the nucleotide sequence and the template or target strand, and are particularly suitable for detecting expression of any of the CARs described herein. It is generally appreciated that conditions can be rendered more stringent by the addition of increasing amounts of formamide.

In an embodiment, the nucleic acids of the invention can be incorporated into a recombinant expression vector. The present disclosure provides recombinant expression vectors comprising any of the nucleic acids of the invention. As used herein, the term "recombinant expression vector" means a genetically-modified oligonucleotide or polynucleotide construct that permits the expression of an mRNA, protein, polypeptide, or peptide by a host cell, when the construct comprises a nucleotide sequence encoding the mRNA, protein, polypeptide, or peptide, and the vector is contacted with the cell under conditions sufficient to have the mRNA, protein, polypeptide, or peptide expressed within the cell. The vectors described herein are not naturally-occurring as a whole; however, parts of the vectors can be naturally-occurring. The described recombinant expression vectors can comprise any type of nucleotides, including, but not limited to DNA and RNA, which can be single-stranded or double-stranded, synthesized or obtained in part from natural sources, and which can contain natural, non-natural or altered nucleotides. The recombinant expression vectors can comprise naturally-occurring or non-naturally-occurring internucleotide linkages, or both types of linkages. The non-naturally occurring or altered nucleotides or internucleotide linkages do not hinder the transcription or replication of the vector.

In an embodiment, the recombinant expression vector of the invention can be any suitable recombinant expression vector, and can be used to transform or transfect any suitable host. Suitable vectors include those designed for propagation and expansion or for expression or both, such as plasmids and viruses. The vector can be selected from the group consisting of the pUC series (Fermentas Life Sciences, Glen Burnie, Md.), the pBluescript series (Stratagene, LaJolla, Calif.), the pET series (Novagen, Madison, Wis.), the pGEX series (Pharmacia Biotech, Uppsala, Sweden), and the pEX series (Clontech, Palo Alto, Calif.). Bacteriophage vectors, such as λGT10, λGT11, λEMBL4, and λNM1149, λZapII (Stratagene) can be used. Examples of plant expression vectors include pBI01, pBI01.2, pBI121, pBI101.3, and pBIN19 (Clontech). Examples of animal expression vectors include pEUK-Cl, pMAM, and pMAM-neo (Clontech). The recombinant expression vector may be a viral vector, e.g., a retroviral vector, e.g., a gamma retroviral vector.

In an embodiment, the recombinant expression vectors of the invention are prepared using standard recombinant DNA techniques described in, for example, Sambrook et al., supra, and Ausubel et al., supra. Constructs of expression vectors, which are circular or linear, can be prepared to contain a replication system functional in a prokaryotic or eukaryotic host cell. Replication systems can be derived, e.g., from ColEl, SV40, 2μ plasmid, λ, bovine papilloma virus, and the like.

The recombinant expression vector may comprise regulatory sequences, such as transcription and translation initiation and termination codons, which are specific to the type of host (e.g., bacterium, plant, fungus, or animal) into which the vector is to be introduced, as appropriate, and taking into consideration whether the vector is DNA- or RNA-based.

The recombinant expression vector can include one or more marker genes, which allow for selection of transformed or transfected hosts. Marker genes include biocide resistance, e.g., resistance to antibiotics, heavy metals, etc., complementation in an auxotrophic host to provide prototrophy, and the like. Suitable marker genes for the described expression vectors include, for instance, neomycin/G418 resistance genes, histidinol×resistance genes, histidinol resistance genes, tetracycline resistance genes, and ampicillin resistance genes.

The recombinant expression vector can comprise a native or normative promoter operably linked to the nucleotide sequence encoding the CAR, polypeptide, or protein (including functional portions and functional variants thereof), or to the nucleotide sequence which is complementary to or which hybridizes to the nucleotide sequence encoding the CAR, polypeptide, or protein. The selection of promoters, e.g., strong, weak, tissue-specific, inducible and developmental-specific, is within the ordinary skill of the artisan. Similarly, the combining of a nucleotide sequence with a promoter is also within the skill of the artisan. The promoter can be a non-viral promoter or a viral promoter, e.g., a cytomegalovirus (CMV) promoter, an RSV promoter, an SV40 promoter, or a promoter found in the long-terminal repeat of the murine stem cell virus.

The recombinant expression vectors can be designed for either transient expression, for stable expression, or for both. Also, the recombinant expression vectors can be made for constitutive expression or for inducible expression.

Further, the recombinant expression vectors can be made to include a suicide gene. As used herein, the term "suicide gene" refers to a gene that causes the cell expressing the suicide gene to die. The suicide gene can be a gene that confers sensitivity to an agent, e.g., a drug, upon the cell in which the gene is expressed, and causes the cell to die when the cell is contacted with or exposed to the agent. Suicide genes are known in the art and include, for example, the Herpes Simplex Virus (HSV) thymidine kinase (TK) gene, cytosine daminase, purine nucleoside phosphorylase, and nitroreductase.

Included in the scope of the invention are conjugates, e.g., bioconjugates, comprising any of the CARs, polypeptides, or proteins (including any of the functional portions or variants thereof), host cells, nucleic acids, recombinant expression vectors, populations of host cells, or antibodies, or antigen binding portions thereof. Conjugates, as well as methods of synthesizing conjugates in general, are known in the art (See, for instance, Hudecz, F., *Methods Mol. Biol.* 298: 209-223 (2005) and Kirin et al., Inorg Chem. 44(15): 5405-5415 (2005)).

An embodiment of the invention further provides an antibody, or antigen binding portion thereof, which binds, e.g., specifically binds, to an epitope of the CARs of the invention.

The antibody can be any type of immunoglobulin that is known in the art. Immunoglobulins may be assigned to five major classes, IgA, IgD, IgE, IgG and IgM. IgA and IgG are further classified as the isotypes IgA1, IgA2, IgG1, IgG2, IgG3 and IgG4. Antibody light chains of vertebrate species can be assigned to one of two types, kappa (κ) and lambda (λ), based on the amino acid sequences of their constant domains. The antibody can be of any class or isotype.

The antibodies include immunoglobulin molecules including monoclonal antibodies including murine, human, humanized and chimeric monoclonal antibodies, polyclonal, antigen-binding fragments, bispecific or multispecific antibodies, monomeric, dimeric, tetrameric or multimeric antibodies, single chain antibodies, domain antibodies and any other modified configuration of the immunoglobulin molecule that comprises an antigen binding site of the required specificity. The antibody can be a naturally-occurring antibody, e.g., an antibody isolated and/or purified from a mammal, e.g., a murine, primate, mouse, rabbit, goat, horse, chicken, hamster, human, etc. Alternatively, the antibody can be an engineered (e.g., genetically-engineered) antibody.

"Human antibody" refers to an antibody that is optimized to have minimal immune response when administered to a human subject. Variable regions of human antibody are derived from human immunoglobulin sequences. If human antibody contains a constant region or a portion of the constant region, the constant region is also derived from human immunoglobulin sequences. Human antibody comprises heavy and light chain variable regions that are "derived from" sequences of human origin if the variable regions of the human antibody are obtained from a system that uses human germline immunoglobulin or rearranged immunoglobulin genes. Such exemplary systems are human immunoglobulin gene libraries displayed on phage, and transgenic non-human animals such as mice or rats carrying human immunoglobulin loci. "Human antibody" typically contains amino acid differences when compared to the immunoglobulins expressed in humans due to differences between the systems used to obtain the human antibody and human immunoglobulin loci, introduction of somatic mutations or intentional introduction of substitutions into the frameworks or CDRs, or both. Typically, "human antibody" is at least about 80%, 81%, 82%, 83%, 84%, 85%, 86%, 87%, 88%, 89%, 90%, 91%, 92%, 93%, 94%, 95%, 96%, 97%, 98% or 99% identical in amino acid sequence to an amino acid sequence encoded by human germline immunoglobulin or rearranged immunoglobulin genes. In some cases, "human antibody" may contain consensus framework sequences derived from human framework sequence analyses, for example as described in Knappik et al., (2000) J Mol Biol 296:57-86, or a synthetic HCDR3 incorporated into human immunoglobulin gene libraries displayed on phage, for example as described in Shi et al., (2010) J Mol Biol 397:385-96, and in Int. Patent Publ. No. WO2009/085462. Antibodies in which at least one CDR is derived from a non-human species are not included in the definition of "human antibody".

"Humanized antibody" refers to an antibody in which at least one CDR is derived from non-human species and at least one framework is derived from human immunoglobulin sequences. Humanized antibody may include substitutions in the frameworks so that the frameworks may not be exact copies of expressed human immunoglobulin or human immunoglobulin germline gene sequences.

Typically, humanized antibodies have antigen binding sites derived from non-human species and the variable region frameworks are derived from human immunoglobulin sequences. Human antibodies have heavy and light chain variable regions in which both the framework and the antigen binding site are derived from sequences of human origin.

Also, the antibody can have any level of affinity or avidity for the functional portion of the CAR. In some embodiments, the antibody may bind the GPRC5D antigen with a range of affinities ($K_D$). In one embodiment according to the invention, and in some embodiments of each and every one of the numbered embodiments listed below, the antibody binds to the GPRC5D antigen with high affinity, for example, with a $K_D$ equal to or less than about $10^{-7}$M, such as but not limited to, 1-9.9 (or any range or value therein, such as 1, 2, 3, 4, 5, 6, 7, 8, or 9)$\times 10^{-8}$M, $10^{-9}$M, $10^{-10}$ M, $10^{-11}$ M, $10^{-12}$ M, $10^{-13}$ M, $10^{-14}$ M, $10^{-15}$M or any range or value therein, as determined by surface plasmon resonance or the Kinexa method, as practiced by those of skill in the art. One example affinity is equal to or less than $1 \times 10^{-8}$M. Another example affinity is equal to or less than $1 \times 10^{-9}$M.

Methods of testing antibodies for the ability to bind to any functional portion of the CARs are known in the art and include any antibody-antigen binding assay, such as, for example, radioimmunoassay (RIA), Western blot, enzyme-linked immunosorbent assay (ELISA), immunoprecipitation, and competitive inhibition assays.

Suitable methods of making antibodies are known in the art. For instance, standard hybridoma methods are described in, e.g., Köhler and Milstein, *Eur. J. Immunol.*, 5, 511-519 (1976), Harlow and Lane (eds.), *Antibodies: A Laboratory*

Manual, CSH Press (1988), and C. A. Janeway et al. (eds.), *Immunobiology*, 5th Ed., Garland Publishing, New York, N.Y. (2001)). Alternatively, other methods, such as EBV-hybridoma methods (Haskard and Archer, J. *Immunol. Methods*, 74(2), 361-67 (1984), and Roder et al., *Methods Enzymol.*, 121, 140-67 (1986)), and bacteriophage vector expression systems (see, e.g., Huse et al., *Science*, 246, 1275-81 (1989)) are known in the art. Further, methods of producing antibodies in non-human animals are described in, e.g., U.S. Pat. Nos. 5,545,806, 5,569,825, and 5,714,352, and U.S. Patent Application Publication No. 2002/0197266 A1).

Phage display can also be used to generate an antibody. In this regard, phage libraries encoding antigen-binding variable (V) domains of antibodies can be generated using standard molecular biology and recombinant DNA techniques (see, e.g., Sambrook et al., supra, and Ausubel et al., supra). Phage encoding a variable region with the desired specificity are selected for specific binding to the desired antigen (i.e., GPRC5D), and a complete or partial antibody is reconstituted comprising the selected variable domain. Nucleic acid sequences encoding the reconstituted antibody are introduced into a suitable cell line, such as a myeloma cell used for hybridoma production, such that antibodies having the characteristics of monoclonal antibodies are secreted by the cell (see, e.g., Janeway et al., supra, Huse et al., supra, and U.S. Pat. No. 6,265,150).

Antibodies can be produced by transgenic mice that are transgenic for specific heavy and light chain immunoglobulin genes. Such methods are known in the art and described in, for example U.S. Pat. Nos. 5,545,806 and 5,569,825, and Janeway et al., supra.

Methods for generating humanized antibodies are known in the art and are described in, for example, Janeway et al., supra, U.S. Pat. Nos. 5,225,539, 5,585,089 and 5,693,761, European Patent No. 0239400 B1, and United Kingdom Patent No. 2188638. Humanized antibodies can also be generated using the antibody resurfacing technology described in U.S. Pat. No. 5,639,641 and Pedersen et al., J. Mol. Biol., 235, 959-973 (1994).

Antibodies, as utilized herein, can be multiple or single chain, or intact immunoglobulins, and may be derived from natural sources or from recombinant sources. Antibodies can be tetramers of immunoglobulin molecules.

In some embodiments, the antibody is a bispecific antibody. "Bispecific" refers to a molecule (such as an antibody) that specifically binds two distinct antigens or two distinct epitopes within the same antigen. The bispecific molecule may have cross-reactivity to other related antigens, for example to the same antigen from other species (homologs), such as human or monkey, for example *Macaca cynomolgus* (cynomolgus, cyno) or Pan troglodytes, or may bind an epitope that is shared between two or more distinct antigens. The VL and/or the VH regions of existing antibodies or the VL and VH regions identified de novo as described herein may be engineered into bispecific full-length antibodies. Such bispecific antibodies may be made by modulating the CH3 interactions in antibody Fc to form bispecific antibodies using technologies such as those described in U.S. Pat. No. 7,695,936; Int. Pat. Publ. No. WO04/111233; U.S. Pat. Publ. No. U52010/0015133; U.S. Pat. Publ. No. US2007/0287170; Int. Pat. Publ. No. WO2008/119353; U.S. Pat. Publ. No. US2009/0182127; U.S. Pat. Publ. No. US2010/0286374; U.S. Pat. Publ. No. US2011/0123532; Int. Pat. Publ. No. WO2011/131746; Int. Pat. Publ. No. WO2011/143545; or U.S. Pat. Publ. No. US2012/0149876. For example, bispecific antibodies of the invention may be generated in vitro in a cell-free environment by introducing asymmetrical mutations in the CH3 regions of two mono-specific homodimeric antibodies and forming the bispecific heterodimeric antibody from two parent monospecific homodimeric antibodies in reducing conditions to allow disulfide bond isomerization according to methods described in Intl. Pat. Publ. No. WO2011/131746. In the methods, the first monospecific bivalent antibody and the second monospecific bivalent antibody are engineered to have certain substitutions at the CH3 domain that promote heterodimer stability; the antibodies are incubated together under reducing conditions sufficient to allow the cysteines in the hinge region to undergo disulfide bond isomerization; thereby generating the bispecific antibody by Fab arm exchange. The incubation conditions may optimally be restored to non-reducing. Example reducing agents that may be used are 2-mercaptoethylamine (2-MEA), dithiothreitol (DTT), dithioerythritol (DTE), glutathione, tris(2-carboxyethyl)phosphine (TCEP), L-cysteine and beta-mercaptoethanol, preferably a reducing agent selected from the group consisting of: 2-mercaptoethylamine, dithiothreitol and tris(2-carboxyethyl)phosphine. For example, incubation for at least 90 min at a temperature of at least 20° C. in the presence of at least 25 mM 2-MEA or in the presence of at least 0.5 mM dithiothreitol at a pH of from 5-8, for example at pH of 7.0 or at pH of 7.4 may be used.

The term "antibody fragment" refers to at least one portion of an intact antibody, or recombinant variants thereof, that retains the antigen binding properties of the parental full length antibody. It refers to, for example, the antigen binding domain, e.g., an antigenic determining variable region of an intact antibody, that is sufficient to confer recognition and binding, e.g., specific binding of the antibody fragment to a target, such as an antigen. "Antigen-binding fragment" refers to a portion of an immunoglobulin molecule Examples of antibody fragments include, but are not limited to, Fab, Fab', F(ab')$_2$, and Fv fragments, single chain antibodies (scFv), linear antibodies, single domain antibodies such as sdAb (either VL or VH), camelid VHH domains, and multi-specific antibodies formed from antibody fragments.

The term "scFv" refers to a protein comprising at least one antibody fragment comprising a variable region of a light chain and at least one antibody fragment comprising a variable region of a heavy chain. In some embodiments, the light and heavy chain variable regions are contiguously linked via a short flexible polypeptide linker, and capable of being expressed as a single chain polypeptide, and wherein the scFv retains the specificity of the intact antibody from which it is derived. Unless specified, as used herein an scFv may have the VL and VH variable regions in either order, e.g., with respect to the N-terminal and C-terminal ends of the polypeptide, the scFv may comprise VL-linker-VH or may comprise VH-linker-VL.

An embodiment of the invention also provides antigen binding portions of any of the antibodies described herein. The antigen binding portion can be any portion that has at least one antigen binding site, such as Fab, F(ab')$_2$, dsFv, sFv, diabodies, and triabodies.

In some embodiments, antigen-binding fragments are heavy chain complementarity determining regions (HCDR) 1, 2 and/or 3, light chain complementarity determining regions (LCDR) 1, 2 and/or 3, a heavy chain variable region (VH), or a light chain variable region (VL), Fab, F(ab')$_2$, Fd and Fv fragments and domain antibodies (dAb) comprising (e.g., consisting of) either one VH domain or one VL domain. VH and VL domains may be linked together via a linker, e.g., a synthetic linker.

"Complementarity determining regions (CDR)" are antigen binding sites in an antibody. CDRs may be defined using various terms: (i) Complementarity Determining Regions (CDRs), three in the VH (HCDR1, HCDR2, HCDR3) and three in the VL (LCDR1, LCDR2, LCDR3) are based on sequence variability (Wu and Kabat, J Exp Med 132:211-50, 1970; Kabat et al., Sequences of Proteins of Immunological Interest, 5th Ed. Public Health Service, National Institutes of Health, Bethesda, Md., 1991). (ii) "Hypervariable regions", "HVR", or "HV", three in the VH (H1, H2, H3) and three in the VL (L1, L2, L3) refer to the regions of an antibody variable domains which are hypervariable in structure as defined by Chothia and Lesk (Chothia and Lesk, Mol Biol 196:901-17, 1987). The International ImMunoGeneTics (IMGT) database (http://www_imgt_org) provides a standardized numbering and definition of antigen-binding sites. The correspondence between CDRs, HVs and IMGT delineations is described in Lefranc et al., Dev Comparat Immunol 27:55-77, 2003. The term "CDR", "HCDR1", "HCDR2", "HCDR3", "LCDR1", "LCDR2" and "LCDR3" as used herein includes CDRs defined by any of the methods described supra, Kabat, Chothia or IMGT, unless otherwise explicitly stated in the specification.

Also, the antibody, or antigen binding portion thereof, can be modified to comprise a detectable label, such as, for instance, a radioisotope, a fluorophore (e.g., fluorescein isothiocyanate (FITC), phycoerythrin (PE)), an enzyme (e.g., alkaline phosphatase, horseradish peroxidase), and element particles (e.g., gold particles).

Also provided by the present disclosure is a nucleic acid comprising a nucleotide sequence encoding any of the CARs, polypeptides, or proteins described herein (including functional portions and functional variants thereof).

The portion of the CAR comprising an antibody or antibody fragment thereof may exist in a variety of forms where the antigen binding domain is expressed as part of a contiguous polypeptide chain including, for example, a single domain antibody fragment (sdAb), a scFv and a human chimeric or humanized antibody (Harlow et al., 1999, In: Using Antibodies: A Laboratory Manual, Cold Spring Harbor Laboratory Press, N.Y.; Harlow et al., 1989, In: Antibodies: A Laboratory Manual, Cold Spring Harbor, N.Y.; Houston et al., 1988, Proc. Natl. Acad. Sci. USA 85:5879-5883; Bird et al., 1988, Science 242:423-426). In one aspect, the antigen binding domain of a CAR composition of the invention comprises an antibody fragment. In one aspect, the CAR comprises an antibody fragment that comprises a scFv.

The term "recombinant antibody" refers to an antibody which is generated using recombinant DNA technology, such as, for example, an antibody expressed by a bacteriophage or yeast expression system. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using recombinant DNA or amino acid sequence technology which is available and known in the art.

The term "antigen" refers to a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full-length nucleotide sequence of a gene. It is apparent that the present disclosure includes, but is not limited to, the use of partial nucleotide sequences of more than one gene and that these nucleotide sequences are arranged in various combinations to encode polypeptides that elicit the desired immune response.

In one aspect, the disclosure provides a CAR, comprising an extracellular antigen-binding domain, a transmembrane domain and an intracellular signaling domain, wherein the extracellular antigen-binding domain binds the GPRC5D antigen.

In one aspect, the disclosure provides a CAR, comprising an extracellular antigen-binding domain, a transmembrane domain and an intracellular signaling domain, wherein the extracellular antigen-binding domain comprises:
  a heavy chain complementarity determining region 1 (CDR1) having the amino acid sequence of SEQ ID NO: 66, a heavy chain CDR2 having the amino acid sequence of SEQ ID NO: 67, and a heavy chain CDR3 having the amino acid sequence of SEQ ID NO: 68;
  a heavy chain complementarity determining region 1 (CDR1) having the amino acid sequence of SEQ ID NO: 58, a heavy chain CDR2 having the amino acid sequence of SEQ ID NO: 59, and a heavy chain CDR3 having the amino acid sequence of SEQ ID NO: 60;
  a heavy chain complementarity determining region 1 (CDR1) having the amino acid sequence of SEQ ID NO: 39, a heavy chain CDR2 having the amino acid sequence of SEQ ID NO: 40, and a heavy chain CDR3 having the amino acid sequence of SEQ ID NO: 41;
  a heavy chain CDR1 having the amino acid sequence of SEQ ID NO: 42, a heavy chain CDR2 having the amino acid sequence of SEQ ID NO: 43, and a heavy chain CDR3 having the amino acid sequence of SEQ ID NO: 44; or
  a heavy chain CDR1 having the amino acid sequence of SEQ ID NO: 45, a heavy chain CDR2 having the amino acid sequence of SEQ ID NO: 46, and a heavy chain CDR3 having the amino acid sequence of SEQ ID NO: 47;
    wherein the extracellular antigen-binding domain binds the GPRC5D antigen.

In one aspect, the disclosure provides a CAR, comprising an extracellular antigen-binding domain, a transmembrane domain and an intracellular signaling domain, wherein the extracellular antigen-binding domain comprises:
  a heavy chain complementarity determining region 1 (CDR1) having the amino acid sequence of SEQ ID NO: 66, a heavy chain CDR2 having the amino acid sequence of SEQ ID NO: 67, and a heavy chain CDR3 having the amino acid sequence of SEQ ID NO: 68;
    wherein the extracellular antigen-binding domain binds the GPRC5D antigen.

In one aspect, the disclosure provides a CAR, comprising an extracellular antigen-binding domain, a transmembrane domain and an intracellular signaling domain, wherein the extracellular antigen-binding domain comprises:
  a heavy chain complementarity determining region 1 (CDR1) having the amino acid sequence of SEQ ID NO: 58, a heavy chain CDR2 having the amino acid sequence of SEQ ID NO: 59, and a heavy chain CDR3 having the amino acid sequence of SEQ ID NO: 60; wherein the extracellular antigen-binding domain binds the GPRC5D antigen.

In one aspect, the disclosure provides a CAR, comprising an extracellular antigen-binding domain, a transmembrane domain and an intracellular signaling domain, wherein the extracellular antigen-binding domain comprises:
a heavy chain complementarity determining region 1 (CDR1) having the amino acid sequence of SEQ ID NO: 39, a heavy chain CDR2 having the amino acid sequence of SEQ ID NO: 40, and a heavy chain CDR3 having the amino acid sequence of SEQ ID NO: 41; wherein the extracellular antigen-binding domain binds the GPRC5D antigen.

In one aspect, the disclosure provides a CAR, comprising an extracellular antigen-binding domain, a transmembrane domain and an intracellular signaling domain, wherein the extracellular antigen-binding domain comprises:
a heavy chain CDR1 having the amino acid sequence of SEQ ID NO: 42, a heavy chain CDR2 having the amino acid sequence of SEQ ID NO: 43, and a heavy chain CDR3 having the amino acid sequence of SEQ ID NO: 44 wherein the extracellular antigen-binding domain binds the GPRC5D antigen.

In one aspect, the disclosure provides a CAR, comprising an extracellular antigen-binding domain, a transmembrane domain and an intracellular signaling domain, wherein the extracellular antigen-binding domain comprises: a heavy chain CDR1 having the amino acid sequence of SEQ ID NO: 45, a heavy chain CDR2 having the amino acid sequence of SEQ ID NO: 46, and a heavy chain CDR3 having the amino acid sequence of SEQ ID NO: 47;
wherein the extracellular antigen-binding domain binds the GPRC5D antigen.

In one embodiment, the extracellular antigen-binding domain comprises the extracellular antigen-binding domain comprising the heavy chain CDR1 having the amino acid sequence of SEQ ID NO: 66, the heavy chain CDR2 having the amino acid sequence of SEQ ID NO: 67, and the heavy chain CDR3 having the amino acid sequence of SEQ ID NO: 68, and further comprises a light chain CDR1 having the amino acid sequence of SEQ ID NO: 69, a light chain CDR2 having the amino acid sequence of SEQ ID NO: 70, and a light chain CDR3 having the amino acid sequence of SEQ ID NO: 71;
the extracellular antigen-binding domain comprising the heavy chain CDR1 having the amino acid sequence of SEQ ID NO: 58, the heavy chain CDR2 having the amino acid sequence of SEQ ID NO: 59, and the heavy chain CDR3 having the amino acid sequence of SEQ ID NO: 60, and further comprises a light chain CDR1 having the amino acid sequence of SEQ ID NO: 61, a light chain CDR2 having the amino acid sequence of SEQ ID NO: 62, and a light chain CDR3 having the amino acid sequence of SEQ ID NO: 63
the heavy chain CDR1 having the amino acid sequence of SEQ ID NO: 39, the heavy chain CDR2 having the amino acid sequence of SEQ ID NO: 40, and the heavy chain CDR3 having the amino acid sequence of SEQ ID NO: 41, and further comprises a light chain CDR1 having the amino acid sequence of SEQ ID NO: 48, a light chain CDR2 having the amino acid sequence of SEQ ID NO: 49, and a light chain CDR3 having the amino acid sequence of SEQ ID NO: 50;
the extracellular antigen-binding domain comprises the heavy chain CDR1 having the amino acid sequence of SEQ ID NO: 42, the heavy chain CDR2 having the amino acid sequence of SEQ ID NO: 43, and the heavy chain CDR3 having the amino acid sequence of SEQ ID NO: 44, and further comprises a light chain CDR1 having the amino acid sequence of SEQ ID NO: 51, a light chain CDR2 having the amino acid sequence of SEQ ID NO: 52, and a light chain CDR3 having the amino acid sequence of SEQ ID NO: 53; or
the extracellular antigen-binding domain comprises the heavy chain CDR1 having the amino acid sequence of SEQ ID NO: 45, the heavy chain CDR2 having the amino acid sequence of SEQ ID NO: 46, and the heavy chain CDR3 having the amino acid sequence of SEQ ID NO: 47, and further comprises a light chain CDR1 having the amino acid sequence of SEQ ID NO: 54, a light chain CDR2 having the amino acid sequence of SEQ ID NO: 55, and a light chain CDR3 having the amino acid sequence of SEQ ID NO: 56.

In one aspect, the disclosure provides a CAR, comprising an extracellular antigen-binding domain, a transmembrane domain and an intracellular signaling domain, wherein the extracellular antigen-binding domain comprises:
a heavy chain CDR1 having an amino acid sequence selected from the group consisting of SEQ ID NO: 66, SEQ ID NO: 58, SEQ ID NO: 39, SEQ ID NO: 42, and SEQ ID NO: 45, and conservative modifications thereof, wherein the extracellular antigen-binding domain binds the GPRC5D antigen.

In one aspect, the disclosure provides a CAR, comprising an extracellular antigen-binding domain, a transmembrane domain and an intracellular signaling domain, wherein the extracellular antigen-binding domain comprises:
a heavy chain CDR2 having an amino acid sequence selected from the group consisting of SEQ ID NO: 67, SEQ ID NO: 59, SEQ ID NO: 40, SEQ ID NO: 43, and SEQ ID NO: 46, and conservative modifications thereof, wherein the extracellular antigen-binding domain binds the GPRC5D antigen.

In one aspect, the disclosure provides a CAR, comprising an extracellular antigen-binding domain, a transmembrane domain and an intracellular signaling domain, wherein the extracellular antigen-binding domain comprises:
a heavy chain CDR3 having an amino acid sequence selected from the group consisting of SEQ ID NO: 68, SEQ ID NO: 60, SEQ ID NO: 41, SEQ ID NO: 44, and SEQ ID NO: 47, and conservative modifications thereof, wherein the extracellular antigen-binding domain binds the GPRC5D antigen.

In one aspect, the disclosure provides a CAR, comprising an extracellular antigen-binding domain, a transmembrane domain and an intracellular signaling domain, wherein the extracellular antigen-binding domain comprises:
a heavy chain CDR1 having an amino acid sequence selected from the group consisting of SEQ ID NO: 66, SEQ ID NO: 58, SEQ ID NO: 39, SEQ ID NO: 42, and SEQ ID NO: 45, and conservative modifications thereof;
a heavy chain CDR2 having an amino acid sequence selected from the group consisting of SEQ ID NO: 67, SEQ ID NO: 59, SEQ ID NO: 40, SEQ ID NO: 43, and SEQ ID NO: 46, and conservative modifications thereof; and
a heavy chain CDR3 having an amino acid sequence selected from the group consisting of SEQ ID NO: 68, SEQ ID NO: 60, SEQ ID NO: 41, SEQ ID NO: 44, and SEQ ID NO: 47, and conservative modifications thereof;

wherein the extracellular antigen-binding domain binds the GPRC5D antigen.

In one aspect, the disclosure provides a CAR, comprising an extracellular antigen-binding domain, a transmembrane domain and an intracellular signaling domain, wherein the extracellular antigen-binding domain comprises:
 a light chain CDR1 having an amino acid sequence selected from the group consisting of SEQ ID NO: 69, SEQ ID NO: 54, SEQ ID NO: 48, SEQ ID NO: 51, and SEQ ID NO: 54, and conservative modifications thereof, wherein the extracellular antigen-binding domain binds the GPRC5D antigen.

In one aspect, the disclosure provides a CAR, comprising an extracellular antigen-binding domain, a transmembrane domain and an intracellular signaling domain, wherein the extracellular antigen-binding domain comprises:
 a light chain CDR2 having an amino acid sequence selected from the group consisting of SEQ ID NO: 70, SEQ ID NO: 55, SEQ ID NO: 49, SEQ ID NO: 52, and SEQ ID NO: 55, and conservative modifications thereof, wherein the extracellular antigen-binding domain binds the GPRC5D antigen.

In one aspect, the disclosure provides a CAR, comprising an extracellular antigen-binding domain, a transmembrane domain and an intracellular signaling domain, wherein the extracellular antigen-binding domain comprises:
 a light chain CDR3 having an amino acid sequence selected from the group consisting of SEQ ID NO: 71, SEQ ID NO: 56, SEQ ID NO: 50, SEQ ID NO: 53, and SEQ ID NO: 56, and conservative modifications thereof, wherein the extracellular antigen-binding domain binds the GPRC5D antigen.

In one aspect, the disclosure provides a CAR, comprising an extracellular antigen-binding domain, a transmembrane domain and an intracellular signaling domain, wherein the extracellular antigen-binding domain comprises:
 a light chain CDR1 having an amino acid sequence selected from the group consisting of SEQ ID NO: 69, SEQ ID NO: 54, SEQ ID NO: 48, SEQ ID NO: 51, and SEQ ID NO: 54, and conservative modifications thereof;
 a light chain CDR2 having an amino acid sequence selected from the group consisting of SEQ ID NO: 70, SEQ ID NO: 55, SEQ ID NO: 49, SEQ ID NO: 52, and SEQ ID NO: 55, and conservative modifications thereof; and
 a light chain CDR3 having an amino acid sequence selected from the group consisting of SEQ ID NO: 71, SEQ ID NO: 56, SEQ ID NO: 50, SEQ ID NO: 53, and SEQ ID NO: 56, and conservative modifications thereof; wherein the extracellular antigen-binding domain binds the GPRC5D antigen.

In one aspect, the disclosure provides a CAR, comprising an extracellular antigen-binding domain, a transmembrane domain and an intracellular signaling domain, wherein the extracellular antigen-binding domain comprises:
 a heavy chain CDR1 having an amino acid sequence selected from the group consisting of SEQ ID NO: 66, SEQ ID NO: 58, SEQ ID NO: 39, SEQ ID NO: 42, and SEQ ID NO: 45, and conservative modifications thereof;
 a heavy chain CDR2 having an amino acid sequence selected from the group consisting of SEQ ID NO: 67, SEQ ID NO: 59, SEQ ID NO: 40, SEQ ID NO: 43, and SEQ ID NO: 46, and conservative modifications thereof; and a heavy chain CDR3 having an amino acid sequence selected from the group consisting of SEQ ID NO: 68, SEQ ID NO: 60, SEQ ID NO: 41, SEQ ID NO: 44, and SEQ ID NO: 47, and conservative modifications thereof; and
 a light chain CDR1 having an amino acid sequence selected from the group consisting of SEQ ID NO: 69, SEQ ID NO: 54, SEQ ID NO: 48, SEQ ID NO: 51, and SEQ ID NO: 54, and conservative modifications thereof;
 a light chain CDR2 having an amino acid sequence selected from the group consisting of SEQ ID NO: 70, SEQ ID NO: 55, SEQ ID NO: 49, SEQ ID NO: 52, and SEQ ID NO: 55, and conservative modifications thereof; and
 a light chain CDR3 having an amino acid sequence selected from the group consisting of SEQ ID NO: 71, SEQ ID NO: 56, SEQ ID NO: 50, SEQ ID NO: 53, and SEQ ID NO: 56, and conservative modifications thereof;
wherein the extracellular antigen-binding domain binds the GPRC5D antigen.

In one aspect, the disclosure provides a CAR, comprising an extracellular antigen-binding domain, a transmembrane domain and an intracellular signaling domain, wherein the extracellular antigen-binding domain comprises:
 a heavy chain CDR1 having the amino acid sequence of SEQ ID NO: 66, a heavy chain CDR2 having the amino acid sequence of SEQ ID NO: 67, and a heavy chain CDR3 having the amino acid sequence of SEQ ID NO: 68, and further comprises a light chain CDR1 having the amino acid sequence of SEQ ID NO: 69, a light chain CDR2 having the amino acid sequence of SEQ ID NO: 70, and a light chain CDR3 having the amino acid sequence of SEQ ID NO: 71

In one aspect, the disclosure provides a CAR, comprising an extracellular antigen-binding domain, a transmembrane domain and an intracellular signaling domain, wherein the extracellular antigen-binding domain comprises:
 a heavy chain CDR1 having the amino acid sequence of SEQ ID NO: 58, a heavy chain CDR2 having the amino acid sequence of SEQ ID NO: 59, and a heavy chain CDR3 having the amino acid sequence of SEQ ID NO: 60, and further comprises a light chain CDR1 having the amino acid sequence of SEQ ID NO: 61, a light chain CDR2 having the amino acid sequence of SEQ ID NO: 62, and a light chain CDR3 having the amino acid sequence of SEQ ID NO: 63.

In one aspect, the disclosure provides a CAR, comprising an extracellular antigen-binding domain, a transmembrane domain and an intracellular signaling domain, wherein the extracellular antigen-binding domain comprises:
 a heavy chain CDR1 having the amino acid sequence of SEQ ID NO: 39, a heavy chain CDR2 having the amino acid sequence of SEQ ID NO: 40, and a heavy chain CDR3 having the amino acid sequence of SEQ ID NO: 41, and further comprises a light chain CDR1 having the amino acid sequence of SEQ ID NO: 48, a light chain CDR2 having the amino acid sequence of SEQ ID NO: 49, and a light chain CDR3 having the amino acid sequence of SEQ ID NO: 50.

In one aspect, the disclosure provides a CAR, comprising an extracellular antigen-binding domain, a transmembrane domain and an intracellular signaling domain, wherein the extracellular antigen-binding domain comprises:
 a heavy chain CDR1 having the amino acid sequence of SEQ ID NO: 42, a heavy chain CDR2 having the amino acid sequence of SEQ ID NO: 43, and a heavy chain CDR3 having the amino acid sequence of SEQ ID NO: 44, and further comprises a light chain CDR1 having the amino acid sequence of SEQ ID NO: 51, a light chain CDR2 having the amino acid sequence of SEQ ID NO: 52, and a light chain CDR3 having the amino acid sequence of SEQ ID NO: 53.

In one aspect, the disclosure provides a CAR, comprising an extracellular antigen-binding domain, a transmembrane domain and an intracellular signaling domain, wherein the extracellular antigen-binding domain comprises:

a heavy chain CDR1 having the amino acid sequence of SEQ ID NO: 45, a heavy chain CDR2 having the amino acid sequence of SEQ ID NO: 46, and a heavy chain CDR3 having the amino acid sequence of SEQ ID NO: 47, and further comprises a light chain CDR1 having the amino acid sequence of SEQ ID NO: 54, a light chain CDR2 having the amino acid sequence of SEQ ID NO: 55, and a light chain CDR3 having the amino acid sequence of SEQ ID NO: 56.

In one embodiment, the extracellular antigen-binding domain comprises a light chain variable region (LCVR) comprising an amino acid sequence selected from the group consisting of SEQ ID NOS: 73, 65, 1, 3 and 5, or a heavy chain variable region (HCVR) comprising an amino acid sequence selected from the group consisting of SEQ ID NOS: 72, 64, 2, 4, and 6, or a combination of a LCVR comprising an amino acid sequence selected from the group consisting of SEQ ID NOS: 73, 65, 1, 3 and 5, and a HCVR comprising an amino acid sequence selected from the group consisting of SEQ ID NOS: 72, 64, 2, 4, and 6.

In some embodiments, the extracellular antigen-binding domain comprises a light chain variable region (LCVR) comprising an amino acid sequence of any one of SEQ ID NOS: 73, 65, 1, 3 or 5. In some embodiments, the extracellular antigen-binding domain comprises a light chain variable region (LCVR) comprising an amino acid sequence having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98% or at least 99%, sequence identity with any one of SEQ ID NOS: 73, 65, 1, 3 or 5. In some embodiments, the extracellular antigen-binding domain comprises a light chain variable region (LCVR) comprising an amino acid sequence of SEQ ID NO: 73. In some embodiments, the extracellular antigen-binding domain comprises a light chain variable region (LCVR) comprising an amino acid sequence having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98% or at least 99%, sequence identity with SEQ ID NO: 73. In some embodiments, the extracellular antigen-binding domain comprises a light chain variable region (LCVR) comprising an amino acid sequence of SEQ ID NO: 65. In some embodiments, the extracellular antigen-binding domain comprises a light chain variable region (LCVR) comprising an amino acid sequence having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98% or at least 99%, sequence identity with SEQ ID NO: 65. In some embodiments, the extracellular antigen-binding domain comprises a light chain variable region (LCVR) comprising an amino acid sequence of SEQ ID NO: 1. In some embodiments, the extracellular antigen-binding domain comprises a light chain variable region (LCVR) comprising an amino acid sequence having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98% or at least 99%, sequence identity with SEQ ID NO: 1. In some embodiments, the extracellular antigen-binding domain comprises a light chain variable region (LCVR) comprising an amino acid sequence of SEQ ID NO: 3. In some embodiments, the extracellular antigen-binding domain comprises a light chain variable region (LCVR) comprising an amino acid sequence having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98% or at least 99%, sequence identity with SEQ ID NO: 3. In some embodiments, the extracellular antigen-binding domain comprises a light chain variable region (LCVR) comprising an amino acid sequence of SEQ ID NO: 5. In some embodiments, the extracellular antigen-binding domain comprises a light chain variable region (LCVR) comprising an amino acid sequence having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98% or at least 99%, sequence identity with SEQ ID NO: 5.

In some embodiments, the extracellular antigen-binding domain comprises a light chain variable region (LCVR) comprising an amino acid sequence of any one of SEQ ID NOS: 72, 64, 2, 4, or 6. In some embodiments, the extracellular antigen-binding domain comprises a heavy chain variable region (HCVR) comprising an amino acid sequence having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98% or at least 99%, sequence identity with any one of SEQ ID NOS: 72, 64, 2, 4, or 6. In some embodiments, the extracellular antigen-binding domain comprises a light chain variable region (LCVR) comprising an amino acid sequence of SEQ ID NO: 72. In some embodiments, the extracellular antigen-binding domain comprises a heavy chain variable region (HCVR) comprising an amino acid sequence having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98% or at least 99%, sequence identity with SEQ ID NO: 72. In some embodiments, the extracellular antigen-binding domain comprises a light chain variable region (LCVR) comprising an amino acid sequence of SEQ ID NO: 2. In some embodiments, the extracellular antigen-binding domain comprises a heavy chain variable region (HCVR) comprising an amino acid sequence having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98% or at least 99%, sequence identity with SEQ ID NO: 64. In some embodiments, the extracellular antigen-binding domain comprises a heavy chain variable region (HCVR) comprising an amino acid sequence having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98% or at least 99%, sequence identity with SEQ ID NO: 2. In some embodiments, the extracellular antigen-binding domain comprises a light chain variable region (LCVR) comprising an amino acid sequence of SEQ ID NO: 6. In some embodiments, the extracellular antigen-binding domain comprises a heavy chain variable region (HCVR) comprising an amino acid sequence having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98% or at least 99%, sequence identity with SEQ ID NO: 4. In some embodiments, the extracellular antigen-binding domain comprises a heavy chain variable region (HCVR) comprising an amino acid sequence having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98% or at least 99%, sequence identity with SEQ ID NO: 6.

In one embodiment, the extracellular antigen-binding domain comprises: a light chain variable region comprising an amino acid sequence of SEQ ID NO: 73, or an amino acid sequence having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98% or at least 99%, sequence identity thereto, and a heavy chain variable region comprising an amino acid sequence of SEQ ID NO: 72, or an amino acid sequence having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98% or at least 99%, sequence identity thereto.

In one embodiment, the extracellular antigen-binding domain comprises: a light chain variable region comprising an amino acid sequence of SEQ ID NO: 65 or an amino acid sequence having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98% or at least 99%, sequence identity thereto, and a heavy chain variable region comprising an amino acid sequence of SEQ ID NO: 64 or an amino acid sequence having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98% or at least 99%, sequence identity thereto.

In one embodiment, the extracellular antigen-binding domain comprises: a light chain variable region comprising an amino acid sequence of SEQ ID NO: 1, or an amino acid sequence having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98% or at least 99%, sequence identity thereto, and a heavy chain variable region comprising an amino acid sequence of SEQ ID NO: 2, or an amino acid sequence having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98% or at least 99%, sequence identity thereto.

In one embodiment, the extracellular antigen-binding domain comprises: a light chain variable region comprising an amino acid sequence of SEQ ID NO: 3 or an amino acid sequence having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98% or at least 99%, sequence identity thereto, and a heavy chain variable region comprising an amino acid sequence of SEQ ID NO: 4, or an amino acid sequence having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98% or at least 99%, sequence identity thereto.

In one embodiment, the extracellular antigen-binding domain comprises: a light chain variable region comprising an amino acid sequence of SEQ ID NO: 5 or an amino acid sequence having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98% or at least 99%, sequence identity thereto, and a heavy chain variable region comprising an amino acid sequence of SEQ ID NO: 6 or an amino acid sequence having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98% or at least 99%, sequence identity thereto.

In one embodiment, the extracellular antigen-binding domain comprises: a light chain variable region comprising an amino acid sequence of SEQ ID NO: 73 and a heavy chain variable region comprising an amino acid sequence of SEQ ID NO: 72.

In one embodiment, the extracellular antigen-binding domain comprises: a light chain variable region comprising an amino acid sequence of SEQ ID NO: 65 and a heavy chain variable region comprising an amino acid sequence of SEQ ID NO: 64.

In one embodiment, the extracellular antigen-binding domain comprises: a light chain variable region comprising an amino acid sequence of SEQ ID NO: 1 and a heavy chain variable region comprising an amino acid sequence of SEQ ID NO: 2.

In one embodiment, the extracellular antigen-binding domain comprises: a light chain variable region comprising an amino acid sequence of SEQ ID NO: 3 and a heavy chain variable region comprising an amino acid sequence of SEQ ID NO: 4.

In one embodiment, the extracellular antigen-binding domain comprises: a light chain variable region comprising an amino acid sequence of SEQ ID NO: 5 and a heavy chain variable region comprising an amino acid sequence of SEQ ID NO: 6.

Herein, in embodiments wherein the amino acid sequence of the VH domain exhibits less than 100% sequence identity with a given reference VH sequence may nevertheless comprise heavy chain CDRs which are identical to HCDR1, HCDR2 and HCDR3 of the reference sequence whilst exhibiting amino acid sequence variation within the framework regions. Likewise, embodiments wherein the amino acid sequence of the VL domain exhibits less than 100% sequence identity with a given reference sequence may nevertheless comprise light chain CDRs which are identical to LCDR1, LCDR2 and LCDR3 of the reference sequence whilst exhibiting amino acid sequence variation within the framework regions. Similarly, where a scFv or extracellular domain of a CAR of the disclosure exhibits less than 100% sequence identity with a given reference VH sequence may nevertheless comprise heavy chain CDRs which are identical to HCDR1, HCDR2 and HCDR3 of the reference sequence and light chain CDRs which are identical to LCDR1, LCDR2 and LCDR3 of the reference sequence, whilst exhibiting amino acid sequence variation within the framework regions.

In one embodiment, the extracellular antigen-binding domain comprises a scFv. In some embodiments, the scFv comprises a linker polypeptide between the light chain variable region and the heavy chain variable region. In certain embodiments, the extracellular antigen-binding domain is a scFv which comprises an amino acid sequence selected from the group consisting of SEQ ID NOS: 78, 77, 75, 76, 8, 9, 10, 24, 25, and 26, and specifically binds to a GPRC5D polypeptide (e.g., a human GPRC5D polypeptide having the amino acid sequence of SEQ ID NO: 57, or fragments thereof).

In some embodiments, the scFv comprises, from the N- to C-terminus, a VH, a linker and a VL (VH-Linker-VL).

In some embodiments, the scFv comprises, from the N- to C-terminus, the VL, the linker and the VH (VL-Linker-VH).

In recombinant expression systems, the linker is a peptide linker and may include any naturally occurring amino acid. Exemplary amino acids that may be included into the linker are Gly, Ser Pro, Thr, Glu, Lys, Arg, Ile, Leu, His and The. The linker should have a length that is adequate to link the VH and the VL in such a way that they form the correct conformation relative to one another so that they retain the desired activity, such as binding to GPRC5D.

The linker may be about 5-50 amino acids long. In some embodiments, the linker is about 10-40 amino acids long. In some embodiments, the linker is about 10-35 amino acids long. In some embodiments, the linker is about 10-30 amino acids long. In some embodiments, the linker is about 10-25 amino acids long. In some embodiments, the linker is about 10-20 amino acids long. In some embodiments, the linker is about 15-20 amino acids long. In some embodiments, the linker is 6 amino acids long. In some embodiments, the linker is 7 amino acids long. In some embodiments, the linker is 8 amino acids long. In some embodiments, the linker is 9 amino acids long. In some embodiments, the linker is 10 amino acids long. In some embodiments, the linker is 11 amino acids long. In some embodiments, the linker is 12 amino acids long. In some embodiments, the linker is 13 amino acids long. In some embodiments, the linker is 14 amino acids long. In some embodiments, the linker is 15 amino acids long. In some embodiments, the linker is 16 amino acids long. In some embodiments, the linker is 17 amino acids long. In some embodiments, the linker is 18 amino acids long. In some embodiments, the linker is 19 amino acids long. In some embodiments, the linker is 20 amino acids long. In some embodiments, the linker is 21 amino acids long. In some embodiments, the linker is 22 amino acids long. In some embodiments, the linker is 23 amino acids long. In some embodiments, the linker is 24 amino acids long. In some embodiments, the linker is 25 amino acids long. In some embodiments, the linker is 26 amino acids long. In some embodiments, the linker is 27 amino acids long. In some embodiments, the linker is 28 amino acids long. In some embodiments, the linker is 29 amino acids long. In some embodiments, the linker is 30 amino acids long. In some embodiments, the linker is 31 amino acids long. In some embodiments, the linker is 32 amino acids long. In some embodiments, the linker is 33 amino acids long. In some embodiments, the linker is 34 amino acids long. In some embodiments, the linker is 35 amino acids long. In some embodiments, the linker is 36 amino acids long. In some embodiments, the linker is 37 amino acids long. In some embodiments, the linker is 38 amino acids long. In some embodiments, the linker is 39 amino acids long. In some embodiments, the linker is 40 amino acids long. Exemplary linkers that may be used are Gly rich linkers, Gly and Ser containing linkers, Gly and Ala containing linkers, Ala and Ser containing linkers, and other flexible linkers.

In one embodiment, the linker polypeptide comprises an amino acid sequence of SEQ ID NO: 7.

Other linker sequences may include portions of immunoglobulin hinge area, CL or CH1 derived from any immunoglobulin heavy or light chain isotype. Exemplary linkers that may be used are shown in Table 1. Additional linkers are described for example in Int. Pat. Publ. No. WO2019/060695, incorporated by reference herein in its entirety.

In one embodiment, the linker polypeptide comprises an amino acid sequence of any one of SEQ ID NOs: 91-123.

TABLE 1

| Linker name | Amino acid sequence | SEQ ID NO: |
|---|---|---|
| Linker 1 | GGSEGKSSGSGSESKSTGGS | 91 |
| Linker 2 | GGGSGGGS | 92 |
| Linker 3 | GGGSGGGSGGGS | 93 |
| Linker 4 | GGGSGGGSGGGSGGGS | 94 |
| Linker 5 | GGGSGGGSGGGSGGGSGGGS | 95 |
| Linker 6 | GGGGSGGGSGGGGS | 96 |
| Linker 7 | GGGGSGGGGSGGGGSGGGGS | 97 |
| Linker 8 | GGGGSGGGGSGGGGSGGGGSGGGGS | 98 |
| Linker 9 | GSTSGSGKPGSGEGSTKG | 99 |
| Linker 10 | IRPRAIGGSKPRVA | 100 |
| Linker 11 | GKGGSGKGGSGKGGS | 101 |
| Linker 12 | GGKGSGGKGSGGKGS | 102 |
| Linker 13 | GGGKSGGGKSGGGKS | 103 |
| Linker 14 | GKGKSGKGKSGKGKS | 104 |
| Linker 15 | GGGKSGGKGSGKGGS | 105 |
| Linker 16 | GKPGSGKPGSGKPGS | 106 |
| Linker 17 | GKPGSGKPGSGKPGSGKPGS | 107 |
| Linker 18 | GKGKSGKGKSGKGKSGKGKS | 108 |
| Linker 19 | STAGDTHLGGEDFD | 109 |
| Linker 20 | GEGGSGEGGSGEGGS | 110 |
| Linker 21 | GGEGSGGEGSGGEGS | 111 |
| Linker 22 | GEGESGEGESGEGES | 112 |
| Linker 23 | GGGESGGEGSGEGGS | 113 |
| Linker 24 | GEGESGEGESGEGESGEGES | 114 |
| Linker 25 | GSTSGSGKPGSGEGSTKG | 115 |
| Linker 26 | PRGASKSGSASQTGSAPGS | 116 |
| Linker 27 | GTAAAGAGAAGGAAAGAAG | 117 |

TABLE 1-continued

| Linker name | Amino acid sequence | SEQ ID NO: |
|---|---|---|
| Linker 28 | GTSGSSGSGSGGSGSGGGG | 118 |
| Linker 29 | GKPGSGKPGSGKPGSGKPGS | 119 |
| Linker 30 | GSGS | 120 |
| Linker 31 | APAPAPAPAP | 121 |
| Linker 32 | APAPAPAPAPAPAPAPAP | 122 |
| Linker 33 | AEAAAKEAAAKEAAAAKEAAAAKEAAAAKAAA | 123 |

In one embodiment, the scFv comprises an amino acid sequence selected from the group consisting of SEQ ID NOS: 78, 77, 75, 76, 8, 9, 10, 24, 25, and 26. In some embodiments, the scFv comprises an amino acid sequence having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98% or at least 99%, sequence identity with any one of SEQ ID NOS: 78, 77, 75, 76, 8, 9, 10, 24, 25, and 26. In some embodiments, the scFv comprises an amino acid sequence of SEQ ID NO:78. In some embodiments, the scFv comprises an amino acid sequence having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98% or at least 99%, sequence identity with SEQ ID NO: 78. In some embodiments, the scFv comprises an amino acid sequence of SEQ ID NO:77. In some embodiments, the scFv comprises an amino acid sequence having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98% or at least 99%, sequence identity with SEQ ID NO: 77. In some embodiments, the scFv comprises an amino acid sequence of SEQ ID NO:75. In some embodiments, the scFv comprises an amino acid sequence having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98% or at least 99%, sequence identity with SEQ ID NO: 75. In some embodiments, the scFv comprises an amino acid sequence of SEQ ID NO:76. In some embodiments, the scFv comprises an amino acid sequence having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98% or at least 99%, sequence identity with SEQ ID NO: 76. In some embodiments, the scFv comprises an amino acid sequence of SEQ ID NO: 8. In some embodiments, the scFv comprises an amino acid sequence having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98% or at least 99%, sequence identity with SEQ ID NO: 8. In some embodiments, the scFv comprises an amino acid sequence of SEQ ID NO: 9. In some embodiments, the scFv comprises an amino acid sequence having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98% or at least 99%, sequence identity with SEQ ID NO: 9. In some embodiments, the scFv comprises an amino acid sequence of SEQ ID NO:10. In some embodiments, the scFv comprises an amino acid sequence having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98% or at least 99%, sequence identity with SEQ ID NO: 10. In some embodiments, the scFv comprises an amino acid sequence of SEQ ID NO: 24. In some embodiments, the scFv comprises an amino acid sequence having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98% or at least 99%, sequence identity with SEQ ID NO: 24. In some embodiments, the scFv comprises an amino acid sequence of SEQ ID NO:25. In some embodiments, the scFv comprises an amino acid sequence having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98% or at least 99%, sequence identity with SEQ ID NO: 25. In some embodiments, the scFv comprises an amino acid sequence of SEQ ID NO: 26. In some embodiments, the scFv comprises an amino acid sequence having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98% or at least 99%, sequence identity with SEQ ID NO: 26.

In one embodiment, the extracellular antigen-binding domain comprises a signal polypeptide. In some embodiments, the signal polypeptide comprises an amino acid sequence of SEQ ID NO: 11. In some embodiments, the extracellular antigen-binding domain comprises an amino acid sequence having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98% or at least 99%, sequence identity with SEQ ID NO: 11.

In one aspect, the disclosure provides a CAR, comprising an extracellular antigen-binding domain, a transmembrane domain and an intracellular signaling domain, wherein the extracellular antigen-binding domain comprises an amino acid sequence selected from the group consisting of SEQ ID NOS: 82, 81, 80, 79, 17, 18, 19, 20, 21, and 22, or a sequence having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98% or at least 99%, sequence identity thereto. Another feature of the CAR having an extracellular antigen-binding domain comprising an amino acid sequence selected from the group consisting of SEQ ID NOS: 82, 81, 80, 79, 17, 18, 19, 20, 21, and 22 is that the extracellular antigen-binding domain binds the GPRC5D antigen.

In one embodiment, the intracellular signaling domain comprises a polypeptide component selected from the group consisting of a TNF receptor superfamily member 9 (CD137) component, a T-cell surface glycoprotein CD3 zeta chain (CD3z) component, a cluster of differentiation (CD27)

component, a cluster of differentiation superfamily member (such as, e.g., CD28 or inducible T-cell co-stimulator (ICOS)) component, and a combination thereof.

In one embodiment, the CD137 component comprises an amino acid sequence of SEQ ID NO: 12. In some embodiments, the CD137 component comprises an amino acid sequence having at least 50%, at least 55%, at least 60%, at least 65%, at least 70%, at least 75%, at least 80%, at least 85%, at least 90%, at least 95%, at least 98% or at least 99%, sequence identity with SEQ ID NO: 12.

In one embodiment, the CD3z component comprises an amino acid sequence of SEQ ID NO: 13. In some embodiments, the CD3z component comprises an amino acid sequence having at least 50%, at least 55%, at least 60%, at least 65%, at least 70%, at least 75%, at least 80%, at least 85%, at least 90%, at least 95%, at least 98% or at least 99%, sequence identity with SEQ ID NO: 13.

In some embodiments, the intracellular signaling domain comprises a CD137 component and a CD3z component.

In one embodiment, the intracellular signaling domain comprises an amino acid sequence of SEQ ID NO: 14. In some embodiments, the intracellular signaling domain comprises an amino acid sequence having at least 50%, at least 55%, at least 60%, at least 65%, at least 70%, at least 75%, at least 80%, at least 85%, at least 90%, at least 95%, at least 98% or at least 99%, sequence identity with SEQ ID NO: 14.

The transmembrane domain of the CAR may be derived from the transmembrane domain of CD8, an α, β or ζ chain of a T-cell receptor, CD28, CD3 epsilon, CD45, CD4, CD5, CD8, CD9, CD16, CD22, CD33, CD37, CD64, CD80, CD86, CD134, CD137, CD154, KIRDS2, OX40, CD2, CD27, LFA-1 (CDI 1a, CD18), ICOS (CD278), 4-1 BB (CD137), 4-1 BBL, GITR, CD40, BAFFR, HVEM (LIGHTR), SLAMF7, NKp80 (KLRFI), CD160, CD1 9, IL2R beta, IL2R gamma, IL7R a, ITGA1, VLA1, CD49a, ITGA4, IA4, CD49D, ITGA6, VLA-6, CD49f, ITGAD, CDI Id, ITGAE, CD103, ITGAL, CDI 1a, LFA-1, ITGAM, CDI 1b, ITGAX, CDI 1c, ITGB1, CD29, ITGB2, CD1 8, LFA-1, ITGB7, TNFR2, DNAM1 (CD226), SLAMF4 (CD244, 2B4), CD84, CD96 (Tactile), CEACAM1, CRT AM, Ly9 (CD229), CD160 (BY55), PSGL1, CD100 (SEMA4D), SLAMF6 (NTB-A, Ly108), SLAM (SLAMF1, CD150, IPO-3), BLAME (SLAMF8), SELPLG (CD162), LTBR, PAG/Cbp, NKp44, NKp30, NKp46, NKG2D, and/or NKG2C.

In one embodiment, the transmembrane domain comprises a CD8a transmembrane region (CD8a-TM) polypeptide. In some embodiments, the CD8a-TM polypeptide comprises an amino acid sequence of SEQ ID NO: 15. In some embodiments, the CD8a-TM polypeptide comprises an amino acid sequence having at least 50%, at least 55%, at least 60%, at least 65%, at least 70%, at least 75%, at least 80%, at least 85%, at least 90%, at least 95%, at least 98% or at least 99%, sequence identity with SEQ ID NO: 15.

In one embodiment, the transmembrane domain comprises at least the transmembrane region(s) of the α, β or ζ chain of the T-cell receptor, CD28, CD3 epsilon, CD45, CD4, CD5, CD8, CD8a, CD9, CD16, CD22, CD33, CD37, CD40, CD64, CD80, CD86, CD134, CD137, or CD154. In another embodiment, the transmembrane domain comprises at least the transmembrane domain of λ, η or FcεR1γ and -β, MB1 (Igα.), B29 or CD3-γ, ζ, or η. In another embodiment, the transmembrane domain is synthetic, e.g., comprising predominantly hydrophobic residues such as leucine and valine, a triplet of phenylalanine, or tryptophan.

In one embodiment, the CAR further comprises a hinge region linking the transmembrane domain to the extracellular antigen-binding domain. In some embodiments, the hinge region is a CD8a-hinge region. In some embodiments, CD8a-hinge region comprises an amino acid sequence of SEQ ID NO: 16. In some embodiments, the CD8a-hinge region comprises an amino acid sequence having at least 50, at least 55, at least 60, at least 65, at least 70, at least 75, at least 80, at least 85, at least 90, at least 95, at least 98 or at least 99%, sequence identity with SEQ ID NO: 16. In some embodiments, the hinge region comprises the sequence EPKSCDKTHTCPPCP (SEQ ID NO: 124), or comprises an amino acid sequence having at least 50, at least 55, at least 60, at least 65, at least 70, at least 75, at least 80, at least 85, at least 90, at least 95, at least 98 or at least 99%, sequence identity with EPKSCDKTHTCPPCP (SEQ ID NO: 124). In some embodiments, the hinge region comprises the sequence ERKCCVECPPCP (SEQ ID NO: 125), or comprises an amino acid sequence having at least 50, at least 55, at least 60, at least 65, at least 70, at least 75, at least 80, at least 85, at least 90, at least 95, at least 98 or at least 99%, sequence identity with ERKCCVECPPCP (SEQ ID NO: 125). In some embodiments, the hinge region comprises the sequence ELKTPLGDTTHTCPRCP (EPKSCDTPPPCPRCP)$_3$ SEQ ID NO: 126), or comprises an amino acid sequence having at least 50, at least 55, at least 60, at least 65, at least 70, at least 75, at least 80, at least 85, at least 90, at least 95, at least 98 or at least 99%, sequence identity with ELKTPLGDTTHTCPRCP (EPKSCDTPPPCPRCP)$_3$ SEQ ID NO: 126). In some embodiments, the hinge region comprises the sequence ESKYGPPCPSCP (SEQ ID NO: 127), or comprises an amino acid sequence having at least 50, at least 55, at least 60, at least 65, at least 70, at least 75, at least 80, at least 85, at least 90, at least 95, at least 98 or at least 99%, sequence identity with ESKYGPPCPSCP (SEQ ID NO: 127).

In one embodiment, the CAR comprises an extracellular antigen-binding domain, a hinge region, a transmembrane domain and an intracellular signaling domain. In one such embodiment, the hinge region is a CD8a hinge region, the transmembrane domain is a CD8a-TM domain, and the intracellular signaling domain comprises a CD3-zeta domain and a 4-1BB/CD137 domain. In one such embodiment, the hinge region is a CD8a hinge region comprising the amino acid sequence of SEQ ID No: 16, the transmembrane domain is a CD8a-TM domain comprising the amino acid sequence of SEQ ID NO: 15, and the intracellular signaling domain comprises a CD3-zeta domain and a 4-1BB/CD137 domain, wherein the intracellular signaling domain comprises the amino acid sequence of SEQ ID No: 14.

In one embodiment, the extracellular antigen-binding domain comprises an amino acid sequence selected from the group consisting of SEQ ID NOS: 82, 81, 80, 79, 17, 18, 19, 20, 21, and 22. In some embodiments, the extracellular antigen-binding domain comprises an amino acid sequence having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98% or at least 99%, sequence identity with any one of SEQ ID NOS: 82, 81, 80, 79, 17, 18, 19, 20, 21, and 22.

In some embodiments, the extracellular antigen-binding domain comprises an amino acid sequence of SEQ ID NO: 82. In some embodiments, the extracellular antigen-binding domain comprises an amino acid sequence having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98% or at least 99%, sequence identity with SEQ ID NO: 82.

In some embodiments, the extracellular antigen-binding domain comprises an amino acid sequence of SEQ ID NO: 81. In some embodiments, the extracellular antigen-binding domain comprises an amino acid sequence having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98% or at least 99%, sequence identity with SEQ ID NO: 81.

In some embodiments, the extracellular antigen-binding domain comprises an amino acid sequence of SEQ ID NO: 80. In some embodiments, the extracellular antigen-binding domain comprises an amino acid sequence having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98% or at least 99%, sequence identity with SEQ ID NO: 80.

In some embodiments, the extracellular antigen-binding domain comprises an amino acid sequence of SEQ ID NO: 79. In some embodiments, the extracellular antigen-binding domain comprises an amino acid sequence having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98% or at least 99%, sequence identity with SEQ ID NO: 79.

In some embodiments, the extracellular antigen-binding domain comprises an amino acid sequence of SEQ ID NO: 17. In some embodiments, the extracellular antigen-binding domain comprises an amino acid sequence having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98% or at least 99%, sequence identity with SEQ ID NO: 17.

In some embodiments, the extracellular antigen-binding domain comprises an amino acid sequence of SEQ ID NO: 18. In some embodiments, the extracellular antigen-binding domain comprises an amino acid sequence having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98% or at least 99%, sequence identity with SEQ ID NO: 18.

In some embodiments, the extracellular antigen-binding domain comprises an amino acid sequence of SEQ ID NO: 19. In some embodiments, the extracellular antigen-binding domain comprises an amino acid sequence having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98% or at least 99%, sequence identity with SEQ ID NO: 19.

In some embodiments, the extracellular antigen-binding domain comprises an amino acid sequence of SEQ ID NO: 20. In some embodiments, the extracellular antigen-binding domain comprises an amino acid sequence having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98% or at least 99%, sequence identity with SEQ ID NO: 20.

In some embodiments, the extracellular antigen-binding domain comprises an amino acid sequence of SEQ ID NO: 21. In some embodiments, the extracellular antigen-binding domain comprises an amino acid sequence having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98% or at least 99%, sequence identity with SEQ ID NO: 21.

In some embodiments, the extracellular antigen-binding domain comprises an amino acid sequence of SEQ ID NO: 22. In some embodiments, the extracellular antigen-binding domain comprises an amino acid sequence having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98% or at least 99%, sequence identity with SEQ ID NO: 22.

In one embodiment, a CAR of the present disclosure comprises an amino acid sequence selected from the group consisting of SEQ ID NOS: 86, 85, 83, 84, 27, 28, 29, 30, 31 and 32. In some embodiments, the CAR of the present disclosure comprises an amino acid sequence having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98% or at least 99%, sequence identity with any one of SEQ ID NOS: 86, 85, 83, 84, 27, 28, 29, 30, 31 and 32.

In some embodiments, the CAR of the present disclosure comprises an amino acid sequence of SEQ ID NO: 86. In some embodiments, the CAR of the present disclosure comprises an amino acid sequence having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98% or at least 99%, sequence identity with SEQ ID NO: 86.

In some embodiments, the CAR of the present disclosure comprises an amino acid sequence of SEQ ID NO: 85. In some embodiments, the CAR of the present disclosure comprises an amino acid sequence having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98% or at least 99%, sequence identity with SEQ ID NO: 85.

In some embodiments, the CAR of the present disclosure comprises an amino acid sequence of SEQ ID NO: 83. In some embodiments, the CAR of the present disclosure comprises an amino acid sequence having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98% or at least 99%, sequence identity with SEQ ID NO: 83.

In some embodiments, the CAR of the present disclosure comprises an amino acid sequence of SEQ ID NO: 84. In some embodiments, the CAR of the present disclosure comprises an amino acid sequence having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98% or at least 99%, sequence identity with SEQ ID NO: 84.

In some embodiments, the CAR of the present disclosure comprises an amino acid sequence of SEQ ID NO: 27. In some embodiments, the CAR of the present disclosure comprises an amino acid sequence having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98% or at least 99%, sequence identity with SEQ ID NO: 27.

In some embodiments, the CAR of the present disclosure comprises an amino acid sequence of SEQ ID NO: 28. In some embodiments, the CAR of the present disclosure comprises an amino acid sequence having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98% or at least 99%, sequence identity with SEQ ID NO: 28.

In some embodiments, the CAR of the present disclosure comprises an amino acid sequence of SEQ ID NO: 29. In some embodiments, the CAR of the present disclosure comprises an amino acid sequence having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98% or at least 99%, sequence identity with SEQ ID NO: 29.

In some embodiments, the CAR of the present disclosure comprises an amino acid sequence of SEQ ID NO: 30. In some embodiments, the CAR of the present disclosure comprises an amino acid sequence having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98% or at least 99%, sequence identity with SEQ ID NO: 30.

In some embodiments, the CAR of the present disclosure comprises an amino acid sequence of SEQ ID NO: 31. In some embodiments, the CAR of the present disclosure comprises an amino acid sequence having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98% or at least 99%, sequence identity with SEQ ID NO: 31.

In some embodiments, the CAR of the present disclosure comprises an amino acid sequence of SEQ ID NO: 32. In some embodiments, the CAR of the present disclosure comprises an amino acid sequence having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98% or at least 99%, sequence identity with SEQ ID NO: 32.

In certain embodiments, the CAR may comprise a signal peptide. In certain embodiments the signal peptide is at the N-terminus of the CAR sequence. In certain embodiments the signal peptide is at the C-terminus of the CAR sequence. In certain embodiments, the signal peptide comprises or consists of the amino acid sequence of SEQ ID No: 11.

CAR Constructs and Immunoresponsive Cells Expressing CARs

In one aspect, the disclosure provides isolated nucleic acid molecules encoding the CARs described herein. In some embodiments, the nucleic acid molecule comprises a nucleic acid sequence selected from the group consisting of SEQ ID NOS: 90, 89, 87, 88, 33, 34, 35, 36, 37, and 38. In some embodiments, the isolated nucleic acid molecule comprises a nucleotide sequence that is at least about 80%, 81%, 82%, 83%, 84%, 85%, 86%, 87%, 88%, 89%, 90%, 91%, 92%, 93%, 94%, 95%, 96%, 97%, 98%, or 99% identical to a nucleotide sequence of SEQ ID NOS: 90, 89, 87, 88, 33, 34, 35, 36, 37, or 38.

In some embodiments, the nucleic acid molecule comprises a nucleic acid sequence of SEQ ID NO: 90. In some embodiments, the isolated nucleic acid molecule comprises a nucleotide sequence that is at least about 80%, 81%, 82%, 83%, 84%, 85%, 86%, 87%, 88%, 89%, 90%, 91%, 92%, 93%, 94%, 95%, 96%, 97%, 98%, or 99% identical to a nucleotide sequence of SEQ ID NO: 90. In some embodiments, the nucleic acid molecule comprises a nucleic acid sequence of SEQ ID NO: 89. In some embodiments, the isolated nucleic acid molecule comprises a nucleotide sequence that is at least about 80%, 81%, 82%, 83%, 84%, 85%, 86%, 87%, 88%, 89%, 90%, 91%, 92%, 93%, 94%, 95%, 96%, 97%, 98%, or 99% identical to a nucleotide sequence of SEQ ID NO: 89. In some embodiments, the nucleic acid molecule comprises a nucleic acid sequence of SEQ ID NO: 87. In some embodiments, the isolated nucleic acid molecule comprises a nucleotide sequence that is at least about 80%, 81%, 82%, 83%, 84%, 85%, 86%, 87%, 88%, 89%, 90%, 91%, 92%, 93%, 94%, 95%, 96%, 97%, 98%, or 99% identical to a nucleotide sequence of SEQ ID NO: 87. In some embodiments, the nucleic acid molecule comprises a nucleic acid sequence of SEQ ID NO: 88. In some embodiments, the isolated nucleic acid molecule comprises a nucleotide sequence that is at least about 80%, 81%, 82%, 83%, 84%, 85%, 86%, 87%, 88%, 89%, 90%, 91%, 92%, 93%, 94%, 95%, 96%, 97%, 98%, or 99% identical to a nucleotide sequence of SEQ ID NO: 88. In some embodiments, the nucleic acid molecule comprises a nucleic acid sequence of SEQ ID NO: 33. In some embodiments, the isolated nucleic acid molecule comprises a nucleotide sequence that is at least about 80%, 81%, 82%, 83%, 84%, 85%, 86%, 87%, 88%, 89%, 90%, 91%, 92%, 93%, 94%, 95%, 96%, 97%, 98%, or 99% identical to a nucleotide sequence of SEQ ID NO: 33. In some embodiments, the nucleic acid molecule comprises a nucleic acid sequence of SEQ ID NO: 34. In some embodiments, the isolated nucleic acid molecule comprises a nucleotide sequence that is at least about 80%, 81%, 82%, 83%, 84%, 85%, 86%, 87%, 88%, 89%, 90%, 91%, 92%, 93%, 94%, 95%, 96%, 97%, 98%, or 99% identical to a nucleotide sequence of SEQ ID NO: 34. In some embodiments, the nucleic acid molecule comprises a nucleic acid sequence of SEQ ID NO: 35. In some embodiments, the isolated nucleic acid molecule comprises a nucleotide sequence that is at least about 80%, 81%, 82%, 83%, 84%, 85%, 86%, 87%, 88%, 89%, 90%, 91%, 92%, 93%, 94%, 95%, 96%, 97%, 98%, or 99% identical to a nucleotide sequence of SEQ ID NO: 35. In some embodiments, the nucleic acid molecule comprises a nucleic acid sequence of SEQ ID NO: 36. In some embodiments, the isolated nucleic acid molecule comprises a nucleotide sequence that is at least about 80%, 81%, 82%, 83%, 84%, 85%, 86%, 87%, 88%, 89%, 90%, 91%, 92%, 93%, 94%, 95%, 96%, 97%, 98%, or 99% identical to a nucleotide sequence of SEQ ID NO: 36. In some embodiments, the nucleic acid molecule comprises a nucleic acid sequence of SEQ ID NO: 37. In some embodiments, the isolated nucleic acid molecule comprises a nucleotide sequence that is at least about 80%, 81%, 82%, 83%, 84%, 85%, 86%, 87%, 88%, 89%, 90%, 91%, 92%, 93%, 94%, 95%, 96%, 97%, 98%, or 99% identical to a nucleotide sequence of SEQ ID NO: 37. In some embodiments, the nucleic acid molecule comprises a nucleic acid sequence of SEQ ID NO: 38. In some embodiments, the isolated nucleic acid molecule comprises a nucleotide sequence that is at least about 80%, 81%, 82%, 83%, 84%, 85%, 86%, 87%, 88%, 89%, 90%, 91%, 92%, 93%, 94%, 95%, 96%, 97%, 98%, or 99% identical to a nucleotide sequence of SEQ ID NO: 38.

The term "encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (e.g., rRNA, tRNA and mRNA) or a defined sequence of amino acids and the biological properties resulting therefrom. Thus, a gene, cDNA, or RNA, encodes a protein if transcription and translation of mRNA corresponding to that gene produces the protein in a cell or other biological system. Both the coding strand, the nucleotide sequence of which is identical to the mRNA sequence, and the non-coding strand, used as the template for transcription of a gene or cDNA, can be referred to as encoding the protein or other product of that gene or cDNA.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or a RNA may also include introns to the extent that the nucleotide sequence encoding the protein may in some version contain an intron(s).

The term "isolated" refers to a homogenous population of molecules (such as synthetic polynucleotides or polypeptides) which have been substantially separated and/or purified away from other components of the system the molecules are produced in, such as a recombinant cell, as well as a protein that has been subjected to at least one purification or isolation step. "Isolated" refers to a molecule that is substantially free of other cellular material and/or chemicals and encompasses molecules that are isolated to a higher purity, such as to 80%, 81%, 82%, 83%, 84%, 85%, 86%, 87%, 88%, 89%, 90%, 91%, 92%, 93%, 94%, 95%, 96%, 97%, 98%, 99% or 100% purity.

In some embodiments, the present disclosure provides an expression vector comprising the nucleic acid molecules described (e.g., SEQ ID NOS: 90, 89, 87, 88, 33, 34, 35, 36, 37, or 38). In some embodiments, the expression vector comprises a nucleic acid molecule comprising a nucleotide sequence that is at least about 80%, 81%, 82%, 83%, 84%, 85%, 86%, 87%, 88%, 89%, 90%, 91%, 92%, 93%, 94%, 95%, 96%, 97%, 98%, or 99% identical to a nucleotide sequence of SEQ ID NOS: 90, 89, 87, 88, 33, 34, 35, 36, 37, or 38.

In some embodiments, the expression vector comprises a nucleic acid molecule of SEQ ID NO: 90. In some embodiments, the expression vector comprises a nucleic acid molecule comprising a nucleotide sequence that is at least about 80%, 81%, 82%, 83%, 84%, 85%, 86%, 87%, 88%, 89%, 90%, 91%, 92%, 93%, 94%, 95%, 96%, 97%, 98%, or 99% identical to a nucleotide sequence of SEQ ID NO: 90. In some embodiments, the expression vector comprises a nucleic acid molecule of SEQ ID NO: 89. In some embodiments, the expression vector comprises a nucleic acid molecule comprising a nucleotide sequence that is at least about 80%, 81%, 82%, 83%, 84%, 85%, 86%, 87%, 88%, 89%, 90%, 91%, 92%, 93%, 94%, 95%, 96%, 97%, 98%, or 99% identical to a nucleotide sequence of SEQ ID NO: 89. In some embodiments, the expression vector comprises a nucleic acid molecule of SEQ ID NO: 87. In some embodiments, the expression vector comprises a nucleic acid molecule comprising a nucleotide sequence that is at least about 80%, 81%, 82%, 83%, 84%, 85%, 86%, 87%, 88%, 89%, 90%, 91%, 92%, 93%, 94%, 95%, 96%, 97%, 98%, or 99% identical to a nucleotide sequence of SEQ ID NO: 87. In some embodiments, the expression vector comprises a nucleic acid molecule of SEQ ID NO: 88. In some embodiments, the expression vector comprises a nucleic acid molecule comprising a nucleotide sequence that is at least about 80%, 81%, 82%, 83%, 84%, 85%, 86%, 87%, 88%, 89%, 90%, 91%, 92%, 93%, 94%, 95%, 96%, 97%, 98%, or 99% identical to a nucleotide sequence of SEQ ID NO: 88. In some embodiments, the expression vector comprises a nucleic acid molecule of SEQ ID NO: 33. In some embodiments, the expression vector comprises a nucleic acid molecule comprising a nucleotide sequence that is at least about 80%, 81%, 82%, 83%, 84%, 85%, 86%, 87%, 88%, 89%, 90%, 91%, 92%, 93%, 94%, 95%, 96%, 97%, 98%, or 99% identical to a nucleotide sequence of SEQ ID NO: 33. In some embodiments, the expression vector comprises a nucleic acid molecule of SEQ ID NO: 34. In some embodiments, the expression vector comprises a nucleic acid molecule comprising a nucleotide sequence that is at least about 80%, 81%, 82%, 83%, 84%, 85%, 86%, 87%, 88%, 89%, 90%, 91%, 92%, 93%, 94%, 95%, 96%, 97%, 98%, or 99% identical to a nucleotide sequence of SEQ ID NO: 34. In some embodiments, the expression vector comprises a nucleic acid molecule of SEQ ID NO: 35. In some embodiments, the expression vector comprises a nucleic acid molecule comprising a nucleotide sequence that is at least about 80%, 81%, 82%, 83%, 84%, 85%, 86%, 87%, 88%, 89%, 90%, 91%, 92%, 93%, 94%, 95%, 96%, 97%, 98%, or 99% identical to a nucleotide sequence of SEQ ID NO: 35. In some embodiments, the expression vector comprises a nucleic acid molecule of SEQ ID NO: 36. In some embodiments, the expression vector comprises a nucleic acid molecule comprising a nucleotide sequence that is at least about 80%, 81%, 82%, 83%, 84%, 85%, 86%, 87%, 88%, 89%, 90%, 91%, 92%, 93%, 94%, 95%, 96%, 97%, 98%, or 99% identical to a nucleotide sequence of SEQ ID NO: 36. In some embodiments, the expression vector comprises a nucleic acid molecule of SEQ ID NO: 37. In some embodiments, the expression vector comprises a nucleic acid molecule comprising a nucleotide sequence that is at least about 80%, 81%, 82%, 83%, 84%, 85%, 86%, 87%, 88%, 89%, 90%, 91%, 92%, 93%, 94%, 95%, 96%, 97%, 98%, or 99% identical to a nucleotide sequence of SEQ ID NO: 37. In some embodiments, the expression vector comprises a nucleic acid molecule of SEQ ID NO: 38. In some embodiments, the expression vector comprises a nucleic acid molecule comprising a nucleotide sequence that is at least about 80%, 81%, 82%, 83%, 84%, 85%, 86%, 87%, 88%, 89%, 90%, 91%, 92%, 93%, 94%, 95%, 96%, 97%, 98%, or 99% identical to a nucleotide sequence of SEQ ID NO: 38.

The nucleic acid molecules described encode for amino acids with sequences selected from the group consisting of SEQ ID NOS: 86, 85, 83, 84, 27, 28, 29, 30, 31 and 32, or a variant thereof. In some embodiments, the expression vector comprises a nucleic acid molecule encoding the amino acid sequence of SEQ ID NO: 86. In some embodiments, the expression vector comprises a nucleic acid molecule encoding an amino acid sequence that is at least about 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence of SEQ ID NO: 86. In some embodiments, the expression vector comprises a nucleic acid molecule encoding the amino acid sequence of SEQ ID NO: 85. In some embodiments, the expression vector comprises a nucleic acid molecule encoding an amino acid sequence that is at least about 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence of SEQ ID NO: 85. In some embodiments, the expression vector comprises a nucleic acid molecule encoding the amino acid sequence of SEQ ID NO: 83. In some embodiments, the expression vector comprises a nucleic acid molecule encoding an amino acid sequence that is at least about 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence of SEQ ID NO: 83. In some embodiments, the expression vector comprises a nucleic acid molecule encoding the amino acid sequence of SEQ ID NO: 84. In some embodiments, the expression vector comprises a nucleic acid molecule encoding an amino acid sequence that is at least about 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence of SEQ ID NO: 84. In some embodiments, the expression vector comprises a nucleic acid molecule encoding the amino acid sequence of SEQ ID NO: 27. In some embodiments, the expression vector comprises a nucleic acid molecule encoding an amino acid sequence that is at least about 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence of SEQ ID NO: 27. In some embodiments, the expression vector comprises a nucleic acid molecule encoding the amino acid sequence of SEQ ID NO: 28. In some embodiments, the expression vector comprises a nucleic acid molecule encoding an amino acid sequence that is at least about 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence of SEQ ID NO: 28. In some embodiments, the expression vector comprises a nucleic acid molecule encoding the amino acid sequence of SEQ ID NO: 29. In some embodiments, the expression vector comprises a nucleic acid molecule encoding an amino acid sequence that is at least about 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence of SEQ ID NO: 29. In some embodiments, the expression vector comprises a nucleic acid molecule encoding the amino acid sequence of SEQ ID NO: 30. In some embodiments, the expression vector comprises a nucleic acid molecule encoding an amino acid sequence that is at least about 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence of SEQ ID NO: 30. In some embodiments, the expression vector comprises a nucleic acid molecule encoding the amino acid sequence of SEQ ID NO: 31. In some embodiments, the expression vector comprises a nucleic acid molecule encoding an amino acid sequence that is at least about 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence of SEQ ID NO: 31. In some embodiments, the expression vector comprises a nucleic acid molecule encoding the amino acid sequence of SEQ ID NO: 32. In some embodiments, the expression vector comprises a nucleic acid molecule encoding an amino acid sequence that is at least about 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence of SEQ ID NO: 32.

Herein, the structure of nucleic acid molecules is in places defined in the basis of % sequence identity with a recited reference sequence (with a given SEQ ID NO). In this context, % sequence identity regarding nucleic acid molecules refers to the similarity between at least two different nucleic acid sequences. When a position in both of the two compared sequences is occupied by the same base e.g., if a position in each of two DNA molecules is occupied by adenine, then the molecules are identical at that position. The percent of identity between two sequences is a function of the number of matching or homologous positions shared by the two sequences divided by the number of positions compared and multiplied by 100. For example, if 6 of 10 of the positions in two sequences are matched or homologous then the two sequences are 60% identical (or homologous). By way of example, the DNA sequences ATTGCC and TATGGC share 50% identity (or homology). Generally, a comparison is made when two sequences are aligned to give maximum homology. The respective percent identity can be determined by standard alignment algorithms, for example, the Basic Local Alignment Search Tool (BLAST) described by Altshul et al. ((1990) J. Mol. Biol. 215:403-10); the algorithm of Needleman et al. ((1970) J. Mol. Biol. 48:444-53); or the algorithm of Meyers et al. ((1988) Comput. Appl. Biosci. 4:11-17). A set of parameters may be the Blosum 62 scoring matrix with a gap penalty of 12, a gap extend penalty of 4, and a frameshift gap penalty of 5. The percent identity between two nucleotide sequences can also be determined using the algorithm of Meyers and Miller ((1989) CABIOS 4:11-17), which has been incorporated into the ALIGN program (version 2.0), using a PAM120 weight residue table, a gap length penalty of 12, and a gap penalty of 4. The percent identity is usually calculated by comparing sequences of similar length.

The term "expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, including cosmids, plasmids (e.g., naked or contained in liposomes) and viruses (e.g., lentiviruses, retroviruses, adenoviruses, and adeno-associated viruses) that incorporate the recombinant polynucleotide.

In one embodiment, the present disclosure provides a cell expressing the nucleic acid molecule described herein. In one embodiment, the present disclosure provides a cell expressing a CAR of the present disclosure. In one embodiment, the CAR of the present disclosure comprises an amino acid sequence selected from the group consisting of SEQ ID NOS: 86, 85, 83, 84, 27, 28, 29, 30, 31 and 32. In some embodiments, the CAR of the present disclosure comprises an amino acid sequence having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98% or at least 99%, sequence identity with any one of SEQ ID NOS: 86, 85, 83, 84, 27, 28, 29, 30, 31 and 32.

In some embodiments, the CAR comprises an amino acid sequence of SEQ ID NO: 86. In some embodiments, the CAR comprises an amino acid sequence of SEQ ID NO: 85. In some embodiments, the CAR comprises an amino acid sequence of SEQ ID NO: 83. In some embodiments, the CAR comprises an amino acid sequence of SEQ ID NO: 84. In some embodiments, the CAR comprises an amino acid sequence of SEQ ID NO: 27. In some embodiments, the CAR comprises an amino acid sequence of SEQ ID NO: 28. In some embodiments, the CAR comprises an amino acid sequence of SEQ ID NO: 29. In some embodiments, the CAR comprises an amino acid sequence of SEQ ID NO: 30. In some embodiments, the CAR comprises an amino acid sequence of SEQ ID NO: 31. In some embodiments, the CAR comprises an amino acid sequence of SEQ ID NO: 32.

In some embodiments, the CAR comprises an amino acid sequence having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98% or at least 99%, sequence identity with SEQ ID NO: 86. In some embodiments, the CAR comprises an amino acid sequence having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98% or at least 99%, sequence identity with SEQ ID NO: 85. In some embodiments, the CAR comprises an amino acid sequence having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98% or at least 99%, sequence identity with SEQ ID NO: 83. In some embodiments, the CAR comprises an amino acid sequence having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98% or at least 99%, sequence identity with SEQ ID NO: 84. In some embodiments, the CAR comprises an amino acid sequence having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98% or at least 99%, sequence identity with SEQ ID NO: 27. In some embodiments, the CAR comprises an amino acid sequence having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 9'7%, at least 98% or at least 99%, sequence identity with SEQ ID NO: 28. In some embodiments, the CAR comprises an amino acid sequence having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98% or at least 99%, sequence identity with SEQ ID NO: 29. In some embodiments, the CAR comprises an amino acid sequence having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98% or at least 99%, sequence identity with SEQ ID NO: 30. In some embodiments, the CAR comprises an amino acid sequence having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98% or at least 99%, sequence identity with SEQ ID NO: 31. In some embodiments, the CAR comprises an amino acid sequence having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98% or at least 99%, sequence identity with SEQ ID NO: 32.

In one aspect, the present disclosure provides isolated immunoresponsive cells comprising the CARs described herein. In some embodiments, the isolated immunoresponsive cell is transduced with the CAR, for example, the CAR is constitutively expressed on the surface of the immunoresponsive cell. In certain embodiments, the isolated immunoresponsive cell is further transduced with at least one co-stimulatory ligand such that the immunoresponsive cell expresses the at least one co-stimulatory ligand. In certain embodiments, the at least one co-stimulatory ligand is selected from the group consisting of 4-1BBL, CD48, CD70, CD80, CD86, OX40L, TNFRSF14, and combinations thereof. In certain embodiments, the isolated immunoresponsive cell is further transduced with at least one cytokine such that the immunoresponsive cell secretes the at least one cytokine. In certain embodiments, the at least cytokine is selected from the group consisting of IL-2, IL-3, IL-6, IL-7, IL-11, IL-12, IL-15, IL-17, IL-21, and combinations thereof. In some embodiments, the isolated immunoresponsive cell is selected from the group consisting of a T lymphocyte (T cell), a Natural Killer (NK) cell, a cytotoxic T lymphocyte (CTL), a regulatory T cell, a human embryonic stem cell, a lymphoid progenitor cell, a T cell-precursor cell, and a pluripotent stem cell from which lymphoid cells may be differentiated.

The inventive nucleic acid sequence encoding a CAR may be introduced into a cell by "transfection", "transformation", or "transduction". "Transfection", "transformation", or "transduction", as used herein, refer to the introduction of one or more exogenous polynucleotides into a host cell by using physical or chemical methods. Many transfection techniques are known in the art and include, for example, calcium phosphate DNA co-precipitation (see, e.g., Murray E. J. (ed.), Methods in Molecular Biology, Vol. 7, Gene Transfer and Expression Protocols, Humana Press (1991)); DEAE-dextran; electroporation; cationic liposome-mediated transfection; tungsten particle-facilitated microparticle bombardment (Johnston, Nature, 346: 776-777 (1990)); and strontium phosphate DNA co-precipitation (Brash et al., Mol. Cell Biol., 7: 2031-2034 (1987)). Phage or viral vectors can be introduced into host cells, after growth of infectious particles in suitable packaging cells, many of which are commercially available.

In one embodiment, the CAR T cells of the disclosure can be generated by introducing a lentiviral vector comprising a desired CAR, for example, a CAR comprising anti-GPRC5D, CD8a hinge and transmembrane domain, and human 4-1BB and CD3-zeta signaling domains, into the cells. The CAR T cells of the invention are able to replicate in vivo resulting in long-term persistence that can lead to sustained tumor control.

Embodiments of the invention further provide host cells comprising any of the recombinant expression vectors described herein. As used herein, the term "host cell" refers to any type of cell that can contain the recombinant expression vector. The host cell can be a eukaryotic cell, e.g., plant, animal, or algae, fungi, or can be a prokaryotic cell, e.g., bacteria or protozoa. The host cell can be a cultured cell or a primary cell, i.e., isolated directly from an organism, e.g., a human. The host cell can be an adherent cell or a suspended cell, i.e., a cell that grows in suspension. Suitable host cells are known in the art and include, for instance, DH5a E. coli cells, Chinese hamster ovarian cells, monkey VERO cells, COS cells, HEK293 cells, and the like. For purposes of amplifying or replicating the recombinant expression vector, the host cell may be a prokaryotic cell, e.g., a DH5α cell. For purposes of producing a recombinant CAR, polypeptide, or protein, the host cell may be a mammalian cell. The host cell may be a human cell. While the host cell can be of any cell type, can originate from any type of tissue, and can be of any developmental stage, the host cell may be a peripheral blood lymphocyte (PBL). The host cell may be a T cell.

For purposes herein, the T cell can be any T cell, such as a cultured T cell, e.g., a primary T cell, or a T cell from a cultured T cell line, e.g., Jurkat, SupT1, etc., or a T cell obtained from a mammal. If obtained from a mammal, the T cell can be obtained from numerous sources, including but not limited to bone marrow, blood, lymph node, the thymus, or other tissues or fluids. T cells can also be enriched for or purified. The T cell may be a human T cell. The T cell may be a T cell isolated from a human. The T cell can be any type of T cell and can be of any developmental stage, including but not limited to, $CD4^+/CD8^+$ double positive T cells, $CD8^+$ T cells (e.g., cytotoxic T cells), $CD4^+$ helper T cells, e.g., $Th_1$ and $Th_2$ cells, peripheral blood mononuclear cells (PBMCs), peripheral blood leukocytes (PBLs), tumor infiltrating cells, memory T cells, naïve T cells, and the like. The T cell may be a $CD8^+$ T cell or a $CD4^+$ T cell.

T cells may also include "NKT cells", which refer to a specialized population of T cells that express a semi-invariant $\alpha\beta$ T-cell receptor, but also express a variety of molecular markers that are typically associated with NK cells, such as NK1.1. NKT cells include NK1.1+ and NK1.1−, as well as CD4+, CD4−, CD8+ and CD8− cells. The TCR on NKT cells is unique in that it recognizes glycolipid antigens presented by the MHC I-like molecule CD Id. NKT cells can have either protective or deleterious effects due to their abilities to produce cytokines that promote either inflammation or immune tolerance. Also included are "gamma-delta T cells ($\gamma\delta$ T cells)," which refer to a specialized population that to a small subset of T cells possessing a distinct TCR on their surface, and unlike the majority of T cells in which the TCR is composed of two glycoprotein chains designated $\alpha$- and $\beta$-TCR chains, the TCR in $\gamma\delta$ T cells is made up of a $\gamma$-chain and a $\delta$-chain. $\gamma\delta$ T cells can play a role in immunosurveillance and immunoregulation, and were found to be an important source of IL-17 and to induce robust CD8+ cytotoxic T cell response. Also included are "regulatory T cells" or "Tregs" which refer to T cells that suppress an abnormal or excessive immune response and play a role in immune tolerance. Tregs cells are typically transcription factor Foxp3-positive CD4+T cells and can also include transcription factor Foxp3-negative regulatory T cells that are IL-10-producing CD4+T cells.

T-cell lines are available from, e.g., the American Type Culture Collection (ATCC, Manassas, VA), and the German Collection of Microorganisms and Cell Cultures (DSMZ) and include, for example, Jurkat cells (ATCC TIB-152), Sup-Tl cells (ATCC CRL-1942), RPMI 8402 cells (DSMZ ACC-290), Karpas 45 cells (DSMZ ACC-545), and derivatives thereof.

In another embodiment, the host cell is a natural killer (NK) cell. NK cells are a type of cytotoxic lymphocyte that plays a role in the innate immune system. NK cells are defined as large granular lymphocytes and constitute the third kind of cells differentiated from the common lymphoid progenitor which also gives rise to B and T lymphocytes (see, e.g., Immunobiology, 5th ed., Janeway et al., eds., Garland Publishing, New York, NY (2001)). NK cells differentiate and mature in the bone marrow, lymph node, spleen, tonsils, and thymus. Following maturation, NK cells enter into the circulation as large lymphocytes with distinctive cytotoxic granules. NK cells are able to recognize and kill some abnormal cells, such as, for example, some tumor cells and virus-infected cells, and are thought to be important in the innate immune defense against intracellular pathogens. As described above with respect to T-cells, the NK cell can be any NK cell, such as a cultured NK cell, e.g., a primary NK cell, or an NK cell from a cultured NK cell line, or an NK cell obtained from a mammal. If obtained from a mammal, the NK cell can be obtained from numerous sources, including but not limited to blood, bone marrow, lymph node, the thymus, or other tissues or fluids. NK cells can also be enriched for or purified. The NK cell preferably is a human NK cell (e.g., isolated from a human). NK cell lines are available from, e.g., the American Type Culture Collection (ATCC, Manassas, VA) and include, for example, NK-92 cells (ATCC CRL-2407), NK92MI cells (ATCC CRL-2408), and derivatives thereof.

Also provided are a population of cells comprising at least one host cell described herein. The population of cells can be a heterogeneous population comprising the host cell comprising any of the recombinant expression vectors described, in addition to at least one other cell, e.g., a host cell (e.g., a T cell), which does not comprise any of the recombinant expression vectors, or a cell other than a T cell, e.g., a B cell, a macrophage, an erythrocyte, a neutrophil, a hepatocyte, an endothelial cell, an epithelial cell, a muscle cell, a brain cell, etc. Alternatively, the population of cells can be a substantially homogeneous population, in which the population comprises mainly host cells (e.g., consisting essentially of) comprising the recombinant expression vector. The population also can be a clonal population of cells, in which all cells of the population are clones of a single host cell comprising a recombinant expression vector, such that all cells of the population comprise the recombinant expression vector. In one embodiment, the population of cells is a clonal population comprising host cells comprising a recombinant expression vector as described herein.

Pharmaceutical Compositions/Administration

In embodiments of the present disclosure, the CAR-expressing cells may be provided in compositions, e.g., suitable pharmaceutical composition(s) comprising the CAR-expressing cells and a pharmaceutically acceptable carrier. In one aspect, the present disclosure provides pharmaceutical compositions comprising an effective amount of a lymphocyte expressing one or more of the CARs described and a pharmaceutically acceptable excipient. Pharmaceutical compositions of the present disclosure may comprise a CAR-expressing cell, e.g., a plurality of CAR-expressing cells, as described herein, in combination with one or more pharmaceutically or physiologically acceptable carriers, excipients or diluents. A pharmaceutically acceptable carrier can be an ingredient in a pharmaceutical composition, other than an active ingredient, which is nontoxic to the subject.

A pharmaceutically acceptable carrier can include, but is not limited to, a buffer, excipient, stabilizer, or preservative. Examples of pharmaceutically acceptable carriers are solvents, dispersion media, coatings, antibacterial and antifungal agents, isotonic and absorption delaying agents, and the like that are physiologically compatible, such as salts, buffers, antioxidants, saccharides, aqueous or non-aqueous carriers, preservatives, wetting agents, surfactants or emulsifying agents, or combinations thereof. The amounts of pharmaceutically acceptable carrier(s) in the pharmaceutical compositions may be determined experimentally based on the activities of the carrier(s) and the desired characteristics of the formulation, such as stability and/or minimal oxidation Such compositions may comprise buffers such as acetic acid, citric acid, formic acid, succinic acid, phosphoric acid, carbonic acid, malic acid, aspartic acid, histidine, boric acid, Tris buffers, HEPPSO, HEPES, neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); antibacterial and antifungal agents; and preservatives.

Compositions of the present disclosure can be formulated for a variety of means of parenteral or non-parenteral administration. In one embodiment, the compositions can be formulated for infusion or intravenous administration. Compositions disclosed herein can be provided, for example, as sterile liquid preparations, e.g., isotonic aqueous solutions, emulsions, suspensions, dispersions, or viscous compositions, which may be buffered to a desirable pH. Formulations suitable for oral administration can include liquid solutions, capsules, sachets, tablets, lozenges, and troches, powders liquid suspensions in an appropriate liquid and emulsions.

The term "pharmaceutically acceptable," as used herein with regard to pharmaceutical compositions, means approved by a regulatory agency of the Federal or a state government or listed in the U.S. Pharmacopeia or other generally recognized pharmacopeia for use in animals and/or in humans.

In one aspect, the disclosure relates to administering a genetically modified T cell expressing a CAR for the treatment of a subject having cancer or at risk of having cancer using lymphocyte infusion. In at least one embodiment, autologous lymphocyte infusion is used in the treatment. Autologous PBMCs are collected from a subject in need of treatment and T cells are activated and expanded using the methods described herein and known in the art and then infused back into the subject.

In one aspect, the disclosure relates generally to the treatment of a subject at risk of developing cancer. The invention also includes treating a malignancy or an autoimmune disease in which chemotherapy and/or immunotherapy in a subject results in significant immunosuppression, thereby increasing the risk of the subject developing cancer. In one aspect, the present disclosure provides methods of preventing cancer, the methods comprising administering an amount of a lymphocyte expressing one or more of the CARs described to a subject in need thereof.

In one aspect, the present disclosure provides methods of treating a subject having cancer, the methods comprising administering a therapeutically effective amount of a lymphocyte expressing one or more of the CARs described to a subject in need thereof, whereby the lymphocyte induces or modulates killing of cancer cells in the subject.

In another aspect, the present disclosure provides methods of reducing tumor burden in a subject having cancer, the methods comprising administering a therapeutically effective amount of a lymphocyte expressing one or more of the CARs described herein to a subject in need thereof, whereby the lymphocyte induces killing of cancer cells in the subject. In another aspect, the present disclosure provides methods of increasing survival of a subject having cancer, the methods comprising administering a therapeutically effective amount of a lymphocyte expressing one or more of the CARs described to a subject in need thereof, whereby the survival of the subject is lengthened. Generally, the lymphocytes expressing the CAR(s) induce killing of cancer cells in the subject and result in reduction or eradication of the tumors/cancer cells in the subject. A non-limiting list of cancers, inclusive of metastatic lesions, that can be targeted, includes lung cancer, gastric cancer, colon cancer, hepatocellular carcinoma, renal cell carcinoma, bladder urothelial carcinoma, metastatic melanoma, breast cancer, ovarian cancer, cervical cancer, head and neck cancer, pancreatic cancer, glioma, glioblastoma, non-Hodgkin's lymphoma (NHL), acute lymphocytic leukemia (ALL), chronic lymphocytic leukemia (CLL), chronic myelogenous leukemia (CML), smoldering multiple myeloma (SMM), multiple myeloma (MM), acute myeloid leukemia (AML), and combinations thereof. In one embodiment, the cancer being treated in a subject is multiple myeloma.

In one aspect, the methods described herein are applicable to treatment of non-cancerous conditions that are at risk of developing into a cancerous condition, such as, e.g., monoclonal gammopathy of undetermined significance (MGUS), which is at risk of developing into a blood cancer, such as MM or lymphoma, and myelodysplastic syndrome, which is at risk of developing into a blood cancer, such as leukemia.

In one aspect, methods of treating a subject having cancer are provided that comprise administering a therapeutically effective amount of a lymphocyte expressing a CAR, the CAR having an extracellular antigen-binding domain that binds the GPRC5D antigen, to a subject in need thereof, whereby the lymphocyte induces killing of cancer cells in the subject. In some embodiments, the at least one of the CARs comprises an amino acid sequence selected from the group consisting of SEQ ID NOS: 86, 85, 83, 84, 27, 28, 29, 30, 31 and 32.

In one aspect, a method of targeted killing of a cancer cell is disclosed, the method comprising contacting the cancer cell with a lymphocyte expressing one or more of the CARs described, whereby the lymphocyte induces killing of the cancer cell. A non-limiting list of cancer cells, inclusive of metastatic cancer cells, that can be targeted include a lung cancer cell, a gastric cancer cell, a colon cancer cell, a hepatocellular carcinoma cell, a renal cell carcinoma cell, a bladder urothelial carcinoma cell, a metastatic melanoma cell, a breast cancer cell, an ovarian cancer cell, a cervical cancer cell, a head and neck cancer cell, a pancreatic cancer cell, a glioma cell, a glioblastoma cell, and a non-Hodgkin's lymphoma (NHL) cell, an acute lymphocytic leukemia (ALL) cell, a chronic lymphocytic leukemia (CLL) cell, a chronic myelogenous leukemia (CML) cell, a smoldering multiple myeloma (SMM) cell, a multiple myeloma (MM) cell, an acute myeloid leukemia (AML) cell, and combinations thereof. In one embodiment, the cancer cell is a multiple myeloma cell.

Pharmaceutical compositions of the present disclosure may be administered in a manner appropriate to the disease to be treated (or prevented). The quantity and frequency of administration will be determined by such factors as the condition of the subject, and the type and severity of the subject's disease, although appropriate dosages may be determined by clinical trials.

The terms "treat" or "treatment" refer to therapeutic treatment wherein the object is to slow down (lessen) an undesired physiological change or disease, or provide a beneficial or desired clinical outcome during treatment. Beneficial or desired clinical outcomes include alleviation of symptoms, diminishment of extent of disease, stabilized (i.e., not worsening) state of disease, delay or slowing of disease progression, amelioration or palliation of the disease state, and/or remission (whether partial or total), whether detectable or undetectable. "Treatment" can also mean prolonging survival as compared to expected survival if a subject was not receiving treatment. Those in need of treatment include those subjects already with the undesired physiological change or disease as well as those subjects prone to have the physiological change or disease.

A "therapeutically effective amount" or "effective amount", used interchangeably herein, refers to an amount effective, at dosages and for periods of time necessary, to achieve a desired therapeutic result. A therapeutically effective amount may vary according to factors such as the disease state, age, sex, and weight of the individual, and the ability of a therapeutic or a combination of therapeutics to elicit a desired response in the individual. Example indicators of an effective therapeutic or combination of therapeutics that include, for example, improved well-being of the patient, reduction of a tumor burden, arrested or slowed growth of a tumor, and/or absence of metastasis of cancer cells to other locations in the body.

As used herein, the term "subject" refers to an animal. The terms "subject" and "patient" may be used interchangeably herein in reference to a subject. As such, a "subject" includes a human that is being treated for a disease, or prevention of a disease, as a patient.

The methods described herein may be used to treat an animal subject belonging to any classification. Examples of such animals include mammals. Mammals, include, but are not limited to, mammals of the order Rodentia, such as mice and hamsters, and mammals of the order Logomorpha, such as rabbits. The mammals may be from the order Carnivora, including Felines (cats) and Canines (dogs). The mammals may be from the order Artiodactyla, including Bovines (cows) and Swines (pigs) or of the order Perssodactyla, including Equines (horses). The mammals may be of the order Primates, Ceboids, or Simoids (monkeys) or of the order Anthropoids (humans and apes). In one embodiment, the mammal is a human.

When a therapeutically effective amount is indicated, the precise amount of the compositions of the present disclosure to be administered can be determined by a physician with consideration of individual differences in age, weight, tumor size, extent of infection or metastasis, and condition of the subject. It can generally be stated that a pharmaceutical composition comprising the T cells described herein may be administered at a dosage of about $10^4$ to about $10^{10}$ cells/kg body weight, in some instances about $10^5$ to about $10^6$ cells/kg body weight, including all integer values within those ranges. In some embodiments, a pharmaceutical composition comprising the T cells described herein may be administered at a dosage of about $10^6$ cells/kg body weight. T cell compositions may also be administered multiple times at these dosages. The cells can be administered by using infusion techniques that are commonly known in immunotherapy (see, e.g., Rosenberg et al., *New Eng. J. of Med.* 319:1676, 1988).

Delivery systems useful in the context of embodiments of the invention may include time-released, delayed release, and sustained release delivery systems such that the delivery of the T cell compositions occurs prior to, and with sufficient time to cause, sensitization of the site to be treated. The composition can be used in conjunction with other therapeutic agents or therapies. Such systems can avoid repeated administrations of the composition, thereby increasing convenience to the subject and the physician, and may be particularly suitable for certain composition embodiments of the invention.

Many types of release delivery systems are available and known to those of ordinary skill in the art. They include polymer base systems such as poly(lactide-glycolide), copolyoxalates, polyesteramides, polyorthoesters, polycaprolactones, polyhydroxybutyric acid, and polyanhydrides. Microcapsules of the foregoing polymers containing drugs are described in, for example, U.S. Pat. No. 5,075,109. Delivery systems also include non-polymer systems that are lipids including sterols such as cholesterol, cholesterol esters, and fatty acids or neutral fats such as mono-di- and tri-glycerides; sylastic systems; peptide based systems; hydrogel release systems; wax coatings; compressed tablets using conventional binders and excipients; partially fused implants; and the like. Specific examples include, but are not limited to: (a) erosional systems in which the active composition is contained in a form within a matrix such as those described in U.S. Pat. Nos. 4,452,775; 4,667,014; 4,748,034; and 5,239,660 and (b) diffusional systems in which an active component permeates at a controlled rate from a polymer such as described in U.S. Pat. Nos. 3,854,480 and 3,832,253. In addition, pump-based hardware delivery systems can be used, some of which are adapted for implantation.

In certain aspects, it may be desirable to administer activated T cells to a subject and then subsequently redraw blood (or have an apheresis performed), activate the T cells according to the present disclosure, and reinfuse the subject with these activated and expanded T cells. This process can be carried out multiple times every few weeks. In certain aspects, T cells can be activated from blood draws of from 10 cc to 400 cc. In certain aspects, T cells are activated from blood draws of 20 cc, 30 cc, 40 cc, 50 cc, 60 cc, 70 cc, 80 cc, 90 cc, or 100 cc.

The administration of the CAR-T cells and compositions may be carried out in any manner, e.g., by parenteral or nonparenteral administration, including by aerosol inhalation, injection, infusions, ingestion, transfusion, implantation or transplantation. For example, the CAR-T cells and compositions described herein may be administered to a patient trans-arterially, intradermally, subcutaneously, intratumorally, intramedullary, intranodally, intramuscularly, by intravenous (i.v.) injection, or intraperitoneally. In one aspect, the compositions of the present disclosure are administered by i.v. injection. In one aspect, the compositions of the present disclosure are administered to a subject by intradermal or subcutaneous injection. The compositions of T cells may be injected, for instance, directly into a tumor, lymph node, tissue, organ, or site of infection.

Administration can be autologous or non-autologous. For example, immunoresponsive cells expressing a G-protein coupled receptor (e.g., GPRC5D)-specific CAR can be obtained from one subject, and administered to the same subject or a different, compatible subject. Peripheral blood derived T cells of the present disclosure, or expanded T cells (e.g., in vivo, ex vivo or in vitro derived) can be administered via, e.g., intravenous injection, localized injection, systemic injection, catheter administration, or parenteral administration.

In particular embodiments, subjects may undergo leukapheresis, wherein leukocytes are collected, enriched, or depleted ex vivo to select and/or isolate the cells of interest, e.g., T cells. These T cell isolates may be expanded by methods known in the art and treated such that one or more CAR constructs of the present disclosure may be introduced, thereby creating a CAR-T cell. Subjects in need thereof may subsequently undergo standard treatment with high dose chemotherapy followed by peripheral blood stem cell transplantation. In certain aspects, following or concurrent with the transplant, subjects receive an infusion of the expanded CAR-T cells. In one aspect, expanded cells are administered before or following surgery.

The dosage administered to a patient having a malignancy is sufficient to alleviate or at least partially arrest the disease being treated ("therapeutically effective amount"). The dosage of the above treatments to be administered to a subject will vary with the precise nature of the condition being treated and the recipient of the treatment. The scaling of dosages for human administration can be performed according to practices generally accepted in the art.

The CART T cells of the invention can undergo in vivo T cell expansion and can establish GPRC5D-specific memory cells that persist at high levels for an extended amount of time in blood and bone marrow. In some instances, the CAR T cells of the invention infused into a subject can eliminate cancer cells, e.g., leukemia cells, in vivo in subjects with advanced chemotherapy-resistant cancer.

In one embodiment, a CAR of the present disclosure is introduced into T cells, e.g., using in vitro transcription, and the subject (e.g., human) receives an initial administration of CAR-T cells of the disclosure, and one or more subsequent administrations of the CAR-T cells, wherein the one or more subsequent administrations are administered less than 15 days, e.g., 14, 13, 12, 11, 10, 9, 8, 7, 6, 5, 4, 3, or 2 days after the previous administration. In one embodiment, more than one administration of the CAR-T cells are administered to the subject (e.g., human) per week, e.g., 2, 3, or 4 administrations of the CAR-T cells are administered per week. In one embodiment, the subject receives more than one administration of the CAR-T cells per week (e.g., 2, 3 or 4 administrations per week) (also referred to herein as a cycle), followed by a week of no CAR-T cell administrations, and then one or more additional administration of the CAR-T cells (e.g., more than one administration of the CAR-T cells per week) is administered to the subject. In another embodiment, the subject receives more than one cycle of CAR-T cells, and the time between each cycle is less than 10, 9, 8, 7, 6, 5, 4, or 3 days. In one embodiment, the CAR-T cells are administered every other day for 3 administrations per week. In one embodiment, the CAR-T cells are administered for at least two, three, four, five, six, seven, eight or more weeks.

In one embodiment, administration may be repeated after one day, two days, three days, four days, five days, six days, one week, two weeks, three weeks, one month, five weeks, six weeks, seven weeks, two months, three months, four months, five months, six months or longer. Repeated courses of treatment are also possible, as is chronic administration. The repeated administration may be at the same dose or at a different dose.

The CAR-T cells may be administered in the methods of the invention by maintenance therapy, such as, e.g., once a week for a period of 6 months or more.

In one embodiment, CAR-T cells are generated using lentiviral viral vectors, such as lentivirus. CAR-T cells generated with such viral vectors will generally have stable CAR expression.

In one embodiment, CAR-T cells transiently express CAR vectors for 4, 5, 6, 7, 8, 9, 10, 11, 12, 13, 14, 15 days after transduction. Transient expression of CARs can be affected by RNA CAR vector delivery. In one embodiment, the CAR RNA is transduced into the T cell by electroporation.

If a patient is at high risk of generating an anti-CAR antibody response during the course of transient CAR therapy (such as those generated by RNA transductions), CAR-T infusion breaks should not last more than ten to fourteen days.

A CAR-expressing cell described herein may be used in combination with other known agents and therapies. Administered "in combination", as used herein, means that two (or more) different treatments are delivered to the subject during the course of the subject's treatment e.g., the two or more treatments are delivered after the subject has been diagnosed with the cancer and before the cancer has been cured or eliminated or treatment has ceased for other reasons. In some embodiments, the delivery of one treatment is still occurring when the delivery of the second begins, so that there is overlap in terms of administration. This is sometimes referred to herein as "simultaneous" or "concurrent delivery". In other embodiments, the delivery of one treatment ends before the delivery of the other treatment begins. In some embodiments of either case, the treatment is more effective because of combined administration. For example, the second treatment is more effective, e.g., an equivalent effect is seen with less of the second treatment, or the second treatment reduces symptoms to a greater extent, than would be seen if the second treatment were administered in the absence of the first treatment, or the analogous situation is seen with the first treatment. In some embodiments, delivery is such that the reduction in a symptom, or other parameter related to the disorder is greater than what would be observed with one treatment delivered in the absence of the other. The effect of the two treatments can be partially additive, wholly additive, or greater than additive. The delivery can be such that an effect of the first treatment delivered is still detectable when the second is delivered.

In one embodiment, other therapeutic agents such as factors may be administered before, after, or at the same time (simultaneous with) as the CAR-T cells, including, but not limited to, interleukins, e.g. IL-2, IL-3, IL 6, IL-7, IL-11, IL-12, IL-15, IL-21, as well as the other interleukins, colony stimulating factors, such as G-, M- and GM-CSF, and interferons, e.g., γ-interferon.

A CAR-expressing cell described herein and the at least one additional therapeutic agent can be administered simultaneously, in the same or in separate compositions, or sequentially. For sequential administration, the CAR-expressing cell described herein can be administered first, and the additional agent can be administered second, or the order of administration can be reversed.

In further embodiments, a CAR-expressing cell described herein may be used in a treatment regimen in combination with surgery, radiation, chemotherapy, immunosuppressive agents, such as methotrexate, cyclosporin, azathioprine, mycophenolate, and FK506, antibodies, or other immunoablative agents such as anti-CD3 antibodies or other antibody therapies, cytoxin, fludarabine, cyclosporin, FK506, rapamycin, mycophenolic acid, steroids, FR901228, cytokines, and irradiation.

In one embodiment, a CAR-expressing cell described herein can be used in combination with a chemotherapeutic agent. Example chemotherapeutic agents include, but are not limited to, an anthracycline (e.g., doxorubicin (e.g., liposomal doxorubicin)), a *vinca* alkaloid (e.g., vinblastine, vincristine, vindesine, vinorelbine), an alkylating agent (e.g., cyclophosphamide, decarbazine, melphalan, ifosfamide, temozolomide), an immune cell antibody (e.g., alemtuzamab, gemtuzumab, rituximab, tositumomab), an antimetabolite (including, e.g., folic acid antagonists, pyrimidine analogs, purine analogs and adenosine deaminase inhibitors (e.g., fludarabine)), an mTOR inhibitor, a TNFR glucocorticoid induced TNFR related protein (GITR) agonist, a proteasome inhibitor (e.g., aclacinomycin A, gliotoxin or bortezomib), an immunomodulator such as thalidomide or a thalidomide derivative (e.g., lenalidomide).

A non-exhaustive list of chemotherapeutic agents considered for use in combination therapies include anastrozole (Arimidex®), bicalutamide (Casodex®), bleomycin sulfate (Blenoxane®), busulfan (Myleran®), leucovorin calcium, melphalan (Alkeran®), 6-mercaptopurine (Purinethol®), methotrexate (Folex®), mitoxantrone (Novantrone®), mylotarg, paclitaxel (Taxol®), phoenix (Yttrium90/MX-DTPA), pentostatin, polifeprosan 20 with carmustine implant (Gliadel®), dactinomycin (Actinomycin D, Cosmegan), daunorubicin hydrochloride (Cerubidine®), daunorubicin citrate liposome injection (DaunoXome®), dexamethasone, docetaxel (Taxotere®), doxorubicin hydrochloride (Adriamycin®, Rubex®), etoposide (Vepesid®), busulfan injection (Busulfex®), capecitabine (Xeloda®), N4-pentoxycarbonyl-5-deoxy-5-fluorocytidine, carboplatin (Paraplatin®), carmustine (BiCNU®), chlorambucil (Leukeran®), cisplatin (Platinol®), cladribine (Leustatin®), cyclophosphamide (Cytoxan® or Neosar®), cytarabine, cytosine arabinoside (Cytosar-U®), cytarabine liposome injection (DepoCyt®), dacarbazine (DTIC-Dome®), fludarabine phosphate (Fludara®), 5-fluorouracil (Adrucil®, Efudex®), flutamide (Eulexin®), tezacitibine, Gemcitabine (difluorodeoxycitidine), hydroxyurea (Hydrea®), Idarubicin (Idamycin®), ifosfamide (IFEX®), irinotecan (Camptosar®), L-asparaginase (ELSPAR®), tamoxifen citrate (Nolvadex®), teniposide (Vumon®), 6-thioguanine, thiotepa, tirapazamine (Tirazone®), topotecan hydrochloride for injection (Hycamptin®), vinblastine (Velban®), vincristine (Oncovin®), and vinorelbine (Navelbine®).

Example alkylating agents include, without limitation, nitrogen mustards, ethylenimine derivatives, alkyl sulfonates, nitrosoureas and triazenes): uracil mustard (Aminouracil Mustard®, Chlorethaminacil®, Haemanthamine®, Nordopan®, Uracil Nitrogen Mustard®, Uracillost®, Uracilmostaza®, Uramustin®, Uramustine®), chlormethine (Mustargen®), cyclophosphamide (Cytoxan®, Neosar®, Clafen®, Endoxan®, Procytox®, Revimmune™), ifosfamide (Mitoxana®), melphalan (Alkeran®), Chlorambucil (Leukeran®), pipobroman (Amedel®, Vercyte®), triethylenemelamine (Hemel®, Hexylen®, Hexastat®), Demethyldopan®, Desmethyldopan®, triethylenethiophosphoramine, Temozolomide (Temodar®), thiotepa (Thioplex®), busulfan (Busilvex®, Myleran®), carmustine (BiCNU®), lomustine (CeeNU®), streptozocin (Zanosar®), and Dacarbazine (DTIC-Dome®). Additional example alkylating agents include, without limitation, Oxaliplatin (Eloxatin®); Melphalan (also known as L-PAM, L-sarcolysin, and phenylalanine mustard, Alkeran®); Altretamine (also known as hexamethylmelamine (HMM), Hexylen®); Carmustine (BiCNU®); Bendamustine (Treanda®); Busulfan (Busulfex® and Myleran®); Carboplatin (Paraplatin®); Temozolomide (Temodar® and Temodal®); Dactinomycin (also known as actinomycin-D, Cosmegen®); Lomustine (also known as CCNU, CeeNU®); Cisplatin (also known as CDDP, Platinol® and Platinol®-AQ); Chlorambucil (Leukeran®); Cyclophosphamide (Cytoxan® and Neosar®); Dacarbazine (also known as DTIC, DIC and imidazole carboxamide, DTIC-Dome®); Altretamine (also known as hexamethylmelamine (HMM), Hexylen®); Ifosfamide (Ifex®); Prednumustine; Procarbazine (Matulane®); Mechlorethamine (also known as nitrogen mustard, mustine and mechloroethamine hydrochloride, Mustargen®); Streptozocin (Zanosar®); Thiotepa (also known as thiophosphoamide, TESPA and TSPA, Thioplex®); Cyclophosphamide (Endoxan®, Cytoxan®, Neosar®, Procytox®, Revimmune®); and Bendamustine HCl (Treanda®).

Examples of immunomodulators useful herein include, but are not limited to, e.g., afutuzumab (available from Roche®); pegfilgrastim (Neulasta®); lenalidomide (CC-5013, Revlimid®); thalidomide (Thalomid®), actimid (CC4047); and IRX-2 (mixture of human cytokines including interleukin 1, interleukin 2, and interferon γ, CAS 951209-71-5, available from IRX Therapeutics).

In one embodiment, the subject can be administered an agent which enhances the activity of a CAR-expressing cell. For example, in one embodiment, the agent can be an agent which inhibits an inhibitory molecule. Inhibitory molecules, e.g., Programmed Death 1 (PD1), can, in some embodiments, decrease the ability of a CAR-expressing cell to mount an immune effector response. Examples of inhibitory molecules include PD1, PD-L1, CTLA4, TIM3, LAG3, VISTA, BTLA, TIGIT, LAIR1, CD160, 2B4 and TGFR beta.

A description of example embodiments follows.

Embodiment 1

A chimeric antigen receptor (CAR), comprising an extracellular antigen-binding domain, a transmembrane domain and an intracellular signaling domain, wherein the extracellular antigen-binding domain comprises:
- a heavy chain complementarity determining region 1 (CDR1) having the amino acid sequence of SEQ ID NO: 66, a heavy chain CDR2 having the amino acid sequence of SEQ ID NO: 67, and a heavy chain CDR3 having the amino acid sequence of SEQ ID NO: 68;
- a heavy chain complementarity determining region 1 (CDR1) having the amino acid sequence of SEQ ID NO: 58, a heavy chain CDR2 having the amino acid sequence of SEQ ID NO: 59, and a heavy chain CDR3 having the amino acid sequence of SEQ ID NO: 60;
- a heavy chain complementarity determining region 1 (CDR1) having the amino acid sequence of SEQ ID NO: 39, a heavy chain CDR2 having the amino acid sequence of SEQ ID NO: 40, and a heavy chain CDR3 having the amino acid sequence of SEQ ID NO: 41;
- a heavy chain CDR1 having the amino acid sequence of SEQ ID NO: 42, a heavy chain CDR2 having the amino acid sequence of SEQ ID NO: 43, and a heavy chain CDR3 having the amino acid sequence of SEQ ID NO: 44; or
- a heavy chain CDR1 having the amino acid sequence of SEQ ID NO: 45, a heavy chain CDR2 having the amino acid sequence of SEQ ID NO: 46, and a heavy chain CDR3 having the amino acid sequence of SEQ ID NO: 47;
- wherein the extracellular antigen-binding domain binds the anti-G protein receptor family C group 5 member D (GPRC5D) antigen.

Embodiment 2

The CAR of Embodiment 1, wherein
the extracellular antigen-binding domain comprising the heavy chain CDR1 having the amino acid sequence of SEQ ID NO: 66, the heavy chain CDR2 having the amino acid sequence of SEQ ID NO: 67, and the heavy chain CDR3 having the amino acid sequence of SEQ ID NO: 68, and further comprises a light chain CDR1 having the amino acid sequence of SEQ ID NO: 69, a light chain CDR2 having the amino acid sequence of SEQ ID NO: 70, and a light chain CDR3 having the amino acid sequence of SEQ ID NO: 71;

the extracellular antigen-binding domain comprising the heavy chain CDR1 having the amino acid sequence of SEQ ID NO: 58, the heavy chain CDR2 having the amino acid sequence of SEQ ID NO: 59, and the heavy chain CDR3 having the amino acid sequence of SEQ ID NO: 60, and further comprises a light chain CDR1 having the amino acid sequence of SEQ ID NO: 61, a light chain CDR2 having the amino acid sequence of SEQ ID NO: 62, and a light chain CDR3 having the amino acid sequence of SEQ ID NO: 63;

the extracellular antigen-binding domain comprising the heavy chain CDR1 having the amino acid sequence of SEQ ID NO: 39, the heavy chain CDR2 having the amino acid sequence of SEQ ID NO: 40, and the heavy chain CDR3 having the amino acid sequence of SEQ ID NO: 41, and further comprises a light chain CDR1 having the amino acid sequence of SEQ ID NO: 48, a light chain CDR2 having the amino acid sequence of SEQ ID NO: 49, and a light chain CDR3 having the amino acid sequence of SEQ ID NO: 50;

the extracellular antigen-binding domain comprising the heavy chain CDR1 having the amino acid sequence of SEQ ID NO: 42, the heavy chain CDR2 having the amino acid sequence of SEQ ID NO: 43, and the heavy chain CDR3 having the amino acid sequence of SEQ ID NO: 44, and further comprises a light chain CDR1 having the amino acid sequence of SEQ ID NO: 51, a light chain CDR2 having the amino acid sequence of SEQ ID NO: 52, and a light chain CDR3 having the amino acid sequence of SEQ ID NO: 53; or the extracellular antigen-binding domain comprising the heavy chain CDR1 having the amino acid sequence of SEQ ID NO: 45, the heavy chain CDR2 having the amino acid sequence of SEQ ID NO: 46, and the heavy chain CDR3 having the amino acid sequence of SEQ ID NO: 47, and further comprises a light chain CDR1 having the amino acid sequence of SEQ ID NO: 54, a light chain CDR2 having the amino acid sequence of SEQ ID NO: 55, and a light chain CDR3 having the amino acid sequence of SEQ ID NO: 56.

Embodiment 3

The CAR of Embodiment 1 or 2, wherein the extracellular antigen-binding domain comprises a light chain variable region (LCVR) comprising an amino acid sequence selected from the group consisting of SEQ ID NOS: 73, 65, 1, 3 and 5, or a heavy chain variable region (HCVR) comprising an amino acid sequence selected from the group consisting of SEQ ID NOS: 72, 64, 2, 4, and 6, or a combination of a LCVR comprising an amino acid sequence selected from the group consisting of SEQ ID NOS: 73, 65, 1, 3 and 5, and a HCVR comprising an amino acid sequence selected from the group consisting of SEQ ID NOS: 72, 64, 2, 4, and 6.

Embodiment 4

The CAR of Embodiments 1-3, wherein the extracellular antigen-binding domain comprises:

a light chain variable region comprising an amino acid sequence of SEQ ID NO: 73 and a heavy chain variable region comprising an amino acid sequence of SEQ ID NO: 72;

a light chain variable region comprising an amino acid sequence of SEQ ID NO: 65 and a heavy chain variable region comprising an amino acid sequence of SEQ ID NO: 64;

a light chain variable region comprising an amino acid sequence of SEQ ID NO: 1 and a heavy chain variable region comprising an amino acid sequence of SEQ ID NO: 2;

a light chain variable region comprising an amino acid sequence of SEQ ID NO: 3 and a heavy chain variable region comprising an amino acid sequence of SEQ ID NO: 4; or a light chain variable region comprising an amino acid sequence of SEQ ID NO: 5 and a heavy chain variable region comprising an amino acid sequence of SEQ ID NO: 6.

Embodiment 5

The CAR of any of Embodiments 1-4, wherein the extracellular antigen-binding domain comprises a single-chain variable fragment (scFv).

Embodiment 6

The CAR of Embodiment 5, wherein the scFv comprises a linker polypeptide between the light chain variable region and the heavy chain variable region.

Embodiment 7

The CAR of Embodiment 6, wherein the linker polypeptide comprises an amino acid sequence of SEQ ID NO: 7.

Embodiment 8

The CAR of any of Embodiments 5-7, wherein the scFv comprises an amino acid sequence selected from the group consisting of SEQ ID NOS: 78, 77, 75, 76, 8, 9, 10, 24, 25, and 26.

Embodiment 9

The CAR of any of Embodiments 1-8, wherein the extracellular antigen-binding domain comprises a signal polypeptide.

Embodiment 10

The CAR of Embodiment 9, wherein the signal polypeptide comprises an amino acid sequence of SEQ ID NO: 11.

Embodiment 11

The CAR of any of Embodiments 1-10, wherein the intracellular signaling domain comprises a polypeptide component selected from the group consisting of a TNF receptor superfamily member 9 (CD137) component, a T-cell surface glycoprotein CD3 zeta chain (CD3z) component, a cluster of differentiation (CD27) component, a cluster of differentiation superfamily member component, and a combination thereof.

Embodiment 12

The CAR of Embodiment 11, wherein the CD137 component comprises an amino acid sequence of SEQ ID NO: 12.

Embodiment 13

The CAR of Embodiment 11, wherein the CD3z component comprises an amino acid sequence of SEQ ID NO: 13.

Embodiment 14

The CAR of Embodiment 11, wherein the intracellular signaling domain comprises an amino acid sequence of SEQ ID NO: 14.

Embodiment 15

The CAR of any of Embodiments 1-14, wherein the transmembrane domain comprises a CD8a transmembrane region (CD8a-TM) polypeptide.

Embodiment 16

The CAR of Embodiment 15, wherein the CD8a-TM polypeptide comprises an amino acid sequence of SEQ ID NO: 15.

Embodiment 17

The CAR of any of Embodiments 1-16, further comprising a hinge region linking the transmembrane domain to the extracellular antigen-binding domain.

Embodiment 18

The CAR of Embodiment 17, wherein the hinge region is a CD8a-hinge region.

Embodiment 19

The CAR of Embodiment 18, wherein the CD8a-hinge region comprises an amino acid sequence of SEQ ID NO: 16.

Embodiment 20

The CAR of any of Embodiments 1-19, wherein the extracellular antigen-binding domain comprises an amino acid sequence selected from the group consisting of SEQ ID NOS: 82, 81, 80, 79, 17, 18, 19, 20, 21, and 22.

Embodiment 21

The CAR of any of Embodiments 1-20, wherein the CAR comprises an amino acid sequence selected from the group consisting of SEQ ID NOS: 86, 85, 83, 84, 27, 28, 29, 30, 31 and 32.

Embodiment 22

An isolated lymphocyte expressing the CAR of any of Embodiments 1-21.

Embodiment 23

The isolated lymphocyte of Embodiment 22, wherein the lymphocyte is a T lymphocyte.

Embodiment 24

An isolated nucleic acid molecule encoding the CAR of any of Embodiments 1-21.

Embodiment 25

The isolated nucleic acid molecule of Embodiment 24, wherein the nucleic acid molecule comprises a nucleic acid sequence selected from the group consisting of SEQ ID NOS: 90, 89, 87, 88, 33, 34, 35, 36, 37, and 38.

Embodiment 26

The isolated nucleic acid molecule of Embodiment 24, wherein the nucleic acid molecule comprises a nucleotide sequence that is at least about 80%, 81%, 82%, 83%, 84%, 85%, 86%, 87%, 88%, 89%, 90%, 91%, 92%, 93%, 94%, 95%, 96%, 97%, 98%, or 99% identical to a nucleotide sequence of SEQ ID NOS: 90, 89, 87, 88, 33, 34, 35, 36, 37, and 38.

Embodiment 27

A vector comprising the nucleic acid molecule of any of Embodiments 24-26.

Embodiment 28

A cell expressing the nucleic acid molecule of any of Embodiments 24-26.

Embodiment 29

A pharmaceutical composition, comprising an effective amount of the lymphocyte of any of Embodiments 22-23.

Embodiment 30

A pharmaceutical composition, comprising an effective amount of the lymphocyte of any of Embodiments 22-23 and a pharmaceutically acceptable excipient.

Embodiment 31

The CAR of any of Embodiments 1-21 or the pharmaceutical composition of Embodiments 29 or 30 for use in therapy.

Embodiment 32

The CAR of any of Embodiments 1-21 or the pharmaceutical composition of Embodiments 29 or 30 for use in a method of treating a subject having cancer.

Embodiment 33

A method of treating a subject having cancer, the method comprising:
 administering a therapeutically effective amount of the lymphocyte of any of Embodiments 22-23 to a subject in need thereof, whereby the lymphocyte induces killing of cancer cells in the subject.

Embodiment 34

The method of Embodiment 33, or the CAR or the pharmaceutical composition for use in a method of Embodiment 32, wherein the cancer is selected from the group consisting of a lung cancer, a gastric cancer, a colon cancer, a hepatocellular carcinoma, a renal cell carcinoma, a bladder urothelial carcinoma, a metastatic melanoma, a breast cancer, an ovarian cancer, a cervical cancer, a head and neck cancer, a pancreatic cancer, a glioma, a glioblastoma, and a non-Hodgkin's lymphoma (NHL), an acute lymphocytic leukemia (ALL), a chronic lymphocytic leukemia (CLL), a chronic myelogenous leukemia (CML), a smoldering multiple myeloma (SMM), a multiple myeloma (MM), an acute myeloid leukemia (AML), and combinations thereof.

Embodiment 35

The method of Embodiment 33 or 34, or the CAR or the pharmaceutical composition for use in a method of Embodiment 32 or 34 wherein the cancer is multiple myeloma.

Embodiment 36

A method of targeted killing of a cancer cell, the method comprising:
contacting the cancer cell with the lymphocyte of any of Embodiments 22-23, whereby the lymphocyte induces killing of the cancer cell.

Embodiment 37

The method of Embodiment 36, wherein the cancer cell is selected from the group consisting of a lung cancer, a gastric cancer, a colon cancer, a hepatocellular carcinoma, a renal cell carcinoma, a bladder urothelial carcinoma, a metastatic melanoma, a breast cancer, an ovarian cancer, a cervical cancer, a head and neck cancer, a pancreatic cancer, a glioma, a glioblastoma, and other solid tumors, and a non-Hodgkin's lymphoma (NHL), an acute lymphocytic leukemia (ALL), a chronic lymphocytic leukemia (CLL), a chronic myelogenous leukemia (CML), a smoldering multiple myeloma (SMM), a multiple myeloma (MM), an acute myeloid leukemia (AML), and other liquid tumors, and combinations thereof.

Embodiment 38 The method of Embodiment 36 or 37, wherein the cancer cell is a multiple myeloma cell.

Embodiment 39

A method of detecting the presence of cancer in a subject, comprising:
(a) contacting a cell sample obtained from the subject with the CAR of claim 1, thereby forming a CAR-cell complex, and
(b) detecting the complex, wherein detection of the complex is indicative of the presence of cancer in the subject. Preferably the embodiment is performed in vitro.

EXAMPLES

The following examples are provided to further describe some of the embodiments disclosed herein. The examples are intended to illustrate, not to limit, the disclosed embodiments.

Example 1—Expression of α-GPRC5D scFv CARs

Primary human pan T cells were electroporated with no mRNA (mock) or 10 μg of mRNA expressing either an α-GPRC5D scFv CAR or isotype control CAR. 24 hours post-electroporation CAR surface expression was measured by flow cytometry following stain with biotinylated L-protein and streptavidin-conjugated PE. (FIG. 1). Percent CAR expression was determined by staining with Protein L. Expression was determined to be 95, 88, 70, and 67% positive for CAR A, CAR B, CAR C, and Isotype CAR, respectively. Mock T cells were electroporated only, but no mRNA was added to the cells. The Mock T cells did not express any CAR structure, as expected. These data indicated that the T cells expressed the CAR structure at a high degree. Open histogram is mock, filled grey histogram is CAR-T population.

The amino acid sequences for the components of the GPRC5D-targeting CAR constructs were as shown in Table 2.

TABLE 2

| Domain | Sequence |
| --- | --- |
| signal sequence | MAWVWTLLFLMAAAQSIQA (SEQ ID NO: 11) |
| extracellular GPRC5D-specific scFv | EIVLTQSPATLSLSPGERATLSCRASQSVSSYL AWYQQKPGQAPRLLIYDASNRATGIPARFSGSG SGTDFTLTISSLEPEDFAVYYCQQRSNWPLTFG QGTKVEIKGTEGKSSGSGSESKSTEVQLVQSGA EVKKPGESLKISCKGSGYSFTSYFIGWVRQMPG KGLEWMGIIYPGKSDTRYSPSFQGQVTISADKS ISTAYLQWSSLKASDTAMYYCARVYSFGGRHKA LFDYWGQGTLVTVSS (SEQ ID NO: 8) DIQMTQSPSSLSASVGDRVTITCRASQSISSYL NWYQQKPGKAPKLLIYAASSLQSGVPSRFSGSG SGTDFTLTISSLQPEDFATYYCQQSYSTPLTFG QGTKVEIKGTEGKSSGSGSESKSTQVQLVQSGA EVKKPGSSVKVSCKASGGTFSSYAISWVRQAPG QGLEWMGGIIPIFGTANYAQKFQGRVTITADES TSTAYMELSSLRSEDTAVYYCARESRWRGYKLD YWGQGTLVTVSS (SEQ ID NO: 9) DIQMTQSPSSLSASVGDRVTITCKASQNVATHV GWYQQKPGKAPKRLIYSASYRYSGVPSRFSGSG SGTEFTLTISNLQPEDFATYYCQQYNRYPYTFG QGTKLEIKGTEGKSSGSGSESKSTQVQLVQSGA EVKKPGASVKVSCKASGYSFTGYTMNWVRQAPG QGLEWMGLINPYNSDTNYAQKLQGRVTMTTDTS TSTAYMELRSLRSDDTAVYYCARVALRVALDYW GQGTLVTVSS (SEQ ID NO: 10) EVQLVQSGAEVKKPGESLKISCKGSGYSFTSYF IGWVRQMPGKGLEWMGIIYPGKSDTRYSPSFQG QVTISADKSISTAYLQWSSLKASDTAMYYCARV YSFGGRHKALFDYWGQGTLVTVSSGTEGKSSGS GSESKSTEIVLTQSPATLSLSPGERATLSCRAS QSVSSYLAWYQQKPGQAPRLLIYDASNRATGIP ARFSGSGSGTDFTLTISSLEPEDFAVYYCQQRS NWPLTFGQGTKVEIK (SEQ ID NO: 24) QVQLVQSGAEVKKPGSSVKVSCKASGGTFSSYA ISWVRQAPGQGLEWMGGIIPIFGTANYAQKFQG RVTITADESTSTAYMELSSLRSEDTAVYYCARE SRWRGYKLDYWGQGTLVTVSSGTEGKSSGSGSE SKSTDIQMTQSPSSLSASVGDRVTITCRASQSI SSYLNWYQQKPGKAPKLLIYAASSLQSGVPSRF SGSGSGTDFTLTISSLQPEDFATYYCQQSYSTP LTFGQGTKVEIK (SEQ ID NO: 25) QVQLVQSGAEVKKPGASVKVSCKASGYSFTGYT MNWVRQAPGQGLEWMGLINPYNSDTNYAQKLQG RVTMTTDTSTSTAYMELRSLRSDDTAVYYCARV ALRVALDYWGQGTLVTVSSGTEGKSSGSGSESK |

TABLE 2-continued

| Domain | Sequence |
| --- | --- |
|  | STDIQMTQSPSSLSASVGDRVTITCKASQNVAT<br>HVGWYQQKPGKAPKRLIYSASYRYSGVPSRFSG<br>SGSGTEFTLTISNLQPEDFATYYCQQYNRYPYT<br>FGQGTKLEIK<br>(SEQ ID NO: 26) |
|  | QLQLQESGPGLVKPSETLSLTCTVSGGSLSSSS<br>YWWGWTRQPPGRGLEWIGTMYYSGNIYYNPSLQ<br>SRATISVDTSKNQFSLKLSSVTAADTAVYYCAR<br>HVGYSYGRRFWYFDLWGRGTLVTVSSGGSEGKS<br>SGSGSESKSTGGSEIVLTQSPATLSLSPGERAT<br>LSCRASQSVSSYLAWYQQKPGQAPRLLIYDASN<br>RATGIPARFSGSGSGTDFTLTISSLEPEDFAVY<br>YCQQRSNWPPTFGQGTKVEIK<br>(SEQ ID NO: 75) |
|  | EIVLTQSPATLSLSPGERATLSCRASQSVSSYL<br>AWYQQKPGQAPRLLIYDASNRATGIPARFSGSG<br>SGTDFTLTISSLEPEDFAVYYCQQRSNWPPTFG<br>QGTKVEIKGGSEGKSSGSGSESKSTGGSQLQLQ<br>ESGPGLVKPSETLSLTCTVSGGSLSSSSYWWGW<br>TRQPPGRGLEWIGTMYYSGNIYYNPSLQSRATI<br>SVDTSKNQFSLKLSSVTAADTAVYYCARHVGYS<br>YGRRFWYFDLWGRGTLVTVSS<br>(SEQ ID NO: 76) |
|  | QVTLKESGPVLVKPTETLTLTCTVSGFSLTNIR<br>MSVSWIRQPPGKALEWLAHIFSNDEKSYSSSLK<br>SRLTISRDTSKSQVVLTLTNVDPVDTATYYCAR<br>MRLPYGMDVWGQGTTVTVSSGGSEGKSSGSGSE<br>SKSTGGSDIVMTQTPLSSPVTLGQPASISCRSS<br>QSLVHSDGNTYLSWLQQRPGQPPRLLIYKISNR<br>FFGVPDRFSGSGAGTDFTLKISRVEAEDVGVYY<br>CMQATQFPHTFGQGTKLEIK<br>(SEQ ID NO: 77) |
|  | DIVMTQTPLSSPVTLGQPASISCRSSQSLVHSD<br>GNTYLSWLQQRPGQPPRLLIYKISNRFFGVPDR<br>FSGSGAGTDFTLKISRVEAEDVGVYYCMQATQF<br>PHTFGQGTKLEIKGGSEGKSSGSGSESKSTGGS<br>QVTLKESGPVLVKPTETLTLTCTVSGFSLTNIR<br>MSVSWIRQPPGKALEWLAHIFSNDEKSYSSSLK<br>SRLTISRDTSKSQVVLTLTNVDPVDTATYYCAR<br>MRLPYGMDVWGQGTTVTVSS<br>(SEQ ID NO: 78) |
| human CD8<br>hinge sequence | TSTPAPRPPTPAPTIASQPLSLRPEACRPAAGG<br>AVHTRGLDFACD<br>(SEQ ID NO: 16) |
| human CD8<br>TM domain<br>sequence | IYIWAPLAGTCGVLLLSLVITLYC<br>(SEQ ID NO: 15) |
| human CD137<br>intracellular<br>sequence | KRGRKKLLYIFKQPFMRPVQTTQEEDGCSCRFP<br>EEEEGGCEL<br>(SEQ ID NO: 12) |
| human CD3<br>zeta<br>intracellular<br>domain | RVKFSRSADAPAYKQGQNQLYNELNLGRREEYD<br>VLDKRRGRDPEMGGKPRRKNPQEGLYNELQKDK<br>MAEAYSEIGMKGERRRGKGHDGLYQGLSTATKD<br>TYDALHMQALPPR<br>(SEQ ID NO: 13) |

Example 2—Induction of Activation Markers in Antigen-Stimulated CAR-T Cells

Figure 2:
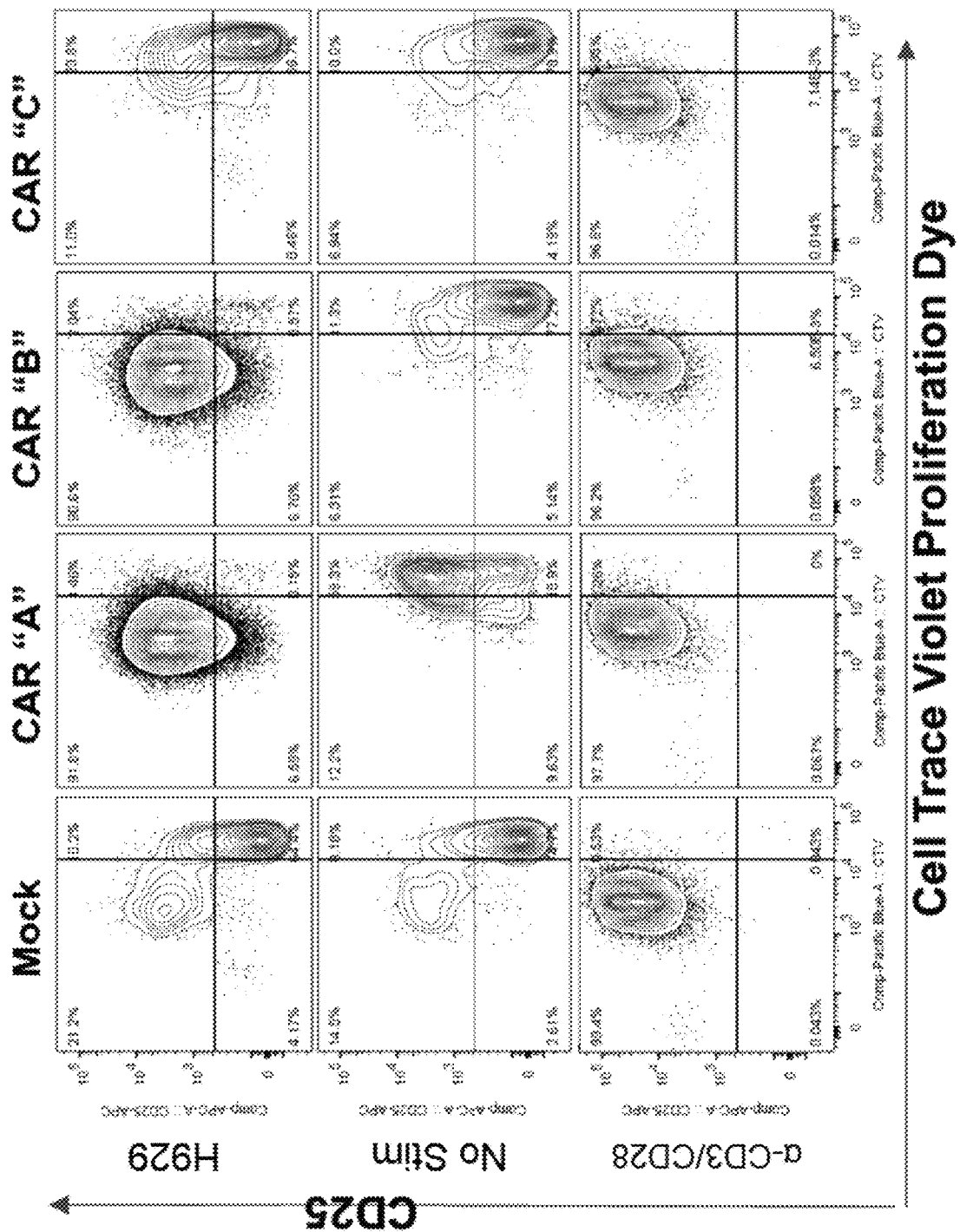
FIG. 2 shows flow cytometric analyses of transiently transfected pan T cells co-cultured with a multiple myeloma cell line. Twenty-four hours after transient transfection, primary pan T cells were labeled with Cell Trace Violet (CTV) fluorescent proliferation dye and then co-cultured with a multiple myeloma cell line, H929. Four days post co-culture, cells were pre-gated on the CD8+CD4− population and surface expression of activation markers CD25 and CD71 on CAR-T were compared to T cells cultured alone or in the presence of α-CD3/CD28 beads.
Figure 2:
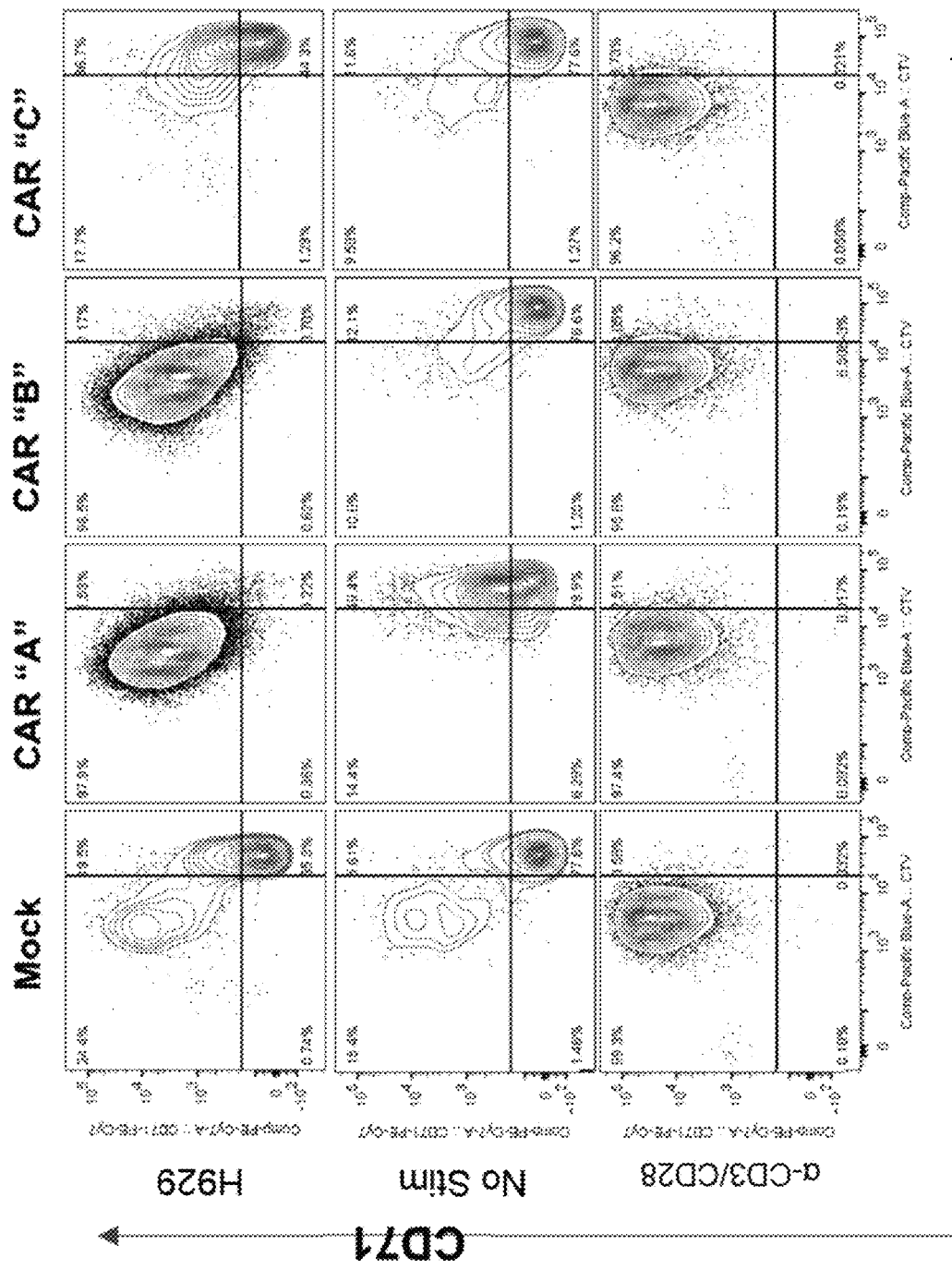

Twenty-four hours after transient transfection, primary pan T cells were labeled with Cell Trace Violet (CTV) fluorescent proliferation dye and then co-cultured with multiple myeloma cell line, H929. Four days post co-culture, cells were pre-gated on the CD8+CD4− population and surface expression of activation markers CD25 and CD71 on CAR-T were compared to T cells cultured alone or in the presence of α-CD3/CD28 beads. (FIG. 2). The same CAR T cells from FIG. 1 were analyzed for a T cell activation response to GPRC5D antigen expressing-H929 cells. Four days after electroporation, CAR A and CAR B showed an increase in T cell activation response, shown by an increase in CD25 and CD71 expression in response to culture with H929 cells. In comparison, the Mock and CAR C-expressing cells demonstrated diminished T cell activation in response to H929 cells. As a negative control, the same cells were grown in the absence of any GPRC5D or T cell antigen and showed minimal increases in CD25 or CD71. As a positive control, Mock, CAR A, CAR B, and CAR C cells were co-cultured with CD3/CD28 beads. Each of the four cell populations showed similar increases in CD25 and CD71 expression. In totality, these data show that CAR A and CAR B cells demonstrated the greatest T cell activation response to GPRC5D-expressing H929 cells.

Example 3—Cytokine Profiling of Antigen-Stimulated CAR-T Cells

Figure 3:
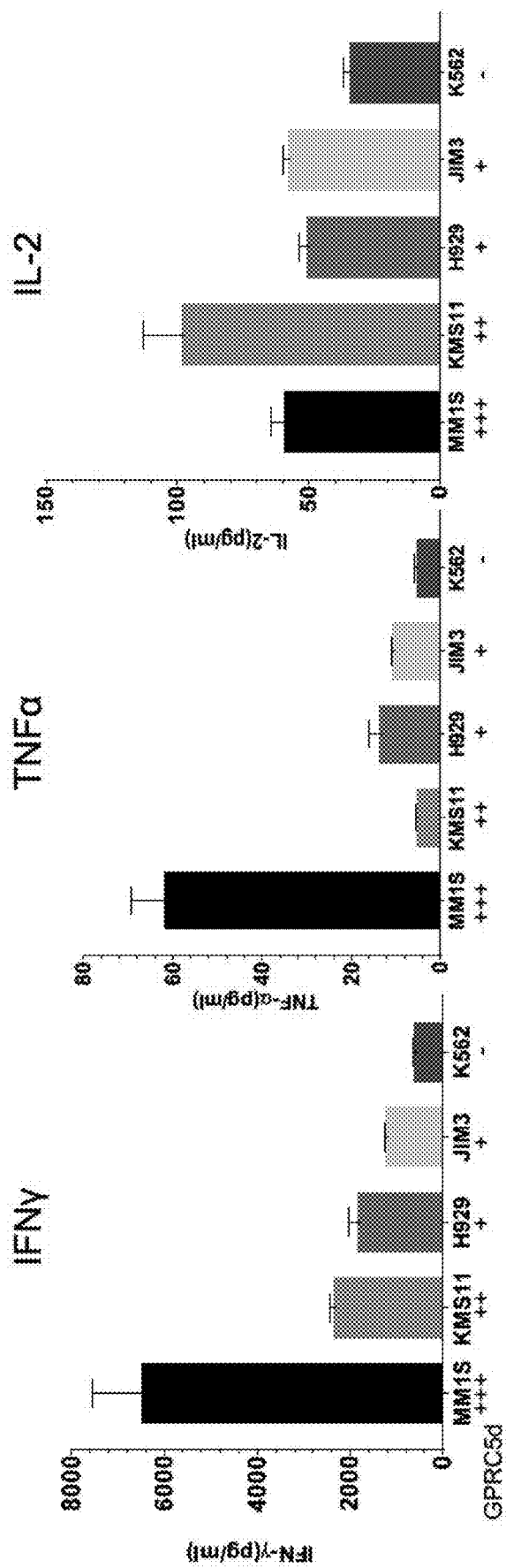
FIG. 3 shows a cytokine profile analysis for primary pan T cells transiently transfected with CAR-expressing mRNA and co-cultured with various myeloma cell lines. Primary pan T cells transiently transfected 24 hours prior with CAR-expressing mRNA were co-cultured at a 1:1 ratio with various myeloma cell lines expressing target antigen, GPRC5D, at high (+++), medium (++), low (+) or negative (−) levels. Sixteen hours post co-culture, supernatants were harvested and cytokine profile analysis by Meso Scale Discovery (MSD) of supernatants from co-cultures was performed.

Primary pan T cells transiently transfected 24 hours prior with CAR-expressing mRNA were co-cultured at a 1:1 ratio with various myeloma cell lines, expressing target antigen, GPRC5D, at high (+++), medium (++), low (+) or negative (−) levels. Sixteen hours post co-culture, supernatants were harvested and cytokine profile analysis by Meso Scale Discovery (MSD) of supernatants from co-cultures was performed. (FIG. 3). Supernatants from GPRC5D CAR-T cells showed an increase in pro-inflammatory cytokines INF-γ, TNF-α, or IL-2. Increases in each of the pro-inflammatory cytokines was respective of GPRC5D expression the cell lines co-cultured with the GPRC5D CAR-T cells. Co-culture with MM.1S resulted in the highest INF-γ and TNF-α expression, whereas co-culture with KMS11 cells resulted in highest IL-2 levels. The K562 cell line was used as negative control, demonstrating basal background cytokines levels with a non-GPRC5D-expressing cell line.

Figure 4:
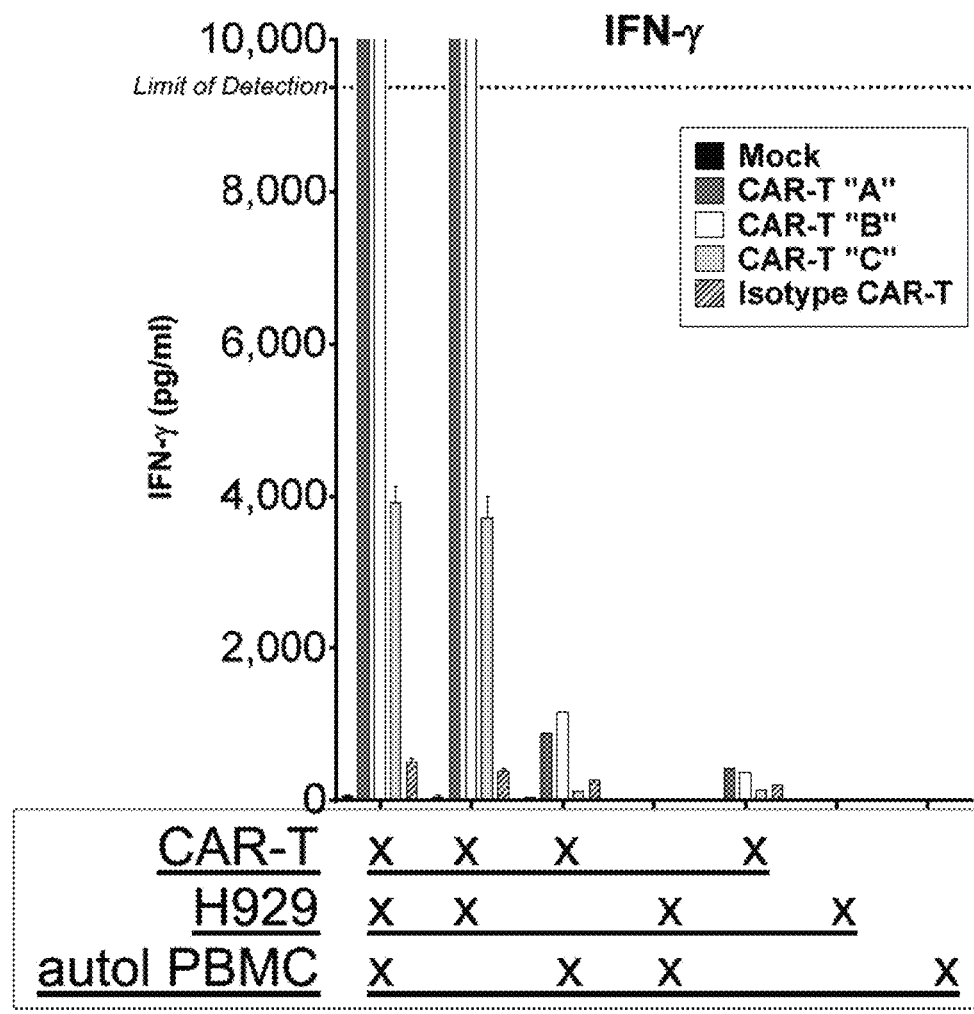
FIG. 4 shows a cytokine profile analysis for primary pan T cells transiently transfected with CAR-expressing mRNA and co-cultured with autologous peripheral blood mononuclear cells (PBMCs) and a multiple myeloma cell line. Twenty-four hours after transient transfection with CAR-expressing mRNA, primary pan T cells were co-cultured (at a 1:1:1 ratio) with autologous PBMCs and the multiple myeloma cell line, H929. Sixteen hours post co-culture, supernatants were harvested. Cytokine profile analysis by MSD of supernatants from co-cultures containing all three populations (CAR-T, H929, autologous PBMC) were compared to control co-cultures lacking CAR-T cells, PBMC or H929, to each population of cells cultured in isolation.
Figure 4:
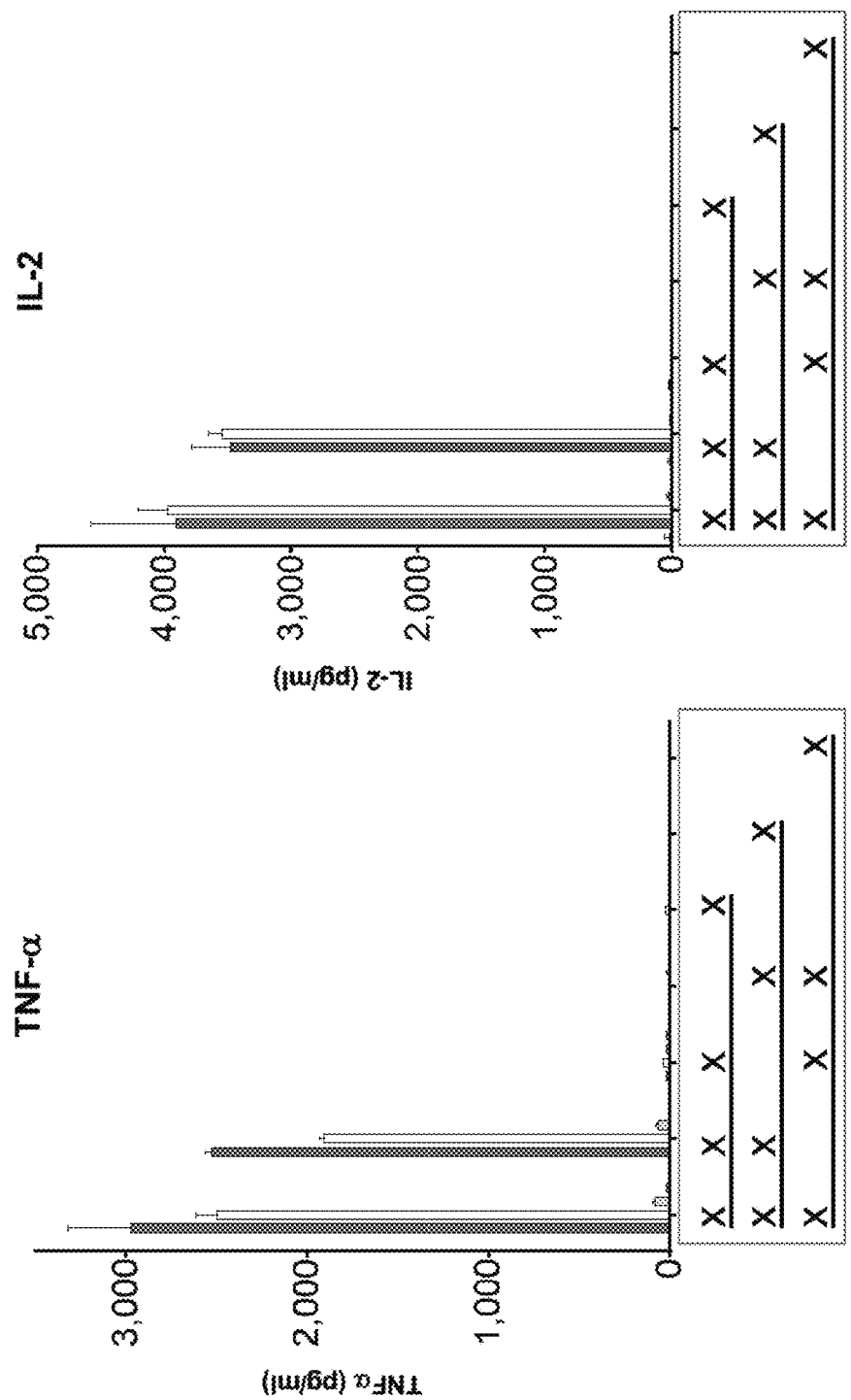

Twenty-four hours after transient transfection with CAR-expressing mRNA, primary pan T cells were co-cultured (at a 1:1:1 ratio) with autologous peripheral blood mononuclear cells (PBMC) and the multiple myeloma cell line, H929. Sixteen hours post co-culture, supernatants were harvested. Cytokine profile analysis by MSD of supernatants from co-cultures containing all three populations (CAR-T, H929, autologous PBMC) were compared to control co-cultures lacking CAR-T cells, PBMC or H929, to each population of cells cultured in isolation. (FIG. 4). Similar to FIG. 3, Mock, CAR-T A, CAR-T B, CAR-T C, or Isotype CAR-T cells were co-cultured with H929 and/or autologous PBMCs. Increases in TNF-α and IL-2 were observed with CAR-T A and CAR-T B cells when H929 cells were co-cultured with PBMCs. When the CAR-T C cells were co-cultured with H929 and PBMC, limited-to-no detectable levels of INF-γ release were observed. Overall, CAR-T C cells demonstrated a diminished cytokine release, consistent with reduced T cell activation markers in FIG. 2. CAR-T, H929, and PBMC cells were cultured alone as negative controls and showed background cytokine levels.

Figure 5:
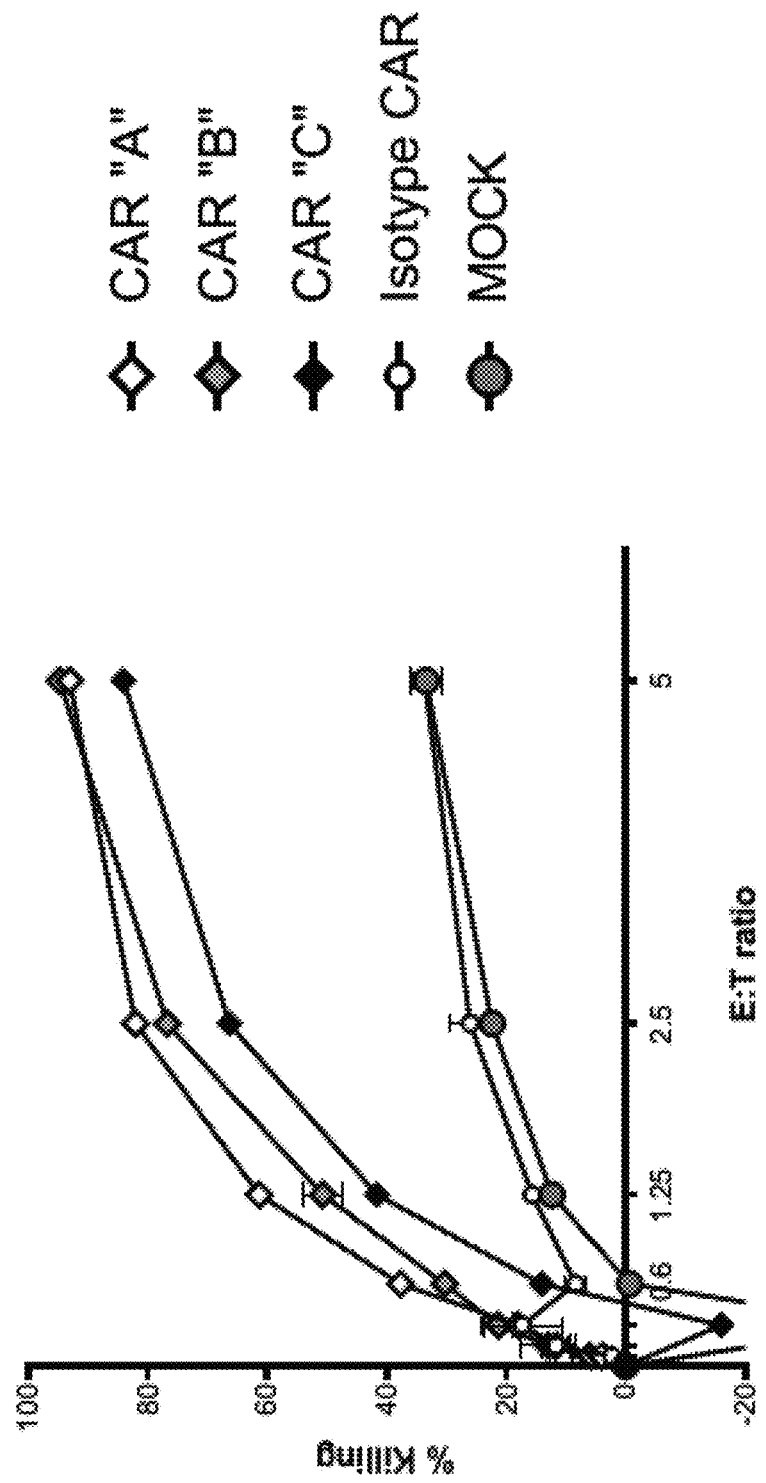
FIG. 5 shows flow cytometric analyses of cytotoxic potential of CAR-T cells on GPRC5D-expressing myeloma cells. Primary pan T cells (transiently expressing one of three CARs as described previously) were co-cultured at the indicated Effector:Target (E:T) ratios with fluorescently labeled myeloma cell lines, MM1R, H929 and K562, for eight hours, at which time co-cultures were stained with viability dye. Percent killing is the ratio of the absolute number of live (viability dye negative) target (CTV positive) cells remaining in the co-culture relative to the number of live targets cultured without CAR-T cells.
Figure 5:
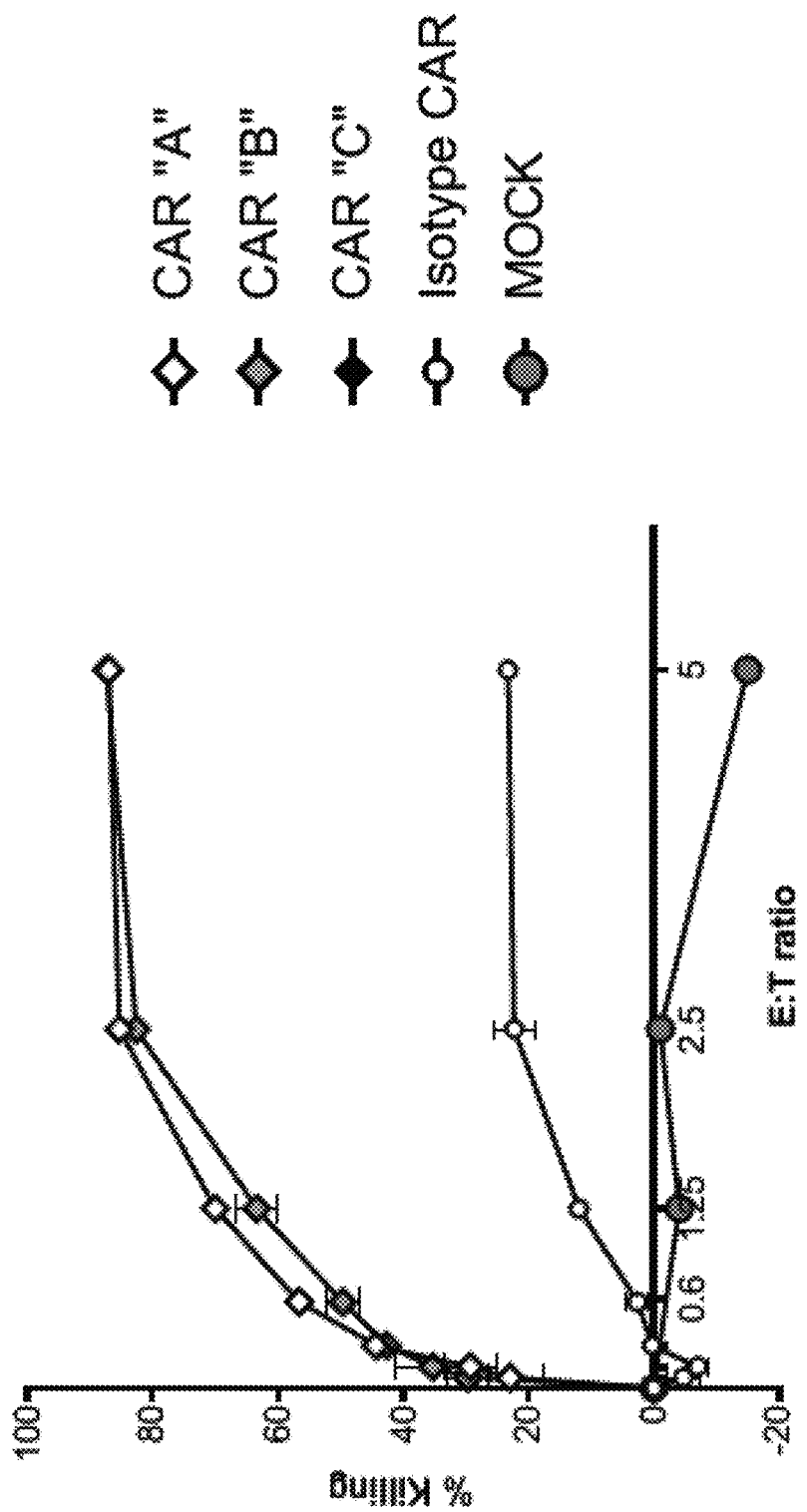
Figure 5:
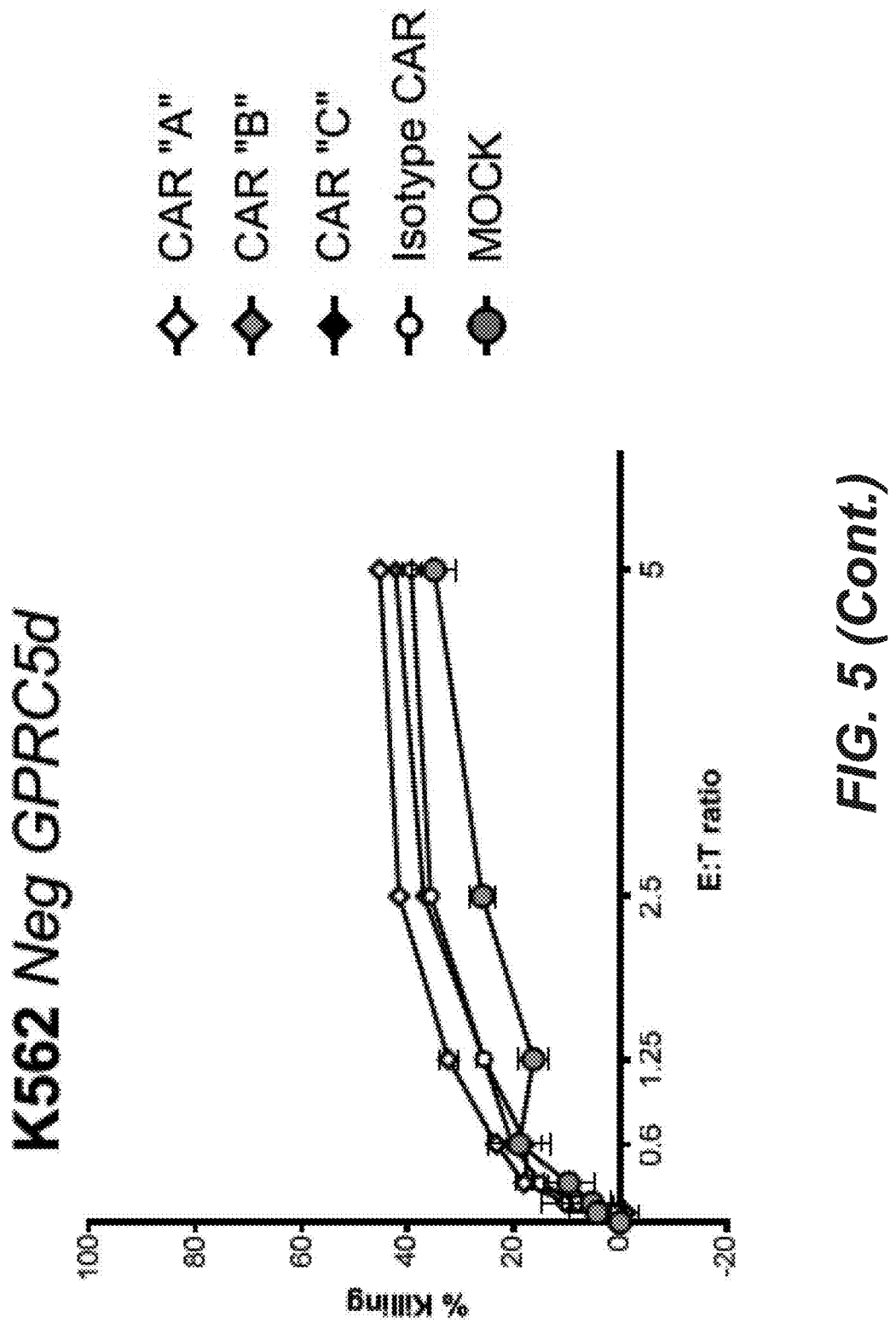

Example 4—Targeted Cytotoxicity of Gprc5D-Expressing Tumor Cell Lines: High/Low/Non-Expressing Gprc5D Target Cell Lines Cytotoxic potential of CAR-T cells on GPRC5D-expressing myeloma cells was assessed by flow-cytometry. Primary pan T cells (transiently expressing one of three CARs as described previously) were co-cultured at the indicated Effector:Target (E:T) ratios with fluorescently labeled myeloma cell lines, MM1R, H929 and K562 for eight hours, at which time co-cultures were stained with viability dye. Percent killing is the ratio of the absolute number of live (viability dye negative) target (CTV positive) cells remaining in the co-culture relative to the number of live targets cultured without CAR-T cells. (FIG. 5). CAR A, CAR B, CAR C, Isotype CAR and Mock T cells were co-cultured with GPRC5D+ cell lines MM1R and H929 or GPRC5D− K562 cells for eight hours. Various effector-to-target ratios were analyzed, showing that the CAR A, CAR B, and CAR C cells were able to induce cytotoxicity of MIVI1R cells. Increases in cytotoxicity correlated with higher effector-to-target ratios. The Isotype and Mock controls are included as controls and showed approximately 20-30% cytotoxicity. Similarly, CAR A and CAR B cells induced cytotoxicity of H929 cells. The CAR A and CAR B cells demonstrated similar cytotoxicity activity to Isotype and Mock cells. These data demonstrate the specificity of CAR A and CAR B cells to MM1R and H929 cells but not to K562 cells (GPRC5D).

Figure 6:
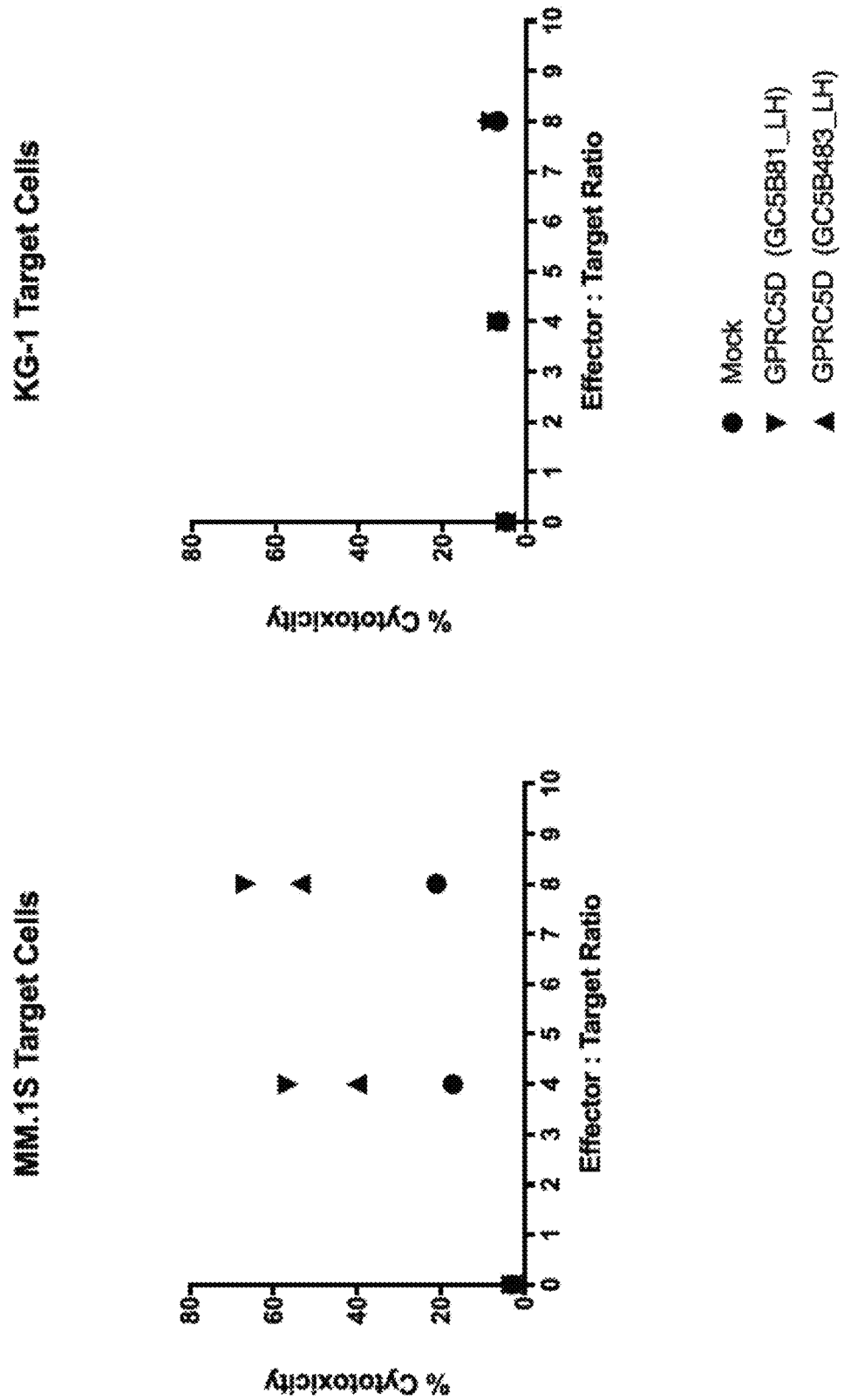
FIG. 6 shows flow cytometric analyses of cytotoxic potential of CAR-T cells on GPRC5D-expressing myeloma cells. Primary multiple myeloma patient T cells (transiently expressing one of two CARs as described previously) were co-cultured at the indicated Effector:Target (E:T) ratios with fluorescently labeled myeloma cell line MM.1S or control GPRC5d-negative cell line KG-1 for 48 hours, at which time co-cultures were stained with viability dye. Percent cytotoxicity was determined as percent fluorescently-labeled cells that stained positive for viability dye, indicating cell death.

Example 5—Targeted Cytotoxicity of GPRC5D-Expressing Tumor Cell Lines: Multiple Myeloma Patient-Derived T-Cells Cytotoxic potential of CAR-T cells on GPRC5D-expressing myeloma cells was assessed by flow-cytometry. Primary multiple myeloma patient T cells (transiently expressing one of two CARs as described previously) were co-cultured at the indicated Effector:Target (E:T) ratios with fluorescently labeled myeloma cell line MM.1S or control GPRC5D-negative cell line KG-1 for 48 hours, at which time co-cultures were stained with viability dye. Percent cytotoxicity was determined as percent fluorescently-labeled cells that stained positive for viability dye, indicating cell death. (FIG. 6). Primary multiple myeloma patient T cells transduced with either GC5B81 LH or GC5B483 LH both induced cytotoxicity of GPRC5D+MM.1S cells with increasing amounts of effector cells compared to Mock T cells. There was no observable cytotoxicity with the GC5B81_LH or GC5B483_LH GPRC5D CAR-T cells when co-cultured with the GPRC5D− KG-1 cell line. These data show multiple myeloma T cells transduced with GPRC5D CAR's can elicit the killing of GPRC5D+ cells, but not GPRC5D cells.

Example 6—Antigen-Stimulated Proliferative Response of α-GPRC5D CAR-T Cells

Figure 7:
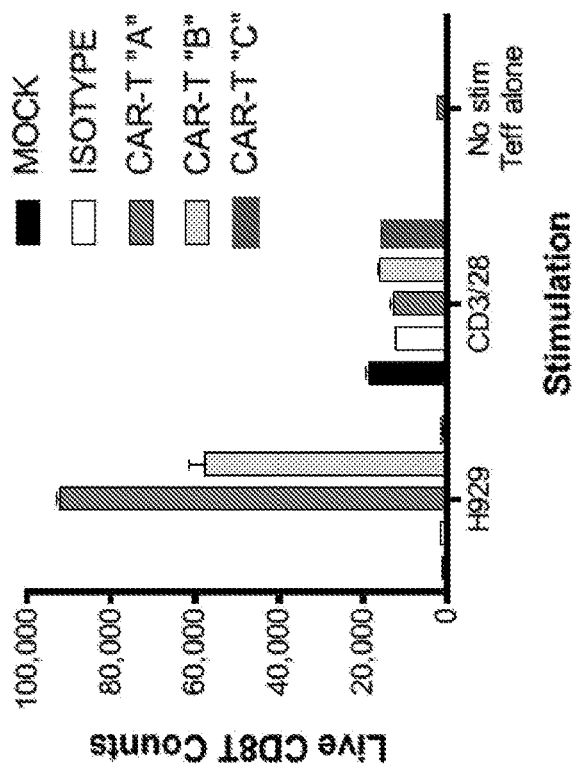
FIG. 7 shows results of flow cytometric analyses of the proliferative capacity of α-GPRC5D-CAR-T cells. Fluorescently labeled pan T cells (transiently expressing an α-GPRC5D CAR or isotype CAR control) were co-cultured at an E:T ratio of 1 with H929 for four days. Proliferation was measured as the absolute number of live (viability dye negative) CAR-T cells which had diluted fluorescent label (CTV). Proliferation in response to H929 was compared to CAR-T proliferation after four days of α-CD3/CD28 bead stimulation and CAR-T cultured alone (no stimulation control).
Figure 7:
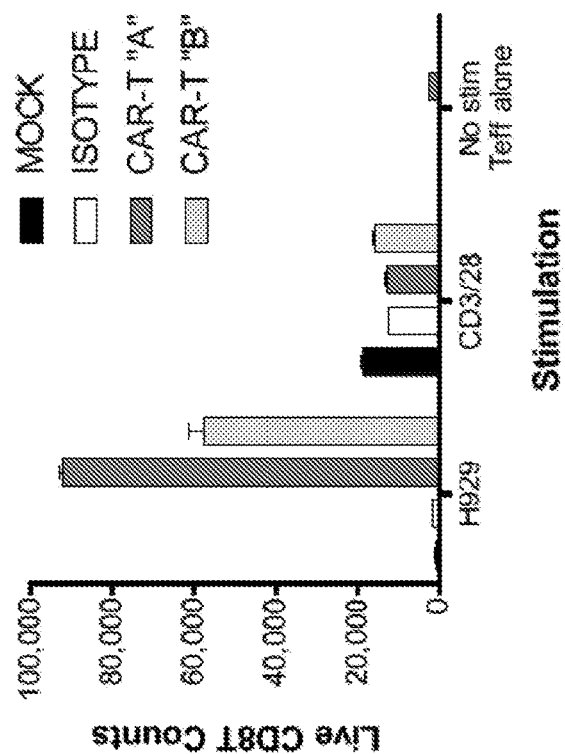
Figure 7:
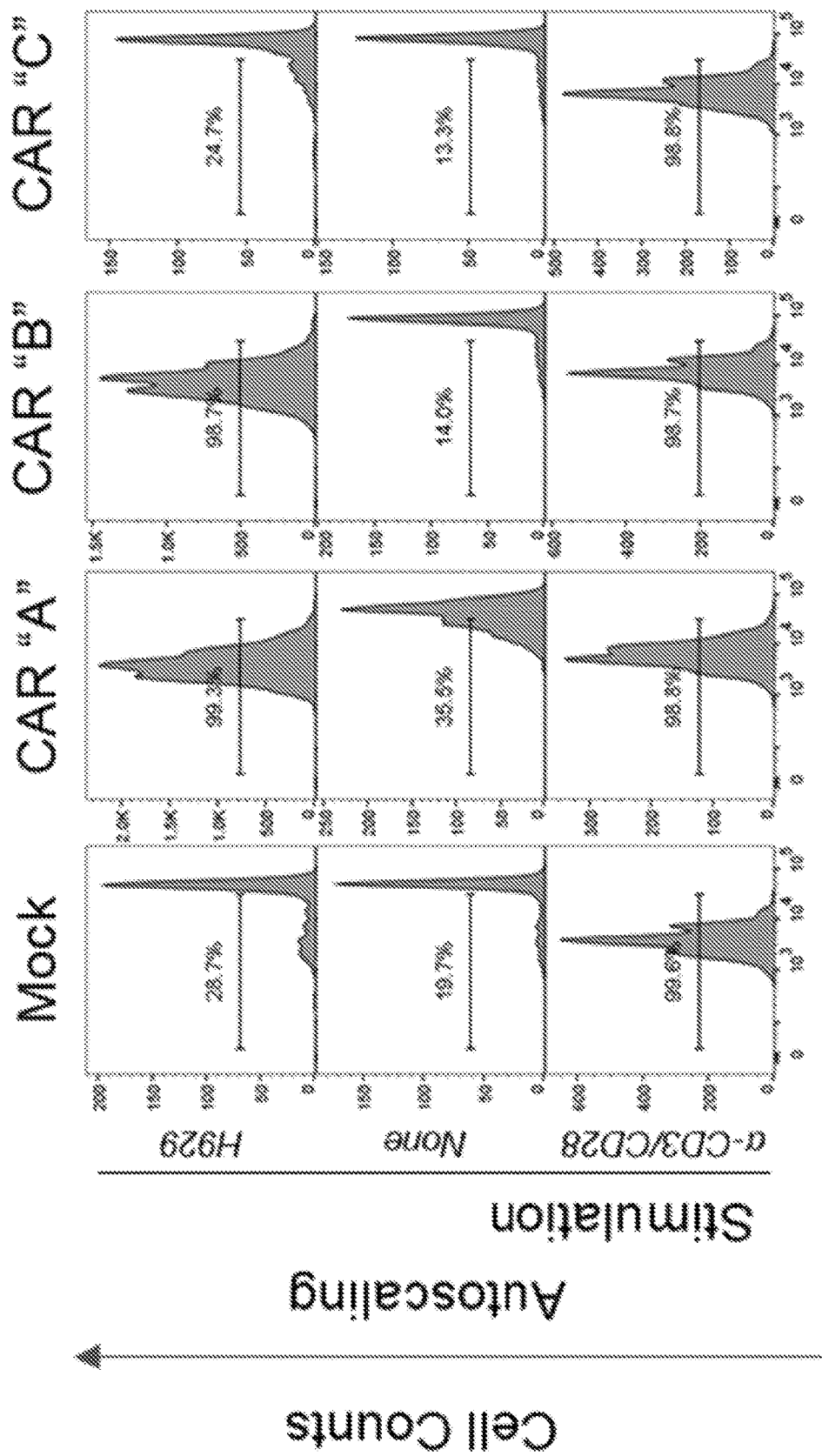
Figure 7:
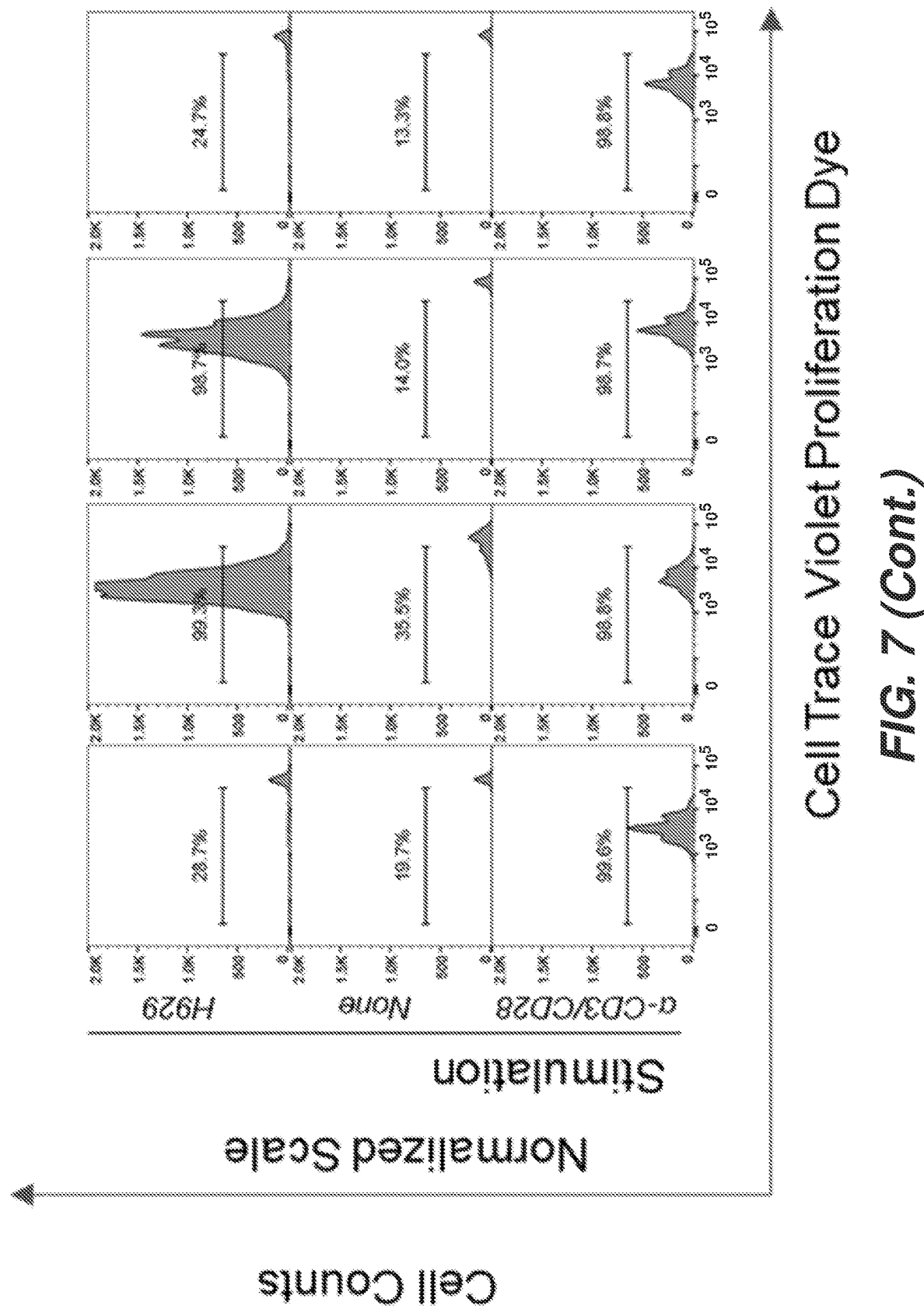

The proliferative capacity of α-GPRC5D CAR-T cells was assessed by flow-cytometry. Fluorescently labeled pan T cells (transiently expressing an α-GPRC5D CAR or isotype CAR control) were co-cultured at a 1 Effector: 1Target ratio with H929 for four days. Proliferation was measured as the absolute number of live (viability dye negative) CAR-T cells which had diluted fluorescent label (CTV). Proliferation in response to H929 was compared to CAR-T proliferation after four days of α-CD3/CD28 bead stimulation and CAR-T cultured alone (no stimulation control). (FIG. 7). Mock, Isotype CAR, CAR-T A, CAR-T B, and CAR-T C cells were co-cultured with GPRC5D+ H929 cells, CD3/CD28 beads or without stimulations. After four days, CD4 and CD8 populations were analyzed for total live counts, reflecting the proliferative ability of the cells in response to GPRC5D antigen. In the CD4 population, CD3/CD28 beads were used as a positive control and all cell populations demonstrated an increase in CD4 events compared to no stimulation. Only the CAR-T A and CAR-T B cells showed a robust increase in counts in response to H929 cells compared to isotype and mock. Similar results were observed for the CD8 population; however, CAR-T C did not show a response in proliferation in response to H929 cells. Taken together, these data show that CAR-T A and CAR-T B cells proliferate in response to GPRC5D+H929 cells.

Example 7—Expression of GPRC5D-CAR on Healthy Donor T Cells

Figure 8:
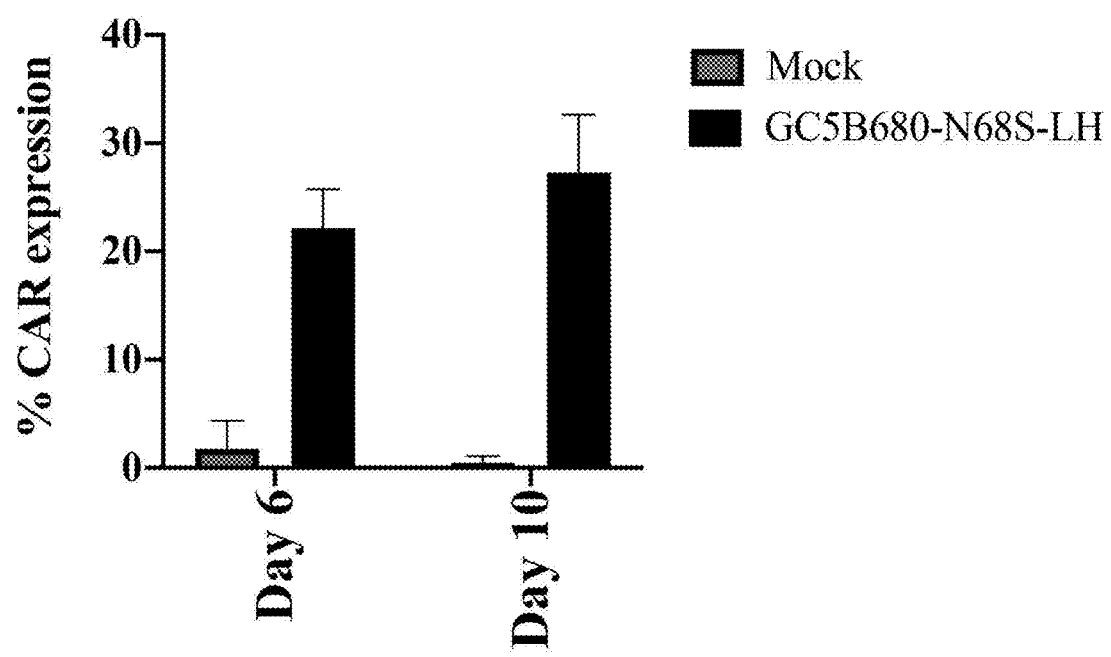
FIG. 8 shows a bar graph depicting the percentage of GPRC5D-CAR expression on healthy donor T cells, as measured by flow cytometry. The shaded gray bars represent background CAR detection in untransduced (mock) cells. The black bars show GPRC5D GC5B680-N68S-LH in transduced CAR-T cells. The values shown represent the mean±SD with 6 healthy donors.

Six primary human pan T cells were activated and expanded using Miltenyi Biotec T cell TRANSACT system. 24 hours post-activation, T cells were transduced with lentivirus comprising a nucleotide sequence encoding the GPRC5D GC5B680-N68S-LH CAR (SEQ ID NO:90). The cells were allowed to expand for 12 days, with surface CAR expression measured by flow cytometry at Days 6 and 10 using a commercially available rabbit anti-human H+L detection antibody. The results are shown in FIG. 8, with the data representing the mean±SD from 6 healthy donors. The bars shaded gray (Mock) that are immediately to the left of the black bars (GCB6800-N68S-LH) represent background CAR detection using the commercial antibody in untransduced (mock) cells. The black bars represent GPRC5D GC5B680-N68S-LH transduced CAR-T cells.

Example 8—Expression of CD4, CD8, and Memory Markers on GPRC5D CAR-T Cells

Figures 9A, 9B, 9C:
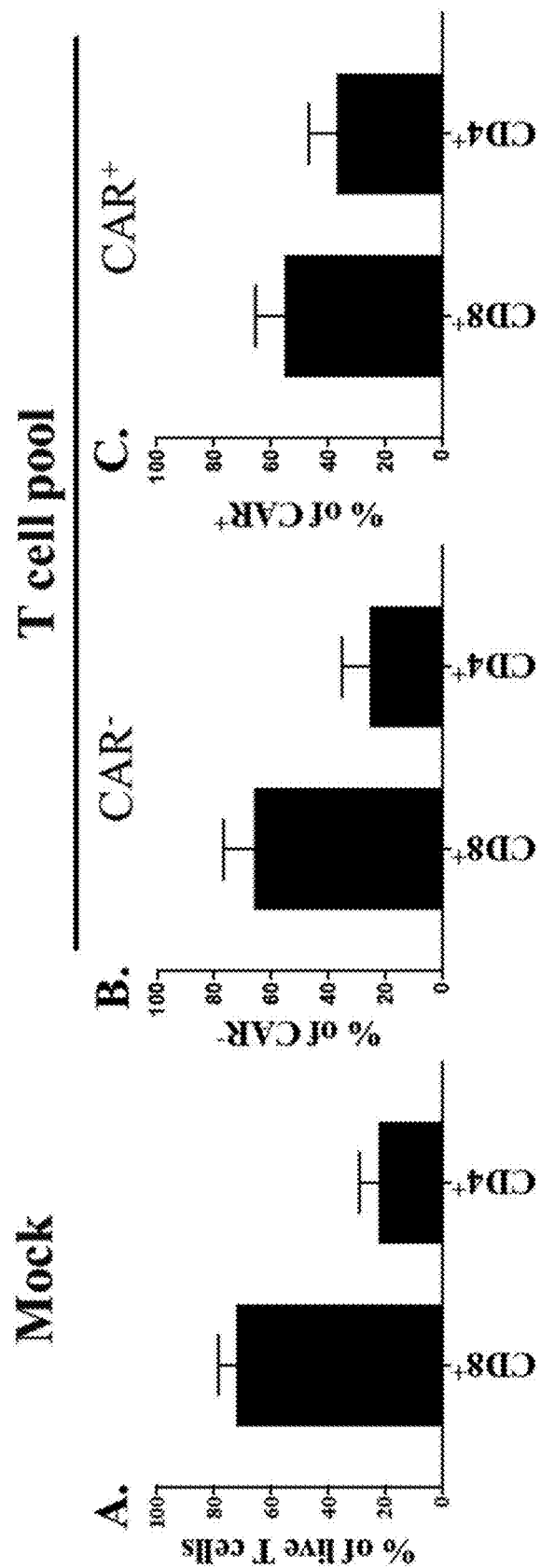
FIGS. 9A-9F depict data showing expression of CD4, CD8, and memory markers on GPRC5D CAR-T cells.

Pan T cells from six healthy donors were transduced with lentivirus comprising a nucleotide sequence encoding the GPRC5D GC5B680-N68S-LH CAR (GPRC5D CAR; SEQ ID NO:90). Mock (untransduced) cells and transduced cells ("T cell pool" including cells with surface CAR (CAR expressing or CAR⁺) and cells without surface CAR (CAR non-expressing or CAR⁻)] were evaluated for proportion of cells with surface CD4 (CD4⁺) and for proportion of cells with surface CD8 (CD8⁺). The data are shown in FIGS. 9A-9C. The data in FIG. 9C show that the GPRC5D CAR was detected in both CD4⁺ and CD8⁺ T cells, as expected. FIGS. 9A-9C also show that the CD4:CD8 ratio was similar among all cell populations evaluated, including CAR⁺ cells, CAR⁻ cells, and mock cells.

Figure 9D:
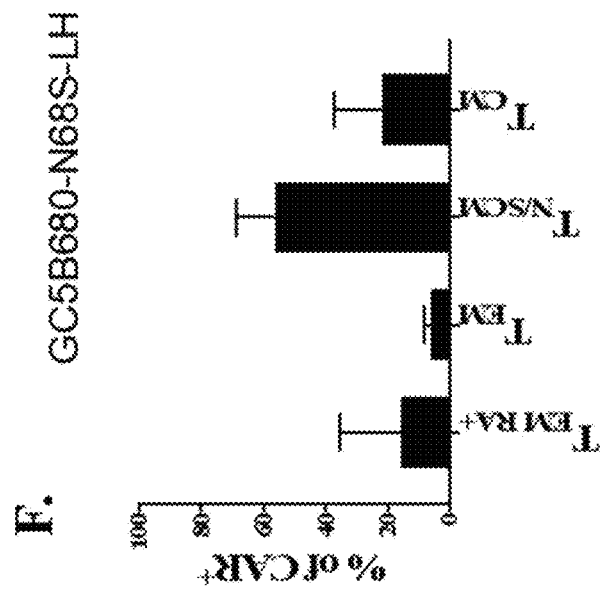
Figure 9E:
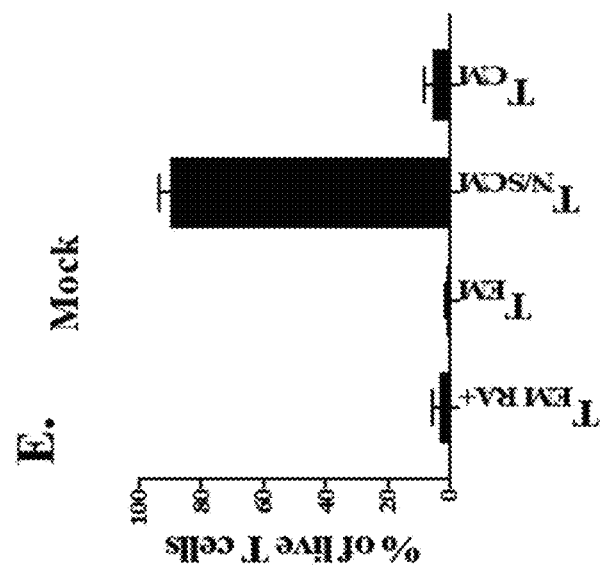
Figure 9F:
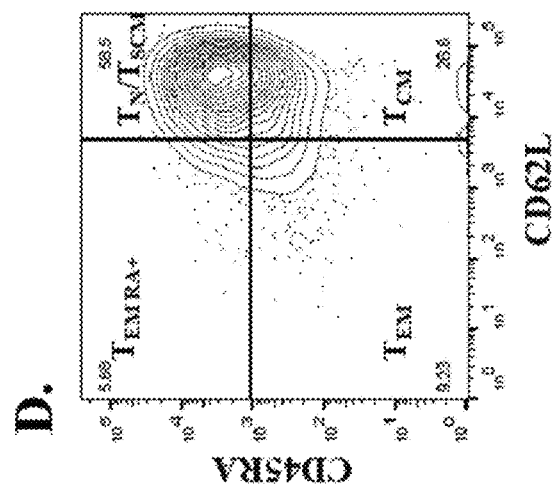

T cell subtypes in the CAR-T population were determined using two surface markers CD45RA and CD62L to differentiate between four memory cell populations: effector memory RA⁺ T cells ($T_{EM\ RA+}$), effector memory cells $T_{EM}$, naïve T cells and memory stem cells $T_{N/SCM}$, and central memory T cells ($T_{CM}$). The data are shown in FIGS. 9D-9F. FIG. 9D is a flow cytogram representative of one donor sample highlighting a gating strategy for distinguishing the four different memory populations using the two surface markers. FIGS. 9E and 9F show that GPRC5D GC5B680-N68S-LH was expressed mostly on $T_{N/SCM}$ and $T_{CM}$ cells, which are known to have high proliferative capacity, survival, and therapeutic efficacy.

Example 9—Assay of GPRC5D CAR-T Cytotoxicity at 6 Hours and 24 Hours

Figure 10A:
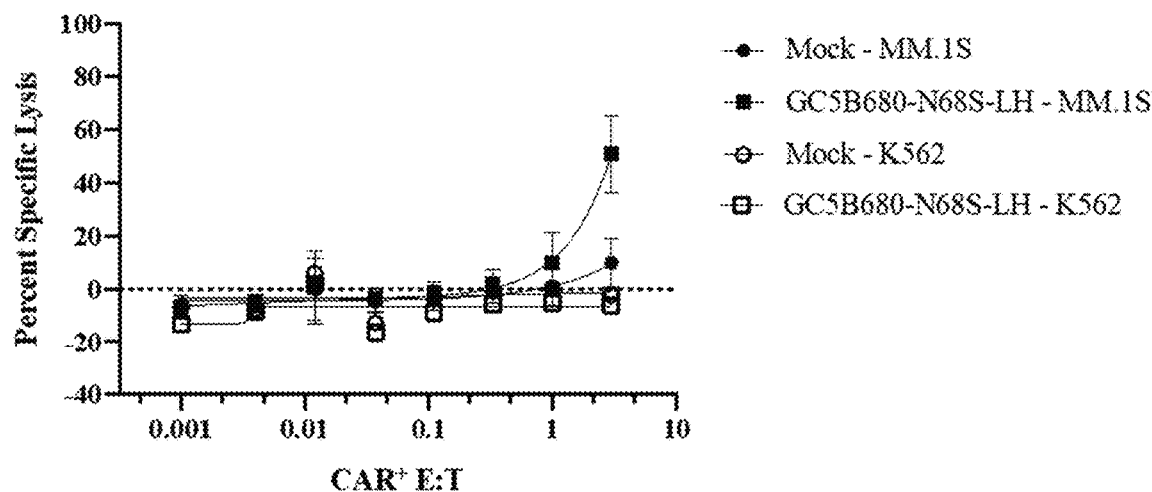
FIGS. 10A-10B show scatter plots demonstrating GPRC5D CAR-T toxicity. GPRC5D GC5B680-N68S-LH or untransduced (Mock) T cells were added at various E:T ratios to $GPRC5D^+$ MM.1S cells or $GPRC5D^-$ K562 cells containing a luciferase transgene. CAR-Ts were made from six healthy donors. The values are expressed as the mean±SD for 6 hours (FIG. 10A) or 24 hours (FIG. 10B). The percent specific lysis was calculated (i) by measuring luciferase signal in tumor cells in the presence of CAR-Ts at 6 or 24 hours divided by luciferase signal in tumor cells alone at the same time points and multiplied by 100 and (ii) by subtracting that number from 100. The equation is: 100−[(CAR-T+tumor luminescence/average tumor alone luminescence)×100]. The dotted line represents a percent specific lysis equal to zero. Negative lysis is indicative of cell growth.
Figure 10B:
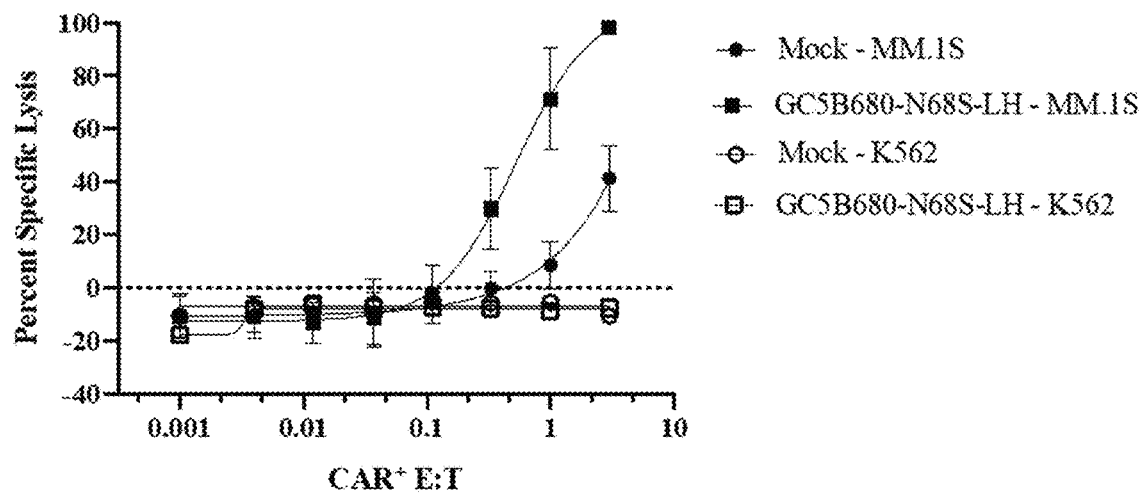
Figure 11A:
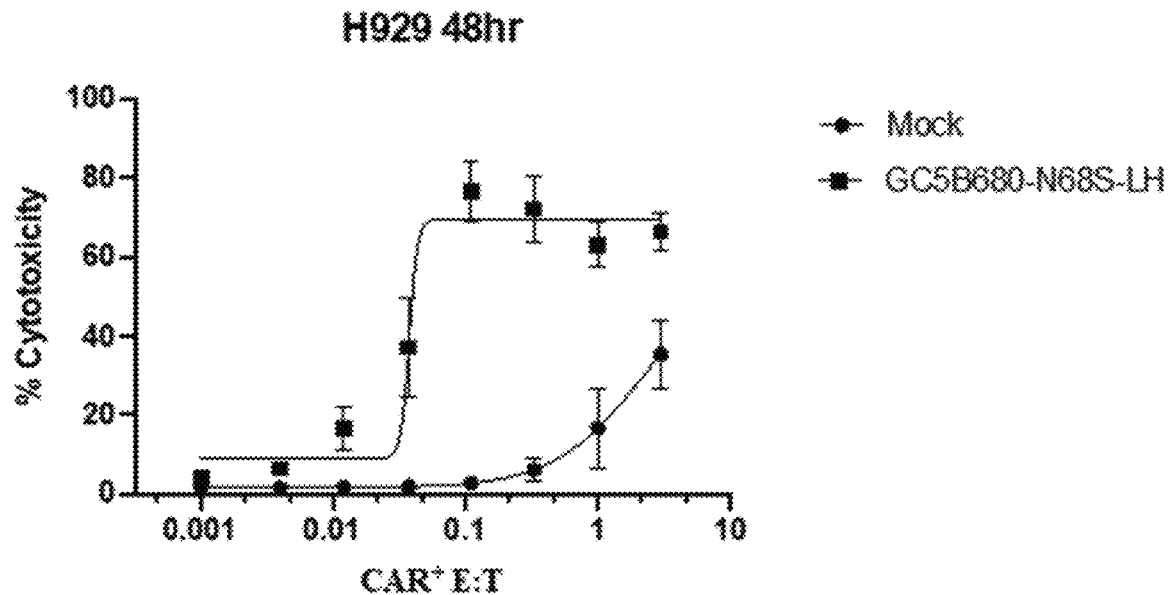
FIGS. 11A-11F illustrate scatter plots demonstrating cytotoxicity of GPRC5D CAR-T cells added at indicated E:T ratios was assessed using $GPRC5D^+$ H929, MM.1S, MM.1R, MOLP-2, and EJM cells or $GPRC5D^-$K562 cells. The GPRC5D CAR-T cells showed cytotoxicity against all the $GPRC5D^+$ cell lines.
Figure 11B:
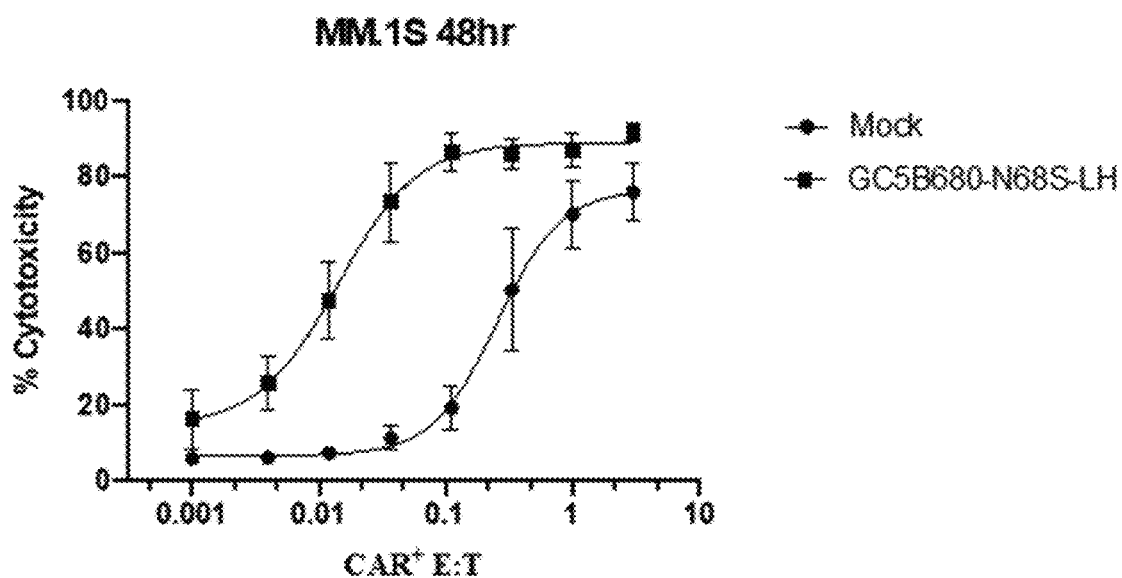
Figure 11C:
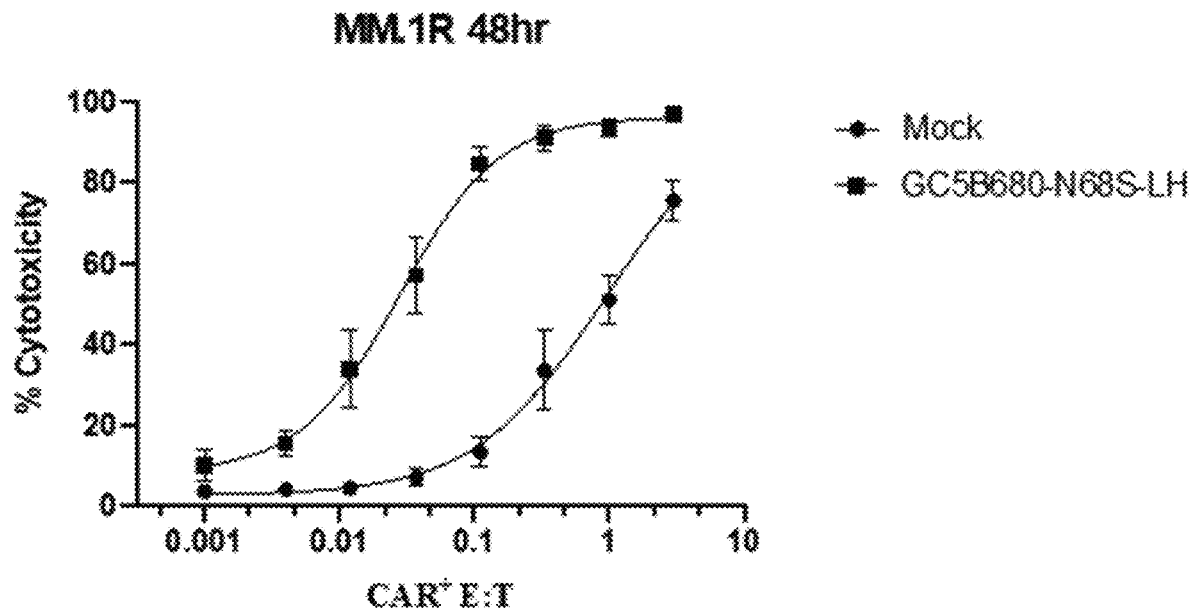
Figure 11D:
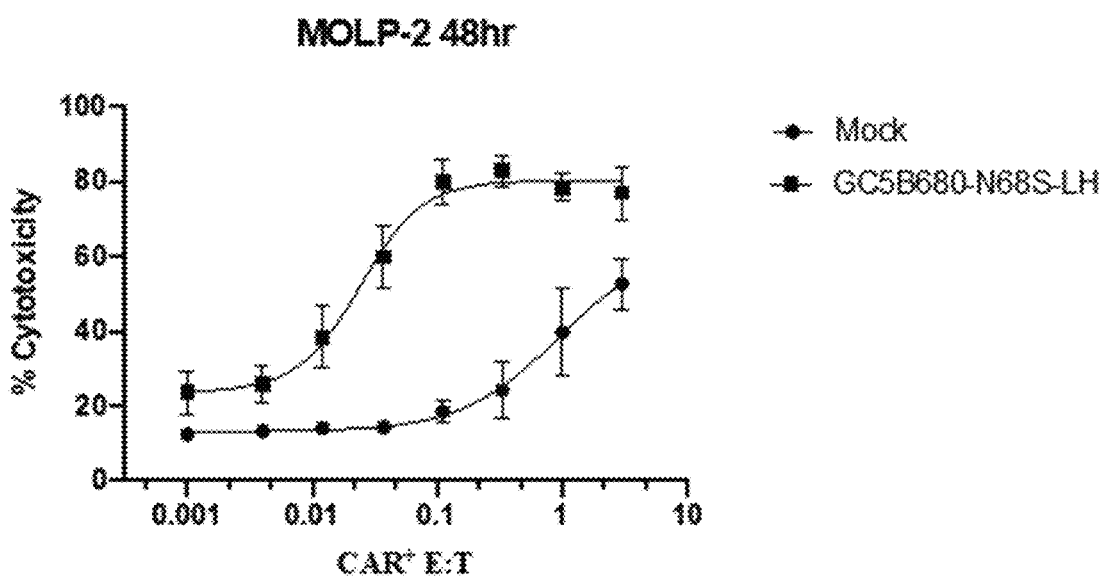
Figure 11E:
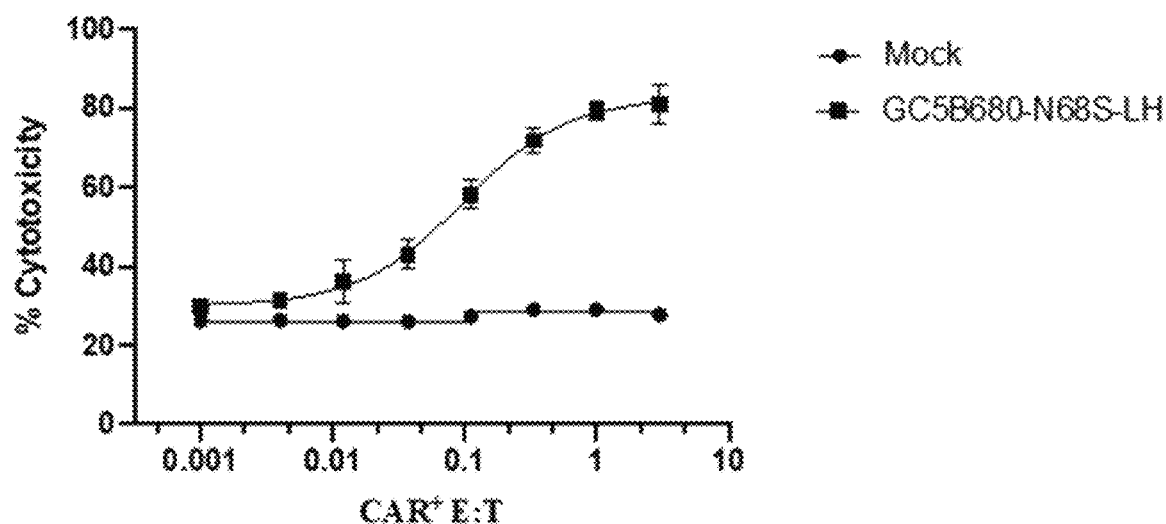
Figure 11F:
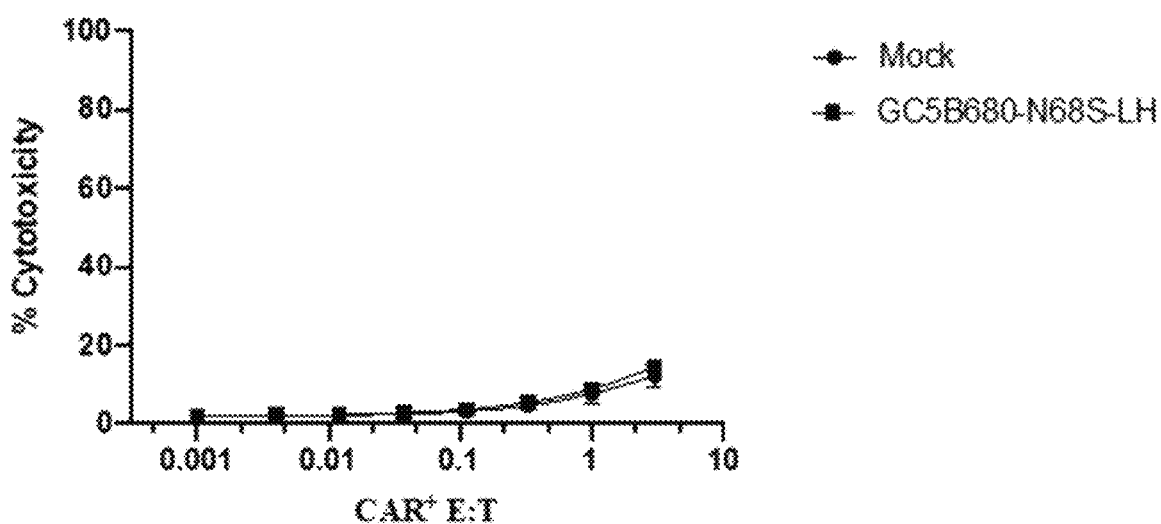

GPRC5D GC5B680-N68S-LH transduced T cells from one of six healthy donors, or untransduced (Mock) T cells, were added at various E:T ratios to (i) cultures of GPRC5D⁺ mM.1S tumor cells comprising a luciferase transgene or to (ii) cultures of GPRC5D⁻ K562 tumor cells comprising a luciferase transgene. Cytotoxicity was assessed at each E:T ratio after 6 hours or 24 hours of incubation. The data are shown in FIG. 10A for the 6 hour time point, and in FIG. 10B for the 24 hour time point. The percent specific lysis was calculated (i) by measuring luciferase signal in tumor cells incubated in the presence of CAR-Ts at 6 or 24 hours divided by luciferase signal in the tumor cells incubated alone at the same time points and multiplied by 100 and (ii) by subtracting that number from 100. The equation is: 100−[(CAR-T+tumor luminescence)/(average tumor alone luminescence)]×100. The dotted line highlights zero lysis. Negative lysis is indicative of cell growth.

Example 10—Assay of GPRC5D CAR-T Cytotoxicity at 48 Hours

GPRC5D GC5B680-N68S-LH transduced and untransduced (Mock) T cells were prepared from healthy donors. Either (i) GPRC5D GC5B680-N68S-LH transduced T cells or (ii) untransduced (Mock) T cells were added at various E:T ratios to carboxyfluorescein succinimidyl ester (CFSE) labeled GPRC5D+ H929, GPRC5D+ MM.1S, GPRC5D+ MM.1R, GPRC5D+ MOLP-2, GPRC5D+ EJM and GPRC5D− K562 cells. After 48 hours of incubation, the cells were stained with a live/dead-dye and evaluated for percentage of dead and CFSE+ cells (% cytotoxicity). The percent cytotoxicity was plotted against a log transformed x-axis (E:T ratios) with a 4-parameter non-linear regression curve fit, with data shown in FIGS. 11A-11F as mean±SD. Mock negative control T cells did induce some degree of cytotoxicity in all GPRC5D+ cell lines other than EJM, but to a lesser degree than GPRC5D GC5B680-N68S-LH cells, especially at the higher E:T ratios. Without wishing to be bound by theory, the reduced cytotoxicity likely arose from an allogeneic response. In addition, cytotoxicity of the GPRC5D CAR cells varied depending on cell line.

Example 11—Assay of GPRC5D CAR-T Activation at 48 Hours

Figure 12:
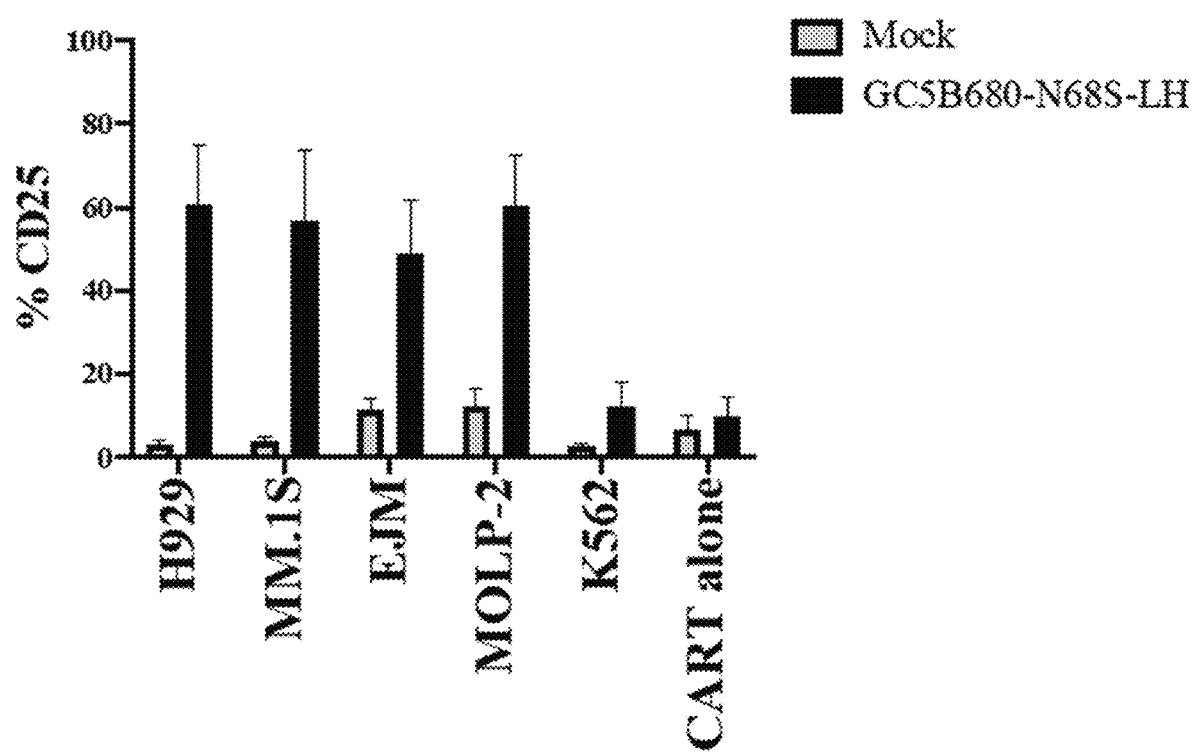
FIG. 12 shows a bar graph depicting levels of surface CD25 expression (% CD25) by untransduced (mock) or GC5B680-N68S-LH cells in the presence of K562 cells at an E:T ratio of 3:1. CAR-Ts were made from six healthy donors. The data is expressed as the mean±SD.

GPRC5D GC5B680-N68S-LH transduced and untransduced (Mock) T cells were prepared from healthy donors. GPRC5D GC5B680-N68S-LH transduced or untransduced (Mock) T cells were added at a 3:1 E:T ratio to carboxyfluorescein succinimidyl ester (CFSE) labeled GPRC5D+ H929, GPRC5D+ MM.1S, GPRC5D+ MOLP-2, GPRC5D+ EJM, and GPRC5D− K562 cells. After 48 hours of incubation, the cells were stained with a live/dead-dye, anti-CD25, anti-CD3, and anti-CAR visual markers. The cells were then evaluated for surface CD25 expression. The data are expressed in FIG. 12 as the mean±SD. As shown in FIG. 12, less than 13% background surface CD25 expression was observed in mock cells (i.e., no activation). In contrast, GC5B680-N68S-LH CAR-T cells were activated in the presence of GPRC5D+ cell lines, as shown by heightened CD25 expression levels. In both (i) mock and (ii) GC5B680-N68S-LH CAR-T cells only, low levels of surface CD25 expression was observed upon incubation with K562 cells or upon incubation alone.

Example 12—Assay of GPRC5D CAR-T Polyfunctionality

GC5B680-N68S-LH transduced (CAR-T) cells were incubated with either PMA/ionomycin (as a positive control), a GPRC5D+ cell line H929 (H929), GPRC5D− K562 (K562) cells (CFSE-labeled), or alone, for 18 hours. The cells were incubated at an E:T ratio of 1:2 when incubated in the presence of H929 or K562 cells. The cells were then first surface-stained with a live/dead dye, anti-CD3, and anti-idiotype followed by fixation, permeabilization, and intracellularly staining with anti-IFN-γ, anti-IL-2, and anti-TNF-α. Stained cells were then analyzed by flow cytometry. The percentages of individual cytokine levels were calculated following analysis of flow cytograms using Boolean (hierarchical) gating, with the percentages represented in Tables 3-6 below. Also in Tables 3-6, the levels of polyfunctional cytokine release for each group are highlighted in gray with the sums of averages represented.

TABLE 3

Cytokine expression in CAR-T cells incubated in the presence of H929

| CAR-T | Target | T cell donor ID | Polyfunctional Populations | | | | | | | |
|---|---|---|---|---|---|---|---|---|---|---|
| | | | IFNγ+ IL2+ TNFα+ | IFNγ+ IL2+ TNFα− | IFNγ+ IL2− TNFα+ | IFNγ− IL2+ TNFα+ | IFNγ+ IL2− TNFα− | IFNγ− IL2+ TNFα− | IFNγ− IL2− TNFα+ | IFNγ− IL2− TNFα− |
| GC5B680-N68S-LH | H929 | D204071 | 2.1 | 0.2 | 4.4 | 18.1 | 0.8 | 1.8 | 43.2 | 29.4 |
| GC5B680-N68S-LH | H929 | D270235 | 4.1 | 0.5 | 8.5 | 10.9 | 3.8 | 2.2 | 31.4 | 38.6 |
| GC5B680-N68S-LH | H929 | 110039522 | 1.3 | 0.1 | 1.8 | 19.1 | 0.5 | 0.5 | 42.2 | 34.6 |
| GC5B680-N68S-LH | H929 | D202896 | 13.5 | 0.0 | 30.7 | 6.8 | 2.1 | 0.4 | 27.1 | 19.5 |
| GC5B680-N68S-LH | H929 | D328058 | 7.0 | 0.1 | 12.2 | 18.2 | 0.8 | 0.2 | 32.9 | 28.7 |
| GC5B680-N68S-LH | H929 | D204395 | 4.3 | 0.0 | 4.6 | 30.5 | 0.4 | 0.3 | 37.9 | 22.1 |
| | | Percent polyfunctional H929 | 33.1 | | | | | | | |

TABLE 4

Cytokine expression in CAR-T cells incubated in the presence of K562

| CAR-T | Target | T cell donor ID | Polyfunctional Populations | | | | | | | |
|---|---|---|---|---|---|---|---|---|---|---|
| | | | IFNγ+ IL2+ TNFα+ | IFNγ+ IL2+ TNFα− | IFNγ+ IL2− TNFα+ | IFNγ− IL2+ TNFα+ | IFNγ+ IL2− TNFα− | IFNγ− IL2+ TNFα− | IFNγ− IL2− TNFα+ | IFNγ− IL2− TNFα− |
| GC5B680-N68S-LH | K562 | D204071 | 0.0 | 0.0 | 0.5 | 0.5 | 1.5 | 3.2 | 5.7 | 88.5 |
| GC5B680-N68S-LH | K562 | D270235 | 0.2 | 0.5 | 2.0 | 1.1 | 2.7 | 3.0 | 7.7 | 83.0 |
| GC5B680-N68S-LH | K562 | 110039522 | 0.1 | 0.3 | 0.3 | 0.2 | 1.0 | 1.1 | 3.6 | 93.4 |
| GC5B680-N68S-LH | K562 | D202896 | 0.2 | 0.2 | 1.3 | 0.5 | 2.3 | 4.5 | 3.7 | 87.4 |
| GC5B680-N68S-LH | K562 | D328058 | 0.2 | 0.1 | 1.4 | 0.3 | 1.6 | 2.1 | 6.1 | 88.1 |
| GC5B680-N68S-LH | K562 | D204395 | 0.1 | 0.2 | 0.5 | 0.5 | 0.7 | 3.1 | 9.4 | 85.5 |
| | | Percent polyfunctional K562 | 1.9 | | | | | | | |

TABLE 5

Cytokine expression in CAR-T cells incubated alone

| CAR-T | Target | T cell donor ID | Polyfunctional Populations | | | | | | | |
|---|---|---|---|---|---|---|---|---|---|---|
| | | | IFNγ+ IL2+ TNFα+ | IFNγ+ IL2+ TNFα− | IFNγ+ IL2− TNFα+ | IFNγ− IL2+ TNFα+ | IFNγ+ IL2− TNFα− | IFNγ− IL2+ TNFα− | IFNγ− IL2− TNFα+ | IFNγ− IL2− TNFα− |
| GC5B680-N68S-LH | CART alone | D204071 | 0.0 | 0.4 | 0.7 | 0.1 | 2.0 | 3.2 | 4.3 | 89.2 |
| GC5B680-N68S-LH | CART alone | D270235 | 0.4 | 0.8 | 1.8 | 0.4 | 4.1 | 3.7 | 6.5 | 82.4 |
| GC5B680-N68S-LH | CART alone | 110039522 | 0.1 | 0.4 | 0.2 | 0.2 | 1.7 | 1.4 | 1.9 | 94.0 |
| GC5B680-N68S-LH | CART alone | D202896 | 0.1 | 0.6 | 1.8 | 0.4 | 2.4 | 6.8 | 2.1 | 86.0 |
| GC5B680-N68S-LH | CART alone | D328058 | 0.2 | 0.4 | 1.0 | 0.3 | 1.4 | 3.2 | 3.9 | 89.6 |
| GC5B680-N68S-LH | CART alone | D204395 | 0.1 | 0.3 | 0.7 | 0.5 | 1.6 | 5.0 | 7.2 | 84.5 |
| | | Percent polyfunctional CAR-T alone | 2.0 | | | | | | | |

TABLE 6

Cytokine expression in CAR-T cells incubated in the presence of PMA/Ionomycin

| CAR-T | Target | T cell donor ID | Polyfunctional Populations | | | | | | | |
|---|---|---|---|---|---|---|---|---|---|---|
| | | | IFNγ+ IL2+ TNFα+ | IFNγ+ IL2+ TNFα− | IFNγ+ IL2− TNFα+ | IFNγ− IL2+ TNFα+ | IFNγ+ IL2− TNFα− | IFNγ− IL2+ TNFα− | IFNγ− IL2− TNFα+ | IFNγ− IL2− TNFα− |
| GC5B680-N68S-LH | PMA/Ionomycin | D204071 | 10.8 | 0.1 | 6.0 | 62.7 | 0.2 | 1.5 | 15.8 | 2.9 |
| GC5B680-N68S-LH | PMA/Ionomycin | D270235 | 31.0 | 0.2 | 16.7 | 43.9 | 0.3 | 0.4 | 7.0 | 0.6 |
| GC5B680-N68S-LH | PMA/Ionomycin | 110039522 | 10.5 | 0.0 | 2.8 | 68.8 | 0.0 | 0.4 | 16.1 | 1.5 |
| GC5B680-N68S-LH | PMA/Ionomycin | D202896 | 42.8 | 0.3 | 29.1 | 20.0 | 0.5 | 0.1 | 6.2 | 1.0 |

TABLE 6-continued

Cytokine expression in CAR-T cells incubated in the presence of PMA/Ionomycin

| | | | Polyfunctional Populations | | | | | | | |
|---|---|---|---|---|---|---|---|---|---|---|
| CAR-T | Target | T cell donor ID | IFNγ+ IL2+ TNFα+ | IFNγ+ IL2+ TNFα− | IFNγ+ IL2− TNFα+ | IFNγ− IL2+ TNFα+ | IFNγ+ IL2− TNFα− | IFNγ− IL2+ TNFα− | IFNγ− IL2− TNFα+ | IFNγ− IL2− TNFα− |
| GC5B680-N68S-LH | PMA/Ionomycin | D328058 | 33.6 | 0.1 | 15.4 | 42.1 | 0.2 | 0.2 | 7.5 | 0.9 |
| GC5B680-N68S-LH | PMA/Ionomycin | D204395 | 21.2 | 0.0 | 6.1 | 59.3 | 0.4 | 1.0 | 10.7 | 1.3 |
| | | Percent polyfunctional PMA/Ionomycin | 87.3 | | | | | | | |

Example 13—Assay of GPRC5D CAR-T Proliferation

GC5B680-N68S-LH cells were prepared using cells from one donor. The (i) GC5B680-N68S-LH transduced cells and (ii) mock cells were incubated in the presence or absence of GPRC5D+ cells (MM.1S and H929). Mock (untransduced) cells were used as a negative control. The extent of cell proliferation was measured following a 6 day incubation by assaying the extent of dilution of CELLTRACE Violet (CTV) dye concentration in cells, with the quantity represented by the X axis of the graphs of FIG. 13. CAR+ cells were stained using an anti-idiotype antibody, with the degree of staining represented by the Y axis of the graphs of FIG. 13.

Figure 13:
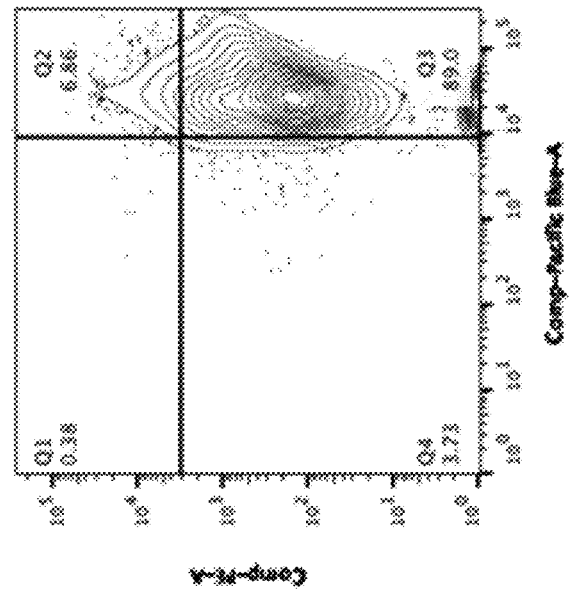
FIG. 13 illustrates flow cytograms demonstrating that GC5B680-N68S-LH proliferates specifically in the presence of GPRC5D+ target cells (H929 or MM.1S) or a positive control (agonist CD3/CD28 beads) and not in the absence of target cells or in the presence of GPRC5D− cells (K562). Cell proliferation was measured using CELLTRACE Violet (CTV) (X-axis). $CAR^+$ events were detected using an anti-idiotype antibody (Y-axis).
Figure 13:
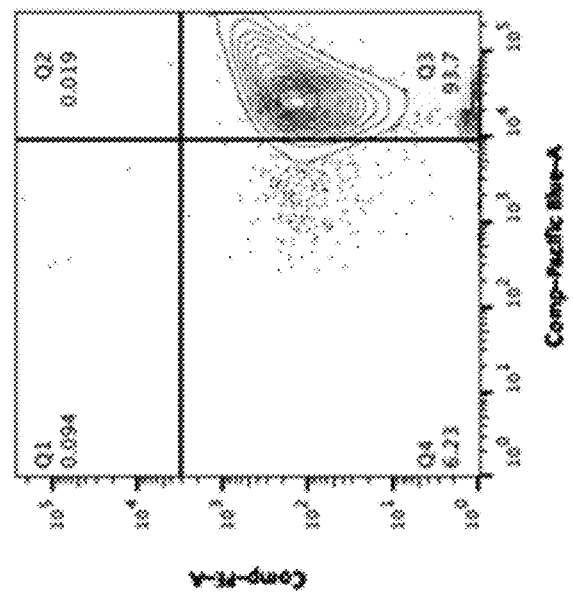
Figure 13:
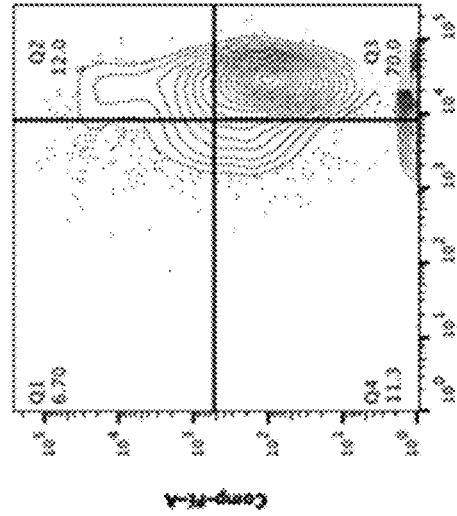
Figure 13:
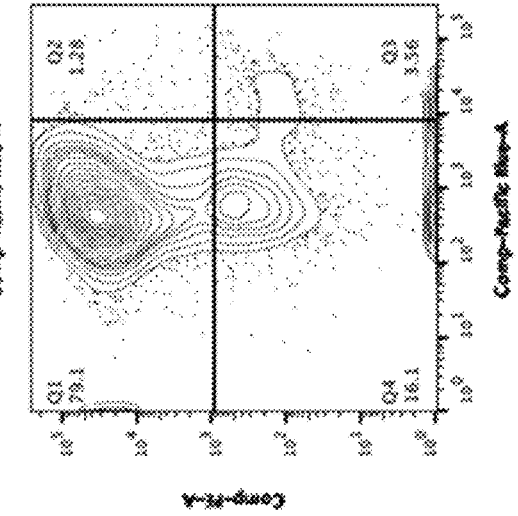
Figure 13:
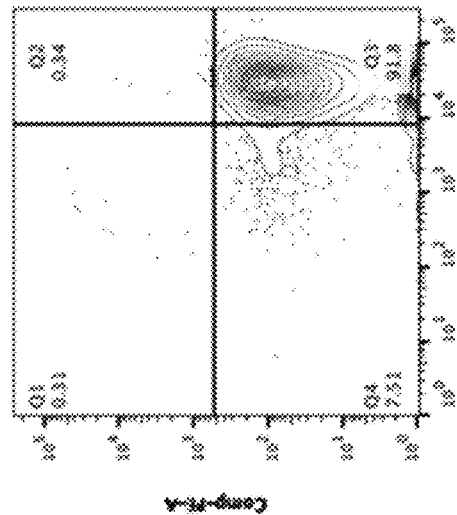
Figure 13:
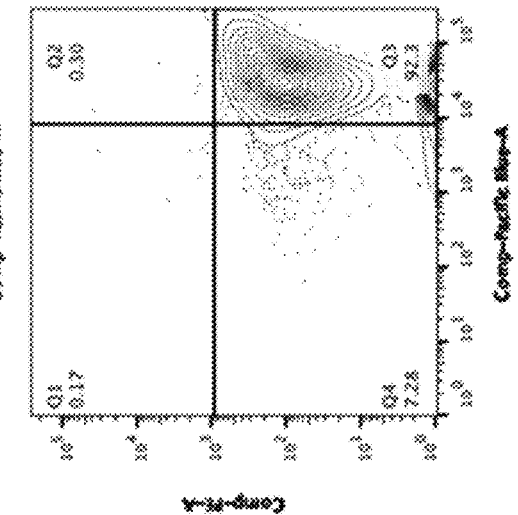
Figure 13:
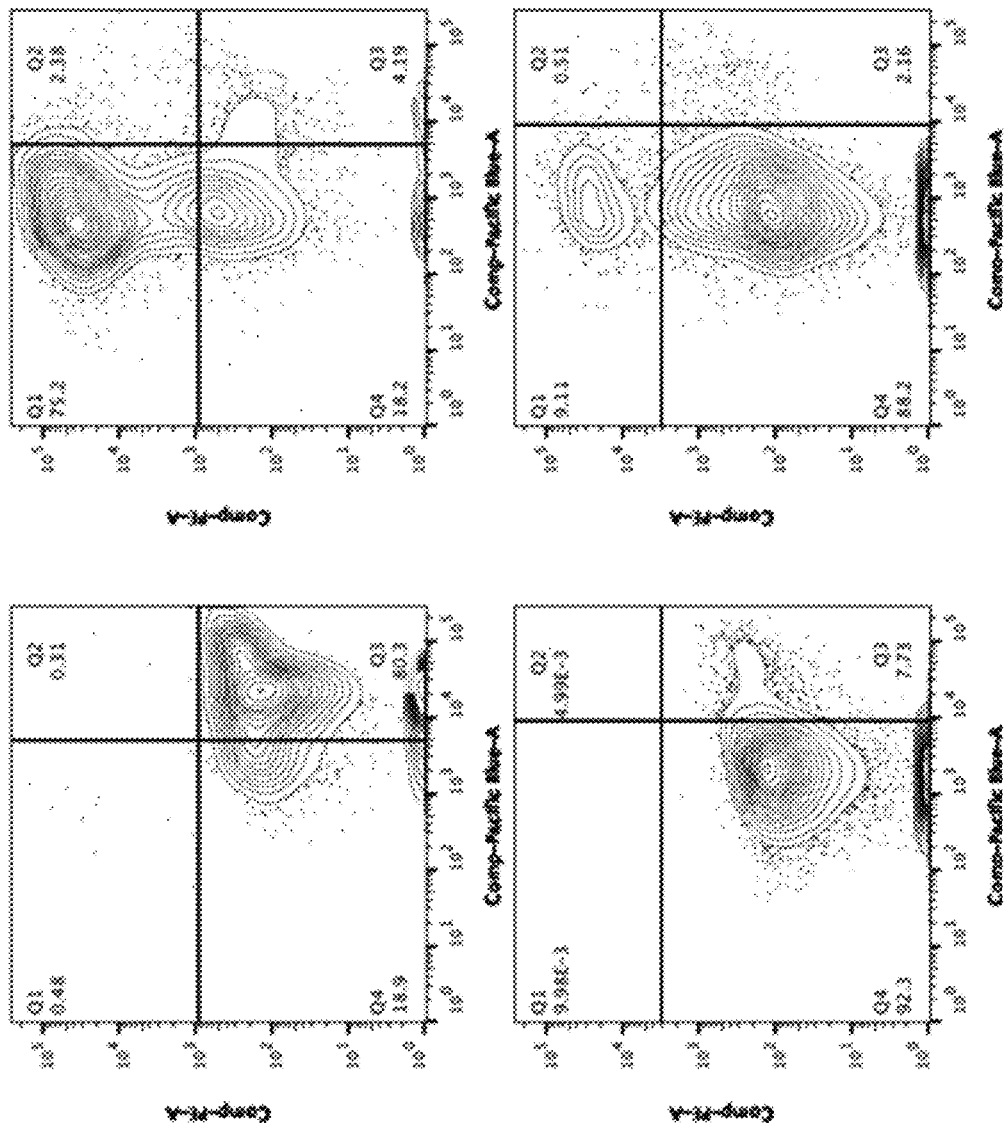

As shown in FIG. 13, mock and CTV-labeled CAR T cells, alone or in the presence of GPRC5D− K562 cells, demonstrated little to no cell proliferation as seen from low to zero dilution of the CTV dye. Agonist CD3/CD28 beads (that served as a positive control) resulted in proliferation of all T cell populations evaluated, as predicted. When CAR-T cells were incubated with GPRC5D+ target cells (H929 or MM.1S), proliferation was primarily enriched in transduced cells expressing GC5B680-N68S-LH on their surface (CAR+) (as shown in the upper quadrants in the graphs of FIG. 13). This result suggested that GC5B680-N68S-LH cell proliferation is enhanced in the presence of GPRC5D+ target cells. The data shown in FIG. 13 is representative of similar observations made using cells prepared from other donors.

Example 14—Assay of GPRC5D CAR-T Proliferation

Figure 14:
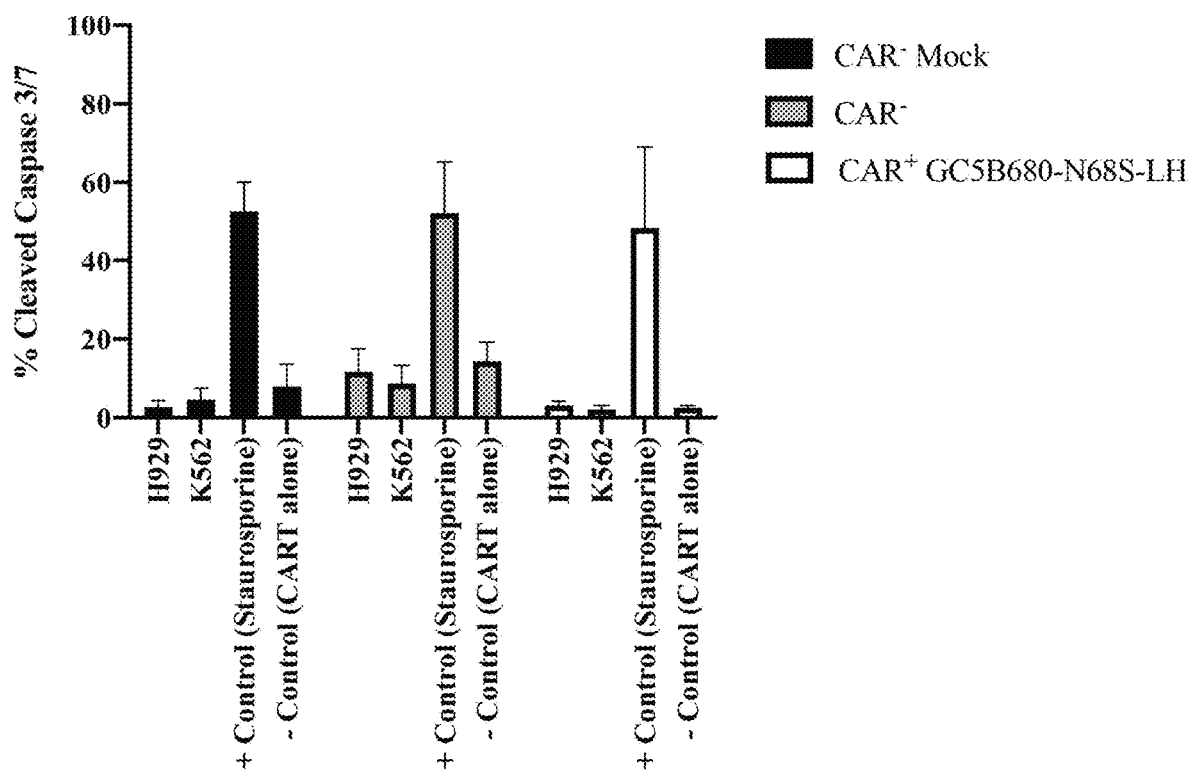
FIG. 14 shows a bar graph demonstrating that levels of cleaved caspase 3/7 levels in CAR-T (GC5B680-N68S-LH) cells incubated with the $GPRC5D^+$ cell line H929 for 24 hours remain unchanged compared to controls (staurosporine, GPRC5D− K562 cells, or alone). E:T ratio 1:2 was used for H929 and K562 cells. $CAR^-$ represents transduced cells not expressing GPRC5D CAR. $CAR^+$ represents transduced cells expressing GPRC5D CAR.

GC5B680-N68S-LH (CAR-T) cells were incubated with either positive control staurosporine, GPRC5D+ H929 cells, GPRC5D− K562 cells, or alone, for 24 hours. An E:T ratio of 1:2 was used for incubations of GC5B680-N68S-LH (CAR-T) cells with H929 or K562 cells. The cells were then stained with a live/dead dye, anti-CD3, anti-idiotype, and anti-cleaved caspase 3/7 dye. The stained cells were analyzed by flow cytometry. The data are expressed in the graph of FIG. 14. As shown in FIG. 14, staurosporine induced cleaved caspase 3/7 staining in both CAR+ and CAR− T cell populations. Also, there were 50-65% positive cells starting from 4 hours after the 24 hour timepoint. Neither CAR+ nor CAR− T cell populations demonstrated significant differences in caspase 3/7 levels between negative control incubations (K562 and CART alone) and incubations in the presence of H929.

Example 15—Assay of Efficacy of GC5B680-N68S-LH, GC5B680-N68S-HL, GP5B83_N24T_N31S-LH, and GP5B83_N24T_N31S-HL on Established MM.1S Human MM Xenografts in NSG-B2M Mice The anti-tumor efficacy of GC5B680-N68S-LH (SEQ ID NO:86), GC5B680-N68S-HL (SEQ ID NO:85), GP5B83_N24T_N31S-LH (SEQ ID NO:84), and GP5B83_N24T_N31S-HL (SEQ ID NO:83) transduced T cells (CAR-T cells) was evaluated in the established subcutaneous (sc) MM.1S human multiple myeloma (MM) xenograft model in female NSG B2m (alternatively referred to as NOD-scid Il2rg$^{null}$ B2mm$^{null}$, or as NOD-scid gamma B2m). The (i) GC5B680-N68S-LH, (ii) GC5B680-N68S-HL, (iii) GP5B83_N24T_N31S-LH, or (iv) GP5B83_N24T_N31S-HL CAR-T cells were administered at a dose of 1×10$^6$ CAR+ cells or 5×10$^6$ CAR+ cells intravenously (iv) on Day 13 for a total of one dose. Three groups of MM.1S xenograft-bearing mice were assessed: (i) mice treated with PBS, (ii) mice that underwent mock transduction, and (iii) mice that were transduced with GPRC5D. The percentage delta tumor growth inhibition (% ΔTGI) of the three groups of mice bearing SC (subcutaneous) MM.1S xenografts was calculated on Day 26 post tumor implantation using the formula: ([(TVc−TVc0)−(TVt−TVt0)]/(TVc−TVc0))×100 where TVC is the mean tumor burden of a given control group, 'TVc0' is the mean initial tumor burden of a given control group, 'TVt' is the mean tumor burden of the treated group, and 'TVt0' is the mean initial tumor burden of the treated group.

Statistical significance was calculated using the linear mixed-effects analysis in R, with treatment and time as fixed effects and animal as random effect. Logarithmic transformation (base 10) was performed if individual longitudinal response trajectories were not linear. The information derived from this statistical model was used to make pairwise treatment comparisons to the PBS control or mock transduced groups, with p values considered statistically significant when <0.05.

Figure 15:
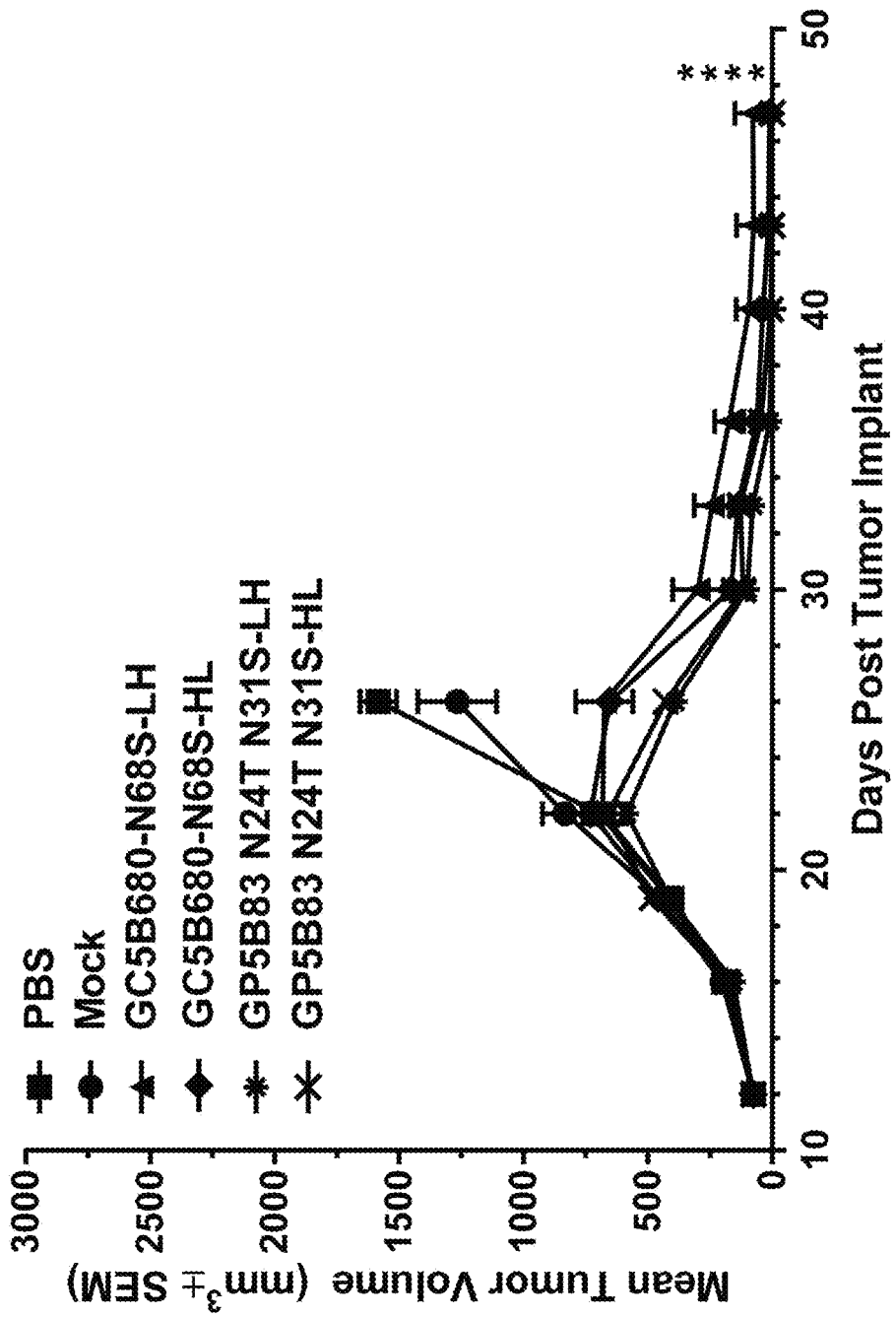
FIG. 15 shows a graph demonstrating the effect of GPRC5D directed CAR-T cells on established MM.1S Human MM Xenografts in NSG-B2M Mice according to Example 15. GC5B680-N68S-LH, GC5B680-N68S-HL, GC5B83-N24T-N31S-LH, and GC5B83-N24T-N31S-HL, GPRC5D-directed CAR-Ts, Mock, untransduced CAR-Ts, PBS, Phosphate-buffered Saline, NSG, non-obese diabetic severe combined immunodeficiency gamma, B2M, Beta-2 microglobulin, MM, Multiple Myeloma. Group tumor volumes are graphed as mean±SEM. Tumor cells were implanted on Day 0, 1×10⁶ CAR+ T cells were implanted on Day 13. The symbol "*" denotes a significant difference on Day 26 vs. PBS control (p<0.05, n=10/group).

All four GPRC5D-directed CAR-T constructs elicited statistically significant % ΔTGI at both 1×10$^6$ and 5×10$^6$ CAR+ T cell dose levels as compared with PBS and Mock CAR-T controls, as summarized in Table 7 and FIG. 15. Complete responses (complete tumor regression, with no palpable tumor) were assessed on Day 47 post-tumor implantation.

TABLE 7

Summary of GPRC5D-directed CAR-T Efficacy on Established
MM.1S Human MM Xenografts in NSG-B2M Mice

| Construct | Dose of CAR+ cells | Total dose of T cells (counting CAR+ and CAR− cells) | % ATGI | CRs (n of group) |
|---|---|---|---|---|
| Mock | — | 28.6 × 10$^6$ | 21% | 0/10 |
| GC5B680-N68S-LH | 1 × 10$^6$ | 5.71 × 10$^6$ | 50% | 8/10 |
|  | 5 × 10$^6$ | 28.6 × 10$^6$ | 97% | 10/10 |
| GC5B680-N68S-HL | 1 × 10$^6$ | 5.71 × 10$^6$ | 52% | 8/10 |
|  | 5 × 10$^6$ | 28.6 × 10$^6$ | 95% | 10/10 |
| GP5B83 N24T N31S-LH | 1 × 10$^6$ | 5.71 × 10$^6$ | 74% | 9/10 |
|  | 5 × 10$^6$ | 28.6 × 10$^6$ | 100% | 10/10 |
| GP5B83 N24T N31S-HL | 1 × 10$^6$ | 5.71 × 10$^6$ | 70% | 10/10 |
|  | 5 × 10$^6$ | 28.6 × 10$^6$ | 99% | 10/10 | p < 0.05 vs. PBS and Mock CAR-T controls except where noted as not significant (ns).
CR = complete response Example 16 Efficacy of GC5B680-N68S-LH, GC5B680-N68S-HL, GP5B83_N24T_N31S-LH, and GP5B83_N24T_N31S-HL on Disseminated H929 IV Human MM Xenografts in NSG Mice The efficacy of GC5B680-N68S-LH (SEQ ID NO:86; encoded by nucleotide of SEQ ID NO: 90), GC5B680-N68S-HL (SEQ ID NO:85; encoded by nucleotide of SEQ ID NO: 89), GP5B83_N24T_N31S-LH (SEQ ID NO:84; encoded by nucleotide of SEQ ID NO: 88), and GP5B83_N24T_N31S-HL (SEQ ID NO:83; encoded by nucleotide of SEQ ID NO: 87) transduced T cells was evaluated on a disseminated (iv) H929 human MM model in female NSG™ (alternatively referred to as NOD scid gamma, or as NOD.Cg-Prkdc$^{scid}$ Il2rg$^{tm1Wjl}$/SzJ) mice. In this example, GC5B680-N68S-LH, GC5B680-N68S-HL, GP5B83_N24T_N31S-LH, or GP5B83_N24T_N31S-HL expressing (CAR+) T cells were administered at a single iv dose of 1×10$^6$ CAR+ cells or 5×10$^6$ CAR+ cells on Day 9 post-tumor engraftment.

A survival assessment was performed in which the percentage survival at various study days was plotted against the study days. Hind-limb paralysis or other clinical signs of excessive disseminated tumor burden were used as surrogate endpoints for death. Median survival was determined using Kaplan-Meier survival analysis. Percent ILS (% ILS) was defined as the difference between median survival of the treated versus control group, and was calculated as ILS= ([MSt−MSc]/MSc)×100 where 'MSc' is the median survival of a given control group and 'MSt' is the median survival of a particular treatment group. Animals failing to reach the surrogate endpoint due to adverse clinical signs (such as ulcerated tumors, body weight loss, etc.) or death unrelated to treatment, were censored for the survival assessment. Survival was graphically represented using a Kaplan-Meier curve and evaluated by log-rank (Mantel-Cox) test using GraphPad Prism software (version 7.0).

Median 50% survival was reached by Day 52 post tumor implantation (43 days post CAR+ injection) for PBS-treated control mice. Median 50% survival was reached by Day 44 post tumor implantation (35 days post CAR-T injection) for Mock CAR-T cell treated mice. Median 50% survival was reached after Day 111 (102 days post CAR-T injection) for mice treated with GC5B680-N68S-LH CAR+ cells administered at a dose of 1×10$^6$. Median 50% survival was reached at Day 63.5 (54.5 days post CAR-T injection) for mice treated with GC5B680-N68S-HL CAR+ cells administered at a dose of 1×10$^6$ cells respectively. Median 50% survival was reached Day 93.5 (84.5 days post CAR-T injection) for mice treated with GP5B83_N24T_N31S-LH CAR+ cells administered at a dose of 1×10$^6$ cells. Median 50% survival was reached after Day 111 (102 days post CAR-T injection) for mice treated with GP5B83_N24T_N31S-HL CAR+ cells administered at a dose of 1×10$^6$ cells. The percent increased lifespan (ILS) was assessed via Kaplan-Meier curve and evaluated by log-rank Mantel-Cox test.

Figure 16:
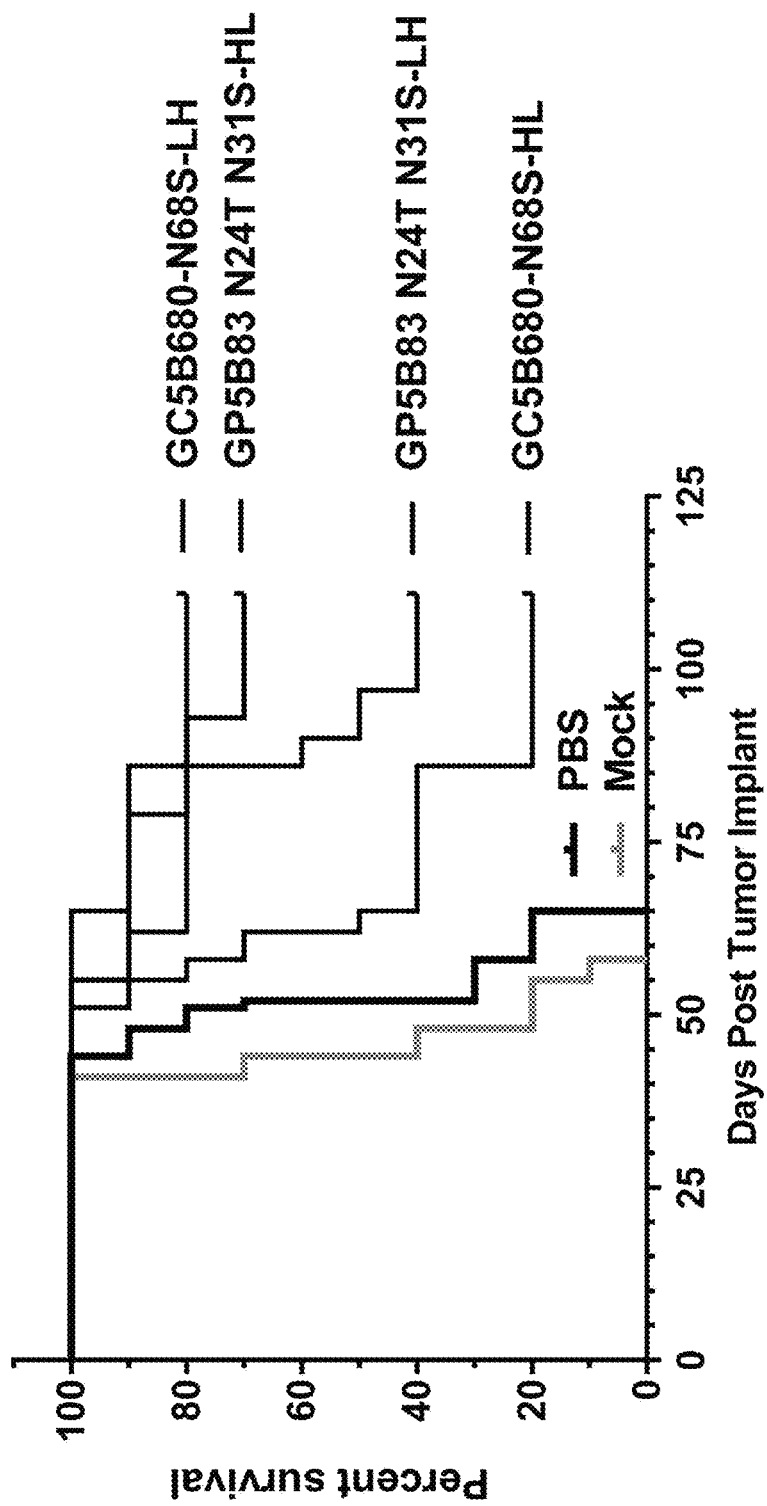
FIG. 16 shows a graph demonstrating the effect of GC5B680-N68S-LH on Survival of NSG Mice Bearing Disseminated H929 human MM Xenografts according to Example 16. GC5B680-N68S-LH, GC5B680-N68S-HL, GC5B83-N24T-N31S-LH, and GC5B83-N24T-N31S-HL, GPRC5D-directed CAR-T, Mock, untransduced CAR-Ts, PBS, Phosphate-buffered Saline, NSG, non-obese diabetic severe combined immunodeficiency gamma, MM, Multiple Myeloma. Tumor cells were implanted on Day 0; 1×10⁶ CAR+T cells were implanted on Day 9. The symbol "*" denotes a significant difference on Day 111 vs. PBS control.

All four GPRC5D-directed CAR-T constructs elicited statistically significant % ILS at the 1×10$^6$ dose level as compared with PBS and Mock CAR-T controls, as discussed below and summarized in Table 8 and FIG. 16. Animals surviving by day 111 were considered CRs.

TABLE 8

Summary of GPRC5D-directed CAR-T Efficacy on Disseminated
H929 Human MM Xenografts in NSG Mice

| Construct | CAR+ T cells | Total T cells | Median Survival Days | % ILS | CRs (n of group) |
|---|---|---|---|---|---|
| PBS | — | — | 52 | — | 0/10 |
| Mock | — | 37.1 × 10$^6$ | 44 | — | 0/10 |
| GC5B680-N685-LH | 1 × 10$^6$ | 7.42 × 10$^6$ | >111 | >113.5% | 8/10 |
| GC5B680-N685-HL | 1 × 10$^6$ | 7.42 × 10$^6$ | 63.5 | 22.1% | 2/10 |
| GP5B83 N24T N31S-LH | 1 × 10$^6$ | 7.42 × 10$^6$ | 93.5 | 79.8% | 4/10 |
| GP5B83 N24T N31S-HL | 1 × 10$^6$ | 7.42 × 10$^6$ | >111 | >113.5% | 7/10 | p < 0.05 vs. PBS and Mock CAR-T controls except where noted as not significant (ns).
CR = complete response Adverse clinical signs associated with progressive tumor disease burden were observed in the PBS-treated control group beginning on day 52 post-tumor engraftment, whereas clinical signs of graft versus host disease developed in the Mock transduced or GPRC5D CAR-T treated groups beginning on day 48 post-tumor engraftment.

The teachings of all patents, published applications and references cited herein are incorporated by reference in their entirety for all purposes.

While example embodiments have been particularly shown and described, it will be understood by those skilled in the art that various changes in form and details may be made therein without departing from the scope of the embodiments encompassed by the appended claims.

SEQUENCE LISTING

Light Chain Sequence 1 (GC5B483)
(SEQ ID NO: 1)
EIVLTQSPATLSLSPGERATLSCRASQSVSSYLAWYQQKPGQAPRLLIYDASNRATGIPARF

SGSGSGTDFTLTISSLEPEDFAVYYCQQRSNWPLTFGQGTKVEIK

Heavy Chain Sequence 1 (GC5B483)
(SEQ ID NO: 2)
EVQLVQSGAEVKKPGESLKISCKGSGYSFTSYFIGWVRQMPGKGLEWMGIIYPGKSDTR

YSPSFQGQVTISADKSISTAYLQWSSLKASDTAMYYCARVYSFGGRHKALFDYWGQGTL

VTVSS

Light Chain Sequence 2 (GC5B81)
(SEQ ID NO: 3)
DIQMTQSPSSLSASVGDRVTITCRASQSISSYLNWYQQKPGKAPKLLIYAASSLQSGVPSR

FSGSGSGTDFTLTISSLQPEDFATYYCQQSYSTPLTFGQGTKVEIK

Heavy Chain Sequence 2 (GC5B81)
(SEQ ID NO: 4)
QVQLVQSGAEVKKPGSSVKVSCKASGGTFSSYAISWVRQAPGQGLEWMGGIIPIFGTAN

YAQKFQGRVTITADESTSTAYMELSSLRSEDTAVYYCARESRWRGYKLDYWGQGTLVTV

SS

Light Chain Sequence 3 (GC5B596)
(SEQ ID NO: 5)
DIQMTQSPSSLSASVGDRVTITCKASQNVATHVGWYQQKPGKAPKRLIYSASYRYSGVPS

RFSGSGSGTEFTLTISNLQPEDFATYYCQQYNRYPYTFGQGTKLEIK

Heavy Chain Sequence 3 (GC5B596)
(SEQ ID NO: 6)
QVQLVQSGAEVKKPGASVKVSCKASGYSFTGYTMNWVRQAPGQGLEWMGLINPYNSD

TNYAQKLQGRVTMTTDTSTSTAYMELRSLRSDDTAVYYCARVALRVALDYWGQGTLVT

VSS

Linker polypeptide Sequence
(SEQ ID NO: 7)
GTEGKSSGSGSESKST scFv Sequence 1 (GC5B483)
(SEQ ID NO: 8)
EIVLTQSPATLSLSPGERATLSCRASQSVSSYLAWYQQKPGQAPRLLIYDASNRATGIPARF

SGSGSGTDFTLTISSLEPEDFAVYYCQQRSNWPLTFGQGTKVEIKGTEGKSSGSGSESKST

EVQLVQSGAEVKKPGESLKISCKGSGYSFTSYFIGWVRQMPGKGLEWMGIIYPGKSDTR

YSPSFQGQVTISADKSISTAYLQWSSLKASDTAMYYCARVYSFGGRHKALFDYWGQGTL

VTVSS scFv Sequence 2 (GC5B81)
(SEQ ID NO: 9)
DIQMTQSPSSLSASVGDRVTITCRASQSISSYLNWYQQKPGKAPKLLIYAASSLQSGVPSR

FSGSGSGTDFTLTISSLQPEDFATYYCQQSYSTPLTFGQGTKVEIKGTEGKSSGSGSESKST

QVQLVQSGAEVKKPGSSVKVSCKASGGTFSSYAISWVRQAPGQGLEWMGGIIPIFGTAN

YAQKFQGRVTITADESTSTAYMELSSLRSEDTAVYYCARESRWRGYKLDYWGQGTLVTV

SS scFv Sequence 3 (GC5B596)
(SEQ ID NO: 10)
DIQMTQSPSSLSASVGDRVTITCKASQNVATHVGWYQQKPGKAPKRLIYSASYRYSGVPS

RFSGSGSGTEFTLTISNLQPEDFATYYCQQYNRYPYTFGQGTKLEIKGTEGKSSGSGSESK

```
STQVQLVQSGAEVKKPGASVKVSCKASGYSFTGYTMNWVRQAPGQGLEWMGLINPYN

SDTNYAQKLQGRVTMTTDTSTSTAYMELRSLRSDDTAVYYCARVALRVALDYWGQGTL

VTVSS

Signal Sequence
                                                    (SEQ ID NO: 11)
MAWVWTLLFLMAAAQSIQA CD137 Sequence
                                                    (SEQ ID NO: 12)
KRGRKKLLYIFKQPFMRPVQTTQEEDGCSCRFPEEEEGGCEL CD3z Sequence
                                                    (SEQ ID NO: 13)
RVKFSRSADAPAYKQGQNQLYNELNLGRREEYDVLDKRRGRDPEMGGKPRRKNPQEGL

YNELQKDKMAEAYSEIGMKGERRRGKGHDGLYQGLSTATKDTYDALHMQALPPR

Intracellular signaling domain
                                                    (SEQ ID NO: 14)
KRGRKKLLYIFKQPFMRPVQTTQEEDGCSCRFPEEEEGGCELRVKFSRSADAPAYKQGQ

NQLYNELNLGRREEYDVLDKRRGRDPEMGGKPRRKNPQEGLYNELQKDKMAEAYSEIG

MKGERRRGKGHDGLYQGLSTATKDTYDALHMQALPPR

CD8a-TM Sequence
                                                    (SEQ ID NO: 15)
IYIWAPLAGTCGVLLLSLVITLYC CD8a hinge Sequence
                                                    (SEQ ID NO: 16)
TSTPAPRPPTPAPTIASQPLSLRPEACRPAAGGAVHTRGLDFACD Extracellular binding domain (GC5B483)
                                                    (SEQ ID NO: 17)
MAWVWTLLFLMAAAQSIQAEIVLTQSPATLSLSPGERATLSCRASQSVSSYLAWYQQKP

GQAPRLLIYDASNRATGIPARFSGSGSGTDFTLTISSLEPEDFAVYYCQQRSNWPLTFGQG

TKVEIKGTEGKSSGSGSESKSTEVQLVQSGAEVKKPGESLKISCKGSGYSFTSYFIGWVR

QMPGKGLEWMGITYPGKSDTRYSPSFQGQVTISADKSISTAYLQWSSLKASDTAMYYCA

RVYSFGGRHKALFDYWGQGTLVTVSS

Extracellular binding domain (GC5B81)
                                                    (SEQ ID NO: 18)
MAWVWTLLFLMAAAQSIQADIQMTQSPSSLSASVGDRVTITCRASQSISSYLNWYQQKP

GKAPKLLIYAASSLQSGVPSRFSGSGSGTDFTLTISSLQPEDFATYYCQQSYSTPLTFGQGT

KVEIKGTEGKSSGSGSESKSTQVQLVQSGAEVKKPGSSVKVSCKASGGTFSSYAISWVRQ

APGQGLEWMGGIIPIFGTANYAQKFQGRVTITADESTSTAYMELSSLRSEDTAVYYCARES

RWRGYKLDYWGQGTLVTVSS

Extracellular binding domain (GC5B596)
                                                    (SEQ ID NO: 19)
MAWVWTLLFLMAAAQSIQADIQMTQSPSSLSASVGDRVTITCKASQNVATHVGWYQQK

PGKAPKRLIYSASYRYSGVPSRFSGSGSGTEFTLTISNLQPEDFATYYCQQYNRYPYTFGQ

GTKLEIKGTEGKSSGSGSESKSTQVQLVQSGAEVKKPGASVKVSCKASGYSFTGYTMN

WVRQAPGQGLEWMGLINPYNSDTNYAQKLQGRVTMTTDTSTSTAYMELRSLRSDDTAV

YYCARVALRVALDYWGQGTLVTVSS

Extracellular binding domain (GC5B483)
                                                    (SEQ ID NO: 20)
MAWVWTLLFLMAAAQSIQAEVQLVQSGAEVKKPGESLKISCKGSGYSFTSYFIGWVRQ

MPGKGLEWMGITYPGKSDTRYSPSFQGQVTISADKSISTAYLQWSSLKASDTAMYYCAR

VYSFGGRHKALFDYWGQGTLVTVSSGTEGKSSGSGSESKSTEIVLTQSPATLSLSPGERAT
```

LSCRASQSVSSYLAWYQQKPGQAPRLLIYDASNRATGIPARFSGSGSGTDFTLTISSLEPE

DFAVYYCQQRSNWPLTFGQGTKVEIK

Extracellular binding domain (GC5B81)
(SEQ ID NO: 21)
MAWVWTLLFLMAAAQSIQAQVQLVQSGAEVKKPGSSVKVSCKASGGTFSSYAISWVRQ

APGQGLEWMGGIIPIFGTANYAQKFQGRVTITADESTSTAYMELSSLRSEDTAVYYCARES

RWRGYKLDYWGQGTLVTVSSGTEGKSSGSGSESKSTDIQMTQSPSSLSASVGDRVTITCR

ASQSISSYLNWYQQKPGKAPKLLIYAASSLQSGVPSRFSGSGSGTDFTLTISSLQPEDFATY

YCQQSYSTPLTFGQGTKVEIK

Extracellular binding domain (GC5B596)
(SEQ ID NO: 22)
MAWVWTLLFLMAAAQSIQAQVQLVQSGAEVKKPGASVKVSCKASGYSFTGYTMNWV

RQAPGQGLEWMGLINPYNSDTNYAQKLQGRVTMTTDTSTSTAYMELRSLRSDDTAVYY

CARVALRVALDYWGQGTLVTVSSGTEGKSSGSGSESKSTDIQMTQSPSSLSASVGDRVTI

TCKASQNVATHVGWYQQKPGKAPKRLIYSASYRYSGVPSRFSGSGSGTEFTLTISNLQPE

DFATYYCQQYNRYPYTFGQGTKLEIK scFv Sequence 4 (GC5B483)
(SEQ ID NO: 24)
EVQLVQSGAEVKKPGESLKISCKGSGYSFTSYFIGWVRQMPGKGLEWMGIIYPGKSDTR

YSPSFQGQVTISADKSISTAYLQWSSLKASDTAMYYCARVYSFGGRHKALFDYWGQGTL

VTVSSGTEGKSSGSGSESKSTEIVLTQSPATLSLSPGERATLSCRASQSVSSYLAWYQQKP

GQAPRLLIYDASNRATGIPARFSGSGSGTDFTLTISSLEPEDFAVYYCQQRSNWPLTFGQG

TKVEIK scFv Sequence 5 (GC5B81)
(SEQ ID NO: 25)
QVQLVQSGAEVKKPGSSVKVSCKASGGTFSSYAISWVRQAPGQGLEWMGGIIPIFGTAN

YAQKFQGRVTITADESTSTAYMELSSLRSEDTAVYYCARESRWRGYKLDYWGQGTLVTV

SSGTEGKSSGSGSESKSTDIQMTQSPSSLSASVGDRVTITCRASQSISSYLNWYQQKPGKA

PKLLIYAASSLQSGVPSRFSGSGSGTDFTLTISSLQPEDFATYYCQQSYSTPLTFGQGTKVEI

K scFv Sequence 6 (GC5B596)
(SEQ ID NO: 26)
QVQLVQSGAEVKKPGASVKVSCKASGYSFTGYTMNWVRQAPGQGLEWMGLINPYNSD

TNYAQKLQGRVTMTTDTSTSTAYMELRSLRSDDTAVYYCARVALRVALDYWGQGTLVT

VSSGTEGKSSGSGSESKSTDIQMTQSPSSLSASVGDRVTITCKASQNVATHVGWYQQKPG

KAPKRLIYSASYRYSGVPSRFSGSGSGTEFTLTISNLQPEDFATYYCQQYNRYPYTFGQGT

KLEIK pDR000074490 GC5B483-LH-CAR sequence
(SEQ ID NO: 27)
MAWVWTLLFLMAAAQSIQAEIVLTQSPATLSLSPGERATLSCRASQSVSSYLAWYQQKP

GQAPRLLIYDASNRATGIPARFSGSGSGTDFTLTISSLEPEDFAVYYCQQRSNWPLTFGQG

TKVEIKGTEGKSSGSGSESKSTEVQLVQSGAEVKKPGESLKISCKGSGYSFTSYFIGWVR

QMPGKGLEWMGIIYPGKSDTRYSPSFQGQVTISADKSISTAYLQWSSLKASDTAMYYCA

RVYSFGGRHKALFDYWGQGTLVTVSSTSTPAPRPPTPAPTIASQPLSLRPEACRPAAGGAV

HTRGLDFACDIYIWAPLAGTCGVLLLSLVITLYCKRGRKKLLYIFKQPFMRPVQTTQEED

-continued

GCSCRFPEEEEGGCELRVKFSRSADAPAYKQGQNQLYNELNLGRREEYDVLDKRRGRDP

EMGGKPRRKNPQEGLYNELQKDKMAEAYSEIGMKGERRRGKGHDGLYQGLSTATKDT

YDALHMQALPPR pDR000074489 GC5B81-LH-CAR sequence
(SEQ ID NO: 28)
MAWVWTLLFLMAAAQSIQADIQMTQSPSSLSASVGDRVTITCRASQRSSYLNWYQQKP

GKAPKLLIYAASSLQSGVPSRFSGSGSGTDFTLTISSLQPEDFATYYCQQSYSTPLTFGQGT

KVEIKGTEGKSSGSGSESKSTQVQLVQSGAEVKKPGSSVKVSCKASGGTFSSYAISWVRQ

APGQGLEWMGGIIPIFGTANYAQKFQGRVTITADESTSTAYMELSSLRSEDTAVYYCARES

RWRGYKLDYWGQGTLVTVSSTSTPAPRPPTPAPTIASQPLSLRPEACRPAAGGAVHTRGL

DFACDIYIWAPLAGTCGVLLLSLVITLYCKRGRKKLLYIFKQPFMRPVQTTQEEDGCSCRF

PEEEEGGCELRVKFSRSADAPAYKQGQNQLYNELNLGRREEYDVLDKRRGRDPEMGGK

PRRKNPQEGLYNELQKDKMAEAYSEIGMKGERRRGKGHDGLYQGLSTATKDTYDALH

MQALPPR pDR000074488 GC5B596-LH-CAR sequence
(SEQ ID NO: 29)
MAWVWTLLFLMAAAQSIQADIQMTQSPSSLSASVGDRVTITCKASQNVATHVGWYQQK

PGKAPKRLIYSASYRYSGVPSRFSGSGSGTEFTLTISNLQPEDFATYYCQQYNRYPYTFGQ

GTKLEIKGTEGKSSGSGSESKSTQVQLVQSGAEVKKPGASVKVSCKASGYSFTGYTMN

WVRQAPGQGLEWMGLINPYNSDTNYAQKLQGRVTMTTDTSTSTAYMELRSLRSDDTAV

YYCARVALRVALDYWGQGTLVTVSSTSTPAPRPPTPAPTIASQPLSLRPEACRPAAGGAVH

TRGLDFACDIYIWAPLAGTCGVLLLSLVITLYCKRGRKKLLYIFKQPFMRPVQTTQEEDG

CSCRFPEEEEGGCELRVKFSRSADAPAYKQGQNQLYNELNLGRREEYDVLDKRRGRDPE

MGGKPRRKNPQEGLYNELQKDKMAEAYSEIGMKGERRRGKGHDGLYQGLSTATKDTY

DALHMQALPPR pDR000074483 GC5B483-HL-CAR sequence
(SEQ ID NO: 30)
MAWVWTLLFLMAAAQSIQAEVQLVQSGAEVKKPGESLKISCKGSGYSFTSYFIGWVRQ

MPGKGLEWMGIIYPGKSDTRYSPSFQGQVTISADKSISTAYLQWSSLKASDTAMYYCAR

VYSFGGRHKALFDYWGQGTLVTVSSGTEGKSSGSGSESKSTEIVLTQSPATLSLSPGERAT

LSCRASQSVSSYLAWYQQKPGQAPRLLIYDASNRATGIPARFSGSGSGTDFTLTISSLEPE

DFAVYYCQQRSNWPLTFGQGTKVEIKTSTPAPRPPTPAPTIASQPLSLRPEACRPAAGGAV

HTRGLDFACDIYIWAPLAGTCGVLLLSLVITLYCKRGRKKLLYIFKQPFMRPVQTTQEED

GCSCRFPEEEEGGCELRVKFSRSADAPAYKQGQNQLYNELNLGRREEYDVLDKRRGRDP

EMGGKPRRKNPQEGLYNELQKDKMAEAYSEIGMKGERRRGKGHDGLYQGLSTATKDT

YDALHMQALPPR SEQ ID NO 30 pDR000074482 GC5B81-HL-CAR sequence
(SEQ ID NO: 31)
MAWVWTLLFLMAAAQSIQAQVQLVQSGAEVKKPGSSVKVSCKASGGTFSSYAISWVRQ

APGQGLEWMGGIIPIFGTANYAQKFQGRVTITADESTSTAYMELSSLRSEDTAVYYCARES

RWRGYKLDYWGQGTLVTVSSGTEGKSSGSGSESKSTDIQMTQSPSSLSASVGDRVTITCR

ASQSISSYLNWYQQKPGKAPKLLIYAASSLQSGVPSRFSGSGSGTDFTLTISSLQPEDFATY

YCQQSYSTPLTFGQGTKVEIKTSTPAPRPPTPAPTIASQPLSLRPEACRPAAGGAVHTRGLD

FACDIYIWAPLAGTCGVLLLSLVITLYCKRGRKKLLYIFKQPFMRPVQTTQEEDGCSCRFP

-continued

EEEEGGCELRVKFSRSADAPAYKQGQNQLYNELNLGRREEYDVLDKRRGRDPEMGGKP

RRKNPQEGLYNELQKDKMAEAYSEIGMKGERRRGKGHDGLYQGLSTATKDTYDALHM

QALPPR pDR000074481 GC5B596-HL-CAR sequence
(SEQ ID NO: 32)
MAWVWTLLFLMAAAQSIQAQVQLVQSGAEVKKPGASVKVSCKASGYSFTGYTMNWV

RQAPGQGLEWMGLINPYNSDTNYAQKLQGRVTMTTDTSTSTAYMELRSLRSDDTAVYY

CARVALRVALDYWGQGTLVTVSSGTEGKSSGSGSESKSTDIQMTQSPSSLSASVGDRVTI

TCKASQNVATHVGWYQQKPGKAPKRLIYSASYRYSGVPSRFSGSGSGTEFTLTISNLQPE

DFATYYCQQYNRYPYTFGQGTKLEIKTSTPAPRPPTPAPTIASQPLSLRPEACRPAAGGAV

HTRGLDFACDIYIWAPLAGTCGVLLLSLVITLYCKRGRKKLLYIFKQPFMRPVQTTQEED

GCSCRFPEEEEGGCELRVKFSRSADAPAYKQGQNQLYNELNLGRREEYDVLDKRRGRDP

EMGGKPRRKNPQEGLYNELQKDKMAEAYSEIGMKGERRRGKGHDGLYQGLSTATKDT

YDALHMQALPPR

DNA sequence for pDR000074490 GC5B483-LH-CDS
(SEQ ID NO: 33)
GAGATCGTGCTGACCCAGAGCCCAGCCACCCTGAGCCTGAGCCCAGGCGAGCGCGC

CACCCTGAGCTGCCGCGCCTCTCAGAGCGTGAGCAGCTACCTGGCTTGGTATCAGCA

GAAGCCCGGACAGGCCCCACGCCTGCTGATCTACGACGCCAGCAACCGCGCCACCG

GCATCCCAGCCCGCTTCAGCGGCAGCGGCAGCGGCACCGACTTCACCCTGACCATC

AGCAGCCTGGAGCCAGAGGACTTCGCCGTGTACTACTGCCAGCAGCGCAGCAACTG

GCCACTGACCTTCGGCCAGGGCACCAAGGTGGAGATCAAGGGTACAGAGGGCAAGT

CTAGTGGAAGTGGTAGCGAAAGTAAGAGTACCGAGGTGCAGCTGGTGCAGAGCGGC

GCTGAGGTCAAAAAGCCAGGCGAAAGCCTTAAAATATCATGCAAAGGAAGTGGATA

TTCCTTTACCAGCTACTTCATCGGCTGGGTGCGCCAGATGCCAGGCAAGGGCCTGGA

GTGGATGGGCATCATCTACCCAGGCAAGAGCGACACCCGCTACAGCCCAAGCTTCC

AGGGCCAGGTGACCATCAGCGCCGACAAGAGCATCAGCACCGCCTACCTGCAGTGG

AGCAGCCTGAAGGCCAGCGACACCGCCATGTACTACTGCGCCCGCGTGTACAGCTT

CGGCGGCCGCCACAAGGCCCTGTTCGACTACTGGGGCCAGGGCACCCTGGTGACCG

TGAGCAGCACTAGTACCCCAGCCCCACGCCCTCCCACCCCTGCTCCTACAATAGCAT

CCCAGCCCTTGTCACTTCGCCCCGAAGCATGCAGACCAGCCGCAGGCGGTGCTGTGC

ATACCCGAGGACTGGACTTCGCCTGCGACATCTACATCTGGGCCCCACTGGCCGGCA

CCTGCGGCGTGCTGCTGCTGAGCCTGGTGATCACCCTGTACTGCAAGCGCGGCCGCA

AGAAGCTGCTGTACATCTTCAAGCAGCCATTCATGCGCCCAGTGCAGACCACCCAG

GAGGAGGACGGCTGCAGCTGCCGCTTCCCAGAGGAGGAGGAGGGCGGCTGCGAGC

TGCGCGTGAAGTTCAGCCGCAGCGCCGACGCCCCAGCCTACAAGCAGGGCCAGAAC

CAGCTGTACAACGAGCTGAACCTGGGCCGCCGCGAGGAGTACGACGTGCTGGACAA

GCGCCGCGGCCGCGACCCAGAGATGGGCGGCAAGCCACGCCGCAAGAACCCACAG

GAGGGCCTGTACAACGAGCTGCAGAAGGACAAGATGGCCGAGGCCTACAGCGAGA

TCGGCATGAAGGGCGAGCGCCGCCGCGGCAAGGGCCACGACGGCCTGTACCAGGGC

CTGAGCACCGCCACCAAGGACACCTACGACGCCCTGCACATGCAGGCCCTGCCACC

ACGC

DNA sequence for pDR000074489 GC5B81-LH-CDS (SEQ ID NO: 34)

GACATCCAGATGACCCAGAGCCCAAGCAGCCTGAGCGCCAGCGTGGGCGACCGCGT

AACCATTACTTGTCGGGCTTCCCAAAGCATTAGTAGCTATTTGAATTGGTATCAACA

AAAACCAGGCAAGGCCCCAAAGCTGCTGATCTACGCCGCCTCTAGCCTGCAGAGCG

GAGTGCCAAGCCGCTTCAGCGGCAGCGGCAGCGGCACCGACTTCACCCTGACCATC

AGCAGCCTGCAGCCAGAGGACTTCGCCACCTACTACTGCCAGCAGAGCTACAGCAC

CCCACTGACCTTCGGCCAGGGCACCAAGGTGGAGATCAAGGGTACAGAGGGCAAGT

CTAGTGGAAGTGGTAGCGAAAGTAAGAGTACCCAGGTGCAGCTGGTGCAGAGCGGC

GCCGAGGTGAAGAAGCCAGGCAGCAGCGTGAAGGTGAGCTGCAAGGCCAGCGGCG

GCACCTTCAGCAGCTACGCCATCAGCTGGGTGCGCCAGGCCCCAGGCCAGGGACTG

GAGTGGATGGGCGGCATCATCCCAATCTTCGGCACCGCCAACTACGCCCAGAAGTT

CCAGGGCCGCGTGACCATCACCGCCGACGAGAGCACCAGCACCGCCTACATGGAGC

TGAGCAGCCTGCGCAGCGAGGACACCGCCGTGTACTACTGCGCACGCGAGAGCCGC

TGGCGCGGCTACAAGCTGGACTACTGGGGCCAGGGCACCCTGGTGACCGTGAGCAG

CACTAGTACCCCAGCCCCACGCCCTCCCACCCCTGCTCCTACAATAGCATCCCAGCC

CTTGTCACTTCGCCCCGAAGCATGCAGACCAGCCGCAGGCGGTGCTGTGCATACCCG

AGGACTGGACTTCGCCTGCGACATCTACATCTGGGCCCCACTGGCCGGCACCTGCGG

CGTGCTGCTGCTGAGCCTGGTGATCACCCTGTACTGCAAGCGCGGCCGCAAGAAGCT

GCTGTACATCTTCAAGCAGCCATTCATGCGCCCAGTGCAGACCACCCAGGAGGAGG

ACGGCTGCAGCTGCCGCTTCCCAGAGGAGGAGGAGGGCGGCTGCGAGCTGCGCGTG

AAGTTCAGCCGCAGCGCCGACGCCCCAGCCTACAAGCAGGGCCAGAACCAGCTGTA

CAACGAGCTGAACCTGGGCCGCCGCGAGGAGTACGACGTGCTGGACAAGCGCCGCG

GCCGCGACCCAGAGATGGGCGGCAAGCCACGCCGCAAGAACCCACAGGAGGGCCT

GTACAACGAGCTGCAGAAGGACAAGATGGCCGAGGCCTACAGCGAGATCGGCATG

AAGGGCGAGCGCCGCCGCGGCAAGGGCCACGACGGCCTGTACCAGGGCCTGAGCA

CCGCCACCAAGGACACCTACGACGCCCTGCACATGCAGGCCCTGCCACCACGC

DNA sequence for pDR000074488 GC5B596-LH-CDS (SEQ ID NO: 35)

GACATCCAGATGACCCAGAGCCCAAGCAGCCTGAGCGCCAGCGTGGGCGACCGCGT

TACAATAACTTGTAAAGCAAGCCAAAATGTTGCTACTCACGTCGGATGGTATCAGCA

AAAGCCAGGCAAGGCCCCAAAGCGCCTGATCTACAGCGCCAGCTACCGCTACAGCG

GAGTGCCAAGCCGCTTCAGCGGCAGCGGCAGCGGCACCGAGTTCACCCTGACCATC

AGCAACCTGCAGCCAGAGGACTTCGCCACCTACTACTGCCAGCAGTACAACCGCTA

CCCATACACCTTCGGCCAGGGCACCAAGCTGGAGATCAAGGGTACAGAGGGCAAGT

CTAGTGGAAGTGGTAGCGAAAGTAAGAGTACCCAGGTGCAGCTGGTGCAGAGCGGA

GCCGAGGTGAAGAAGCCAGGCGCCAGCGTGAAGGTGAGCTGCAAGGCCAGCGGCT

ACAGCTTCACCGGCTACACCATGAACTGGGTGCGCCAGGCCCCAGGCCAGGGACTG

GAGTGGATGGGCCTGATCAACCCATACAACAGCGACACCAACTACGCCCAGAAGCT

GCAGGGCCGCGTGACCATGACCACCGACACCAGCACCAGCACCGCCTACATGGAGC

TGCGCAGCCTGCGCAGCGACGACACCGCCGTGTACTACTGCGCCCGCGTGGCCCTGC

GCGTGGCCCTGGACTACTGGGGACAGGGCACCCTGGTGACCGTGAGCAGCACTAGT

-continued

ACCCCAGCCCCACGCCCTCCCACCCCTGCTCCTACAATAGCATCCCAGCCCTTGTCA

CTTCGCCCCGAAGCATGCAGACCAGCCGCAGGCGGTGCTGTGCATACCCGAGGACT

GGACTTCGCCTGCGACATCTACATCTGGGCCCCACTGGCCGGCACCTGCGGCGTGCT

GCTGCTGAGCCTGGTGATCACCCTGTACTGCAAGCGCGGCCGCAAGAAGCTGCTGT

ACATCTTCAAGCAGCCATTCATGCGCCCAGTGCAGACCACCCAGGAGGAGGACGGC

TGCAGCTGCCGCTTCCCAGAGGAGGAGGAGGGCGGCTGCGAGCTGCGCGTGAAGTT

CAGCCGCAGCGCCGACGCCCCAGCCTACAAGCAGGGCCAGAACCAGCTGTACAACG

AGCTGAACCTGGGCCGCCGCGAGGAGTACGACGTGCTGGACAAGCGCCGCGGCCGC

GACCCAGAGATGGGCGGCAAGCCACGCCGCAAGAACCCACAGGAGGGCCTGTACA

ACGAGCTGCAGAAGGACAAGATGGCCGAGGCCTACAGCGAGATCGGCATGAAGGG

CGAGCGCCGCCGCGGCAAGGGCCACGACGGCCTGTACCAGGGCCTGAGCACCGCCA

CCAAGGACACCTACGACGCCCTGCACATGCAGGCCCTGCCACCACGC

DNA sequence for pDR000074483 GC5B483-HL-CDS (SEQ ID NO: 36)

GAGGTGCAGCTGGTGCAGAGCGGCGCTGAGGTCAAAAAGCCAGGCGAAAGCCTTAA

AATATCATGCAAAGGAAGTGGATATTCCTTTACCAGCTACTTCATCGGCTGGGTGCG

CCAGATGCCAGGCAAGGGCCTGGAGTGGATGGGCATCATCTACCCAGGCAAGAGCG

ACACCCGCTACAGCCCAAGCTTCCAGGGCCAGGTGACCATCAGCGCCGACAAGAGC

ATCAGCACCGCCTACCTGCAGTGGAGCAGCCTGAAGGCCAGCGACACCGCCATGTA

CTACTGCGCCCGCGTGTACAGCTTCGGCGGCCGCCACAAGGGCCCTGTTCGACTACTG

GGGCCAGGGCACCCTGGTGACCGTGAGCAGCGGTACAGAGGGCAAGTCTAGTGGAA

GTGGTAGCGAAAGTAAGAGTACCGAGATCGTGCTGACCCAGAGCCCAGCCACCCTG

AGCCTGAGCCCAGGCGAGCGCGCCACCCTGAGCTGCCGCGCCTCTCAGAGCGTGAG

CAGCTACCTGGCTTGGTATCAGCAGAAGCCCGGACAGGCCCCACGCCTGCTGATCTA

CGACGCCAGCAACCGCGCCACCGGCATCCCAGCCCGCTTCAGCGGCAGCGGCAGCG

GCACCGACTTCACCCTGACCATCAGCAGCCTGGAGCCAGAGGACTTCGCCGTGTACT

ACTGCCAGCAGCGCAGCAACTGGCCACTGACCTTCGGCCAGGGCACCAAGGTGGAG

ATCAAGACTAGTACCCCAGCCCCACGCCCTCCCACCCCTGCTCCTACAATAGCATCC

CAGCCCTTGTCACTTCGCCCCGAAGCATGCAGACCAGCCGCAGGCGGTGCTGTGCAT

ACCCGAGGACTGGACTTCGCCTGCGACATCTACATCTGGGCCCCACTGGCCGGCACC

TGCGGCGTGCTGCTGCTGAGCCTGGTGATCACCCTGTACTGCAAGCGCGGCCGCAAG

AAGCTGCTGTACATCTTCAAGCAGCCATTCATGCGCCCAGTGCAGACCACCCAGGA

GGAGGACGGCTGCAGCTGCCGCTTCCCAGAGGAGGAGGAGGGCGGCTGCGAGCTGC

GCGTGAAGTTCAGCCGCAGCGCCGACGCCCCAGCCTACAAGCAGGGCCAGAACCAG

CTGTACAACGAGCTGAACCTGGGCCGCCGCGAGGAGTACGACGTGCTGGACAAGCG

CCGCGGCCGCGACCCAGAGATGGGCGGCAAGCCACGCCGCAAGAACCCACAGGAG

GGCCTGTACAACGAGCTGCAGAAGGACAAGATGGCCGAGGCCTACAGCGAGATCG

GCATGAAGGGCGAGCGCCGCCGCGGCAAGGGCCACGACGGCCTGTACCAGGGCCTG

AGCACCGCCACCAAGGACACCTACGACGCCCTGCACATGCAGGCCCTGCCACCACG

C

DNA sequence for pDR000074482 GC5B81-HL-CDS
(SEQ ID NO: 37)
CAGGTGCAGCTGGTGCAGAGCGGCGCCGAGGTGAAGAAGCCAGGCAGCAGCGTGA

AGGTGAGCTGCAAGGCCAGCGGCGGCACCTTCAGCAGCTACGCCATCAGCTGGGTG

CGCCAGGCCCCAGGCCAGGGACTGGAGTGGATGGGCGGCATCATCCCAATCTTCGG

CACCGCCAACTACGCCCAGAAGTTCCAGGGCCGCGTGACCATCACCGCCGACGAGA

GCACCAGCACCGCCTACATGGAGCTGAGCAGCCTGCGCAGCGAGGACACCGCCGTG

TACTACTGCGCACGCGAGAGCCGCTGGCGCGGCTACAAGCTGGACTACTGGGGCCA

GGGCACCCTGGTGACCGTGAGCAGCGGTACAGAGGGCAAGTCTAGTGGAAGTGGTA

GCGAAAGTAAGAGTACCGACATCCAGATGACCCAGAGCCCAAGCAGCCTGAGCGCC

AGCGTGGGCGACCGCGTAACCATTACTTGTCGGGCTTCCCAAAGCATTAGTAGCTAT

TTGAATTGGTATCAACAAAAACCAGGCAAGGCCCCAAAGCTGCTGATCTACGCCGC

CTCTAGCCTGCAGAGCGGAGTGCCAAGCCGCTTCAGCGGCAGCGGCAGCGGCACCG

ACTTCACCCTGACCATCAGCAGCCTGCAGCCAGAGGACTTCGCCACCTACTACTGCC

AGCAGAGCTACAGCACCCCACTGACCTTCGGCCAGGGCACCAAGGTGGAGATCAAG

ACTAGTACCCCAGCCCCACGCCCTCCCACCCCTGCTCCTACAATAGCATCCCAGCCC

TTGTCACTTCGCCCCGAAGCATGCAGACCAGCCGCAGGCGGTGCTGTGCATACCCGA

GGACTGGACTTCGCCTGCGACATCTACATCTGGGCCCCACTGGCCGGCACCTGCGGC

GTGCTGCTGCTGAGCCTGGTGATCACCCTGTACTGCAAGCGCGGCCGCAAGAAGCT

GCTGTACATCTTCAAGCAGCCATTCATGCGCCCAGTGCAGACCACCCAGGAGGAGG

ACGGCTGCAGCTGCCGCTTCCCAGAGGAGGAGGAGGGCGGCTGCGAGCTGCGCGTG

AAGTTCAGCCGCAGCGCCGACGCCCCAGCCTACAAGCAGGGCCAGAACCAGCTGTA

CAACGAGCTGAACCTGGGCCGCCGCGAGGAGTACGACGTGCTGGACAAGCGCCGCG

GCCGCGACCCAGAGATGGGCGGCAAGCCACGCCGCAAGAACCCACAGGAGGGCCT

GTACAACGAGCTGCAGAAGGACAAGATGGCCGAGGCCTACAGCGAGATCGGCATG

AAGGGCGAGCGCCGCCGCGGCAAGGGCCACGACGGCCTGTACCAGGGCCTGAGCA

CCGCCACCAAGGACACCTACGACGCCCTGCACATGCAGGCCCTGCCACCACGC

DNA sequence for pDR000074481 GC5B596-HL-CDS
(SEQ ID NO: 38)
CAGGTGCAGCTGGTGCAGAGCGGAGCCGAGGTGAAGAAGCCAGGCGCCAGCGTGA

AGGTGAGCTGCAAGGCCAGCGGCTACAGCTTCACCGGCTACACCATGAACTGGGTG

CGCCAGGCCCCAGGCCAGGGACTGGAGTGGATGGGCCTGATCAACCCATACAACAG

CGACACCAACTACGCCCAGAAGCTGCAGGGCCGCGTGACCATGACCACCGACACCA

GCACCAGCACCGCCTACATGGAGCTGCGCAGCCTGCGCAGCGACGACACCGCCGTG

TACTACTGCGCCCGCGTGGCCCTGCGCGTGGCCCTGGACTACTGGGGACAGGGCAC

CCTGGTGACCGTGAGCAGCGGTACAGAGGGCAAGTCTAGTGGAAGTGGTAGCGAAA

GTAAGAGTACCGACATCCAGATGACCCAGAGCCCAAGCAGCCTGAGCGCCAGCGTG

GGCGACCGCGTTACAATAACTTGTAAAGCAAGCCAAAATGTTGCTACTCACGTCGG

ATGGTATCAGCAAAAGCCAGGCAAGGCCCCAAAGCGCCTGATCTACAGCGCCAGCT

ACCGCTACAGCGGAGTGCCAAGCCGCTTCAGCGGCAGCGGCAGCGGCACCGAGTTC

ACCCTGACCATCAGCAACCTGCAGCCAGAGGACTTCGCCACCTACTACTGCCAGCA

GTACAACCGCTACCCATACACCTTCGGCCAGGGCACCAAGCTGGAGATCAAGACTA

```
GTACCCCAGCCCCACGCCCTCCCACCCCTGCTCCTACAATAGCATCCCAGCCCTTGT

CACTTCGCCCCGAAGCATGCAGACCAGCCGCAGGCGGTGCTGTGCATACCCGAGGA

CTGGACTTCGCCTGCGACATCTACATCTGGGCCCCACTGGCCGGCACCTGCGGCGTG

CTGCTGCTGAGCCTGGTGATCACCCTGTACTGCAAGCGCGGCCGCAAGAAGCTGCTG

TACATCTTCAAGCAGCCATTCATGCGCCCAGTGCAGACCACCCAGGAGGAGGACGG

CTGCAGCTGCCGCTTCCCAGAGGAGGAGGAGGGCGGCTGCGAGCTGCGCGTGAAGT

TCAGCCGCAGCGCCGACGCCCCAGCCTACAAGCAGGGCCAGAACCAGCTGTACAAC

GAGCTGAACCTGGGCCGCCGCGAGGAGTACGACGTGCTGGACAAGCGCCGCGGCCG

CGACCCAGAGATGGGCGGCAAGCCACGCCGCAAGAACCCACAGGAGGGCCTGTAC

AACGAGCTGCAGAAGGACAAGATGGCCGAGGCCTACAGCGAGATCGGCATGAAGG

GCGAGCGCCGCCGCGGCAAGGGCCACGACGGCCTGTACCAGGGCCTGAGCACCGCC

ACCAAGGACACCTACGACGCCCTGCACATGCAGGCCCTGCCACCACGC
```

HCDR1 (GC5B81)                                          (SEQ ID NO: 39)
GGTFSSY

HCDR2 (GC5B81)                                          (SEQ ID NO: 40)
ESRWRGYKLDY

HCDR3 (GC5B81)                                          (SEQ ID NO: 41)
IPIFGT

HCDR1 (GC5B483)                                        (SEQ ID NO: 42)
GYSFTSY

HCDR2 (GC5B483)                                          (SEQ ID NO: 43)
YPGKSD

HCDR3 (GC5B483)                                          (SEQ ID NO: 44)
VYSFGGRHKALFDY

HCDR1 (GC5B596)                                        (SEQ ID NO: 45)
GYSFTGY

HCDR2 (GC5B596)                                        (SEQ ID NO: 46)
NPYNSD

HCDR3 (GC5B596)                                        (SEQ ID NO: 47)
VALRVALDY

LCDR1 (GC5B81)                                          (SEQ ID NO: 48)
RASQSISSYLN

LCDR2 (GC5B81)                                          (SEQ ID NO: 49)
AASSLQS

LCDR3 (GC5B81)                                          (SEQ ID NO: 50)
QQSYSTPLT

LCDR1 (GC5B483)                                        (SEQ ID NO: 51)
RASQSVSSYLA

LCDR2 (GC5B483)                                        (SEQ ID NO: 52)
DASNRAT

LCDR3 (GC5B483)

-continued

QQRSNWPLT (SEQ ID NO: 53)

LCDR1 (GC5B596)
KASQNVATHVG (SEQ ID NO: 54)

LCDR2 (GC5B596)
SASYRYS (SEQ ID NO: 55)

LCDR3 (GC5B596)
QQYNRYPYT (SEQ ID NO: 56)

human GPRC5D polypeptide (SEQ ID NO: 57)
MYKDCIESTGDYFLLCDAEGPWGIILESLAILGIVVTILLLLAFLFLMRKIQDCSQWNVLP
TQLLFLLSVLGLFGLAFAFIIELNQQTAPVRYFLFGVLFALCFSCLLAHASNLVKLVRGCV
SFSWTTILCIAIGCSLLQIIIATEYVTLIMTRGMMFVNMTPCQLNVDFVVLLVYVLFLMAL
TFFVSKATFCGPCENWKQHGRLIFITVLFSIIIWVVWISMLLRGNPQFQRQPQWDDPVVCI
ALVTNAWVFLLLYIVPELCILYRSCRQECPLQGNACPVTAYQHSFQVENQELSRARDSDG
AEEDVALTSYGTPIQPQTVDPTQECFIPQAKLSPQQDAGGV

HCDR1 (GP5B83)
GGSLSSSSY (SEQ ID NO: 58)

HCDR2 (GP5B83)
YYSGN (SEQ ID NO: 59)

HCDR3 (GP5B83)
HVGYSYGRRFWYFDL (SEQ ID NO: 60)

LCDR1 (GP5B83)
RASQSVSSYLA (SEQ ID NO: 61)

LCDR2 (GP5B83)
DASNRAT (SEQ ID NO: 62)

LCDR3 (GP5B83)
QQRSNWPPT (SEQ ID NO: 63)

Heavy Chain Sequence (GP5B83) (SEQ ID NO: 64)
QLQLQESGPGLVKPSETLSLTCTVSGGSLSSSSYWWGWTRQPPGRGLEWIGTMYYSGNI
YYNPSLQSRATISVDTSKNQFSLKLSSVTAADTAVYYCARHVGYSYGRRFWYFDLWGR
GTLVTVSS Light Chain Sequence (GP5B83) (SEQ ID NO: 65)
EIVLTQSPATLSLSPGERATLSCRASQSVSSYLAWYQQKPGQAPRLLIYDASNRATGIPA
RFSGSGSGTDFTLTISSLEPEDFAVYYCQQRSNWPPTFGQGTKVEIK

HCDR1 (GC5B680)
GFSLTNIRM (SEQ ID NO: 66)

HCDR2 (GC5B680)
FSNDE (SEQ ID NO: 67)

HCDR3 (GC5B680)
MRLPYGMDV (SEQ ID NO: 68)

-continued

```
LCDR1 (GC5B680)
                                                     (SEQ ID NO: 69)
RSSQSLVHSDGNTYLS

LCDR2 (GC5B680)
                                                     (SEQ ID NO: 70)
KISNRFF

LCDR3 (GC5B680)
                                                     (SEQ ID NO: 71)
MQATQFPHT

Heavy Chain Sequence (GC5B680)
                                                     (SEQ ID NO: 72)
QVTLKESGPVLVKPTETLTLTCTVSGFSLTNIRMSVSWIRQPPGKALEWLAHIFSNDEKS

YSSSLKSRLTISRDTSKSQVVLTLTNVDPVDTATYYCARMRLPYGMDVWGQGTTVTVS

S

Light Chain Sequence (GC5B680)
                                                     (SEQ ID NO: 73)
DIVMTQTPLSSPVTLGQPASISCRSSQSLVHSDGNTYLSWLQQRPGQPPRLLIYKISNRFF

GVPDRFSGSGAGTDFTLKISRVEAEDVGVYYCMQATQFPHTFGQGTKLEIK

Linker polypeptide Sequence
                                                     (SEQ ID NO: 74)
GGSEGKSSGSGSESKSTGGS scFv Sequence (GP5B83-HL)
                                                     (SEQ ID NO: 75)
QLQLQESGPGLVKPSETLSLTCTVSGGSLSSSSYWWGWTRQPPGRGLEWIGTMYYSGNI

YYNPSLQSRATISVDTSKNQFSLKLSSVTAADTAVYYCARHVGYSYGRRFWYFDLWGRG

TLVTVSSGGSEGKSSGSGSESKSTGGSEIVLTQSPATLSLSPGERATLSCRASQSVSSYLAW

YQQKPGQAPRLLIYDASNRATGIPARFSGSGSGTDFTLTISSLEPEDFAVYYCQQRSNWPP

TFGQGTKVEIK scFv Sequence (GP5B83-LH)
                                                     (SEQ ID NO: 76)
EIVLTQSPATLSLSPGERATLSCRASQSVSSYLAWYQQKPGQAPRLLIYDASNRATGIPARF

SGSGSGTDFTLTISSLEPEDFAVYYCQQRSNWPPTFGQGTKVEIKGGSEGKSSGSGSESKS

TGGSQLQLQESGPGLVKPSETLSLTCTVSGGSLSSSSYWWGWTRQPPGRGLEWIGTMYY

SGNIYYNPSLQSRATISVDTSKNQFSLKLSSVTAADTAVYYCARHVGYSYGRRFWYFDL

WGRGTLVTVSS scFv Sequence (GC5B680-HL)
                                                     (SEQ ID NO: 77)
QVTLKESGPVLVKPTETLTLTCTVSGFSLTNIRMSVSWIRQPPGKALEWLAHIFSNDEKS

YSSSLKSRLTISRDTSKSQVVLTLTNVDPVDTATYYCARMRLPYGMDVWGQGTTVTVS

SGGSEGKSSGSGSESKSTGGSDIVMTQTPLSSPVTLGQPASISCRSSQSLVHSDGNTYLSW

LQQRPGQPPRLLIYKISNRFFGVPDRFSGSGAGTDFTLKISRVEAEDVGVYYCMQATQFP

HTFGQGTKLEIK scFv Sequence (GC5B680-LH)
                                                     (SEQ ID NO: 78)
DIVMTQTPLSSPVTLGQPASISCRSSQSLVHSDGNTYLSWLQQRPGQPPRLLIYKISNRFF

GVPDRFSGSGAGTDFTLKISRVEAEDVGVYYCMQATQFPHTFGQGTKLEIKGGSEGKSS

GSGSESKSTGGSQVTLKESGPVLVKPTETLTLTCTVSGFSLTNIRMSVSWIRQPPGKALE

WLAHIFSNDEKSYSSSLKSRLTISRDTSKSQVVLTLTNVDPVDTATYYCARMRLPYGMD

VWGQGTTVTVSS
```

Extracellular binding domain (GP5B83-HL)
(SEQ ID NO: 79)
MAWVWTLLFLMAAAQSIQAQLQLQESGPGLVKPSETLSLTCTVSGGSLSSSSYWWGWT
RQPPGRGLEWIGTMYYSGNIYYNPSLQSRATISVDTSKNQFSLKLSSVTAADTAVYYCAR
HVGYSYGRRFWYFDLWGRGTLVTVSSGGSEGKSSGSGSESKSTGGSEIVLTQSPATLSLS
PGERATLSCRASQSVSSYLAWYQQKPGQAPRLLIYDASNRATGIPARFSGSGSGTDFTLTI
SSLEPEDFAVYYCQQRSNWPPTFGQGTKVEIK Extracellular binding domain (GP5B83-LH)
(SEQ ID NO: 80)
MAWVWTLLFLMAAAQSIQAEIVLTQSPATLSLSPGERATLSCRASQSVSSYLAWYQQKP
GQAPRLLIYDASNRATGIPARFSGSGSGTDFTLTISSLEPEDFAVYYCQQRSNWPPTFGQG
TKVEIKGGSEGKSSGSGSESKSTGGSQLQLQESGPGLVKPSETLSLTCTVSGGSLSSSSYW
WGWTRQPPGRGLEWIGTMYYSGNIYYNPSLQSRATISVDTSKNQFSLKLSSVTAADTAV
YYCARHVGYSYGRRFWYFDLWGRGTLVTVSS Extracellular binding domain (GC5B680-HL)
(SEQ ID NO: 81)
MAWVWTLLFLMAAAQSIQAQVTLKESGPVLVKPTETLTLTCTVSGFSLTNIRMSVSWIR
QPPGKALEWLAHIFSNDEKSYSSSLKSRLTISRDTSKSQVVLTLTNVDPVDTATYYCAR
MRLPYGMDVWGQGTTVTVSSGGSEGKSSGSGSESKSTGGSDIVMTQTPLSSPVTLGQPA
SISCRSSQSLVHSDGNTYLSWLQQRPGQPPRLLIYKISNRFFGVPDRFSGSGAGTDFTLKIS
RVEAEDVGVYYCMQATQFPHTFGQGTKLEIK Extracellular binding domain (GC5B680-LH)
(SEQ ID NO: 82)
MAWVWTLLFLMAAAQSIQADIVMTQTPLSSPVTLGQPASISCRSSQSLVHSDGNTYLSW
LQQRPGQPPRLLIYKISNRFFGVPDRFSGSGAGTDFTLKISRVEAEDVGVYYCMQATQFP
HTFGQGTKLEIKGGSEGKSSGSGSESKSTGGSQVTLKESGPVLVKPTETLTLTCTVSGFSL
TNIRMSVSWIRQPPGKALEWLAHIFSNDEKSYSSSLKSRLTISRDTSKSQVVLTLTNVDPV
DTATYYCARMRLPYGMDVWGQGTTVTVSS GP5B83-HL-CAR sequence
(SEQ ID NO: 83)
QLQLQESGPGLVKPSETLSLTCTVSGGSLSSSSYWWGWTRQPPGRGLEWIGTMYYSGNI
YYNPSLQSRATISVDTSKNQFSLKLSSVTAADTAVYYCARHVGYSYGRRFWYFDLWGR
GTLVTVSSGGSEGKSSGSGSESKSTGGSEIVLTQSPATLSLSPGERATLSCRASQSVSSYL
AWYQQKPGQAPRLLIYDASNRATGIPARFSGSGSGTDFTLTISSLEPEDFAVYYCQQRSN
WPPTFGQGTKVEIKTSTPAPRPPTPAPTIASQPLSLRPEACRPAAGGAVHTRGLDFACDIY
IWAPLAGTCGVLLLSLVITLYCKRGRKKLLYIFKQPFMRPVQTTQEEDGCSCRFPEEEEG
GCELRVKFSRSADAPAYKQGQNQLYNELNLGRREEYDVLDKRRGRDPEMGGKPRRKN
PQEGLYNELQKDKMAEAYSEIGMKGERRRGKGHDGLYQGLSTATKDTYDALHMQALP
PR GP5B83-LH-CAR sequence
(SEQ ID NO: 84)
EIVLTQSPATLSLSPGERATLSCRASQSVSSYLAWYQQKPGQAPRLLIYDASNRATGIPA
RFSGSGSGTDFTLTISSLEPEDFAVYYCQQRSNWPPTFGQGTKVEIKGGSEGKSSGSGSES
KSTGGSQLQLQESGPGLVKPSETLSLTCTVSGGSLSSSSYWWGWTRQPPGRGLEWIGTM
YYSGNIYYNPSLQSRATISVDTSKNQFSLKLSSVTAADTAVYYCARHVGYSYGRRFWYF
DLWGRGTLVTVSSTSTPAPRPPTPAPTIASQPLSLRPEACRPAAGGAVHTRGLDFACDIYI -continued

WAPLAGTCGVLLLSLVITLYCKRGRKKLLYIFKQPFMRPVQTTQEEDGCSCRFPEEEEG

GCELRVKFSRSADAPAYKQGQNQLYNELNLGRREEYDVLDKRRGRDPEMGGKPRRKN

PQEGLYNELQKDKMAEAYSEIGMKGERRRGKGHDGLYQGLSTATKDTYDALHMQALP

PR

GC5B680-HL-CAR sequence (SEQ ID NO: 85)
QVTLKESGPVLVKPTETLTLTCTVSGFSLTNIRMSVSWIRQPPGKALEWLAHIFSNDEKS

YSSSLKSRLTISRDTSKSQVVLTLTNVDPVDTATYYCARMRLPYGMDVWGQGTTVTVS

SGGSEGKSSGSGSESKSTGGSDIVMTQTPLSSPVTLGQPASISCRSSQSLVHSDGNTYLSW

LQQRPGQPPRLLIYKISNRFFGVPDRFSGSGAGTDFTLKISRVEAEDVGVYYCMQATQFP

HTFGQGTKLEIKTSTPAPRPPTPAPTIASQPLSLRPEACRPAAGGAVHTRGLDFACDIYIW

APLAGTCGVLLLSLVITLYCKRGRKKLLYIFKQPFMRPVQTTQEEDGCSCRFPEEEEGGC

ELRVKFSRSADAPAYKQGQNQLYNELNLGRREEYDVLDKRRGRDPEMGGKPRRKNPQ

EGLYNELQKDKMAEAYSEIGMKGERRRGKGHDGLYQGLSTATKDTYDALHMQALPPR

GC5B680-LH-CAR sequence (SEQ ID NO: 86)
DIVMTQTPLSSPVTLGQPASISCRSSQSLVHSDGNTYLSWLQQRPGQPPRLLIYKISNRFF

GVPDRFSGSGAGTDFTLKISRVEAEDVGVYYCMQATQFPHTFGQGTKLEIKGGSEGKSS

GSGSESKSTGGSQVTLKESGPVLVKPTETLTLTCTVSGFSLTNIRMSVSWIRQPPGKALE

WLAHIFSNDEKSYSSSLKSRLTISRDTSKSQVVLTLTNVDPVDTATYYCARMRLPYGMD

VWGQGTTVTVSSTSTPAPRPPTPAPTIASQPLSLRPEACRPAAGGAVHTRGLDFACDIYI

WAPLAGTCGVLLLSLVITLYCKRGRKKLLYIFKQPFMRPVQTTQEEDGCSCRFPEEEEG

GCELRVKFSRSADAPAYKQGQNQLYNELNLGRREEYDVLDKRRGRDPEMGGKPRRKN

PQEGLYNELQKDKMAEAYSEIGMKGERRRGKGHDGLYQGLSTATKDTYDALHMQALP

PR

DNA Sequence for pDR000084454 GP5B83-HL sequence (SEQ ID NO: 87)
ATGGCTTGGGTGTGGACCTTGCTATTCCTGATGGCAGCTGCCCAAAGTATACAGGCC

CAACTCCAGCTGCAAGAATCTGGTCCTGGACTCGTAAAACCATCAGAAACCCTCTCA

TTGACCTGCACAGTGAGTGGTGGATCATTGTCTTCCAGCAGCTATTGGTGGGGGTGG

ACTCGACAGCCACCAGGTCGCGGTCTCGAGTGGATAGGTACAATGTATTACAGTGGT

AACATTTATTACAACCCTAGCCTCCAAAGCCGGGCAACCATCTCTGTTGACACATCC

AAGAATCAATTTAGCCTGAAATTGTCTAGTGTGACTGCTGCTGATACAGCTGTTTAT

TATTGCGCTAGGCATGTCGGATACTCTTATGGTCGTAGATTCTGGTACTTCGATTTGT

GGGGTCGCGGGACCTTGGTAACAGTCTCCTCCGGAGGATCAGAGGGGAAATCTTCC

GGTAGCGGCAGTGAATCAAAGTCAACTGGTGGTTCCGAAATCGTGCTGACTCAGTC

ACCCGCAACTCTTTCACTGAGTCCTGGAGAACGTGCTACTCTGTCATGTCGGGCTTCT

CAGTCAGTAAGTTCTTATTTGGCATGGTACCAGCAAAAGCCCGGCCAAGCCCCCCGA

CTCTTGATATACGATGCATCAAACCGTGCCACTGGAATCCCAGCACGGTTTTCCGGA

AGTGGTTCCGGAACCGACTTCACCCTCACCATATCCAGTTTGGAGCCCGAGGACTTC

GCAGTTTACTATTGTCAACAACGGTCCAACTGGCCCCCCACATTTGGACAAGGCACC

AAAGTCGAAATAAAGACTAGTACCCCAGCCCCACGCCCTCCCACCCCTGCTCCTACA

ATAGCATCCCAGCCCTTGTCACTTCGCCCCGAAGCATGCAGACCAGCCGCAGGCGGT

GCTGTGCATACCCGAGGACTGGACTTCGCCTGCGACATCTACATCTGGGCCCCACTG

-continued

```
GCCGGCACCTGCGGCGTGCTGCTGCTGAGCCTGGTGATCACCCTGTACTGCAAGCGC

GGCCGCAAGAAGCTGCTGTACATCTTCAAGCAGCCATTCATGCGCCCAGTGCAGAC

CACCCAGGAGGAGGACGGCTGCAGCTGCCGCTTCCCAGAGGAGGAGGAGGGCGGC

TGCGAGCTGCGCGTGAAGTTCAGCCGCAGCGCCGACGCCCCAGCCTACAAGCAGGG

CCAGAACCAGCTGTACAACGAGCTGAACCTGGGCCGCCGCGAGGAGTACGACGTGC

TGGACAAGCGCCGCGGCCGCGACCCAGAGATGGGCGGCAAGCCACGCCGCAAGAA

CCCACAGGAGGGCCTGTACAACGAGCTGCAGAAGGACAAGATGGCCGAGGCCTAC

AGCGAGATCGGCATGAAGGGCGAGCGCCGCCGCGGCAAGGGCCACGACGGCCTGT

ACCAGGGCCTGAGCACCGCCACCAAGGACACCTACGACGCCCTGCACATGCAGGCC

CTGCCACCACGCTGA
```

DNA Sequence for GP5B83-LH sequence (SEQ ID NO: 88)

```
ATGGCTTGGGTGTGGACCTTGCTATTCCTGATGGCAGCTGCCCAAAGTATACAGGCC

GAAATCGTACTGACTCAAAGTCCCGCTACTCTCAGTCTGTCACCCGGCGAGAGAGCC

ACACTGTCATGCCGCGCCAGCCAATCAGTCAGTTCCTACCTTGCTTGGTATCAGCAG

AAACCTGGCCAAGCACCTCGGCTGCTTATCTACGACGCCAGCAATCGCGCCACTGGT

ATCCCAGCTCGGTTTTCAGGTAGCGGCAGTGGGACAGACTTTACCTTGACTATTAGC

TCTCTTGAACCCGAAGACTTTGCCGTTTATTACTGCCAGCAACGGTCAAACTGGCCT

CCCACTTTTGGCCAAGGAACCAAAGTAGAGATAAAAGGTGGTTCAGAAGGTAAATC

AAGTGGGTCCGGTTCCGAAAGTAAGTCCACCGGAGGCTCTCAACTCCAGTTGCAGG

AAAGTGGGCCTGGGCTTGTAAAACCAAGCGAGACATTGTCTCTCACATGCACTGTAT

CAGGGGGATCTCTTTCAAGTTCCTCTTATTGGTGGGGTGGACTCGTCAACCCCCCG

GTAGGGGTCTCGAATGGATCGGTACCATGTATTATTCTGGGAATATATACTATAATC

CAAGCCTTCAAAGTAGAGCTACTATATCCGTGGACACATCCAAGAATCAGTTCTCCT

TGAAACTTTCTAGCGTGACCGCCGCCGATACTGCTGTCTACTACTGCGCACGGCATG

TGGGATACTCCTACGGGAGACGGTTCTGGTATTTCGACTTGTGGGGTCGCGGTACAC

TCGTTACAGTGTCCTCTACTAGTACCCCAGCCCCACGCCCTCCCACCCCTGCTCCTAC

AATAGCATCCCAGCCCTTGTCACTTCGCCCCGAAGCATGCAGACCAGCCGCAGGCG

GTGCTGTGCATACCCGAGGACTGGACTTCGCCTGCGACATCTACATCTGGGCCCCAC

TGGCCGGCACCTGCGGCGTGCTGCTGCTGAGCCTGGTGATCACCCTGTACTGCAAGC

GCGGCCGCAAGAAGCTGCTGTACATCTTCAAGCAGCCATTCATGCGCCCAGTGCAG

ACCACCCAGGAGGAGGACGGCTGCAGCTGCCGCTTCCCAGAGGAGGAGGAGGGCG

GCTGCGAGCTGCGCGTGAAGTTCAGCCGCAGCGCCGACGCCCCAGCCTACAAGCAG

GGCCAGAACCAGCTGTACAACGAGCTGAACCTGGGCCGCCGCGAGGAGTACGACGT

GCTGGACAAGCGCCGCGGCCGCGACCCAGAGATGGGCGGCAAGCCACGCCGCAAG

AACCCACAGGAGGGCCTGTACAACGAGCTGCAGAAGGACAAGATGGCCGAGGCCT

ACAGCGAGATCGGCATGAAGGGCGAGCGCCGCCGCGGCAAGGGCCACGACGGCCT

GTACCAGGGCCTGAGCACCGCCACCAAGGACACCTACGACGCCCTGCACATGCAGG

CCCTGCCACCACGCTGA
```

-continued

DNA Sequence for GC5B680-HL sequence
(SEQ ID NO: 89)
ATGGCTTGGGTGTGGACCTTGCTATTCCTGATGGCAGCTGCCCAAAGTATACAGGCC

CAAGTAACACTCAAGGAGAGCGGACCAGTCTTGGTGAAACCAACTGAGACCTTGAC

TTTGACATGTACTGTAAGTGGCTTCAGCCTTACCAACATCAGGATGTCAGTATCTTG

GATAAGGCAACCACCTGGCAAGGCACTCGAATGGCTGGCACACATCTTTTCTAACG

ACGAAAAATCCTATTCTTCCAGTCTCAAAAGTCGCCTTACCATCAGCCGAGATACCA

GTAAGAGTCAAGTAGTTCTTACATTGACCAATGTAGATCCAGTTGATACAGCCACAT

ACTACTGCGCACGAATGCGGCTTCCATACGGCATGGATGTATGGGGACAGGGAACT

ACTGTTACCGTTAGTTCCGGCGGCTCCGAGGGCAAGAGCAGCGGCAGCGGCAGCGA

GAGCAAGAGCACCGGCGGCAGCGACATTGTGATGACCCAAACACCTCTTAGTAGTC

CTGTAACTCTCGGACAGCCAGCTTCAATATCTTGTCGCTCAAGTCAATCCCTCGTCC

ATTCCGACGGCAACACCTACCTCTCTTGGCTCCAACAGAGACCCGGCCAGCCTCCCA

GACTTCTCATCTACAAAATCAGTAACAGGTTCTTCGGCGTCCCTGACAGGTTCAGTG

GATCTGGAGCAGGTACAGATTTCACCTTGAAGATAAGTAGAGTGGAGGCTGAGGAC

GTAGGCGTCTATTATTGTATGCAAGCTACCCAATTCCCACATACATTCGGCCAAGGC

ACTAAATTGGAAATAAAAACTAGTACCCCAGCCCCACGCCCTCCCACCCCTGCTCCT

ACAATAGCATCCCAGCCCTTGTCACTTCGCCCCGAAGCATGCAGACCAGCCGCAGG

CGGTGCTGTGCATACCCGAGGACTGGACTTCGCCTGCGACATCTACATCTGGGCCCC

ACTGGCCGGCACCTGCGGCGTGCTGCTGCTGAGCCTGGTGATCACCCTGTACTGCAA

GCGCGGCCGCAAGAAGCTGCTGTACATCTTCAAGCAGCCATTCATGCGCCCAGTGC

AGACCACCCAGGAGGAGGACGGCTGCAGCTGCCGCTTCCCAGAGGAGGAGGAGGG

CGGCTGCGAGCTGCGCGTGAAGTTCAGCCGCAGCGCCGACGCCCCAGCCTACAAGC

AGGGCCAGAACCAGCTGTACAACGAGCTGAACCTGGGCCGCCGCGAGGAGTACGAC

GTGCTGGACAAGCGCCGCGGCCGCGACCCAGAGATGGGCGGCAAGCCACGCCGCA

AGAACCCACAGGAGGGCCTGTACAACGAGCTGCAGAAGGACAAGATGGCCGAGGC

CTACAGCGAGATCGGCATGAAGGGCGAGCGCCGCCGCGGCAAGGGCCACGACGGC

CTGTACCAGGGCCTGAGCACCGCCACCAAGGACACCTACGACGCCCTGCACATGCA

GGCCCTGCCACCACGCTGA

DNA Sequence for GC5B680-LH sequence
(SEQ ID NO: 90)
ATGGCTTGGGTGTGGACCTTGCTATTCCTGATGGCAGCTGCCCAAAGTATACAGGCC

GACATTGTGATGACCCAAACACCTCTTAGTAGTCCTGTAACTCTCGGACAGCCAGCT

TCAATATCTTGTCGCTCAAGTCAATCCCTCGTCCATTCCGACGGCAACACCTACCTCT

CTTGGCTCCAACAGAGACCCGGCCAGCCTCCCAGACTTCTCATCTACAAAATCAGTA

ACAGGTTCTTCGGCGTCCCTGACAGGTTCAGTGGATCTGGAGCAGGTACAGATTTCA

CCTTGAAGATAAGTAGAGTGGAGGCTGAGGACGTAGGCGTCTATTATTGTATGCAA

GCTACCCAATTCCCACATACATTCGGCCAAGGCACTAAATTGGAAATAAAAGGCGG

CTCCGAGGGCAAGAGCAGCGGCAGCGGCAGCGAGAGCAAGAGCACCGGCGGCAGC

CAAGTAACACTCAAGGAGAGCGGACCAGTCTTGGTGAAACCAACTGAGACCTTGAC

TTTGACATGTACTGTAAGTGGCTTCAGCCTTACCAACATCAGGATGTCAGTATCTTG

GATAAGGCAACCACCTGGCAAGGCACTCGAATGGCTGGCACACATCTTTTCTAACG

```
-continued
ACGAAAAATCCTATTCTTCCAGTCTCAAAAGTCGCCTTACCATCAGCCGAGATACCA
GTAAGAGTCAAGTAGTTCTTACATTGACCAATGTAGATCCAGTTGATACAGCCACAT
ACTACTGCGCACGAATGCGGCTTCCATACGGCATGGATGTATGGGGACAGGGAACT
ACTGTTACCGTTAGTTCCACTAGTACCCCAGCCCCACGCCCTCCCACCCCTGCTCCTA
CAATAGCATCCCAGCCCTTGTCACTTCGCCCCGAAGCATGCAGACCAGCCGCAGGC
GGTGCTGTGCATACCCGAGGACTGGACTTCGCCTGCGACATCTACATCTGGGCCCCA
CTGGCCGGCACCTGCGGCGTGCTGCTGCTGAGCCTGGTGATCACCCTGTACTGCAAG
CGCGGCCGCAAGAAGCTGCTGTACATCTTCAAGCAGCCATTCATGCGCCCAGTGCA
GACCACCCAGGAGGAGGACGGCTGCAGCTGCCGCTTCCCAGAGGAGGAGGAGGGC
GGCTGCGAGCTGCGCGTGAAGTTCAGCCGCAGCGCCGACGCCCCAGCCTACAAGCA
GGGCCAGAACCAGCTGTACAACGAGCTGAACCTGGGCCGCCGCGAGGAGTACGACG
TGCTGGACAAGCGCCGCGGCCGCGACCCAGAGATGGGCGGCAAGCCACGCCGCAA
GAACCCACAGGAGGGCCTGTACAACGAGCTGCAGAAGGACAAGATGGCCGAGGCC
TACAGCGAGATCGGCATGAAGGGCGAGCGCCGCCGCGGCAAGGGCCACGACGGCC
TGTACCAGGGCCTGAGCACCGCCACCAAGGACACCTACGACGCCCTGCACATGCAG
GCCCTGCCACCACGCTGA
```

Linker sequence
(SEQ ID NO: 91)
GGSEGKSSGSGSESKSTGGS

Linker sequence
(SEQ ID NO: 92)
GGGSGGGS

Linker sequence
(SEQ ID NO: 93)
GGGSGGGSGGGS

Linker sequence
(SEQ ID NO: 94)
GGGSGGGSGGGSGGGS

Linker sequence
(SEQ ID NO: 95)
GGGSGGGSGGGSGGGSGGGS

Linker sequence
(SEQ ID NO: 96)
GGGGSGGGGSGGGGS

Linker sequence
(SEQ ID NO: 97)
GGGGSGGGGSGGGGSGGGGS

Linker sequence
(SEQ ID NO: 98)
GGGGSGGGGSGGGGSGGGGSGGGGS

Linker sequence
(SEQ ID NO: 99)
GSTSGSGKPGSGEGSTKG

Linker sequence
(SEQ ID NO: 100)
IRPRAIGGSKPRVA

Linker sequence
(SEQ ID NO: 101)
GKGGSGKGGSGKGGS

Linker sequence
(SEQ ID NO: 102)
GGKGSGGKGSGGKGS

Linker sequence
GGGKSGGGKSGGGKS (SEQ ID NO: 103)

Linker sequence
GKGKSGKGKSGKGKS (SEQ ID NO: 104)

Linker sequence
GGGKSGGKGSGKGGS (SEQ ID NO: 105)

Linker sequence
GKPGSGKPGSGKPGS (SEQ ID NO: 106)

Linker sequence
GKPGSGKPGSGKPGSGKPGS (SEQ ID NO: 107)

Linker sequence
GKGKSGKGKSGKGKSGKGKS (SEQ ID NO: 108)

Linker sequence
STAGDTHLGGEDFD (SEQ ID NO: 109)

Linker sequence
GEGGSGEGGSGEGGS (SEQ ID NO: 110)

Linker sequence
GGEGSGGEGSGGEGS (SEQ ID NO: 111)

Linker sequence
GEGESGEGESGEGES (SEQ ID NO: 112)

Linker sequence
GGGESGGEGSGEGGS (SEQ ID NO: 113)

Linker sequence
GEGESGEGESGEGESGEGES (SEQ ID NO: 114)

Linker sequence
GSTSGSGKPGSGEGSTKG (SEQ ID NO: 115)

Linker sequence
PRGASKSGSASQTGSAPGS (SEQ ID NO: 116)

Linker sequence
GTAAAGAGAAGGAAAGAAG (SEQ ID NO: 117)

Linker sequence
GTSGSSGSGSGGSGSGGGG (SEQ ID NO: 118)

Linker sequence
GKPGSGKPGSGKPGSGKPGS (SEQ ID NO: 119)

Linker sequence
GSGS (SEQ ID NO: 120)

Linker sequence
APAPAPAPAP (SEQ ID NO: 121)

Linker sequence
APAPAPAPAPAPAPAPAPAP (SEQ ID NO: 122)

```
Linker sequence
                                                        (SEQ ID NO: 123)
AEAAAKEAAAKEAAAAKEAAAAKEAAAAKAAA Hinge sequence
                                                        (SEQ ID NO: 124)
EPKSCDKTHTCPPCP Hinge sequence
                                                        (SEQ ID NO: 125)
ERKCCVECPPCP Hinge sequence
                                                        (SEQ ID NO: 126)
ELKTPLGDTTHTCPRCPEPKSCDTPPPCPRCPEPKSCDTPPPCPRCPEPKSCDTPPPCPRCP Hinge sequence
                                                        (SEQ ID NO: 127)
ESKYGPPCPSCP
```

---

What is claimed is:

1. A chimeric antigen receptor (CAR), comprising an extracellular antigen-binding domain, a transmembrane domain and an intracellular signaling domain, wherein the extracellular antigen-binding domain comprises:
   a heavy chain CDR1 having the amino acid sequence of SEQ ID NO: 66, a heavy chain CDR2 having the amino acid sequence of SEQ ID NO: 67, and a heavy chain CDR3 having the amino acid sequence of SEQ ID NO: 68, and further comprises a light chain CDR1 having the amino acid sequence of SEQ ID NO: 69, a light chain CDR2 having the amino acid sequence of SEQ ID NO: 70, and a light chain CDR3 having the amino acid sequence of SEQ ID NO: 71; or
   a heavy chain CDR1 having the amino acid sequence of SEQ ID NO: 58, a heavy chain CDR2 having the amino acid sequence of SEQ ID NO: 59, and a heavy chain CDR3 having the amino acid sequence of SEQ ID NO: 60, and further comprises a light chain CDR1 having the amino acid sequence of SEQ ID NO: 61, a light chain CDR2 having the amino acid sequence of SEQ ID NO: 62, and a light chain CDR3 having the amino acid sequence of SEQ ID NO: 63;
   wherein the extracellular antigen-binding domain binds the anti-G protein receptor family C group 5 member D (GPRC5D) antigen.

2. The CAR of claim 1, wherein the extracellular antigen-binding domain comprises:
   a light chain variable region comprising an amino acid sequence of SEQ ID NO: 73 and a heavy chain variable region comprising an amino acid sequence of SEQ ID NO: 72; or
   a light chain variable region comprising an amino acid sequence of SEQ ID NO: 65 and a heavy chain variable region comprising an amino acid sequence of SEQ ID NO: 64.

3. The CAR of claim 1, wherein the extracellular antigen-binding domain comprises a single-chain variable fragment (scFv).

4. The CAR of claim 3, wherein the scFv comprises a linker polypeptide between the light chain variable region and the heavy chain variable region.

5. The CAR of claim 4, wherein the linker polypeptide comprises an amino acid sequence of SEQ ID NO: 7.

6. The CAR of claim 3, wherein the scFv comprises an amino acid sequence selected from the group consisting of SEQ ID NOS: 78, 77, 75, and 76.

7. The CAR of claim 1, wherein the extracellular antigen-binding domain comprises a signal polypeptide.

8. The CAR of claim 7, wherein the signal polypeptide comprises an amino acid sequence of SEQ ID NO: 11.

9. The CAR of claim 1, wherein the intracellular signaling domain comprises a polypeptide component selected from the group consisting of a TNF receptor superfamily member 9 (CD137) component, a T-cell surface glycoprotein CD3 zeta chain (CD3z) component, a cluster of differentiation (CD27) component, a cluster of differentiation superfamily member component, and a combination thereof.

10. The CAR of claim 9, wherein the CD137 component comprises an amino acid sequence of SEQ ID NO: 12.

11. The CAR of claim 9, wherein the CD3z component comprises an amino acid sequence of SEQ ID NO: 13.

12. The CAR of claim 9, wherein the intracellular signaling domain comprises an amino acid sequence of SEQ ID NO: 14.

13. The CAR of claim 1, wherein the transmembrane domain comprises a CD8a transmembrane region (CD8a-TM) polypeptide.

14. The CAR of claim 13, wherein the CD8a-TM polypeptide comprises an amino acid sequence of SEQ ID NO: 15.

15. The CAR of claim 1, further comprising a hinge region linking the transmembrane domain to the extracellular antigen-binding domain.

16. The CAR of claim 15, wherein the hinge region is a CD8a-hinge region.

17. The CAR of claim 16, wherein the CD8a-hinge region comprises an amino acid sequence of SEQ ID NO: 16.

18. The CAR of claim 1, wherein the extracellular antigen-binding domain comprises an amino acid sequence selected from the group consisting of SEQ ID NOS: 82, 81, 80, and 79.

19. The CAR of claim 1, wherein the CAR comprises an amino acid sequence selected from the group consisting of SEQ ID NOS: 86, 85, 83, and 84.

20. An isolated lymphocyte expressing the CAR of claim 1.

21. The isolated lymphocyte of claim 20, wherein the lymphocyte is a T lymphocyte.

22. The isolated lymphocyte of claim 21, wherein the T lymphocyte is a naïve T cell.

23. The isolated lymphocyte of claim 21, wherein the T lymphocyte is a memory stem T cell.

24. The isolated lymphocyte of claim 21, wherein the T lymphocyte is a central memory T cell.

25. The isolated lymphocyte of claim 21, wherein the T lymphocyte is CD4+.

26. The isolated lymphocyte of claim 21, wherein the T lymphocyte is CD8+.

27. The isolated lymphocyte of claim 21, wherein the T lymphocyte is CD4+ and CD8+.

28. A pharmaceutical composition, comprising an effective amount of the lymphocyte of claim 20.

29. A pharmaceutical composition, comprising
   an effective amount of the lymphocyte of claim 20 and a pharmaceutically acceptable excipient.

30. A method of treating a subject having a GPRC5D-expressing cancer, the method comprising: administering a therapeutically effective amount of the lymphocyte of claim 20 to a subject in need thereof, whereby the lymphocyte induces killing of GPRC5D-expressing cancer cells in the subject.

31. The method of claim 30, wherein the cancer is selected from the group consisting of a lung cancer, a gastric cancer, a colon cancer, a hepatocellular carcinoma, a renal cell carcinoma, a bladder urothelial carcinoma, a metastatic melanoma, a breast cancer, an ovarian cancer, a cervical cancer, a head and neck cancer, a pancreatic cancer, a glioma, a glioblastoma, and a non-Hodgkin's lymphoma (NHL), an acute lymphocytic leukemia (ALL), a chronic lymphocytic leukemia (CLL), a chronic myelogenous leukemia (CML), a smoldering multiple myeloma (SMM), a multiple myeloma (MM), an acute myeloid leukemia (AML), and combinations thereof.

32. The method of claim 31, wherein the cancer is multiple myeloma.

33. A method of targeted killing of a GPRC5D-expressing cancer cell, the method comprising: contacting the GPRC5D-expressing cancer cell with the lymphocyte of claim 20, whereby the lymphocyte induces killing of the GPRC5D-expressing cancer cell.

34. The method of claim 33, wherein the cancer cell is selected from the group consisting of a lung cancer, a gastric cancer, a colon cancer, a hepatocellular carcinoma, a renal cell carcinoma, a bladder urothelial carcinoma, a metastatic melanoma, a breast cancer, an ovarian cancer, a cervical cancer, a head and neck cancer, a pancreatic cancer, a glioma, a glioblastoma, and a non-Hodgkin's lymphoma (NHL), an acute lymphocytic leukemia (ALL), a chronic lymphocytic leukemia (CLL), a chronic myelogenous leukemia (CML), a smoldering multiple myeloma (SMM), a multiple myeloma (MM), an acute myeloid leukemia (AML), and combinations thereof.

35. The method of claim 33, wherein the cancer cell is a multiple myeloma cell.

36. A method of detecting the presence of a GPRC5D-expressing cancer in a subject, comprising: (a) contacting a cell sample obtained from the subject with the CAR of claim 1, thereby forming a CAR-cell complex, and (b) detecting the complex, wherein detection of the complex is indicative of the presence of a GPRC5D-expressing cancer in the subject.

* * * * *